US008367401B2

(12) United States Patent
Lemon et al.

(10) Patent No.: US 8,367,401 B2
(45) **Date of Patent: *Feb. 5, 2013**

(54) REPLICATION COMPETENT HEPATITIS C VIRUS AND METHODS OF USE

(75) Inventors: Stanley M. Lemon, Galveston, TX (US); MinKyung Yi, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 549 days.

This patent is subject to a terminal disclaimer.

(21) Appl. No.: 11/975,658

(22) Filed: Oct. 19, 2007

(65) Prior Publication Data

US 2008/0311576 A1 Dec. 18, 2008

Related U.S. Application Data

(63) Continuation of application No. 11/006,313, filed on Dec. 6, 2004, now Pat. No. 7,288,369, which is a continuation of application No. 10/259,275, filed on Sep. 27, 2002, now Pat. No. 6,921,634, which is a continuation-in-part of application No. 09/747,419, filed on Dec. 23, 2000, now abandoned.

(60) Provisional application No. 60/338,123, filed on Nov. 13, 2001, provisional application No. 60/325,236, filed on Sep. 27, 2001, provisional application No. 60/171,909, filed on Dec. 23, 1999.

(51) Int. Cl.
*C12Q 1/70* (2006.01)
*C12N 15/63* (2006.01)

(52) U.S. Cl. .................. 435/320.1; 435/69.1; 424/228.1

(58) Field of Classification Search ........................ None
See application file for complete search history.

(56) References Cited

U.S. PATENT DOCUMENTS

| | | | | |
|---|---|---|---|---|
| 5,652,122 | A * | 7/1997 | Frankel et al. | 435/69.7 |
| 5,766,906 | A | 6/1998 | Lemon et al. | |
| 5,846,767 | A | 12/1998 | Halpin et al. | |
| 5,874,565 | A | 2/1999 | Rice et al. | |
| 5,912,167 | A | 6/1999 | Palmenberg et al. | |
| 6,127,116 | A | 10/2000 | Rice et al. | |
| 6,392,028 | B1 | 5/2002 | Rice, III et al. | |
| 6,630,343 | B1 | 10/2003 | Bartenschlager | |
| 6,689,559 | B2 | 2/2004 | Wimmer et al. | |
| 6,921,634 | B2 * | 7/2005 | Lemon et al. | 435/3 |
| 6,930,095 | B2 | 8/2005 | Bichko | |
| 6,943,246 | B2 | 9/2005 | Rice et al. | |
| 7,049,428 | B1 | 5/2006 | Rice, III et al. | |
| 7,276,373 | B2 * | 10/2007 | Pellerin et al. | 435/455 |
| 7,288,369 | B2 * | 10/2007 | Lemon et al. | 435/5 |
| 7,838,207 | B2 * | 11/2010 | Pellerin et al. | 430/370 |
| 2002/0155582 | A1 | 10/2002 | Lemon et al. | |
| 2003/0073080 | A1 | 4/2003 | Rice et al. | |
| 2005/0153281 | A1 | 7/2005 | Lemon et al. | |
| 2007/0292840 | A1 | 12/2007 | Lemon et al. | |

FOREIGN PATENT DOCUMENTS

| | | | |
|---|---|---|---|
| WO | WO 00/14263 | | 3/2000 |
| WO | WO 02/059321 | A2 | 8/2002 |
| WO | WO 02/059321 | A3 | 8/2002 |
| WO | WO 2004/055216 | A2 | 7/2004 |
| WO | WO 2007/055216 | A3 | 7/2004 |
| WO | WO 2005/053516 | A2 | 6/2005 |
| WO | WO 2005/053516 | A3 | 6/2005 |

OTHER PUBLICATIONS

Marzio et al. Proc. Natl. Acad. Sci. U.S.A. 1998, vol. 95, pp. 13519-13524.*
Betti et al. Vaccine 2001, vol. 19, No. 25-26, pp. 3408-3419.*
Rossi et al. Gene Therapy 1997, vol. 4, pp. 1261-1269.*
U.S. Appl. No. 60/525,989, filed Dec. 1, 2003, Lemon et al.
Blight et al., "Highly Permissive Cell Lines for Subgenomic and Genomic Hepatitis C Virus RNA Replication," *J. Virol.*, Dec. 2002; 76(24):13001-13014.
Choo et al., "Genetic Organization and Diversity of the Hepatitis C Virus," *Proc. Natl. Acad. Sci. USA*, Mar. 1991; 88(6):2451-2455.
Duhamel et al., "Secondary structure content of the HDV ribozyme in 95% formamide," *Nucleic Acids Research*, 1996;24(20):3911-3917.
Enomoto et al., "There are Two Major Types of Hepatitis C Virus in Japan," *Biochem. Biophys. Res. Commun.*, Aug. 16, 1990; 170(3):1021-1025.
Fried et al., "Peginterferon Alfa-2a Plus Ribavirin for Chronic Hepatitis C Virus Infection," *N. Engl. J. Med.*, Sep. 26, 2002; 347(13):975-982.
Gale et al., "Repression of the PKR Protein Kinase by the Hepatitis C Virus NS5A Protein: a Potential Mechanism of Interferon Resistance," *Clin. Diagn. Virol.*, Jul. 1998; 10(2-3):157-162.
Gale et al., "Evidence that hepatitis C virus resistance to Interferon is mediated through repression of the PKR protein kinase by the nonstructural 5A protein," *Virology*, 1997;230:217-227.

Inchauspe et al., "Genomic Structure of the Human Prototype Strain H of Hepatitis C Virus: Comparison with American and Japanese Isolates," *Proc. NatL Acad. Sci. USA*, Nov. 15, 1991; 88(22):10292-10296.

Kato, "Molecular Virology of Hepatitis C Virus," *Acta Medica Okayama*, 2001; 55(3):133-159.
Knowles et al., "Human hepatocellular carcinoma cell lines secrete the major plasma proteins and hepatitis B surface antigen," *Science*, Jul. 1980; 209(25):497-499.
Le Pogam et al., "Comparison of DNA Enzyme Immunoassay and Line Probe Assays (Inno-LiPA HCV I and II) for Hepatitis C Virus Genotyping," *J. Clin. Microbiol.*, May 1998; 36(5):1461-1463.
Nakano et al., "General Acid-Base Catalysis in the Mechanism of Hepatitis Delta Virus Ribozyme," *Science*, Feb. 25, 2000; 287:1493-1497.

(Continued)

*Primary Examiner* — Bao Li
(74) *Attorney, Agent, or Firm* — Mueting, Raasch & Gebhardt, P.A.

(57) ABSTRACT

The present invention provides a replication competent hepatitis C virus that includes a heterologous polynucleotide. The invention also includes methods for modifying a hepatitis C virus polynucleotide, selecting a replication competent hepatitis C virus polynucleotide, detecting a replication competent hepatitis C virus polynucleotide, and identifying a compound that inhibits replication of a hepatitis C virus polynucleotide.

20 Claims, 62 Drawing Sheets

OTHER PUBLICATIONS

National Center for Biotechnology Information, National Library of Medicine, National Institutes of Health, Bethesda, MD, GenBank Locus No. HPCCGAA, Accession No. M67463, "Hepatitis C virus subtype 1a, complete genome," [online]. Retrieved from the Internet on Mar. 31, 2009: <URL: http://www.ncbi.nlm.nih.gov/nuccore/329737>, 6 pgs.

Neddermann et al., "Hyperphosphorylation of the Hepatitis C Virus NS5A Protein Requires an Active NS3 Protease, NS4A, NS4B, and NS5A Encoded on the Same Polyprotein," *Journal of Virology*, Dec. 1999; 73(12):9984-9991.

Noguchi et al., "Cell lines from non-neoplastic liver and hepatocellular carcinoma tissue from a single patient," *In Vitro Cell Dev. Biol. Anim.*, Mar. 1996; 32:135-137.

Noguchi et al., "Routes of transmission of hepatitis C virus in an endemic rural area of Japan—Molecular epidemiologic study of hepatitis C virus infection," *Scand J. Infect. Diseases*, 1997; 29:23-28.

Ohno et al., "New Hepatitis C Virus (HCV) Genotyping System that Allows for Identification of HCV Genotypes 1a, 1b, 2a, 2b, 3a, 3b, 4, 5a, and 6a," *J. Clin. Microbiol.*, Jan. 1997; 35(1):201-207.

Perrotta et al., "Core Sequences and a Cleavage Site Wobble Pair Required for HDV Antigenomic Ribozyme Self-Cleavage," *Nucleic Acids Res.*, Apr. 1996; 24(7):1314-1321.

Pietschmann et al., "Persistent and transient replication of full-length hepatitis C virus genomes in cell culture," *J Virology*, 2002; 76:4008-4021.

Sandres et al., "Genetic Heterogeneity of Hypervariable Region 1 of the Hepatitis C Virus (HCV) Genome and Sensitivity of HCV to Alpha Interferon Therapy," *J. Virol.*, Jan. 2000; 74(2):661-668.

Simmonds, "Viral Heterogeneity of the Hepatitis C Virus," *J. Hepatol.*, 1999; 31(Suppl.1):54-60.

Simmonds et al., "Classification of Hepatitis C Virus into Six Major Genotypes and a Series of Subtypes by Phylogenetic Analysis of the NS-5 Region," *J. Gen. Virol.*, Nov. 1993; 74(Pt 11):2391-2399.

Smith et al., "Variation of the Hepatitis C Virus 5' Non-Coding Region: Implications for Secondary Structure, Virus Detection and Typing",*J. Gen. Virol.*, Jul. 1995; 76 (Pt. 7):1749-1761.

Tokita et al., "The Entire Nucleotide Sequences of Three Hepatitis C Virus Isolates in Genetic Groups 7-9 and Comparison with Those in the Other Eight Genetic Groups," *J. Gen. Virol.*, Aug. 1998; 79(Pt 8):1847-1857.

Wright-Minogue et al., "Cross-Genotypic Interaction Between Hepatitis C Virus NS3 Protease Domains and NS4A Cofactors," *J. Hepatol.*, Mar. 2000, 32(3):497-504.

Yao et al., "Molecular Views of Viral Polyprotein Processing Revealed by the Crystal Structure of the Hepatitis C Virus Bifunctional Protease-Helicase," *Structure*, Nov. 1999, 7(11):1353-1363.

Ausubel et al., eds., *Current Protocols in Molecular Biology*, vol. 1-4, John Wiley & Sons, U.S.; title page, publication page and table of contents only, 12 pgs. (1994).

Bartenschlager et al., "Replication of hepatitis C virus," *J. Gen. Virol.*, 2000; 81:1631-1648.

Beard et al., "An Infectious Molecular Clone of a Japanese Genotype 1b Hepatitis C Virus," *Hepatology*, Jul. 1999; 30(1):316-24.

Berger et al., "Secreted Placental Alkaline Phosphatase: A Powerful New Quantitative Indicator of Gene Expression in Eukaryotic Cells," *Gene*, Jun. 15, 1988; 66(1):1-10.

Bieniasz et al., "Highly Divergent Lentiviral Tat Proteins Activate Viral Gene Expression by a Common Mechanism," *Mol. Cell Biol.*, Jul. 1999; 19(7):4592-9.

"BLAST," National Institues of Health, Bethesda, MD [online]. Retrieved from Internet on Apr. 17, 2001. <URL:http://www.ncbi.nlm.nih.gov/gorf/b12.html>, 2 pgs.

Blight et al., "Efficient Initiation of HCV RNA Replication in Cell Culture," *Science*, Dec. 8, 2000; 290(5498):1972-1975.

Blight et al., "Efficient Replication of Hepatitis C Virus Genotype 1a RNAs in Cell Culture," *Journal of Virology*, 2003; 77(5):3181-3190.

Bukh et al., "Sequence analysis of the 5' noncoding region of hepatitis C virus," *Proc. Nat. Acad. Sci. USA*, 1992; 89:4942-46.

Bukh et al., "Mutations that permit efficient replication of hepatitis C virus RNA in Huh-7 cells prevent productive replication in chimpanzees," *PNAS*, Oct. 29, 2002; 99(22):14416-14421.

Cai et al., "Robust Production of Infectious Hepatitis C Virus (HCV) from Stably HCV cDNA-Transfected Human Hepatoma Cells," *J. Virol.*, 2005; 79:13963-13973.

Cullen, "*Trans*-activation of Human Immunodeficiency Virus Occurs via a Bimodal Mechanism," *Cell*, Sep. 26, 1986; 46(7):973-982.

Cullen, Bryan R., "HIV-1 Auxiliary Proteins: Making Connections in a Dying Cell," *Cell*, 1998; 93:685-692.

Forns et al., "Hepatitis C Virus Lacking the Hypervariable Region 1 of the Second Envelope Protein Is Infectious and Causes Acute Resolving or Persistent Infection in Chimpanzees," *Proc Natl Acad Sci U S A*. Nov. 21, 2000;97(24):13318-13323.

Frese et al., "Interferon-α inhibits hepatitis C virus subgenomic RNA replication by an MxA-independent pathway," *J. Gen. Virol.*, 2001; 82:723-733.

Fujisawa et al., "The Indirect Association of Human T-cell Leukemia Virus *tax* Protein with DNA Results in Transcriptional Activation," *J Virol*. Aug. 1991; 65(8):4525-4528.

Graham et al., "A genotype 2b NS5B polymerase with novel substitutions supports replication of a chimeric HCV 1b:2b replicon containing a genotype 1b NS3-5A background," *Antiviral Research*, 2006; 69:24-30.

Grobler et al., "Identification of a Key Determinant of Hepatitis C Virus Cell Culture Adaptation in Domain II of NS3 Helicase," *Journal of Biological Chemistry*, 2003; 278(19):16741-16746.

Gu et al., "Replication Studies Using Genotype 1a Subgenomic Hepatitis C Virus Replicons," *Journal of Virology*, 2003; 77(9):5352-5359.

Guo et al., "Identification of a Novel RNA Species in Cell Lines Expressing HCV Subgenomic Replicons," Abstract P045, 7th International Meeting on Hepatitis C Virus and Related Viruses (Molecular Virology and Pathogenesis), The Marriott Resort Hotel, Gold Coast, Queensland, Australia, Dec. 3-7, 2000.

Guo et al., "Effect of Alpha Interferon on the Hepatitis C Virus Replicon," *J. Virol.*, 2001; 75:8516-8523.

Hadzopoulou-Cladaras et al., "The *rev* (*trs/art*) Protein of Human Immunodeficiency Virus Type 1 Affects Viral mRNA and Protein Expression via a *cis*-acting Sequence in the *env* Region," *J Virol*. Mar. 1989; 63(3):1265-1274.

Harlow et al., *Antibodies: A Laboratory Manual*, Cold Spring Harbor Laboratory Press, Cold Spring Harbor, NY; title page, publisher's page, and table of contents, 9 pages (1988).

Hayashi et al., "Molecular cloning and heterogeneity of the human hepatitis C virus (HCV) genome," *J. Hepatol.*, 1993; 17:S94-S107.

Heller et al., "An in vitro model of hepatitis C virion production," *PNAS*, 2005; 102(7):2579-2583.

Honda et al., "Stability of a stem-loop involving the initiator AUG controls the efficiency of internal initiation of translation of hepatitis C virus RNA," *RNA*, 1996; 2:955-968.

Iacovacci et al., "Molecular Characterization and Dynamics of Hepatitis C Virus Replication in Human Fetal Hepatocytes Infected In Vitro," *Hepatology*, 1997; 26(5):1328-1337.

Ikeda et al., "Human hepatocyte clonal cell lines that support persistent replication of hepatitis C virus," *Virus Research*, 1998; 56:157-167.

Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," *J. Virol.*, Mar. 2002;76(6): 2997-3006.

Kanda et al., "Generation of Infectious Hepatitis C Virus in Immortalized Human Hepatocytes," *J. Virol.*, 2006; 80:4633-4639.

Kato et al., "Susceptibility of Human T-Lymphotropic Virus Type I Infected Cell Line MT-2 to Hepatitis C Virus Infection," *Biochemical and Biophysical Research Communications*, Jan. 26, 1995; 206(3):863-869.

Kato et al., "Replication of Hepatitis C Virus in Cultured Non-neoplastic Human Hepatocytes," *Jpn. J. Cancer Res.*, Aug. 1996; 87:787-792.

Kim et al., "Domains I and II in the 5' Nontranslated Region of the HCV Genome Are Required for RNA Replication," *Biochem Biophys Res Comm*, 2002; 290:105-112.

Kolykhalov et al., "Identification of a Highly Conserved Sequence Element at the 3' Terminus of Hepatitis C Virus Genome RNA," *J. Virol.* Jun. 1996; 70(6):3363-3371.

Kolykhalov et al., "Hepatitis C Virus-encoded Enzymatic Activities and Conserved RNA Elements in the 3' Nontranslated Region Are Essential for Virus Replication in Vivo," *J. Virol.* Feb. 2000; 74(4):2046-2051.
Krieger et al., "Enhancement of Hepatitis C Virus RNA Replication by Cell Culture-Adaptive Mutations," *J. Virol.*, 2001; 75:4614-4624.
Lai et al., "Generation and Characterization of a Hepatitis C Virus NS3 Protease-dependent Bovine Viral Diarrhea Virus," *J. Virol.* Jul. 2000;74(14):6339-6347.
Lanford et al., "Demonstration of in Vitro Infection of Chimpanzee Hepatocytes with Hepatitis C Virus Using Strand-Specific RT/PCR," *Virology*, 1994; 202(2):606-614.
Lanford et al., "Lack of Detection of Negative-strand Hepatitis C Virus RNA in Peripheral Blood Mononuclear Cells and Other Extrahepatic Tissues by the Highly Strand-specific rTth Reverse Transcriptase PCR," *J. Virol.* Dec. 1995;69(12):8079-8083.
Landford et al., "Antiviral Effect and Virus-Host Interactions in Response to Alpha Interferon, Poly(I)-Poly(C), Tumor Necrosis Factor Alpha, and Ribavirin in Hepatitis C Virus Subgenomic Replicons," *Journal of Virology*, 2003; 77(2):1092-1104.
Lemon, "Selection of Cell Culture-adapted Hepatitis C RNA," Grant Abstract for Grant No. 2U19AI40035-050001 [online]. National Institute of Allergy and Infectious Diseases, National Institutes of Health; project dates Aug. 1, 1996 to Jul. 31, 2005. Retrieved from the Internet on Apr. 17, 2001; URL: <http://commons.cit.nih.gov/crisp/crisp_lib.getdoc?textkey=6340699&p_query=&ticket=1907498&p_audit_session_id=4197699&p_keywords=>, 2 pages.
Lemon, "The Southeastern Cooperative Hepatitis C Research Group," Grant Abstract for Grant No. 2U19AI40035-05 [online]. National Institute of Allergy and Infectious Diseases, National Institutes of Health; project dates Aug. 1, 1996 to Jul. 31, 2005. Retrieved from the Internet on Apr. 17, 2001; URL: <http://commons.cit.nih.gov/crisp/crisp_lib.getdoc?textkey=6199426&p_query=&ticket=1907498&p_audit_session_id=4197699&p_keywords=>, 2 pages.
Li et al., "Cellular response to conditional expression of Hepatitis C virus core protein in Huh7 cultured human hepatoma cells," *Hepatology*, May 2002; 35(5):1237-1246.
Lohmann et al., "Replication of Subgenomic Hepatitis C Virus RNAs in a Hepatoma Cell Line," *Science*, Jul. 2, 1999; 285(5424):110-113.
Lohmann et al., "Adaptation of Selectable HCV Replicon to a Human Hepatoma Cell Line," Abstract P038, 7th International Meeting on Hepatitis C Virus and Related Viruses (Molecular Virology and Pathogenesis), The Marriott Resort Hotel, Gold Coast, Queensland, Australia, Dec. 3-7, 2000.
Lohmann et al., "Mutations in Hepatitis C Virus RNAs Conferring Cell Culture Adaptation," *J. Virol.*, Feb. 2001; 75(3):1437-1449.
Murray et al., "Persistant Replication of Hepatitis C Virus Replicons Expressing the β-Lactamase Reporter in Subpopulations of Highly Permissive Huh7 Cells," *J. Virol.*, 2003; 77:2928-2935.
Nakajima et al., "Characterization of Long-Term Cultures of Hepatitis C Virus," *Journal of Virology*, May 1996; 70(5):3325-3329.
Naryshikin et al., "RNA Recognition and Regulation of HIV-1 Gene Expression by Viral Factor Tat," *Biochemistry*, 1998; 63:489-503.
National Center for Biotechnology Information, National Library of Medicine, National Institutes of Health, Bethesda, MD, GenBank Locus No. AB030907, Accession No. AB030907, "Hepatitis C virus type 2b gene for polyprotein, complete cds, isolate:JPUT971017," [online]. Retrieved from the Internet on Apr. 17, 2001:<URL: http://www.ncbi.nlm.nih.gov/entrez/query.fcgi?cmd=Retrieve&db=Nucleotide&list_uids=9757541&dopt=GenBank>, 8 pages.
National Center for Biotechnology Information, National Library of Medicine, National Institutes of Health, Bethesda, MD, GenBank Locus No. AF011751, Accession No. AF011751, "Hepatitis C virus strain H77 pCV-H77C polyprotein gene, complete cds," [online]. Retrieved from the Internet on Apr. 26, 2001:<URL:http://www.ncbi.nlm.nih.gov/entrez/query.fcgi?cmd=Retrieve&db=Nucleotide&list_uids=2327070&dopt=GenBank>, 7 pages.
National Center for Biotechnology Information, National Library of Medicine, National Institutes of Health, Bethesda, MD, GenBank Locus No. AF033819, Accession No. AF033819, "HIV-1, complete genome," [online]. Retrieved from the Internet on Apr. 17, 2001:<URL:http://www.ncbi.nlm.nih.gov/entrez/query.fcgi?cmd=Retrieve&db=Nucleotide&list_uids=4558520&dopt=GenBank>, 9 pages.
National Center for Biotechnology Information, National Library of Medicine, National Institutes of Health, Bethesda, MD, GenBank Locus No. AF139594, Accession No. AF139594, "Hepatitis C virus strain HCV-N, complete genome,"[online]. Retrieved from the Internet on Apr. 17, 2001:<URL:http://www.ncbi.nlm.nih.gov/entrez/query.fcgi?cmd=Retrieve&db=Nucleotide&list_uids=5532421&dopt=GenBank>, 7 pages.
National Center for Biotechnology Information, National Library of Medicine, National Institutes of Health, Bethesda, MD, GenBank Locus No. AF238481, Accession No. AF238481, "Hepatitis C virus 2a polyprotein gene, complete cds,"[online]. Retrieved from the Internet on Apr. 17, 2001:<URL:http://www.ncbi.nlm.nih.gov/entrez/query.fcgi?cmd=Retrieve&db=Nucleotide&list_uids=7329200&dopt=GenBank>, 6 pages.
National Center for Biotechnology Information, National Library of Medicine, National Institutes of Health, Bethesda, MD, GenBank Locus No, SSE242652, Accession No. AJ242652, "Hepatitis C virus replicon I377/NS3-3'UTR,"[online]. Retrieved from the Internet on Feb. 18, 2003:<URL:http://www.ncbi.nlm.nih.gov/entrez/query.fcgi?cmd=Retrieve&db=Nucleotide&list_uids=5441834&dopt=GenBank>, 7 pages.
National Center for Biotechnology Information, National Library of Medicine, National Institutes of Health, Bethesda, MD, GenBank Locus No. HCJ238799, Accession No. AJ238799, "Hepatitis C virus type 1b complete genome, isolate Con1," [online]. Retrieved from the Internet on Apr. 17, 2001:<URL:http://www.ncbi.nlm.nih.gov/entrez/query.fcgi?cmd=Retrieve&db—Nucleotide&list_uids=5420376&dopt=GenBank>, 8 pages.
Pelletier et al., "Internal Initiation of Translation of Eukaryotic mRNA Directed by a Sequence Derived from Poliovirus RNA," *Nature*, Jul. 28, 1988;.334(6180):320-5.
Pietschmann et al., "Characterization of Cell Lines Carrying Self-Replicating Hepatitis C Virus RNAs," *J. Virol.*, 2001; 75:1252-64.
Rethwilm et al., "The Transcriptional Transactivator of Human Foamy Virus Maps to the *bel* 1 Genomic Region," *Proc Natl Acad Sci USA*, Feb. 1, 1991; 88(3):941-5.
Reynolds et al., "Unique features of internal initiation of hepatitis C virus RNA translation," *EMBO J.*, 1995; 14:6010-20.
Reynolds et al., "Internal initiation of translation of hepatitis C virus RNA: The ribosome entry site is at the authentic initiation codon," *RNA*, 1996; 2:867-78.
Rijinbrand et al., "The influence of downstream protein-coding sequence on internal ribosome entry on hepatitis C virus and other flavivirus RNAs," *RNA*, 2001; 7:585-97.
Ryan et al., "Foot-and-Mouth Disease Virus 2A Oligopeptide Mediated Cleavage of an Artificial Polyprotein," *EMBO J.*, Feb. 15, 1994; 13(4):928-33.
Shimizu et al., "Evidence for in vitro replication of hepatitis C virus genome in a human T-cell line," *Proc. Natl. Acad. Sci. USA*, Jun. 1992; 89:5477-5481.
Shimizu et al., "Correlation between the infectivity of hepatits C virus in vivo and its infectivity in vitro," *Proc. Natl. Acad. Sci. USA*, Jul. 1993; 90:6037-6041.
Shimizu et al., "Infection of a chimpanzee with hepatitis C virus grown in cell culture," *J. of General Virology*, 1998; 79:1383-1386.
Simmonds, "Variability of Hepatitis C Virus," *Hepatology*, Feb. 1995; 21(2):570-83.
Takeuchi et al., "Real-time Detection System for Quantification of Hepatitis C Virus Genome," *Gastroenterology*. Mar. 1999;116(3):636-42.
Tatusova, et al. "BLAST 2 Sequences, a New Tool for Comparing Protein and Nucleotide Sequences," *FEMS Microbial Lett*. May 15, 1999;174(2):247-50.
Tautz et al., "Processing of Poly-ubiquitin in the Polyprotein of an RNA Virus," *Virology*. Nov. 1993; 197(1):74-85.
Whetter et al., "Analysis of Hepatitis A Virus Translation in a T7 Polymerase-expressing Cell Line," *Arch Virol Suppl.*, 1994; 9:291-8.
Whetter et al., "Low Efficiency of the 5' Nontranslated Region of Hepatitis A Virus RNA in Directing Cap-Independent Translation in Permissive Monkey Kidney Cells, " *J. Virol.*, 1994; 68:5253-63.

Xu et al., "Synthesis of a novel hepatitis C virus protein by ribosomal frameshift," *EMBO J.*, 2001; 20:3840-3848.

Yamada et al., "Genetic Organization and Diversity of the 3' Noncoding Region of the Hepatitis C Virus Genome," *Virology*, Sep. 1, 1996; 223(1):255-261.

Yanagi et al., "Transcripts from a Single Full-length cDNA Clone of Hepatitis C Virus Are Infectious When Directly Transfected into the Liver of a Chimpanzee," *Proc Natl Acad Sci USA*, Aug. 5, 1997; 94(16):8738-8743.

Yanagi et al., "In vivo Analysis of the 3' Untranslated Region of the Hepatitis C Virus after in vitro Mutagenesis of an Infectious cDNA Clone," *Proc Natl Acad Sci USA*, Mar. 2, 1999; 96(5):2291-2295.

Yi et al., "Infectious Discistronic Hepatitis C Virus (HCV) RNA That Facilitates the Rescue of Virus from Synthetic RNA and the Monitoring of Viral Replication in Cultured Cells," presented at 7th International Meeting on Hepatitis C Virus and Related Viruses (Molecular Virology and Pathogenesis), The Marriott Resort Hotel, Gold Coast, Queensland, Australia, Dec. 3-7, 2000; abstract and poster (30 pages).

Yi et al., "Subgenomic Hepatitis C Virus Replicons Inducing Expression of a Secreted Enzymatic Reporter Protein," *Virology*, 2002; 304(2):197-210.

Yi et al., "Adaptive Mutations Producing Efficient Replication of Genotype 1a Hepatitis C Virus RNA in Normal Huh7 Cells," *Journal of Virology*, 2004; 78(15):7904-7915.

Yoo et al., "Transfection of a Differentiated Human Hepatoma Cell Line (Huh7) with In Vitro-transcribed Hepatitis C Virus (HCV) RNA and Establishment of a Long-term Culture Persistently Infected with HCV," *J Virol*. Jan. 1995; 69(1):32-38.

Zhong et al., "Robust hepatitis C virus infection," PNAS, 2005; 102:9294-9299.

Adams et al., "Complete Coding Sequence of Hepatitis C Virus Genotype 6a," *Biochemical and Biophysical Research Communications*, 1997; 234:393-396.

Bressanelli et al., "Crystal structure of the RNA-dependent RNA polymerase of hepatitis C virus," *PNAS*, Nov. 9, 1999; 96(23):13034-13039.

Bressanelli et al., "Structural Analysis of the Hepatitis C Virus RNA Polymerase in Complex with Ribonucleotides," *Journal of Virology*, Apr. 2002; 76(7):3482-3492.

Chamberlain et al. "Complete nucleotide sequence of a type 4 hepatits C virus variant, the predominant genotype in the Middle East," *Journal of General Virology*, 1997; 78:1341-1347.

Cheney et al., "Mutations in NS5B Polymerase of Hepatitis C Virus: Impacts on in Vitro Enzymatic Activity and Viral RNA Replication in the Subgenomic Replicon Cell Culture," *Virology*, 2002; 297:298-306.

Love et al., "The Crystal Structure of Hepatitis C Virus NS3 Proteinase Reveals a Trypsin-like Fold and a Structural Zinc Binding Site," *Cell*, Oct. 18, 1996; 87:331-342.

Love et al., "Crystallographic Identification of a Noncompetitive Inhibitor Binding Site on the Hepatitis C Virus NS5B RNA Polymerase Enzyme," *Journal of Virology*, Jul. 2003; 77(13):7575-7581.

Simmonds et al., "A Proposed System for the Nomenclature of Hepatitis C Viral Genotypes," *Hepatology*, 1994; 19:1321-1324.

Simmonds et al., "Evolutionary analysis of variants of hepatitis C virus found in South-East Asia: comparison with classifications based upon sequence similarity," *Journal of General Virology*, 1996; 77:3013-3024.

Simmonds et al., "Consensus Proposals for a Unified System of Nomenclature of Hepatitis C Virus Genotypes," *Hepatology*, 2005; 42(4):962-973.

Smith et al., "Characteristics of Nucleotide Substitution in the Hepatitis C Virus Genome: Constraints on Sequence Change in Coding Regions at Both Ends of the Genome," *J. Mol. Evol.*, 1997; 45:238-246.

Yan et al., "Complex of NS3 protease and NS4A peptide of BK strain hepatitis C virus: a 2.2 å resolution structure in a hexagonal crystal form," *Protein Science*, 1998; 7:837-847.

Campbell et al., "What does the structure-function relationship of the HIV-1 Tat protein teach us about developing an AIDS vaccine?" *Retrovirology*, 2009; 6:50.

Jeang et al., "Multifaceted Activities of the HIV-1 Transactivator of Transcription, Tat," *The Journal of Biological Chemistry*, 1999; 274(41):28837-28840.

Kuppuswamy et al., "Multiple functional domains of Tat, the *trans*-activator of HIV-1, defined by mutational analysis," *Nucleic Acids Research*, 1989; 17(9):3551-3561.

\* cited by examiner

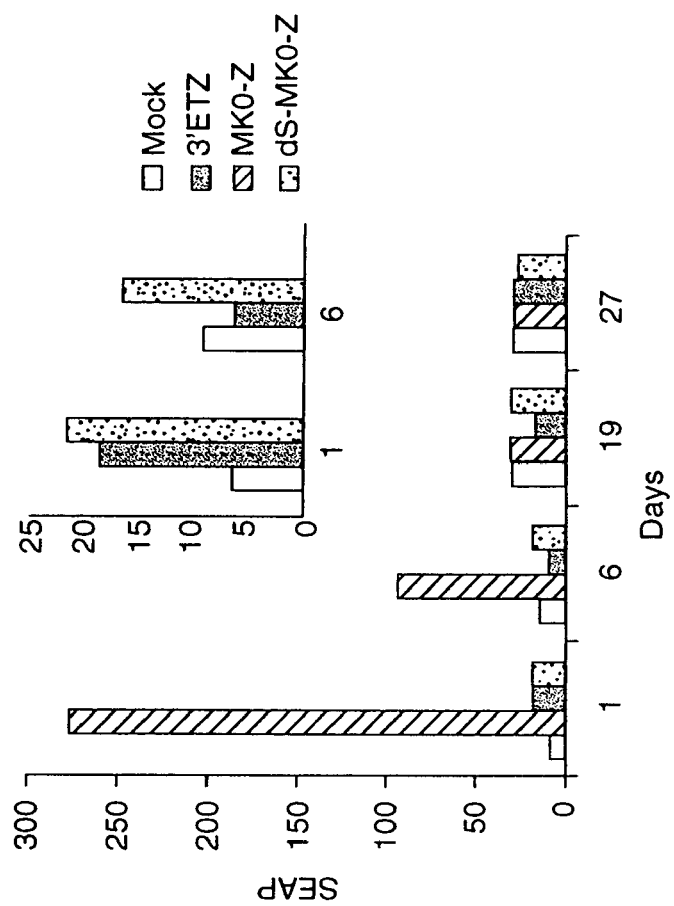
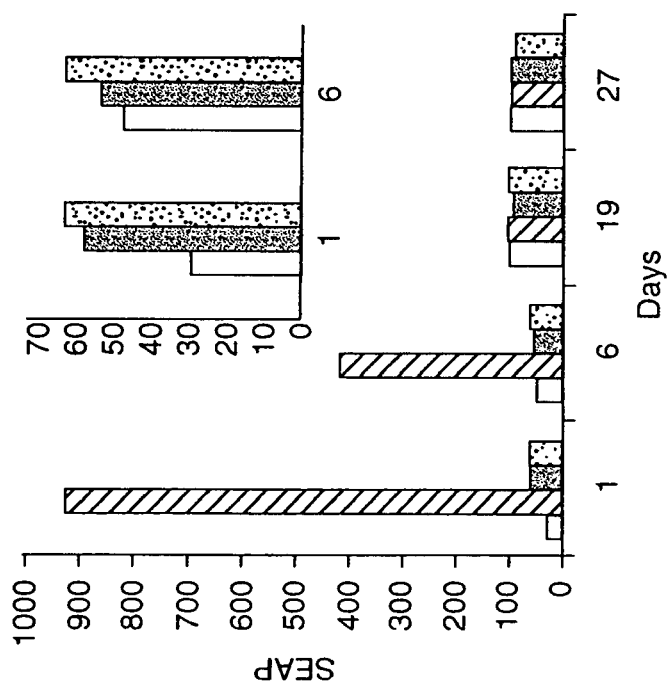
Fig. 4a
Fig. 4b

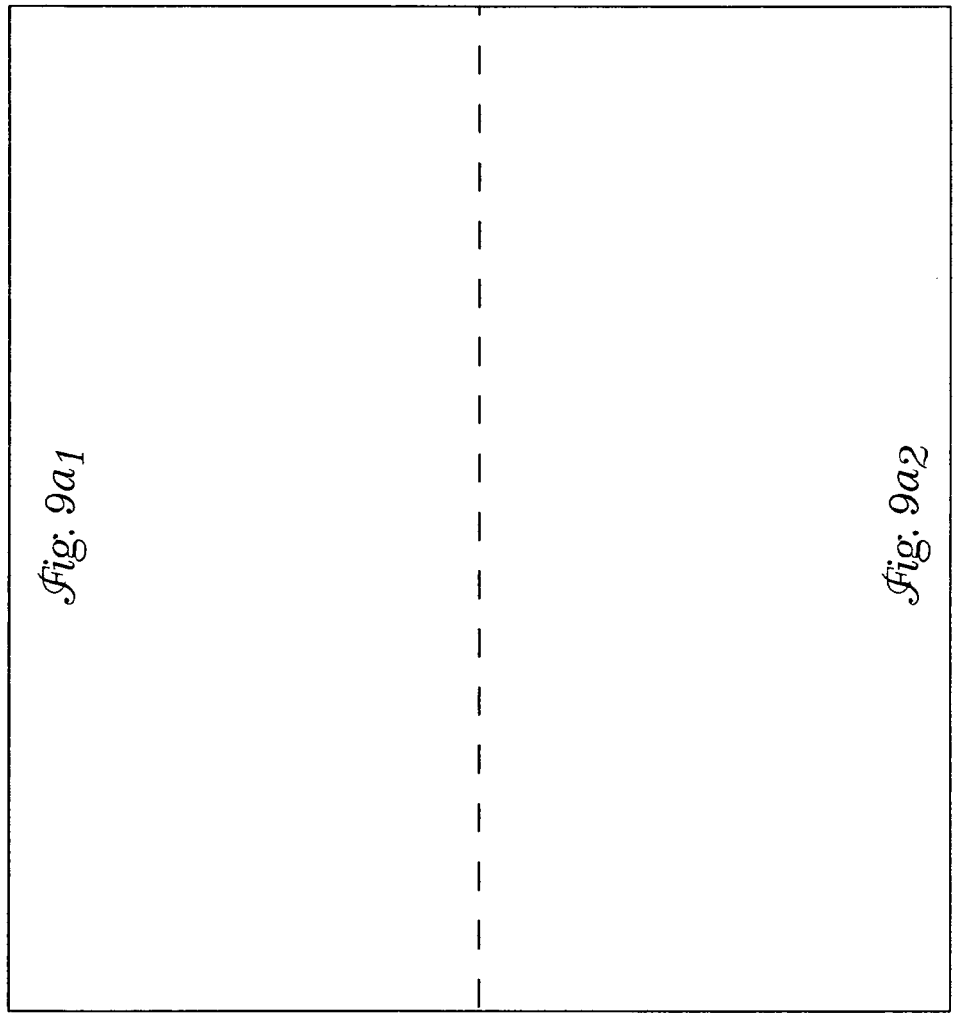

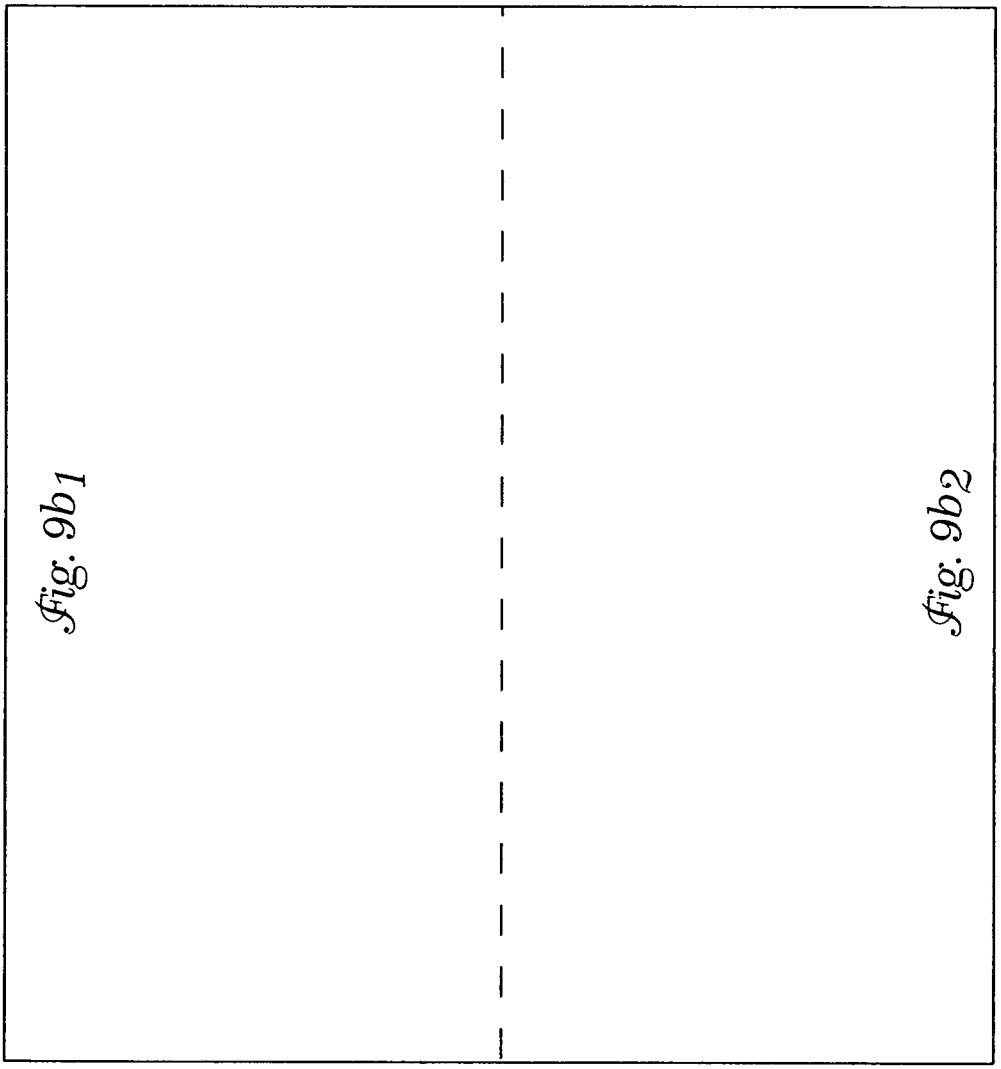

Fig. 9b₁

| | | | | | | | | | | |
|---|---|---|---|---|---|---|---|---|---|---|
|5121|TGCGCTAGGG|CTCAAGCCCC|TCCCCCATCG|TGGACCAGA|TGTGGAAGTG|TTTGATCCGC|CTTAAACCCA|CCCTCCATGG|5200|
|5201|GCCAACACCC|CTGCTATACA|GACTGGGCGC|TGTTCAGAAT|GAAGTCACCC|TGACGCACCC|AATCACCAAA|TACATCATGA|5280|
|5281|CATGCATGTC|GGCCGACCTG|GAGGTCGTCA|CGAGCACCTG|GTGCTCGTT|GGCGGCGTCC|TGGCTGCTCT|GCCCGGTAT|5360|
|5361|TGCCTGTCAA|CAGGCTGCGT|GGTCATAGTG|GGCAGGATCG|TCTTGTCCGG|GAAGCCGGCA|ATTATACCTG|ACAGGAGGT|5440|
|5441|TCTCTACCAG|GAGTTCGATG|AGATGGAAGA|GTGCTCTCAG|CACTTACCGT|ACATCGAGCA|AGGGATGATG|CTCGCTGAGC|5520|
|5521|AGTTCAAGCA|GAAGGCCCTC|GGCCTCCTGC|AGACCGCGTC|CCGCCATGCA|GAGGTTATCA|CCCCTGCTGT|CCAGACCAAC|5600|
|5601|TGGCAGAAAC|TCGAGGTCTT|TTGGGCGAAG|CACATGTGGA|ATTTCATCAG|TGGGATACAA|TACTTGGCGG|GCCTGTCAAC|5680|
|5681|GCTGCCTGGT|AACCCGCCA|TTGCTTCATT|GATGGCTTTT|ACAGCTGCCG|TCACCAGCCC|ACTAACCACT|GGCCAAACCC|5760|
|5761|TCCTCTTCAA|CATATTGGGG|GGGTGGGTGG|CTGCCCAGCT|GCCCGCCCCC|GGTGCCGCTA|CTGCCTTTGT|GGGTGCTGGC|5840|
|5841|CTAGCTGGCG|CCGCCATCGG|CAGCGTTGGA|CTGGGGAAGG|TCCTCGTTGA|CATTCTTGCA|GGGTATGGCG|CGGGCGTGGC|5920|
|5921|GGGAGCTCTT|GTAGCATTCA|AGATCATGAG|CGGTGAGGTC|CCCTCCACGG|AGGACCTGGT|CAATCTGCTG|CCCGCCATCC|6000|
|6001|TCTCGCCTGG|AGCCCTTGTA|GTCGGTGTGG|TCGCGCAGC|AATACTGCGC|CGGCACGTTG|GCCCGGGCGA|GGGGCAGTG|6080|
|6081|CAATGGATGA|ACGGCTAAT|AGCCTTCGCC|TCCCGGGGA|ACCATGTTTC|CCCCACGCAC|TACGTGCCGG|AGAGCGATGC|6160|
|6161|AGCCGCCCGC|GTCACTGCCA|TACTCAGCAG|CCTCACTGTA|ACCAGCTCC|TGAGGCGACT|GCATCAGTGG|ATAAGCTCGG|6240|
|6241|AGTGTACCAC|TCCATGCTCC|GGTTCCTGGC|TAAGGACAT|CTGGGACTGG|ATATGCGAGG|TGCTGAGCGA|CTTTAAGACC|6320|
|6321|TGGCTGAAAG|CCAAGCTCAT|GCCACAACTG|CCTGGGATTC|CCTTTGTGTC|CTGCCAGCGC|GGGTATAGGG|GGGTCTGCCG|6400|
|6401|AGGAGACGGC|ATTATGCACA|CTCGCTGCCA|CTGTGGAGCT|GAGATCACTG|GACATGTCAA|AAACGGGACG|ATGAGGATCG|6480|
|6481|TCGGTCCTAG|GACCTGCAGG|AACATGTGGA|GTGGGACGTT|CCCCATTAAC|GCCTACACCA|CGGGCCCCTG|TACTCCCCTT|6560|
|6561|CCTGCGCCGA|ACTATAAGTT|CGCGCTGTGG|AGGGTGTCTG|CAGAGGAATA|CGTGGAGATA|AGGCGGGTGG|GGGACTTCCA|6640|
|6641|CTACGTATCG|GGTATGACTA|CTGACAATCT|TAAATGCCCG|TGCCAGATCC|CATCGCCCGA|ATTTTTCACA|GAATTGGACG|6720|
|6721|GGGTGCGCCT|ACACAGGTTT|GCGCCCCCTT|GCAAGCCCTT|GCTGCGGAG|GAGGTATCAT|TCAGAGTAGG|ACTCCACGAG|6800|
|6801|TACCCGGTGG|GGTCGCAATT|ACCTTGCGAG|CCCGAACCGG|AGTAGCCGT|GTTGACGTCC|ATGCTCACTG|ATCCCTCCCA|6880|
|6881|TATAACAGCA|GAGGCGGCCG|GGAGAAGGTT|GGCGAGAGGG|TCACCCCCTT|CTATGGCCAG|CTCCTCGGCT|AGCCAGCTGT|6960|
|6961|CCGCTCCATC|TCTCAAGGCA|ACTTGCACCG|CCAACCATGA|CTCCCCTGAC|GCCGAGCTCA|TAGAGGCTAA|CCTCCTGTGG|7040|
|7041|AGGCAGGAGA|TGGGCGGCAA|CATCACCAGG|GTTGAGTCAG|AGAACAAAGT|GGTGATTCTG|GACTCCTTCG|ATCCGTTGT|7120|
|7121|GGCAGAGGAG|GATGAGCGGG|AGGTCTCCGT|ACCTGCAGAA|ATTCTGCGGA|AGTCTCGGAG|ATTCGCCCGG|GCCCTGCCCG|7200|
|7201|TCTGGGCGCG|GCCGGACTAC|AACCCCCCGC|GTCCCCTCCT|TAGTAGAGAC|GTGGAAAAAG|CCTGACTACG|GGTCCATGGC|7280|
|7281|TGCCCGCTAC|CACCTCCACG|GTCCCGAGC|TTGCCACCAA|AGTTTTGGC|AGCTCCTCAA|CTTCCGGCAT|AACCACCTGT|7360|
|7361|ATCTACTGCC|TTGGCCGAGC|CCCCGCCCCT|TCTGGCTGCC|CCCCGACTC|CGACGTTGAG|CGGTCAGTGA|TGGGGCCGAC|AATCAACCCT|7440|
|7441|CATCCTCTGA|GCCCGGATCT|CAGCGACGGG|TCTGGGACT|CATGGTCGA|TGCCGTCAGTAG|CGTCACCCCG|TGCGCTGCGG|GTCCTCACCG|AATACGACAA|7520|
|7521|GAGCCTGGGG|ATCCGGATCT|TATTCCTGGA|CAGGCGCACT|CACAATCTGG|CGTATTCCAC|AAGAACAAAA|TACGGGCGAC|CCTGAGGGG|7600|
|7601|CTCAATGTCT|GCTACGCCAT|GCAAGTTCT|GGACAGCCAT|CACCGCCCG|TGCGCTCCGC|CGGTCAGTGA|ACGAAGATG|ACGCCCATC|TCGTGTCTG|7680|
|7681|GCAACTTGTA|TGCAAGTTCT|GGACAGCCAT|CACAATCTGG|GGACAGCCAT|CACCGCCCG|CGGTCAGTGA|AAGAACAAAA|ACTGCCCATC|AACGCACTGA|7760|
|7761|TTTGACAGAC|TCCGTAGAGG|AAGCTTGCAG|CAGGCGCACT|TGCTCAAGGA|GGTCAAAGCA|AAAGGCAGAA|GCGGCGTCAA|GAAGTCACA|7840|
|7841|TAACTTGCTA|TCCGTAGAGG|AAGCTTGCAG|CAGGCGCACT|CAGGCGCACT|GGTCAAAGCA|CCAATTCAG|GTTTGCTTG|AGTGAAGGC|GGGCAAAAG|7920|
|7921|AGTGCCGTTG|CCATGCCAGA|AAGGCCGTAG|CCCACATCAA|CCCACATCAA|CTCCGTGTGG|AAAGACCTTC|TGGAAGACAG|TGTAACACCA|8000|

```
 8001 ATAGCACTA CCATCATGGC CAAGAACGAG GTTTTCTGCG TTCAGCCTGA GAAGGGGGGT CGTAAGCCAG CTCGTCTCAT 8080
 8081 CGTGTTCCCC GACCTGGGCG TGCGCGTGTG CGAGAAGATG GCCCTGTACG ACGTGGTTAG CAAGCTCCCC CTGGCCGTGA 8160
 8161 TGGGAAGCTC CTACGGATTC CAATACTCAC CAGGACAGCG GGTTGAATTC CTCGTGCAAG CGTGGAAGTC CAAGAAGACC 8240
 8241 CCGATGGGGT TCTCGTATGA TTTGACTTCA CAGTCACTGA GAGCGACATC CGTACGGAGG AGGCAATTTA 8320
 8321 CCAATGTGT GACCTGACC CCCAAGCCCG CGTGGCCATC AAGTCCCTCA CTGAGAGGCT TTATGTTGGG GGCCCTCTTA 8400
 8401 CCAATTCAAG GGGGAAAAC TGCGGCTACC GCAGTGCCG GCGAGTGCCG GTACTGACAA CTAGCTGTGG TAACACCCTC 8480
 8481 ACTTGCTACA TCAAGGCCCG GGCAGCCTGT CGAGCCGAG CGAGGAGGA CTGCACCATG CTCGTGTGTG GCGACGACTT 8560
 8561 AGTCGTTATC TGTGAAAGTG CGGGGTCCA GGAGGACGCG GCGAGCCTGA GAGCCTTCAC GGAGGCTATG ACCAGGTACT 8640
 8641 CCGCCCCCCC CGGGGACCCC CCACAACCAG AATACGACTT GGAGCTTATA ACATCATGCT CCTCCAACGT GTCAGTCGCC 8720
 8721 CACGACGGCG CTGGAAAGAG GGTCTACTAC CTTACCCGTG ACCCTACAAC ATGTTTGCCC CCCACTGTG AGAGCCGCGT GGGAGACAGC 8800
 8801 AAGACACACT CCAGTCAATT CCTGGCTAGG CAACATAATC ATGGCCTCTT GGCGAGGATG ATACTGATGA 8880
 8881 CCCATTTCTT TAGCGTCCTC ATAGCCAGGG ATCAGCTTGA ACAGGCCTCA AACTGTGAGA TCTACGGAGC CTGCTACTCC 8960
 8961 ATAGAACCAC TGGATCTACC TCCAATCATT CAAAGACTCC ATGGCCTCAG CGCATTTCA CTCCACAGTT ACTCTCCAGG 9040
 9041 TGAAATCAAT AGGGTGGCCG CATGCCTCAG GTCCCGCCCT TGCGAGCTTG GAGACACCGG GCCCGAGCG 9120
 9121 TCCGCGTAG GCTTCTGTCC AGAGGAGGCA GGGCTGCCAT ATGTGGCAAG TACCTCTTCA ACTGGGCAGT AAGAACAAAG 9200
 9201 CTCAAACTCA CTCCAATAGC GGCCGCTGGC TGTCCGGTTG GTTCACGGCT TGTCACGGCT GTTCACGGCT GGGGAGACAT 9280
 9281 TTATCACAGC GTGTCTCATG CCCGGCCCCG CTGGTTCTGG TTTTGCCTAC TCCTGCTCGC TGCAGGGGTA GGCATCTACC 9360
 9361 TCCTCCCCAA CCGATGAAGG TTGGGGTAAA CACTCCGGCC TcttaagGTT ATTTTCCACC ATATTGCCGT CTTTTGGCAA 9440
 9441 TGTGAGGGCC CGGAAACCTG GCCCTGTCTT CTTGACGAGC ATTCCTAGGG GTCTTTCCCC TCTGCCAAA GGAATGCAAG 9520
 9521 GTCGTGTTGAA TGTCGTGAAG GAAGCAGTTC CTCTGAAAGC TTCTTGAAGA CAAACAACGT CTGTAGCGAC CCTTTGCAGG 9600
 9601 CAGCGGAACC CCCCACCTGG CGACAGGTGC CTCTGCGGCC AAAAGCCACG TGTATAAGAT ACACCTGCAA AGGCGGCACA 9680
 9681 ACCCCAGTGC CACGTTGTGA GTTGGATAGT TGTGGAAAGA GTCAAATGCC TCTCCTCAAG CGTATTCAAC AAGGGGCTGA 9760
 9761 AGGATGCCCA GAAGGTACCC CATTGTATGG GATCTGATCT GGGGCCTCGG TGCACATGCT TTACGTGTGT TTAGTCGAGG 9840
 9841 TTAAAAAACG TCTAGCCCCC CCGAACCACG AGCCCTGGAA GCATCCAGGA GTCAGCCTA AAAACACGAT GATAATATGA GGCCTATGA 9920
 9921 GCCAGTAGAT CCTAGACTAG GTTTGTTTCA TAACAAAAGC CTTAGGCATC TCCTATGGCA GGAAGAAGCG GAGACAGCGA 10000
10001 AGTGTTGCTT TCAGGCAG TCAGACTCAT CAAGTTTCTC TATCAAAGCA ACCCACCTCC CAATCCCGAC GGGACCCGAC 10080
10081 CGAAGACCTC CTCAAGGCAG GAAGAATTCG ACCTTCTTAA GCTTGCGGGA GACGTCGAGT CCAACCTCTG GCCCGGATCC ATGGCCAAGT 10160
10161 AGGCCCGAAG CGTTCCGGTG CTCACCGCGC GCGACGTCGC GGACCGGTC GAGTTGTCGA CCGACCGGCT CGGGTTCTCC 10240
10241 TGACCAGTGC CGTTGCCAGA CTTCCGGTG GTGGTCCGGT GTGGTCCGGG GGCACGTGAC CCTGTTCATC AGCGCGGTCC AGGACCAGGT 10320
10321 CGGGACTTCG TGGAGGACGA AACACCCTGG CCTGGGTGTG GGTGCCGGC CTGGACGAGC TGGACGAGAG GTGGTCCGA AGCGCGGTCC AGGACCAGGT 10400
10401 GGTGCCGGAC AACACCCTGG GGACGCCTCC CCTGGGTGTG GGTGCCGGCC CTGGACGAGC TGGACGAGAG TGTACGCCGA GTGGTCGGAG 10480
10481 CGAACTTCCG GGACGCCTCC CCTGGGTGTG TGACCGAGAT CGGGCCGGCC CTGGACGAGC CGGGAGCAG CGTGGGGGCC GGGAGTTCGC CCTGTCGCGA GTCGTGTCCA 10560
10561 CGGGCCGGCA ACTGCGTGCA CTTCGTGGCC CTTCGTTCTTT CCTTCTTTTT CCTTCTTTTT gCCATTTCGT GTTTTTTTTT TTAATGGTGG CCCTGCGCAC CCTGCGCAC 10640
10641 TTTTTTTTC TTTTTTTTT TCTTTTCCTT TCTTTCCTTT CCTTCTTTTT TTCCCTTTCT CCTTCCTTT CTCCATCTTA 10720
10721 GCCCTAGTCA CGGCTAGCTG TGAAAGGTCC GTGAGCCGGA TGACTGCAGA GAGTGCTGAT ACTGGCCTCT CTGCAGATCA 10800
     TGT
```

SEQ ID NO:20

```
342/1
atg agc acg aat cct aaa cct caa aga aaa acc aac acc aac cgt cgc cca cag
Met Ser Thr Asn Pro Lys Pro Gln Arg Lys Thr Asn Thr Asn Arg Arg Pro Gln 402/21
gac gtc aag ttc ccg ggt ggc ggt cag atc gtt ggt gga gtt tac ttg ccg cgc agg
Asp Val Lys Phe Pro Gly Gly Gly Gln Ile Val Gly Gly Val Tyr Leu Pro Arg Arg 462/41
ggc cct aga ttg ggt gtg cgc gcg acg agg aag act tcc gag cgg tcg caa cct cga ggt
Gly Pro Arg Leu Gly Val Arg Ala Thr Arg Lys Thr Ser Glu Arg Ser Gln Pro Arg Gly 522/61
aga cgt cag cct atc ccc aag gca cct cgt cgg ccc gag ggc agg acc tgg gct cag ccc ggg
Arg Arg Gln Pro Ile Pro Lys Ala Pro Arg Arg Pro Glu Gly Arg Thr Trp Ala Gln Pro Gly 582/81
tac cct tgg ccc ctc tat ggc aat gag ggt tgc ggg tgg gcg ctc ctg tct ccc
Tyr Pro Trp Pro Leu Tyr Gly Asn Glu Gly Cys Gly Trp Ala Gly Trp Leu Leu Ser Pro 642/101
cgt ggc tct cgg cct agc tgg ggc aca gac ccc cgg cgt agg tcg cgc aat ttg ggt
Arg Gly Ser Arg Pro Ser Trp Gly Thr Asp Pro Arg Arg Ser Arg Asn Leu Gly 702/121
aag gtc atc gat acc ctt acg tgc ggc ttc gcc gac ctc atg ggg tac ata ccg ctc gtc
Lys Val Ile Asp Thr Leu Thr Cys Gly Phe Ala Asp Leu Met Gly Tyr Ile Pro Leu Val 762/141
ggc gcc cct ctt gga ggc ggt gcc agg gcc ctg gcg cat ggc gtc cgg gtt ctg gaa gac
Gly Ala Pro Leu Gly Gly Gly Ala Arg Ala Leu Ala His Gly Val Arg Val Leu Glu Asp 822/161
ggc gtg aac tat gca aca ggg aac ctt cct ggt tgc tct ttc atc ctt ctg gcc
Gly Val Asn Tyr Ala Thr Gly Asn Leu Pro Gly Cys Ser Phe Ile Leu Leu Ala 882/181        CORE →|← E1
ctg ctc tct tgc ctg act gtg ccc gct tca gcc tac caa gtg cgc aat tcc tcg ggg ctt
Leu Leu Ser Cys Leu Thr Val Pro Ala Ser Ala Tyr Gln Val Arg Asn Ser Ser Gly Leu 942/201
tac cat gtc acc aat gat tgc cct aac tcg agt att gtg tac gag gcg gcc gat gcc atc
Tyr His Val Thr Asn Asp Cys Pro Asn Ser Ser Ile Val Tyr Glu Ala Ala Asp Ala Ile
```

```
1002/221
ctg cac act ccg ggg tgt gtc cct tgc gtt cgc gag ggt aac gcc tcg agg tgt tgg gtg
Leu His Thr Pro Gly Cys Val Pro Cys Val Arg Glu Gly Asn Ala Ser Arg Cys Trp Val 1062/241
gcg gtg acc ccc acg gtg gcc agg gac ggc aaa ctc ccc aca acg cag ctt cga cgt
Ala Val Thr Pro Thr Val Ala Thr Arg Asp Gly Lys Leu Pro Thr Thr Gln Leu Arg Arg 1122/261
cat atc gat ctg ctt gtc ggg agc gcc acc ctc tgc gcc ctc tac gtg ggg gac ctg
His Ile Asp Leu Leu Val Gly Ser Ala Thr Leu Cys Ala Leu Tyr Val Gly Asp Leu 1182/281
tgc ggg tct gtc ttt ctt gtt ggt caa ctg ttt acc ttc tct ccc agg cgc cac tgg acg
Cys Gly Ser Val Phe Leu Val Gly Gln Leu Phe Thr Phe Ser Pro Arg Arg His Trp Thr 1242/301
acg caa gac tgc aat tgt tct atc tat ccc ggc cat ata acg ggt cat cgc atg gca tgg
Thr Gln Asp Cys Asn Cys Ser Ile Tyr Pro Gly His Ile Thr Gly His Arg Met Ala Trp 1302/321
gat atg atg aac tgg tcc cct acg gca gcg ttg gta gct cag ctg ctc cgg atc
Asp Met Met Asn Trp Ser Pro Thr Ala Ala Leu Val Ala Gln Leu Leu Arg Ile 1362/341
cca caa gcc atc atg gac atg gct ggt gct gca gtc gga gtc gcg ggc ata gcg
Pro Gln Ala Ile Met Asp Met Ala Gly Ile Ala His Trp Gly Val Leu Ala Gly Ile Ala 1422/361
tat ttc tcc atg ggg gcg aac tgg gcg aag gga gta gtg ctg ctg cta ttt gcc ggc
Tyr Phe Ser Met Gly Ala Asn Trp Ala Lys Gly Val Val Leu Leu Leu Phe Ala Gly
      E1  E2

1482/381
gtc gac gcg gaa acc cac cac gtc ggg gga aat cag gga aac acg gct ggg ctt gtt
Val Asp Ala Glu Thr His Val Gly Gly Asn Gln Gly Asn Thr Ala Gly Leu Val 1542/401
ggt ctc ctt aca cca ggc gcc aag cag aac atc caa ctg atc aac acc aac ggc agt tgg
Gly Leu Leu Thr Pro Gly Ala Lys Gln Asn Ile Gln Leu Ile Asn Thr Asn Gly Ser Trp
```

Fig. 10a2

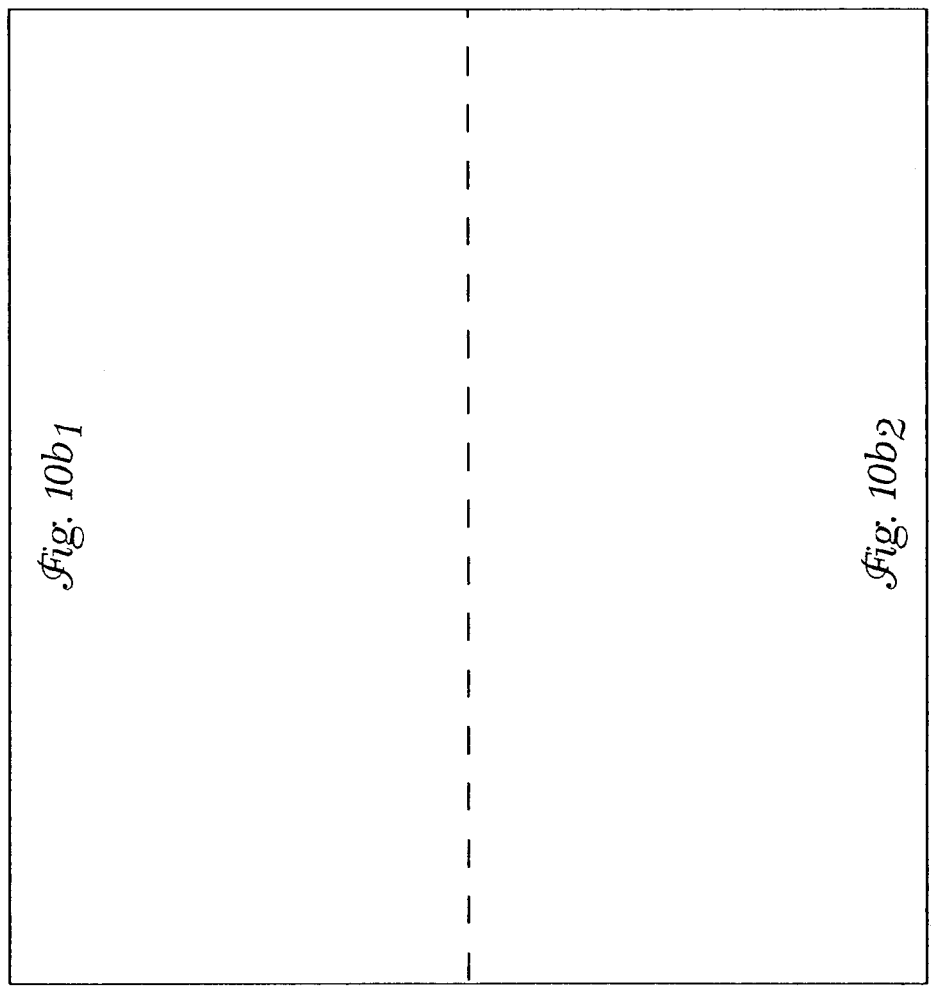

Fig. 10b₁

```
1602/421
cac atc aat agc acg gcc ttg aat tgc aat gaa agc ctt aac acc ggc tgg tta gca ggg
His Ile Asn Ser Thr Ala Leu Asn Cys Asn Glu Ser Leu Asn Thr Gly Trp Leu Ala Gly 1662/441
ctc ttc tat caa cac aaa ttc aac tct tca ggc tgt cct gag agg cct gcc agc tgc cga
Leu Phe Tyr Gln His Lys Phe Asn Ser Ser Gly Cys Pro Glu Arg Pro Ala Ser Cys Arg 1722/461
cgc ctt acc gat tgc ttt gcc cag ggc tgg ggt cct atc agt tat gcc aac gga agc ctc
Arg Leu Thr Asp Phe Ala Gln Gly Trp Gly Pro Ile Ser Tyr Ala Asn Gly Ser Gly Leu 1782/481
gac gaa cgc ccc tac tgc tgg cac tac cct cca aga cct tgt ggc att gtg ccc gca aag
Asp Glu Arg Pro Tyr Cys Trp His Tyr Pro Pro Arg Pro Cys Gly Ile Val Pro Ala Lys 1842/501
agc gtg tgt ggc ccg gta tat tgc ttc act ccc agc ccc gtg gtg gtg gga acg acc gac
Ser Val Cys Gly Pro Val Tyr Cys Phe Thr Pro Ser Pro Val Val Val Gly Thr Thr Asp 1902/521
agg tcg ggc gcg cct acc tac agc tgg gca aat gat acg gat gtc ttc gtc ctt aac
Arg Ser Gly Ala Pro Thr Tyr Ser Trp Gly Ala Asn Asp Thr Asp Val Phe Val Leu Asn 1962/541
aac acc agg cca ccg ctg ggc aat tgg ttc ggt tgt acc tgg atg aac tca act gga ttc
Asn Thr Arg Pro Pro Leu Gly Asn Trp Phe Gly Cys Thr Trp Met Asn Ser Thr Gly Phe 2022/561
aaa gtg tgc gga gcg gcc ccc cct tgt gtc atc gga ggg gtg ggc val gly asn asn thr leu leu
Thr Lys Val Cys Gly Ala Pro Pro Cys Val Ile Gly Gly Val Gly Asn Asn Thr Leu Leu 2082/581
tgc ccc act gat tgc ttc cgc aaa cat ccg gaa gcc aca tct cgg tgc tgg tcc ggt
Cys Pro Thr Asp Cys Phe Arg Lys His Pro Glu Ala Thr Ser Arg Cys Gly Ser Gly 2142/601
ccc tgg att aca ccc agg tgc atg gtc gac tac ccg tat agg ctt tgg cac tat cct tgt
Pro Trp Ile Thr Pro Arg Cys Met Val Asp Tyr Pro Tyr Arg Leu Trp His Tyr Pro Cys 2202/621
acc atc aat tac acc ata ttc aaa gtc agg atg tac gtg gga ggg gtc gag cac agg ctg
Thr Ile Asn Tyr Thr Ile Phe Lys Val Arg Met Tyr Val Gly Gly Val Glu His Arg Leu
```

```
2262/641
gaa gcg gcc tgc aac tgg acg cgg ggc gaa cgc tgt gat ctg gaa gac agg gac agg tcc
Glu Ala Ala Cys Asn Trp Thr Arg Gly Glu Arg Cys Asp Leu Glu Asp Arg Asp Arg Ser 2322/661
gag ctc agc ccg ctg ctg tcc acc aca cag tgg cag gtc ctt ccg tgt tct ttc acg
Glu Leu Ser Pro Leu Leu Ser Thr Thr Gln Trp Gln Val Leu Pro Cys Ser Phe Thr 2382/681
acc ctg cca gcc ttg tcc acc ggc ctc atc cac ctc cac aac att gtg gac gtg cag
Thr Leu Pro Ala Leu Ser Thr Gly Leu Ile His Leu His Gln Asn Ile Val Asp Val Gln 2442/701
tac ttg tac ggg gta ggg tca agc atc gcg tcc tgg gcc att aag tgg gag tac gtc gtt
Tyr Leu Tyr Gly Val Gly Ser Ser Ile Ala Ser Trp Ala Ile Lys Trp Glu Tyr Val Val 2502/721
ctc ctg ttc ctt ctg gca gac gcg cgc tgc tcc tgc gtc tcc ttg tgg atg tta ctc
Leu Leu Phe Leu Leu Ala Asp Ala Arg Cys Ser Cys Val Ser Leu Trp Met Met Leu Leu
                    E2 ← → P7
2562/741
ata tcc caa gcg gag gcg gct ttg gag aac ctc gta ata ctc aat gca tcc ctg gcc
Ile Ser Gln Ala Glu Ala Ala Leu Glu Asn Leu Val Ile Leu Asn Ala Ser Leu Ala 2622/761
ggg acg cac ggt ctt gtg tcc ctc gtg ttc tgc ttt gcg tgg tat ctg aag ggt
Gly Thr His Gly Leu Val Ser Phe Leu Val Phe Cys Phe Ala Trp Tyr Leu Lys Gly 2682/781
agg tgg gtg ccc gga gcg gtc gca gtc tac gcc ctc tac ggg atg tgg cct ctc ctg ctg
Arg Trp Val Pro Gly Ala Val Tyr Ala Leu Tyr Gly Met Trp Pro Leu Leu Leu Leu
                                            P7 ← → NS2
2742/801
ctg gcg ttg cct cag cgg tac gca gca ctg gac acg gag gtg gcc tgt ggc ggc
Leu Ala Leu Pro Gln Arg Ala Tyr Ala Leu Asp Thr Glu Val Ala Ser Cys Gly Gly 2802/821
gtt gtt ctt gtc ggg tta atg ctg act cca tat tac aag cgc tat atc agc
Val Val Leu Val Gly Leu Met Leu Thr Pro Tyr Tyr Lys Arg Tyr Ile Ser 2862/841
tgg tgc atg tgg tgg ctt cag tat ttt ctg acc aga gaa gcg caa ctg cac gtg tgg
Trp Cys Met Trp Trp Leu Gln Tyr Phe Leu Thr Arg Glu Ala Gln Leu His Val Trp 2922/861
gtt ccc ccc ctc aac gtc cgg ggg cgc gat gcc atc tta ctc atg tgt gta gta
Val Pro Pro Leu Asn Val Arg Gly Arg Asp Ala Ile Leu Leu Met Cys Val Val
```

*Fig. 10b₂*

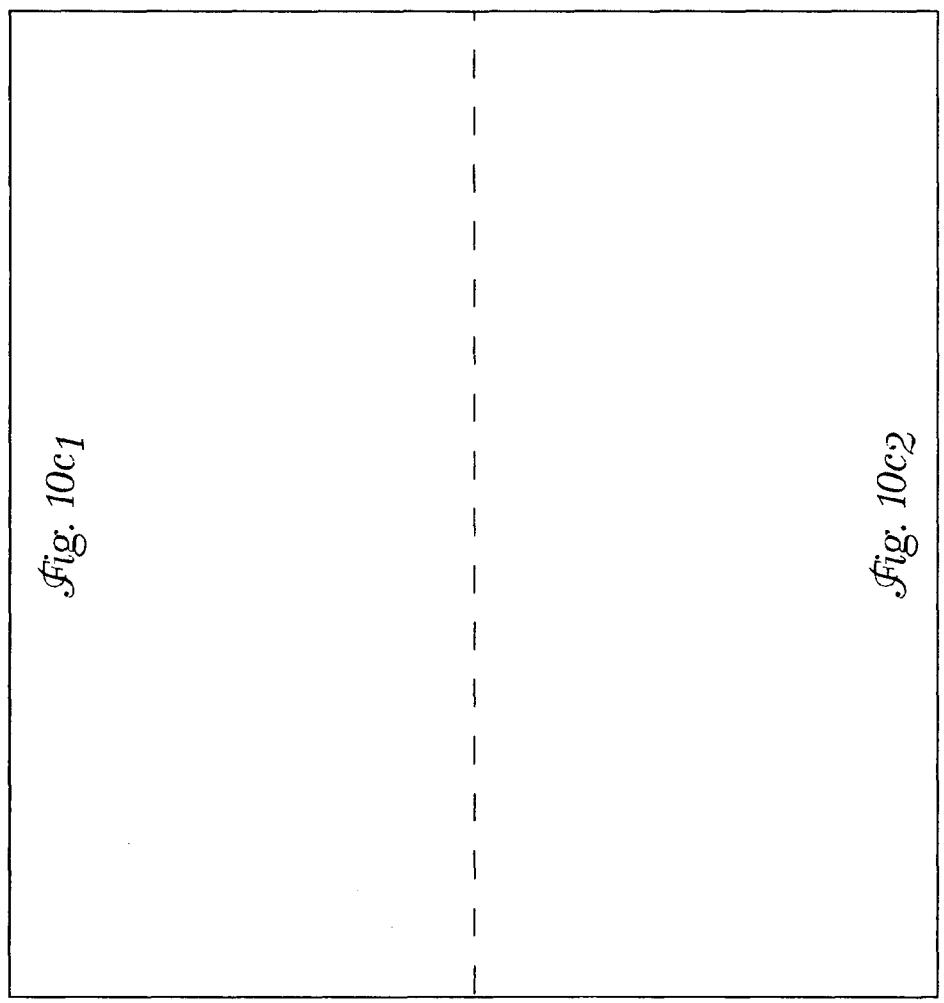

Fig. 10c1

```
2982/881
cac ccg acc ctg gta ttt gac atc acc aaa cta ctc ctg gcc atc ttc gga ccc ctt tgg
His Pro Thr Leu Val Phe Asp Ile Thr Lys Leu Leu Leu Ala Ile Phe Gly Pro Leu Trp 3042/901
att ctt caa gcc agt ttg ctt aaa gtc ccc tac ttc gtg cgc gtt caa ggc gtt ctc cgg
Ile Leu Gln Ala Ser Leu Leu Lys Val Pro Tyr Phe Val Arg Val Gln Gly Leu Leu Arg 3102/921
atc tgc gcg cta gcg cgg aag ata gcc gga tac cat gtg caa atg gcc atc atc aag
Ile Cys Ala Leu Ala Arg Lys Ile Ala Gly His Tyr Val Gln Met Ala Ile Ile Lys 3162/941
tta ggg gcg ctt act ggc acc tat gtg tat aac cat ctc acc cct ctt cga gac tgg gcg
Leu Gly Ala Leu Thr Gly Thr Tyr Val Tyr Asn His Leu Thr Pro Leu Arg Asp Trp Ala 3222/961
cac aac ggc ctg cga gat ctg gcc gtg gct gaa cca gtc gtc ttc tcc cga atg gag
His Asn Gly Leu Arg Asp Leu Ala Val Ala Glu Pro Val Phe Ser Arg Met Glu 3282/981
acc aag ctc atc acg tgg ggg gca gat acc gcc gcg tgc ggt gac atc aac ggc ttg
Thr Lys Leu Ile Thr Trp Gly Ala Asp Thr Ala Cys Gly Asp Ile Asn Gly Leu 3342/1001
ccc gtc tct gcc cgt agg ggc cag gag ata ctg ctt ctc ggg cca gcc gga atg gtc tcc
Pro Val Ser Ala Arg Arg Gly Gln Glu Ile Leu Leu Leu Gly Pro Ala Gly Met Val Ser NS2    NS3
3402/1021
aag ggg tgg agg ttg ctg gcg ccc atc acg gcg cag cag acg aga ggc ctc cta
Lys Gly Trp Arg Leu Leu Ala Pro Ile Thr Ala Gln Gln Thr Arg Gly Leu Leu 3462/1041
ggg tgt ata atc acc agc agc ctg act ggc cgg gac cgg aaa aac caa gtg gag ggt gag gtc cag
Gly Cys Ile Ile Thr Ser Leu Thr Gly Arg Asp Arg Lys Asn Gln Val Glu Gly Glu Val Gln 3522/1061
atc gtg tca act gct acc acc caa acg gca acg tgc atc acg tca ccc aag ggt cct gtc atc cag atg
Ile Val Ser Thr Ala Thr Thr Gln Thr Ala Thr Cys Ile Thr Ser Pro Lys Gly Pro Val Ile Gln Met 3682/1081
gtc tac cac ggg gcc gga acg agg acc atc atc gca ggt cct caa ggt tcc cgc tca ttg
Val Tyr His Gly Ala Gly Thr Arg Thr Ile Ile Ala Gly Pro Gln Gly Ser Arg Ser Leu 3642/1101
tat acc aat gtg gac caa gac ctt gtg ggc ctt gtg gac ctt gtg ggc ctt gtg ccc gct cct caa gaa
Tyr Thr Asn Val Asp Gln Asp Leu Val Gly Leu Val Asp Leu Val Gly Leu Val Pro Ala Pro Gln Ser Arg Ser Leu
```

```
3702/1121
aca ccc tgt acc tgc ggc tcc tcg gac ctt tac ctg gtc acg agg cac gcc gat gtc att
Thr Pro Cys Thr Cys Gly Ser Asp Leu Tyr Leu Val Thr Arg His Ala Asp Val Ile 3762/1141
ccc gtg cgc cgg cga ggt gat agc agg ggt agc ctt tcg ccc cgg ccc att tcc tac
Pro Val Arg Arg Arg Gly Asp Ser Arg Gly Ser Leu Ser Pro Arg Pro Ile Ser Tyr 3822/1161
ttg aaa ggc tcc tcg ggg ggt ccg ctg ttg tgc ccc gcg gga cac gcc gtg ggc cta ttc
Leu Lys Gly Ser Ser Gly Gly Pro Leu Leu Cys Pro Ala Gly His Ala Val Gly Leu Phe 3882/1181
agg gcc gcg acc tgc cgt gga gtg gct aaa gcg gtg gac ttt atc cct gtg gag aac
Arg Ala Ala Thr Cys Arg Gly Val Ala Lys Ala Val Asp Phe Ile Pro Val Glu Asn 3942/1201
cta ggg aca acc atg aga tcc ccg gtg ttc acg gac aac tcc tct cca cca gca gtg ccc
Leu Gly Thr Thr Met Arg Ser Pro Val Phe Thr Asp Asn Ser Ser Pro Pro Ala Val Pro 4002/1221
cag agc ttc cag gtg gcc cac ctg cat gct ccc acc ggc agc ggt aag agc acc aag gtc
Gln Ser Phe Gln Val Ala His Leu His Ala Pro Thr Gly Ser Gly Lys Ser Thr Lys Val 4062/1241
ccg gct gcg tac gca gcc cag ggc tac aag gtg ttg ctc aac ccc tct gtt gct gca
Pro Ala Ala Tyr Ala Ala Gln Gly Tyr Lys Val Leu Leu Asn Pro Ser Val Ala Ala 4122/1261
acg ctg ggc ttt ggt gct atg tcc aag gcc cat ggg gtt gat cct aat atc agg acc
Thr Leu Gly Phe Gly Ala Tyr Met Ser Lys Ala His Gly Val Asp Pro Asn Ile Arg Thr 4182/1281
ggg gtg aga aca att acc act ggc agc ccc atc acg tac tcc acc tac ggc aag ttc ctt
Gly Val Arg Thr Ile Thr Thr Gly Ser Pro Ile Thr Tyr Ser Thr Tyr Gly Lys Phe Leu 4242/1301
gcc gac ggc ggg tgc tca gga ggt gct tat gct ata att tgt gac gag tgc cac tcc
Ala Asp Gly Gly Cys Ser Gly Gly Ala Tyr Asp Ile Ile Cys Asp Glu Cys His Ser 4302/1321
acg gat gcc aca tcc atc ttg ggc atc ggc act gtc ctt gac caa gca gag act gcg ggg
Thr Asp Ala Thr Ser Ile Leu Gly Ile Gly Thr Val Leu Asp Gln Ala Glu Thr Ala Gly
```

*Fig. 10c2*

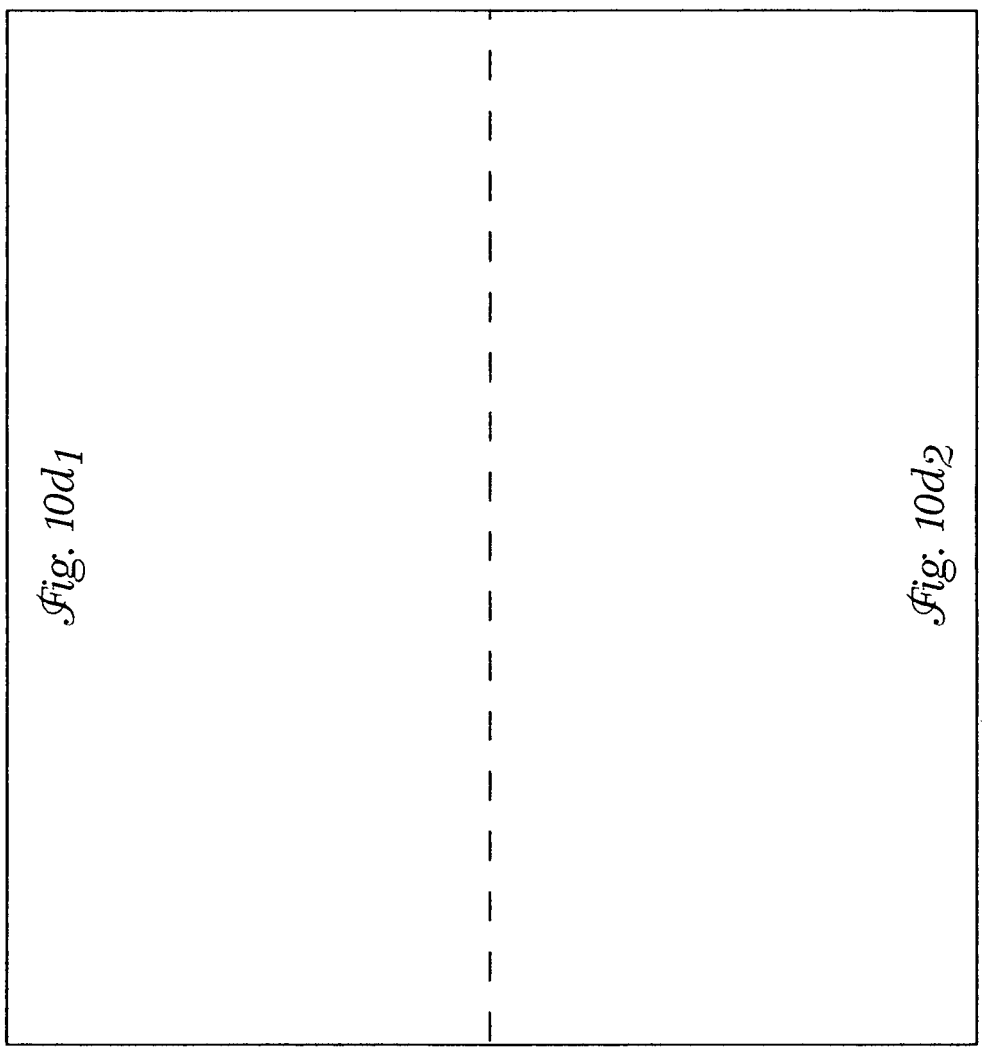
Fig. 10d₁  Fig. 10d₂  Fig. 10d

Fig. 10d₁

```
4362/1341
gcg aga ctg gtt gtg ctc gcc act gct acc cct ccg ggc tcc gtc act gtg tcc cat cct
Ala Arg Leu Val Val Leu Ala Thr Ala Thr Pro Pro Gly Ser Val Thr Val Ser His Pro 4422/1361
aac atc gag gag gtt gct ctg tcc acc acc gga gag atc ccc ttt tac ggc aag gct atc
Asn Ile Glu Glu Val Ala Leu Ser Thr Thr Gly Glu Ile Pro Phe Tyr Gly Lys Ala Ile 4482/1381
ccc ctc gag atc gtg aag gga aga cat ctc atc ttc tgc cac aag aag aag tgc
Pro Leu Glu Ile Val Lys Gly Gly Arg His Leu Ile Phe Cys His Ser Lys Lys Lys Cys 4542/1401
gac gag ctc gcc gcg aag ctg gca ttg ggc gtc aat gcc gtg gcc tac tac cgc ggt
Asp Glu Leu Ala Ala Lys Leu Val Leu Gly Ile Asn Ala Val Ala Tyr Tyr Arg Gly 4602/1421
ctt gac gtg tct gtc atc ccg agc gtt gtc gtg acc gat gct ctc
Leu Asp Val Ser Val Ile Pro Thr Ser Gly Asp Val Val Val Ser Thr Asp Ala Leu 4662/1441
atg act ggc ttt acc ggc gac ttc agc tct gtg ata gac tgt gtc act cag
Met Thr Gly Phe Thr Gly Asp Phe Ser Val Ile Asp Cys Asn Thr Cys Val Thr Gln 4722/1461
aca gtc gat ttc agc ctt gac ctt acc cct acc att gag aca acc acg ctc ccc cag gat
Thr Val Asp Phe Ser Leu Asp Pro Thr Phe Thr Ile Glu Thr Thr Leu Pro Gln Asp 4782/1481
gct gtc tcc agg act caa cgc cgg cgc agg act ggg aag cca ggc atc tat aga
Ala Val Ser Arg Thr Gln Arg Arg Arg Gly Arg Thr Gly Lys Pro Gly Ile Tyr Arg 4842/1501
ttt gtg gca ccg ggg gag cgc ccc tcc ggc atg ttc gac tcc gtc ctc tgt gag tgc
Phe Val Ala Pro Gly Glu Arg Pro Ser Gly Met Phe Asp Ser Val Leu Cys Glu Cys 4902/1521
tat gac gcg ggc tgt gct tat gag ctc tgg acg act ctt gtt agg cta cga
Tyr Asp Ala Gly Cys Ala Trp Tyr Glu Leu Pro Ala Glu Thr Thr Val Arg Leu Arg 4962/1541
gcg tac atg aac acc ccg ggg ctt ccc gtg tgc cag gac cat gaa ttt tgg gag ggc
Ala Tyr Met Asn Thr Pro Gly Leu Pro Val Cys Gln Asp His Leu Glu Phe Trp Glu Gly 5022/1561
gtc ttt acg ggc ctc act cat ata gat gcc cac ttt tta tcc cag aca aag cag agt ggg
Val Phe Thr Gly Leu Thr His Ile Asp Ala His Phe Leu Ser Gln Thr Lys Gln Ser Gly
```

```
5082/1581
gag aac ttt cct tac ctg gta gcg tac caa gcc acc gtg tgc gct agg caa gcc cct
Glu Asn Phe Pro Tyr Leu Val Ala Tyr Gln Ala Thr Val Cys Ala Arg Gln Ala Pro 5142/1601
ccc cca tcg tgg gac atg cag aag tgg tgt ttg atc cgc ctt aaa ccc acc ctc cat ggg
Pro Pro Ser Trp Asp Met Gln Lys Trp Cys Leu Ile Arg Leu Lys Pro Thr Leu His Gly 5202/1621
cca aca ccc ctg cta tac aga ggc ctg gct gtt cag aat gaa gtc acc ctg acg cac cca
Pro Thr Pro Leu Leu Tyr Arg Gly Leu Ala Val Gln Asn Glu Val Thr Leu Thr His Pro
                                                                          NS3   NS4A
5262/1641
atc acc aaa tac atg aca tgc atg tcg gcc gac ctg gag gtc acg agc acc tgg
Ile Thr Lys Tyr Met Thr Cys Met Ser Ala Asp Leu Glu Val Thr Ser Thr Trp 5322/1661
gtg ctc gtt ggc ggc gtc ctg gct gcc gcg gcc tat tgc ctg tca aca ggc tgc gtg
Val Leu Val Gly Gly Val Leu Ala Ala Ala Ala Tyr Cys Leu Ser Thr Gly Cys Val 5382/1681
gtc ata gtg ggc agg atc gtc ttg tcc ggg aag ccg att ata cct gac agg gag gtt
Val Ile Val Gly Arg Ile Val Leu Ser Gly Lys Pro Ala Ile Ile Pro Asp Arg Glu Val
              NS4A            NS4B
5442/1701
ctc tac cag gag gag ttc gat gag atg gaa gag tgc tct cag cac tta ccg tac atc gag caa
Leu Tyr Gln Glu Glu Phe Asp Glu Met Glu Glu Cys Ser Gln His Leu Pro Tyr Ile Glu Gln 5502/1721
ggg atg atg gct ctc gag cag ttc aag cag ttc gcc aag cag ctc ctg cag acc gcg tcc
Gly Met Met Ala Leu Glu Gln Phe Lys Gln Phe Ala Lys Gln Leu Leu Gln Thr Ala Ser 5562/1741
cgc cat gca gag gtt atc acc cct gct gtc cag acc tgg aac tac aaa ctc gag gtc ttt
Arg His Ala Glu Val Ile Thr Pro Ala Val Gln Thr Trp Asn Tyr Lys Leu Glu Val Phe 5622/1761
tgg gcg aag cac atg tgg aat ttc atc agt ggg ata caa ggc ttg gcg ggc ctg tca acg
Trp Ala Lys His Met Trp Asn Phe Ile Ser Gly Ile Gln Gly Leu Ala Gly Leu Ser Thr 5682/1781
ctg cct ggt aac ccc gcc att gct tca ttg atg gct ttt aca gct gcc gtc acc agc cca
Leu Pro Gly Asn Pro Ala Ile Ala Ser Leu Met Ala Phe Thr Ala Ala Val Thr Ser Pro
```

*Fig. 10d2*

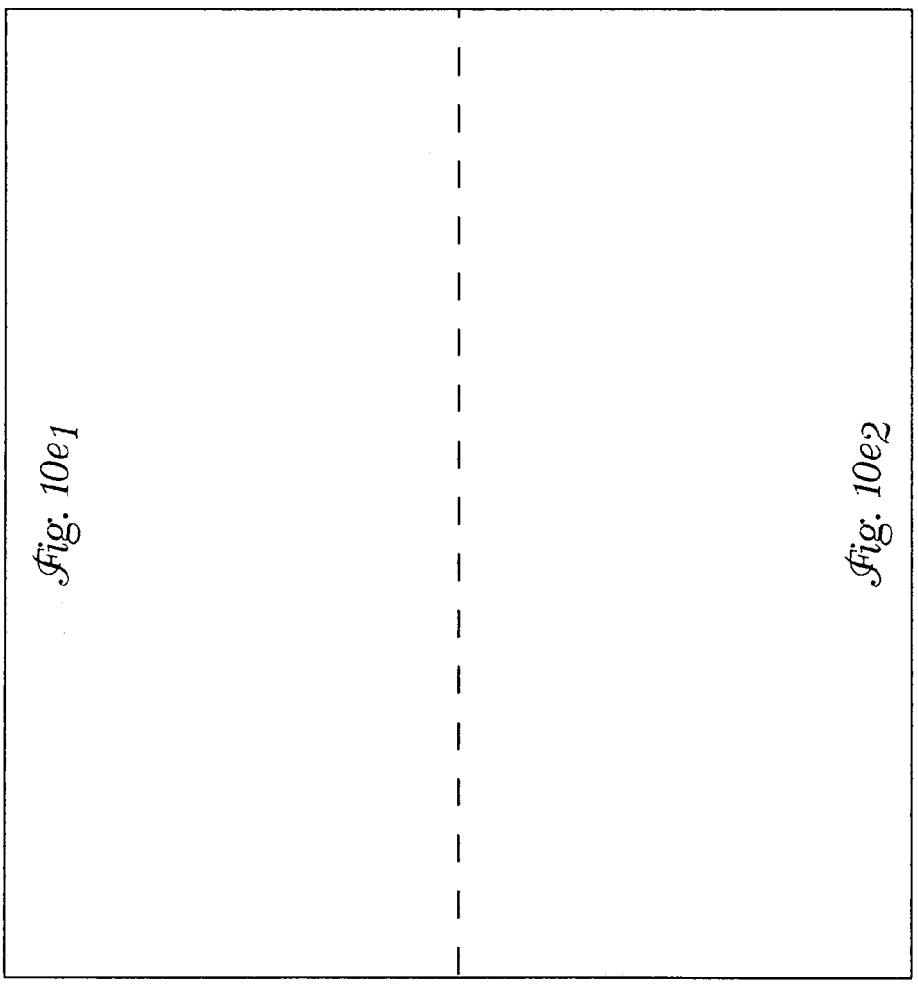

Fig. 10e1

```
5742/1801
cta acc act ggc caa acc ctc ttc aac ata ttg ggg tgg gtg gct gcc cag ctc
Leu Thr Thr Gly Gln Thr Leu Phe Asn Ile Leu Gly Gly Trp Val Ala Ala Gln Leu
5802/1821
gcc gcc ccc ggt gcc gct act gcc ttt gtg gt gct ggc cta gct ggc gcc atc ggc
Ala Ala Pro Gly Ala Ala Thr Ala Phe Val Gly Ala Gly Leu Ala Gly Ala Ile Gly
5862/1841
agc gtt gga ctg ggg aag gtc ctc gtg gac att ctt gca ggg tat ggc gcg ggc gtg gcg
Ser Val Gly Leu Gly Lys Val Leu Val Asp Ile Leu Ala Gly Tyr Gly Ala Gly Val Ala
5922/1861
gga gct ctt gta gca ttc aag atc atg agc ggt gag gtc ccc tcc acg gag gac ctg gtc
Gly Ala Leu Val Ala Phe Lys Ile Met Ser Gly Glu Val Pro Ser Thr Glu Asp Leu Val
5982/1881
aat ctg ctg ccc gcc atc ctc tcg cct gga gcc ctt gta gtc ggt gtg gtg gtc gca gca
Asn Leu Leu Pro Ala Ile Leu Ser Pro Gly Ala Leu Val Val Gly Val Val Cys Ala Ala
6042/1901
ata ctg cgc cgg cac cgt ggc ccg ggc gag ggg gca gtg caa tgg atg aac cgg cta ata
Ile Leu Arg Arg His Arg Val Gly Pro Gly Glu Gly Ala Val Gln Trp Met Asn Arg Leu Ile
6102/1921
gcc ttc gcc tcc cgg ata agc tcg gag gag tgt cat gtt tcc ccc acg cac gtg ccg gag agc gat gca
Ala Phe Ala Ser Arg Ile Ser Ser Glu Glu Cys His Val Ser Pro Thr His Tyr Val Pro Glu Ser Asp Ala
6162/1941
gcc gcc cgc gtc act gcc act gcc ata ctc agc agc ctc act gta acc cag ctc ctg agg cga ctg
Ala Ala Arg Val Thr Ala Ile Leu Ser Ser Leu Thr Val Thr Gln Leu Leu Arg Arg Leu
                                      NS4B    NS5A
6222/1961
cat cag tgg ata agc tcg gag gag tgt cca tgc tcc ggt tgg cta agg gac atc
His Gln Trp Ile Ser Glu Glu Cys Thr Thr Pro Cys Ser Gly Trp Leu Arg Asp Ile
6282/1981
tgg gac tgg ata tgc gag gtg ctg agc gac ttt aag acc tgg ctg aaa gcc aag ctc atg
Trp Asp Trp Ile Cys Glu Val Leu Ser Asp Phe Lys Thr Trp Leu Lys Ala Lys Leu Met
6342/2001
cca caa ctg cct ggg att ccc ttt gtg tcc tgc cag cgc agg ggg tat agg gtc tgg cga
Pro Gln Leu Pro Gly Ile Pro Phe Val Ser Cys Gln Arg Arg Gly Tyr Arg Val Trp Arg
6402/2021
gga gac ggc att atg cac act cgc tgc cac tgt gga gct gag atc act gga cat gtc aaa
Gly Asp Gly Ile Met His Thr Arg Cys His Cys Gly Ala Glu Ile Thr Gly His Val Lys
```

6462/2041
aac ggg acg atg agg atc gtc ggt cct agg acc tgc agg aac atg tgg agt ggg acg ttc
Asn Gly Thr Met Arg Ile Val Gly Pro Arg Thr Cys Arg Asn Met Trp Ser Gly Thr Phe 6522/2061
ccc att aac gcc tac acc acg ggc ccc tgt act ccc ctt cct gcg ccg aac tat aag ttc
Pro Ile Asn Ala Tyr Thr Thr Gly Pro Cys Thr Pro Leu Pro Ala Pro Asn Tyr Lys Phe 6582/2081
gcg ctg tgg agg gtg tct gca gag gaa tac gtg gag ata agg cgg gtg ggg gac ttc cac
Ala Leu Trp Arg Val Ser Ala Glu Glu Tyr Val Glu Ile Arg Arg Val Gly Asp Phe His 6642/2101
tac gta tcg ggt atg act act gac aat ctt aaa tgc ccg tgc cag atc cca tcg ccc gaa
Tyr Val Ser Gly Met Thr Thr Asp Asn Leu Lys Cys Pro Cys Gln Ile Pro Ser Pro Glu 6702/2121
ttt ttc aca gaa ttg gac ggg gtg cgc cta cac agg ttt gcg ccc cct tgc aag ccc ttg
Phe Phe Thr Glu Leu Asp Gly Val Arg Leu His Arg Phe Ala Pro Pro Cys Lys Pro Leu 6762/2141
ctg cgg gag gag gta tca aga gta gga ctc cac gag tac ccg gtg ggg tcg caa tta
Leu Arg Glu Glu Val Ser Arg Val Gly Leu His Glu Tyr Pro Val Gly Ser Gln Leu 6822/2161
cct tgc gag ccc gaa ccg gac gta gcc gtg ttg acg tcc atg ctc act ccc tcc cat
Pro Cys Glu Pro Glu Asp Pro Asp Val Ala Val Leu Thr Ser Met Leu Thr Asp Pro Ser His 6882/2181
ata aca gca gag gcg gcc ggg aga agg ttg gcg aga ggg tca ccc cct tct atg gcc agc
Ile Thr Ala Glu Ala Ala Gly Arg Arg Leu Ala Arg Gly Ser Pro Pro Ser Met Ala Ser 6942/2201
tcc tcg gct agc cag ctg tcc gct cca tct ctc aag gca act tgc acc gcc aac cat gac
Ser Ser Ala Ser Gln Leu Ser Ala Pro Ser Leu Lys Ala Thr Cys Thr Ala Asn His Asp 7002/2221
tcc cct gac gcc gag ctc ata gag gct aac ctg tgg agg cag gag atg gag aac ggc aac
Ser Pro Asp Ala Glu Leu Ile Glu Ala Asn Leu Trp Arg Gln Glu Met Gly Gly Asn 7062/2241
atc acc agg gtt gag tca gag aac aaa gtg gtg att ctg gac tcc ttc gat ccg ctt gtg
Ile Thr Arg Val Glu Ser Glu Asn Lys Val Val Ile Leu Asp Ser Phe Asp Pro Leu Val

Fig. 10e2

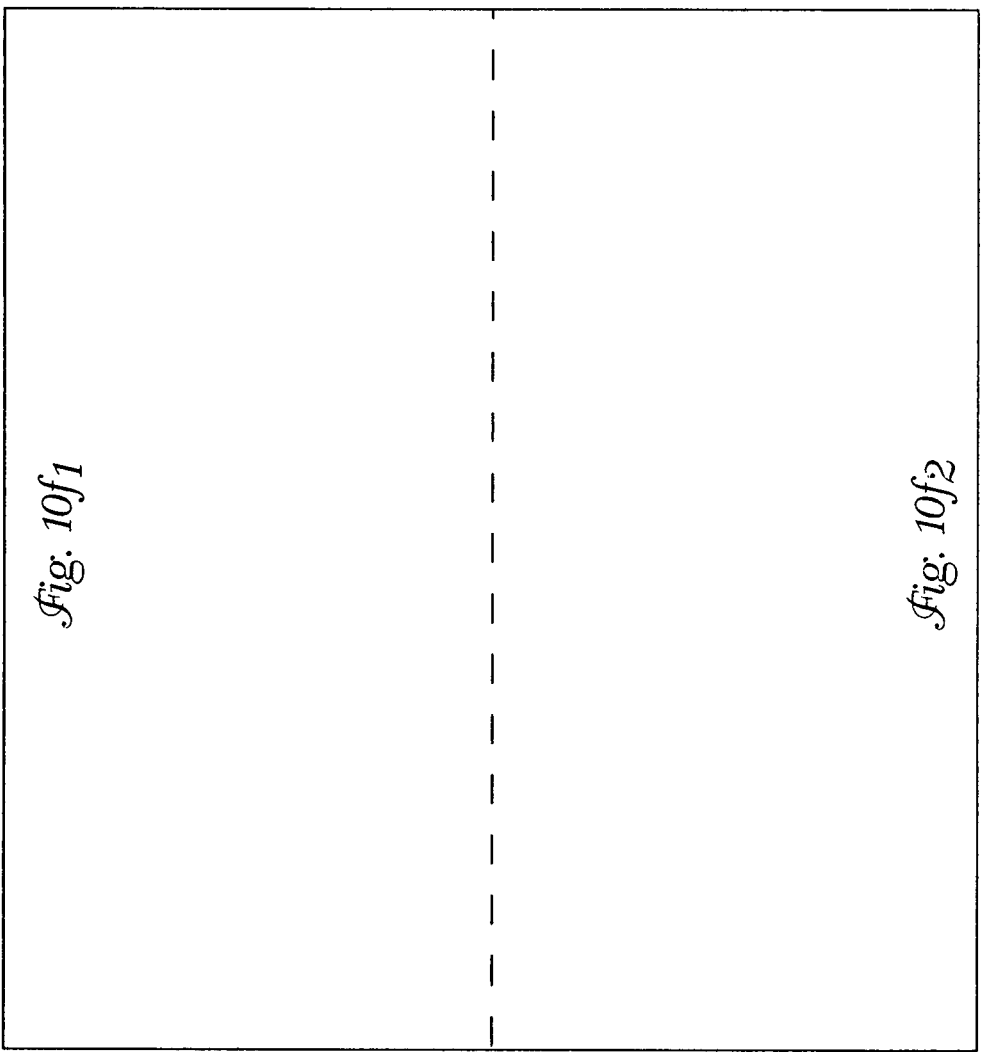

Fig. 10f₁

```
7122/2261
gca gag gag gat gag cgg gag gtc tcc gta cct gca gaa att ctg cgg aag tct cgg aga
Ala Glu Glu Asp Glu Arg Glu Val Ser Val Pro Ala Glu Ile Leu Arg Lys Ser Arg Arg
7182/2281
ttc gcc cgg gcc ctg gcc gtc ccc tgg gcg aac ccc gac tac aac ccc cta gta gag acg
Phe Ala Arg Ala Leu Pro Val Trp Ala Arg Pro Asp Tyr Asn Pro Leu Val Glu Thr
7242/2301
tgg aaa aag cct gac tac gaa cct cca gaa cct gtg gtc cat ggc tgc ccg cta cca cct cca cgg
Trp Lys Lys Pro Asp Tyr Glu Pro Pro Val His Gly Cys Pro Leu Pro Pro Pro Arg
7302/2321
tcc cct cct gtg cct cct ccg cct ccg cgg aaa aag cgt acg gtg gtc ctc acc gaa tca acc cta
Ser Pro Pro Val Pro Pro Pro Arg Lys Lys Arg Thr Val Val Leu Thr Glu Ser Thr Leu
7362/2341
tct act gcc ttg gcc gag ctt gcc acc aaa agt ttt ggc tcc tca act tcc ggc att
Ser Thr Ala Leu Ala Glu Leu Ala Thr Lys Ser Phe Gly Ser Ser Thr Ser Gly Ile
7422/2361
acg ggc gac aat acg aca aca tcc tct gag ccc gcc cct tct ggc tgc ccc ccc gac tcc
Thr Gly Asp Asn Thr Thr Thr Ser Ser Glu Pro Ala Pro Ser Gly Cys Pro Pro Asp Ser
7482/2381
gac gtt gag tcc tat tct tcc atg ccc ccc ctg gag ggg gag cct ggg gat ccg gat ctc
Asp Val Glu Ser Tyr Ser Ser Met Pro Pro Leu Glu Gly Glu Pro Gly Asp Pro Asp Leu
7542/2401
agc gac ggg tca tgg tcg acg gtc agt gca ctc gtc gtc gac gaa gat gtc gtg tgc tgc
Ser Asp Gly Ser Trp Ser Thr Val Ser Ser Gly Ala Asp Thr Glu Asp Val Val Cys Cys
7602/2421
tca atg tct tat tcc tgg aca ggg gca ctc gtc acc ccg tgc gct gcg gaa gaa caa aaa
Ser Met Ser Tyr Ser Trp Thr Gly Ala Leu Val Thr Pro Cys Ala Ala Glu Glu Gln Lys
7662/2441
ctg ccc atc aac gca ctg agc aac agc ctg cta cgc cat cac aat ctg gtg tat tcc acc
Leu Pro Ile Asn Ala Leu Ser Asn Ser Leu Leu Arg His His Asn Leu Val Tyr Ser Thr
7722/2461
act tca cgc agt gct tgc caa agg cag aag gtc aca ttt gac aga ctg caa ctg gtt ctg
Thr Ser Arg Ser Ala Cys Gln Arg Gln Lys Val Thr Phe Asp Arg Leu Gln Val Leu
7782/2481
gac agc cat tac cag gac gtg ctc aag gag gtc aaa gca gcg gcg tca aaa gtg aag gct
Asp Ser His Tyr Gln Asp Val Leu Lys Glu Val Lys Ala Ala Ala Ser Lys Val Lys Ala
```

NS5A → NS5B

```
7842/2501
aac ttg cta tcc gta gag gaa gct tgc agc cct acg ctg acg ccc cca cat tca gcc aaa tcc aag
Asn Leu Leu Ser Val Glu Glu Ala Cys Ser Pro Thr Leu Thr Pro His Ser Ala Lys Ser Lys 7902/2521
ttt ggc tat ggg gca aaa gac gtc cgt tgc cat tgc gcc aga aag gcc gta gcc cac atc aac
Phe Gly Tyr Gly Ala Lys Asp Val Arg Cys His Ala Arg Lys Ala Val Ala His Ile Asn 7962/2541
tcc gtg tgg aaa gac ctt ctg gaa gac agt gta gac ata cca act acc atc atg gcc
Ser Val Trp Lys Asp Leu Leu Glu Asp Ser Val Thr Pro Ile Asp Thr Thr Ile Met Ala 8022/2561
aag aac gag gtt ttc tgc gtt cag cct gag aag ggg ggt cgt aag cca gct cgt ctc atc
Lys Asn Glu Val Phe Cys Val Gln Pro Glu Lys Gly Gly Arg Lys Pro Ala Arg Leu Ile 8082/2581
gtg ttc ccc gac ctg ggc gtg cgc gtg tgc gag aag atg gcc ctg tac gac tyr asp val ser
Val Phe Pro Asp Leu Gly Val Arg Val Cys Glu Lys Met Ala Leu Tyr Asp Val Val Ser 8142/2601
aag ctc ccc ctg gcc gtg atg gga agc tcc tgg tac ttc caa tac tca cca gga cag cag cgg
Lys Leu Pro Leu Ala Val Met Gly Ser Ser Tyr Phe Gln Tyr Ser Pro Gly Gln Arg 8202/2621
gtt gaa ttc ctc gtg caa gcg tgg aag tcc acc atc ccg atg ttc tcg tat gat
Val Glu Phe Leu Val Gln Ala Trp Lys Ser Thr Pro Met Gly Phe Ser Tyr Asp 8262/2641
acc cgc tgt ttt gac tcc aca gtc act gag agc gac atc cgt gag gag gca att tac
Thr Arg Cys Phe Asp Ser Thr Val Thr Glu Ser Asp Ile Arg Glu Glu Ala Ile Tyr 8322/2661
caa tgt tgt gac ctg gac ccc caa gcc cgc gtg gcc atc aag tcc ctc act gag agg ctt
Gln Cys Cys Asp Leu Asp Pro Gln Ala Arg Val Ala Ile Lys Ser Leu Thr Glu Arg Leu 8382/2681
tat gtt ggg ggc cct ctt acc aat tca agg ggg gaa aac tgc ggc tac cgc tac cgc
Tyr Val Gly Gly Pro Leu Thr Asn Ser Arg Gly Glu Asn Cys Gly Tyr Arg Arg Cys Arg 8442/2701
gcg agc ggc gta ctg aca act agc tgt ggt aac acc ctc tac atc tgc tac ile lys ala arg
Ala Ser Gly Val Leu Thr Thr Ser Cys Gly Asn Thr Leu Thr Cys Tyr Ile Lys Ala Arg
```

```
8502/2721
gca gcc tgt cga gcc gca ggg ctc cag gac tgc gac atg ctc gtg tgt ggc gac tta
Ala Ala Cys Arg Ala Ala Gly Leu Gln Asp Cys Asp Met Leu Val Cys Gly Asp Leu
8562/2741
gtc gtt atc tgt gaa agt gcg ggg gtc cag gag gac gcg gcg agc ctg aga gcc ttc acg
Val Val Ile Cys Glu Ser Ala Gly Val Gln Glu Asp Ala Ala Ser Leu Arg Ala Phe Thr
8622/2761
gag gct atg acc agg tac tcc gcc ccc ccc ggg gac cca caa cca gaa tac gac ttg
Glu Ala Met Thr Arg Tyr Ser Ala Pro Pro Pro Gly Asp Pro Gln Pro Glu Tyr Asp Leu
8682/2781
gag ctt ata aca tca tgc tcc aac gtg tca gtc gcc cac gac ggc gct gga aag agg
Glu Leu Ile Thr Ser Cys Ser Asn Val Ser Val Ala His Asp Gly Ala Gly Lys Arg
8742/2801
gtc tac tac ctt acc cgt gac gat cct aca acc ccc ctc gcg aga gcc gcg tgg gag aca gca
Val Tyr Tyr Leu Thr Arg Asp Asp Pro Thr Thr Pro Leu Ala Arg Ala Ala Trp Glu Thr Ala
8802/2821
aga cac act cca gtc aat tcc tgg cta ggc aac ata atc atg ttt gcc ccc aca ctg tgg
Arg His Thr Pro Val Asn Ser Trp Leu Gly Asn Ile Ile Met Phe Ala Pro Thr Leu Trp
8862/2841
gcg agg atg ata ctg atg acc cat cat ttc ttt agc gtc ctc gtc ata gcc agg gat cag ctt gaa
Ala Arg Met Ile Leu Met Thr His His Phe Phe Ser Val Leu Ile Ala Arg Asp Gln Leu Glu
8922/2861
cag gct ctt aac tgt gag atc tac gga gcc tgc tac tcc ata gaa cca ctg gat tac tct cta cct
Gln Ala Leu Asn Cys Glu Ile Tyr Gly Ala Cys Tyr Ser Ile Glu Pro Leu Asp Tyr Ser Pro
8982/2881
cca atc att caa aga ctc cat ggc ctc ggc ctc agc gca ttt gca ttt tca ctc cac agt tac tct cca ggt
Pro Ile Ile Gln Arg Leu His Gly Leu Ser Ala Phe Ala Phe Ser Leu His Ser Tyr Ser Pro Gly
9042/2901
gaa atc aat agg gtg gcc gca gtc tgc aga aaa ctt ctg ccc ctt cga gct tgg
Glu Ile Asn Arg Val Ala Ala Val Cys Leu Arg Lys Leu Leu Leu Pro Pro Leu Arg Ala Trp
9102/2921
aga cac cgg gcc cgg agc gtc gct agg gtc tcc aga gga ggc agg gct gcc ata
Arg His Arg Ala Arg Ser Val Arg Arg Val Ser Arg Gly Arg Ala Ala Ile
9162/2941
tgt ggc aag tac ctc ttc aac tgg gca gta aga aca aag ctc aaa ctc act cca ata gcg
Cys Gly Lys Tyr Leu Phe Asn Trp Ala Val Arg Thr Lys Leu Lys Leu Thr Pro Ile Ala
```

```
9222/2961
gcc gct ggc cgg ctg gac ttg tcc ggt tgg ttc acg gct ggc tac agc ggg gga gac att
Ala Ala Gly Arg Leu Asp Leu Ser Gly Trp Phe Thr Ala Gly Tyr Ser Gly Gly Asp Ile
9282/2981
tat cac agc gtg tct cat gcc cgg ccc cgc tgg ttc tgg ttt tgc cta ctc ctg ctc gct
Tyr His Ser Val Ser His Ala Arg Pro Arg Trp Phe Trp Phe Cys Leu Leu Leu Leu Ala
9342/3001                                NS5B <-> 3'NTR Variable Region
gca ggg gta ggc atc tac ctc ctc ccc aac cga|tga agg ttg ggg taa aca ctc cgg cct
Ala Gly Val Gly Ile Tyr Leu Leu Pro Asn Arg *   Arg Leu Gly *   Thr Leu Arg Pro
9402/3021 -> EMCV IRES
ctt aag|gtt att ttc cac cat att gcc gtc ttt tgg caa tgt gag ggc ccg gaa acc tgg
Leu Lys Val Ile Phe His His Ile Ala Val Phe Trp Gln Cys Glu Gly Pro Glu Thr Trp
9462/3041
ccc tgt ctt ctt gac gag cat tcc tag ggg tct ttc ccc tct cgc caa agg aat gca agg
Pro Cys Leu Leu Asp Glu His Ser *   Gly Ser Phe Pro Ser Arg Gln Arg Asn Ala Arg
9522/3061
tct gtt gaa tgt cgt gaa gga agc agt tcc tct gga agc ttc ttg aag aca aac aac gtc
Ser Val Glu Cys Arg Glu Gly Ser Ser Ser Ser Gly Ser Phe Leu Lys Thr Asn Asn Val
9582/3081
tgt agc gac cct ttg cag gca gcg gaa ccc ccc acc tgg cga cag gtg cct ctg cgg cca
Cys Ser Asp Pro Leu Gln Ala Ala Glu Pro Pro Thr Trp Arg Gln Val Pro Leu Arg Pro
9642/3101
aaa gcc acg tgt ata aga tac acc tgc aaa ggc ggc aca acc cca gtg cca cgt tgt gag
Lys Ala Thr Cys Ile Arg Tyr Thr Cys Lys Gly Gly Thr Thr Pro Val Pro Arg Cys Glu
9702/3121
ttg gat agt tgt gga aag agt caa atg gct ctc ctc aag cgt att caa caa ggg gct gaa
Leu Asp Ser Cys Gly Lys Ser Gln Met Ala Leu Leu Lys Arg Ile Gln Gln Gly Ala Glu
9762/3141
gga tgc cca gaa ggt acc cca ttg tat ggg atc tga tct ggg gcc tcg gtg cac atg ctt
Gly Cys Pro Glu Gly Thr Pro Leu Tyr Gly Ile *   Ser Gly Ala Ser Val His Met Leu
9822/3161
tac gtg tgt tta gtc gag gtt aaa aaa cgt cta ggc ccc ccg aac cac ggg gac gtg gtt
Tyr Val Cys Leu Val Glu Val Lys Lys Arg Leu Gly Pro Pro Asn His Gly Asp Val Val
```

Fig. 10g2

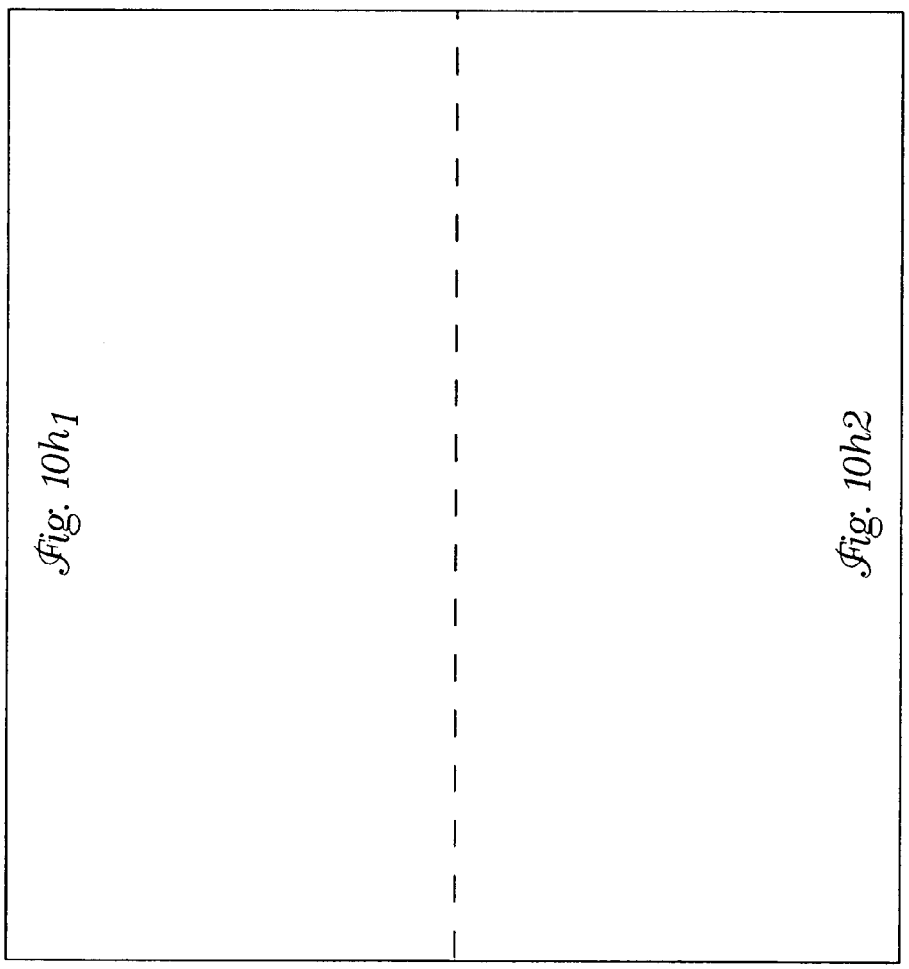
Fig. 10h₁  Fig. 10h2  Fig. 10h

Fig. 10h1

```
                   9882/3181              EMCV IRES<-
                   ttc ctt tga aaa aca cga tga taa t
                   Phe Lue *   Lys Thr Arg *   *
                  -> translation start by EMCV IRES
                   9907/1     -> tat coding sequence
                   atg agg cct atg gag cca gta gat cct aga cta gag ccc tgg aag cat cca gga agt cag
SEQ ID NO:21       Met Arg Pro Met Glu Pro Val Asp Pro Arg Leu Glu Pro Trp Lys His Pro Gly Ser Gln 9967/21
                   cct aaa act gct tgt acc aat tgc tat tgt aaa aag tgt tgc ttt cat tgc caa gtt tgt
                   Pro Lys Thr Ala Cys Thr Asn Cys Tyr Cys Lys Lys Cys Cys Phe His Cys Gln Val Cys 10027/41
                   ttc ata aca aaa gcc tta ggc atc tcc tat ggc agg aag aag cgg aga cag cga cga aga
                   Phe Ile Thr Lys Ala Leu Gly Ile Ser Tyr Gly Arg Lys Lys Arg Arg Gln Arg Arg Arg 10087/61
                   cct cct caa ggc agt cag act cat caa gtt tct cta tca aag caa ccc acc tcc caa tcc
                   Pro Pro Gln Gly Ser Gln Thr His Gln Val Ser Leu Ser Lys Gln Pro Thr Ser Gln Ser 10147/81                         TAT<-       ->FMDV2A
                   cga ggg gac ccg aca ggc ccg aag gaa gaa ttc gac ctt ctt aag ctt gcg gga gac gtc
                   Arg Gly Asp Pro Thr Gly Pro Lys Glu Glu Phe Asp Leu Leu Lys Leu Ala Gly Asp Val 10207/101        FMDV2A<-        -> Zeo
                   gag tcc aac cct ggg ccc gga tcc atg gcc aag ttg acc agt gcc gtt ccg gtg ctc acc
                   Glu Ser Asn Pro Gly Pro Gly Ser Met Ala Lys Leu Thr Ser Ala Val Pro Val Leu Thr 10267/121
                   gcg cgc gac gtc gcc gga gcg gtc gag ttc tgg acc gac cgg ctc ggg ttc tcc cgg gac
                   Ala Arg Asp Val Ala Gly Ala Val Glu Phe Trp Thr Asp Arg Leu Gly Phe Ser Arg Asp
```

```
10327/141
ttc gtg gag gac gac ttc gcc ggt gtc cgg gac gac gtg acc ctg ttc atc agc gcg
Phe Val Glu Asp Asp Phe Ala Gly Val Val Arg Asp Asp Val Thr Leu Phe Ile Ser Ala 10387/161
gtc cag gac cag gtg gtg ccg gac aac acc ctg gcc tgg tgg gtg cgc ggc ctg gac
Val Gln Asp Gln Val Val Pro Asp Asn Thr Leu Ala Trp Trp Val Arg Gly Leu Asp 10447/181
gag ctg tac gcc gag tgg tcg gag gtc gtg tcc acg ttc cgg aac gcc gcc ggg ccg
Glu Leu Tyr Ala Glu Trp Ser Glu Val Val Ser Thr Phe Arg Asn Ala Ala Ser Gly Pro 10507/201
gcc atg acc gag atc ggc gag cag ccg tgg ggg cgg gag ttc gcc cgc gac ccg gcc
Ala Met Thr Glu Ile Gly Glu Gln Pro Trp Gly Arg Glu Phe Ala Leu Arg Asp Pro Ala
                                                              Zeo→

10567/221
ggc aac tgc gtg gtg cac ttc gtg gcc gag gag cag gac gac tga ctt aag cca ttt cct gtt ttt
Gly Asn Cys Val His Phe Val Ala Glu Glu Gln Asp Asp  *

10627/241
ttt ttt ttt ttt ctt ctt taa tgg tgg ctc cat ctt ttt ttt cct ttc ctt ctt ttc ctt 10687/261
tct ttt tcc ctt tcc ctt ctt agc cct agt cac ggc tag ctg tga aag gtc cgt gac cat gac ccg cat gac tgc aga gag tgc aga gag tgc cct ctc tgc aga tca tgt
```

*Fig. 10h₂*

```
SEQ ID NO:18
           |         |         |         |         |         |         |         |
           1        10        20        30        40        50        60        70        80
   1 ACCTGGAAAA ACATGGAGCA ATCACAAGTA GCAATACAGC AGCTACCAAT GCTGCTTGTG CCTGGCTAGA AGCACAAGAG    80
  81 GAGGAGGAGG TGGGTTTTCC AGTCACACCT CAGGTACCTT TAAGACCAAT GACTTACAAG GCAGCTGTAG ATCTTAGCCA   160
 161 CTTTTTAAAA GAAAAGGGGG GACTGGAAGG GCTAATTCAC TCCCAAAGAA GACAAGATAT CCTTGATCTG TGGATCTACC   240
 241 ACACACAAGG CTACTTCCCT GATTAGCAGA ACTACACACC AGGGCCAGGG GTCAGATATC CACTGACCTT TGGATGGTGC   320
 321 TACAAGCTAG TACCAGTTGA GCCAGATAAG ATAGAAGAGG CCAATAAAGG AGAGAACACC AGCTTGTTAC ACCCTGTGAG   400
 401 CCTGCATGGG ATGGATGACC CGGAGAGAGA AGTGTTAGAG TGGAGGTTTG ACAGCCGCCT AGCATTTCAT CACGTGGCCC   480
 481 GAGAGCTGCA TCCGGAGTAC TTCAAGAACT GCTGACATCG CGAGCCCTCA AAGGGACTTT CCGCTGGGGA CTTTCCAGGG   560
 561 AGGCGTGGCC TGGGCGGGAC TGGGGAGTGG CGAGCCTGGG AGCTCTCTGG CTAACTAGGG AAACCCACTG CTTTTTGCC   640
 641 CTCTCTGGTT AGACCAGATC TGAGCCTGCT GCTCTGGGGC CTGAGCCTCA AGCTCTCCCT GGGCATCATC CCAGTTGAGG AGGAGAACCC   720
 721 TGCATGCTGC TGCTGCTGCT AACCGCGAGG CAGCCGAGGC CCTGGGTGCC GCCAAGAAGC TGCAGCCTGC ACAGACAGCC AGGAGAACGC   800
 801 GGACTTCTGG AACCGCGAGG CCTGGGTGCC CAGCCGAGGC CCTGGGTGCC TGCAGCCTGC AGGATCCTAA AGGGCAGAA GCCAAGAACC   880
 881 TCATCATCTT CCTGGGCGAT TGTCTACGGT GGATCCCCAT ATGTGGCTCT GACAAGACA AGGGCAGAA GCCAAGAACC   960
 961 CTGGGGCCTG AGATACCCCT GGAGCCACAG CCACGGCCTA CCTGTGCGGG GTCAAGGGCA ACTTCCAGAC CATTGGCTTG AGTGCAGCCG  1040
1041 GCCAGACAGT GGAGCCACAG CCACGGCCTA ACGACACGCG GCAACGAGGT CATCTCCGTG ATGAAATCGGG CCAAGAAAGC AGGGAAGTCA  1120
1121 CCCGCTTTAA CCAGTGCAAC ACGACACGCG AGAGTGCAG CACGCCCTGC CAGCCCCTCGC CTACGCCCAC ACGTGAACC GCAACTGGTA  1200
1201 GTGGGAGTGG TAACCACCAC GACGTGCCTG CCTCGGCCCG CCAGGAGGGG CCAGGACA TCGCTACGCA GCTCATCTCC AACATGGACA  1280
1281 CTCGGACGCC GACGTGCCTG GGCCGAAAGT ACATGTTTCC CATGGGAACC CCAGACCCTG GAAGCGCCAG GGTGCCCGGT AGTACTACAGC  1360
1361 TTGACGTGAT CCTAGGTGGA CCAGGTGGGA CGGAAGAAT CTGGTGCAGG CCCGTCTGTG AATGGCTGGC ACCCATCTCA TGGCCTGGA ATGTGTGGAA  1440
1441 CAAGGTGGGA CCAGGTGGGA CTCATGCAGG CTTCCCTGGA ACACTGACC CCGTCTGTGA ACCCATCTCA TGGCCTGGA GACATGAAAT  1520
1521 CCGCACTGAG CTCATGCAGG CCGAGACTCC TCTTCCTCTT CGTGGAGGGT GGTCGCATCG GAGGGCGGGC TCATGAAAGC GAGCAGGAAC  1600
1601 ACGAGATCCA CCGAGACTCC TCTTCCTCTT CGTGGAGGGT GGTCGCATCG GAGGGCGGGC ACCATGGTCA TCATGAAAGC GGGCACTGAC  1680
1681 CCCCGCGGCT TCTTCCTCTT ATGTTCGACG ACGCCATTGA GAGGGCGGGC GCTACCCCCT CAGCTCACCA GCGAGGAGGA CTCGTCACTG  1760
1761 TGAGACGATC ATGTTCGACG CCACGTCTTC TCCTTCGGAG GCTACCCCCT CAGCTCACCA GCGAGGAGGA CTCGTCACTG AAGCAGCGA  1840
1841 CCGACCACTC CCACGTCTTC TCCTTCGGAG GCTACCCCCT GGTCCTCCTA TACGCAGAACG GTCCAGGCTA TGTGCTCAAG TGGCAAGGCC  1920
1921 CGGGACAGGA AGGCCTACAC TCCTTCGGAG GCCCCGAGTA TCGGCAGCAG AGAGGACTA GTCCAGGCTA TGTGCTCAAG GGCCGGATGT  2000
2001 TACCGAGAGC GAGAGCGGGA GCCCGCCAGG TCGGCAGCAG CGCACCTGGT TCGACCTGCT CCTTCATAGC GCAGGCGAGG GGCCGGATGT  2080
2081 ACGTGGCGGT GTTCGCGGGC GGCCCGCCAGG CGCACCTGGT TCGACCTGCT CCTTCATAGC GCACGTCATG GCACGTCATG ACGTGGCGGT  2160
2161 GCCTTCGCCG CCTGCCTGGA GCCCTACACC GCCTGCGACC CGCCGGGCACC CGCCGGGCACC ACCGACGCCG CGCACCCCGG  2239
           |         |         |         |         |         |         |         |
          10        20        30        40        50        60        70        80
```

*Fig. 12*

```
NNeo  SGSWLRDVDWDWVCTVLSDFKTWLQSKLLPRLPGVPFLSCQRGYKGVWRGDGIMHTTCPCGAQIAGHVKNGSMRII
BNeo  ............................F.....................Q................T....V

NNeo  GPKTCSNTWHGTFPINAYTTGPCTPSPAPNYSKALWRVAAEEYVEVTRVGDFHYVTGITTDNVKCPCQVPAPEFF
BNeo  ..R................................R...........................M........

NNeo  TEVDGVRLHRYAPVCKPLLRDEVVFQVGLNQYLVGSQLPCEPEPDVAVLTSMLTDPSHITAEAAKRRLARGSPPS
BNeo  ................A..........E..T.L................................T........

NNeo  LASSSASQLSAPSLRATCTTHSSYNLDSPDVDLIAANLLWRQEMGGNITRVESENKVVVLDSFEPLRAEGDENEI
BNeo  ..........K.........R...........A...E.....................I........Q.E.R.V

NNeo  STAAEILRKSKKFPAAIPIWARPDYNPPLLESWKNPDYVPPVVHGCPLPPVKAPPIPPPRRKRTVVLTDSTVSSV
BNeo  .VP....R.R...R.M...........................D............................SE......A

NNeo  LAELATKTFGSSELSAADSGTATAPPDQTSDNGGKDSDAESCSSMPPLEGEPGDPLSDGSWSTVSEEAGESVVCC
BNeo  ...........S..V........S.....P..D.DAG..V..Y................S..D
```

Fig. 15

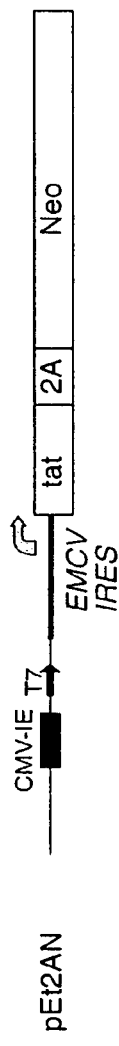
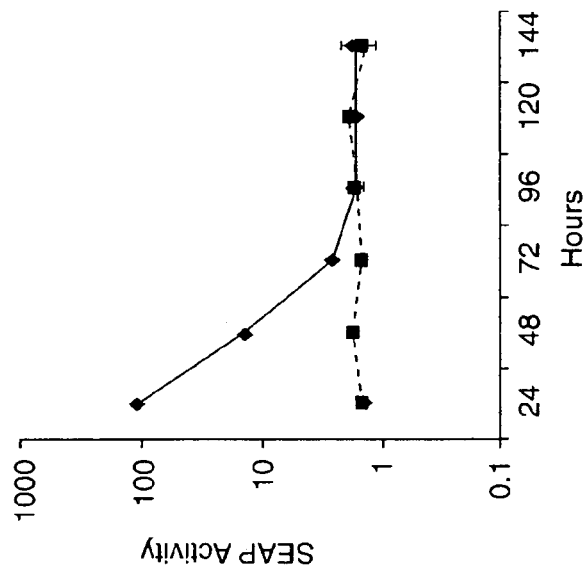
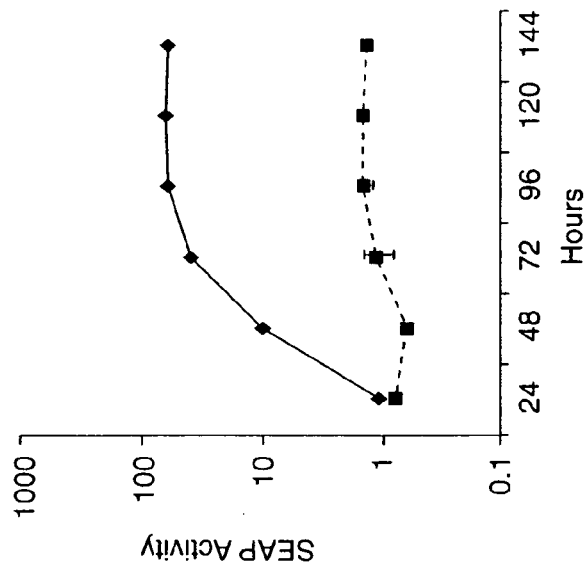
Fig. 16a
Fig. 16b
Fig. 16c

SEQ ID NO:35
GCCAGCCCCC TGATGGGGGC GACACTCCAC CATGAATCAC TCCCCTGTGA GGAACTACTG
TCTTCACGCA GAAAGCGTCT AGCCATGGCG TTAGTATGAG TGTCGTGCAG CCTCCAGGAC
CCCCCCTCCC GGGAGAGCCA TAGTGGTCTG CGGAACCGGT GAGTACACCG GAATTGCCAG
GACGACCGGG TCCTTTCTTG GATAAACCCG CTCAATGCCT GGAGATTTGG GCGTGCCCCC
GCAAGACTGC TAGCCGAGTA GTGTTGGGTC GCGAAAGGCC TTGTGGTACT GCCTGATAGG
GTGCTTGCGA GTGCCCCGGG AGGTCTCGTA GACCGTGCAC C

SEQ ID NO:38
             AGACC ACAACGGTTT CCCTCTAGCG GGATCAATTC CGCCCCCTCTC CCTCCCCCCC
CCCTAACGTT ACTGGCCGAA GCCGCTTGGA ATAAGGCCGG TGTGCGTTTG TCTATATGTT
ATTTTCCACC ATATTGCCGT CTTTTGCCCT CTTTTGCCCT TGTGAGGGCC CGGAAACCTG GCCCTGTCTT
CTTGACGAGC ATTCCTAGGG GTCTTTCCCC TCTCGCCAAA GGAATGCAAG GTCGTTGAA
TGTCGTGAAG GAAGCAGTTC CTCTGGAAGC TTCTTGAAGA CAAACAACGT CTGTAGCGAC
CCTTTGCAGG CAGCGGAAAC CCCCACCTGG CGACAGGTGC CTCTGCGGCC AAAAGCCACG
TGTATAAGAT ACACCTGCAA AGGCGGCACA ACCCCAGTGC CACGTTGTGA GTTGGATAGT
TGTGGAAAGA GTCAAATGGC TCTCCTCAAG CGTATTCAAC AAGGGGCTGA AGGATGCCCA
GAAGTACCCC CATTGTATGG GATCTGATCT GGGGCCTCGG TGCACATGCT TTACATGTGT
TTAGTCGAGG TTAAAAAACG TCTAGGCCCC CCGAACCACG GGGACGTGGT TTTCCTTTGA
AAAACACGAT AATACC

SEQ ID NO:39

```
GGG CAG GGG TGG CGA CTC CTT|gcg CCC ATC ACG GCC TAC TCC CAA CAG ACC CGG GGC CTA CTT GGT TGC ATC ACG AGT CTC ACA GGC
 G   Q   G   W   R   L   L | A   P   I   T   A   Y   S   Q   Q   T   R   G   L   L   G   C   I   I   T   S   L   T   G
5227/1051                                       5257/1061                                       5287/1071
                      NS2 ──┼──► NS3
CGG GAC AAG AAC CAG GTC GAG GGG TCA AAG ACT CTA GCC GCC GTG GTC TCC CCA AAA CAA ACA CAA GCC CTG GCG ACC GTA TGT TGG
 R   D   K   N   Q   V   E   G   S   K   T   L   A   A   V   V   S   P   K   Q   T   Q   A   L   A   T   V   C   W
5317/1081                                       5347/1091                                       5377/1101
ACT GTC TAC CAT GGT GCT GGC TCA AAG ACC CTA GCC GCC GTG GTC TCC CCA AAA CAA ACA CAA GCC ATG TAC ACT AAT GTA GAC CAG GAT CTC GTC
 T   V   Y   H   G   A   G   S   K   T                                                          M   Y   T   N   V   D   Q   D   L   V
5407/1111                                                                                       5437/1121
GGC TGG CCG GCG CCC CCC GGG GCG CGT TCC CTG ACA CCA TGC ACC TGC CAG AGC TCG GAC CTT TAC TTG GTT ACG AGA CAT GCA GAT GTT
 G   W   P   A   P   P   G   A   R   S   L   T   P   C   T   C   Q   S   S   D   L   Y   L   V   T   R   H   A   D   V
5497/1141                                       5527/1151                                       5557/1161
ATT CCG GTG CGC CGG GGC GAC AAT AGA GGG AGC TTG CTC TTC ACC CCC AGG CCT GTC TCC TAC TTG AAG GGC TCG GGT GGC CCA CTG
 I   P   V   R   R   G   D   N   R   G   S   L   L   F   T   P   R   P   V   S   Y   L   K   G   S   G   G   P   L
5587/1171                                       5617/1181                                       5647/1191
CTC TGC CCT TCG GGG GCC GTC TTC CGG GCC GCT GTA TGC ACC CGG GGG GTT GCA AAG GCG GTG TTT GTC GCC CCC GTT GAG
 L   C   P   S   G   A   V   F   R   A   A   V   C   T   R   G   V   A   K   A   V   F   V   A   P   V   E
5677/1201                                       5707/1211                                       5737/1221
TCC ATG GAA ACT ATG CGG GGC GTC GTC TTC ACA GAC AAC TCA TCT CCC CCG GCC GTA CCG CAA ACA TTC CAA GTG GCC CAT CTA CAC
 S   M   E   T   M   R   G   V   V   F   T   D   N   S   S   P   P   A   V   P   Q   T   F   Q   V   A   H   L   H
5767/1231                                       5797/1241                                       5827/1251
GCT CCC ACT GGC AGC ACT ATC TAT GGC ATG GGG GCA TAT GGT ACC GAC TAT GGT AAG GTG CTT GTC CTG AAC CCG TCT GTT GCC
 A   P   T   G   S   T   I   Y   G   M   G   A   Y   G   T   D   Y                AAG GTG CTT GTC CTG AAC CCG TCT GTT GCC
                                                                                    K   V   L   V   L   N   P   S   V   A
5857/1261                                       5887/1271                                       5917/1281
GCT ACC TTA GGT TTT GGG GCG TAT ATG TCT AAA GCA CAT GGT GTC GAC CCT AAC ATC AGG ACT GGG GTA AGG ACC ATT ACC ACG GGC GCC
 A   T   L   G   F   G   A   Y   M   S   K   A   H   G   V   D   P   N   I   R   T   G   V   R   T   I   T   T   G   A
5947/1291                                       5977/1301                                       6007/1311
CCC ATT ACG TAC TCC ACC TAT GGC AAG TTC CTT GCC GAC GGT GGT TGC TCC GGG GGC GCT TAC GAC ATC ATA ATG TGC GAT GAG TGC CAC
 P   I   T   Y   S   T   Y   G   K   F   L   A   D   G   G   C   S   G   G   A   Y   D   I   I   M   C   D   E   C   H
6037/1321                                       6067/1331                                       6097/1341
TCA ACT GAC GCA ACT ACT ATC TTG GGC ATC GGC ACA GTC CTG GAC CAA GCG GAG ACG GCT GGA GCG CGG CTT GTC GTG CTC GCC ACC ACC GCT
 S   T   D   A   T   T   I   L   G   I   G   T   V   L   D   Q   A   E   T   A   G   A   R   L   V   V   L   A   T   T   A
6127/1351                                       6157/1361                                       6187/1371
ACG CCT CCA GGA TCG GTC ACC GTG CCA CAC CCC AAT ATC GAG GAG GTG GCC CTG TCG AAC AAC GGA GAG ATC CCC TTC TAC GGC AAA GCC
 T   P   P   G   S   V   T   V   P   H   P   N   I   E   E   V   A   L   S   N   N   G   E   I   P   F   Y   G   K   A
6217/1381                                       6247/1391                                       6277/1401
ATC CCC ATC GAA GCC ATC AAG GGA GGG AGG CAC CTC ATT TTC TGT CAC TCC AAG AAG AAG TGC GAC GAG CTT GCC GCA AAG CTG TCA GGC
 I   P   I   E   A   I   K   G   G   R   H   L   I   F   C   H   S   K   K   K   C   D   E   L   A   A   K   L   S   G
6307/1411                                       6337/1421                                       6367/1431
CTC GGA ATC AAT GCT GTA GCG TAC TAC CGG GGT CTT GAT GTT TCC GTC ATA CCG ACC AGC GGA GAC GTC GTT GTC GCA ACA GAC GCT
 L   G   I   N   A   V   A   Y   Y   R   G   L   D   V   S   V   I   P   T   S   G   D   V   V   V   A   T   D   A
6397/1441                                       6427/1451                                       6457/1461
CTA ATG ACG GGC TAT ACC GGT GAC TTT GAT TCA GTG ATC GAC TGT AAT ACG TGT GTC ACC CAG ACA GTC GAC TTC AGC TTG GAC CCC ACC
 L   M   T   G   Y   T   G   D   F   D   S   V   I   D   C   N   T   C   V   T   Q   T   V   D   F   S   L   D   P   T
6487/1471                                       6517/1481                                       6547/1491
TTC ACC ATT GAG ACG ACG ACC GTG CCC CAA GAC GCA GTG TCG CGG TCG CAG CGG CGG GGT AGG ACT GGC AGG GGG CGG ATA TAC
 F   T   I   E   T   T   T   V   P   Q   D   A   V   S   R   S   Q   R   R   G   R   T   G   R   G   R   I   Y
6577/1501                                       6607/1511                                       6637/1521
AGG TTT GTA ACT CCG GGA GAA CGG CCC TCG GGC ATG TTC GAT TCC GTC GTC CTG TGC GAG TGC TAT GAC GCG GGT ACT GCA TGG TAC GAG
 R   F   V   T   P   G   E   R   P   S   G   M   F   D   S   V   V   L   C   E   C   Y   D   A   G   T   A   W   Y   E
6667/1531                                       6697/1541                                       6727/1551
CTC ACC CCC GCT GAG ACC CCG GTT AGG CTA CGG GCT TAC CTA AAT ACA CCA GGA TTG CCC GTT TGC CAG GAC CAT CTG GAG TTC TGG GAG
 L   T   P   A   E   T   P   V   R   L   R   A   Y   L   N   T   P   G   L   P   V   C   Q   D   H   L   E   F   W   E
```

REPLICATION COMPETENT HEPATITIS C VIRUS AND METHODS OF USE

This application claims priority to U.S. patent application Ser. No. 11/006,313, filed 6 Dec. 2004, which claims priority to U.S. patent application Ser. No. 10/259,275, filed Sep. 27, 2002, which is a Continuation-In-Part of U.S. patent application Ser. No. 09/747,419, filed Dec. 23, 2000, which claims the benefit of U.S. Provisional Application Ser. No. 60/171,909, filed Dec. 23, 1999, each of which are incorporated by reference herein. U.S. patent application Ser. No. 10/259,275 also claims the benefit of U.S. Provisional Applications Ser. No. 60/325,236, filed Sep. 27, 2001, and Ser. No. 60/338,123, filed Nov. 13, 2001, each of which are incorporated by reference herein.

GOVERNMENT FUNDING

The present invention was made with government support under Grant No. U19-A140035, awarded by the National Institute of Allergy and Infectious Diseases. The Government has certain rights in this invention.

BACKGROUND

Hepatitis C virus is the most common cause of chronic viral hepatitis within the United States, infecting approximately 4 million Americans and responsible for the deaths of 8,000-10,000 persons annually due to progressive hepatic fibrosis leading to cirrhosis and/or the development of hepatocellular carcinoma. Hepatitis C virus is a single stranded, positive-sense RNA virus with a genome length of approximately 9.6 kb. It is currently classified within a separate genus of the flavivirus family, the genus *Hepacivirus*. The hepatitis C virus genome contains a single large open reading frame (ORF) that follows a 5' non-translated RNA of approximately 342 bases containing an internal ribosome entry segment (IRES) directing cap-independent initiation of viral translation. The large ORF encodes a polyprotein which undergoes post-translational cleavage, under control of cellular and viral proteinases. This yields a series of structural proteins which include a core or nucleocapsid protein, two envelope glycoproteins, E1 and E2, and at least six nonstructural replicative proteins. These include NS2 (which with the adjacent NS3 sequence demonstrates cis-active metalloproteinase activity at the NS2/NS3 cleavage site), NS3 (a serine proteinase/NTPase/RNA helicase), NS4A (serine proteinase accessory factor), NS4B, NS5A, and NS5B (RNA-dependent RNA polymerase).

With the exception of the 5' non-translated RNA, there is substantial genetic heterogeneity among different stains of hepatitis C virus. Phylogenetic analyses have led to the classification of Hepatitis C virus strains into a series of genetically distinct "genotypes," each of which contains a group of genetically related viruses. The genetic distance between some of these genotypes is large enough to suggest that there may be biologically significant serotypic differences as well. There is little understanding of the extent to which infection with a virus of any one genotype might confer protection against viruses of a different genotype.

Several types of human interferon have proven effective in the treatment of infection by hepatitis C virus, either alone as monotherapy, or in combination with ribavirin. However, treatment with interferon-ribavirin carries a high risk of treatment failure, either primary failure of virus elimination, or relapse of the infection upon cessation of therapy. Moreover, these therapeutic agents are relatively toxic and are associated with a high frequency of adverse reactions. The development of better (more effective and safer) antiviral agents capable of suppressing or eliminating hepatitis C virus infection has been hindered by the fact that this virus replicates with very low efficiency, or not at all, in cultured cells. The absence of a highly permissive cell culture system that is capable of supporting robust replication of the virus has prevented the development of high throughput antiviral screens for use in the development of inhibitors of viral replication, and has delayed the investigation of the virus and relevant aspects of its molecular and cellular biology. It has also stymied efforts at vaccine development and the immunologic characterization of the virus, the human response to hepatitis C virus, and the diseases associated with infection. The development of infectious molecular cDNA clones of the viral genome has done little to solve this problem, since virus can be rescued from the RNA transcribed from such clones only by its injection into the liver of a living chimpanzee or other susceptible primate.

SUMMARY OF THE INVENTION

The present invention provides methods for identifying a compound that inhibits replication of an HCV RNA. The methods include contacting a cell that contains a replication competent HCV RNA with a compound. The replication competent HCV RNA includes a heterologous polynucleotide that contains a first coding sequence encoding a transactivator. The transactivator may include an amino acid sequence having at least about 70% identity with the amino acid sequence SEQ ID NO:19 or amino acids 4-89 of SEQ ID NO:21. The cells are incubated under conditions where the replication competent HCV RNA replicates in the absence of the compound, and the replication competent HCV RNA is detected. A decrease the replication competent HCV RNA in the cell contacted with the compound compared to the replication competent HCV RNA in a cell not contacted with the compound indicates the compound inhibits replication of the replication competent HCV RNA.

The HCV RNA may include a second coding sequence encoding a hepatitis C virus polyprotein and a 3' non-translated RNA, and the heterologous polynucleotide may be present in the 3' non-translated RNA or 5' of the second coding sequence. Alternatively, the HCV RNA may include a 3' non-translated RNA and a second coding sequence encoding a subgenomic hepatitis C virus polyprotein, and the heterologous polynucleotide may be present in the 3' non-translated RNA or 5' of the second coding sequence.

The heterologous polynucleotide may include a second coding sequence encoding a selectable marker, and the first coding sequence and the second coding sequence together encode a fusion polypeptide. The heterologous polynucleotide may further include a third coding sequence encoding a cis-active proteinase present between the first coding sequence encoding the transactivator and the second coding sequence encoding the selectable marker. The first coding sequence, the third coding sequence, and the second coding sequence together encode a fusion polypeptide.

The cell may include a polynucleotide that includes a transactivated coding sequence encoding a detectable marker and an operator sequence operably linked to the transactivated coding sequence. The transactivator interacts with the operator sequence and alters expression of the transactivated coding sequence. Detecting the replication competent HCV RNA in the cell includes detecting the detectable marker encoded by the transactivated coding sequence. The present invention is also directed to the cell.

The present invention also provides a method for selecting a replication competent HCV RNA. The method includes incubating a vertebrate cell in the presence of a selecting agent, for instance, an antibiotic. The cell includes an HCV RNA that includes a first coding sequence encoding a hepatitis C virus polyprotein, and a heterologous polynucleotide, and the heterologous polynucleotide includes a second coding sequence encoding a selectable marker that confers resistance to the selecting agent. The selecting agent inhibits replication of a cell that does not express the selectable marker. A cell that replicates in the presence of the selecting agent is detected, and the presence of such a cell indicates the HCV RNA is replication competent.

The method may further include obtaining a virus particle produced by the first cell and exposing a second vertebrate cell to the isolated virus particle and incubating the second vertebrate cell in the presence of the selecting agent. A second cell that replicates in the presence of the selecting agent is detected, wherein the presence of such a cell indicates the HCV RNA present in the first cell produces an infectious virus particle.

The HCV RNA may include a 3' non-translated RNA, and the heterologous polynucleotide may be present in the 3' non-translated RNA or 5' of the first coding sequence.

The present invention also provides a method for detecting a replication competent HCV RNA. The method includes incubating a vertebrate cell comprising an HCV RNA. The HCV RNA includes a first coding sequence encoding a hepatitis C virus polyprotein, or a subgenomic hepatitis C virus polyprotein, and a heterologous polynucleotide includes a second coding sequence encoding a transactivator. The cell includes a transactivated coding region and an operator sequence operably linked to the transactivated coding region, where the transactivated coding region encodes a detectable marker and the transactivator alters transcription of the transactivated coding region. The detectable marker is detected, and the presence of the detectable marker indicates the cell contains a replication competent HCV RNA.

The heterologous polynucleotide may further include a third coding sequence encoding a selectable marker, and the second coding sequence and the third coding sequence together encode a fusion polypeptide. Alternatively, the heterologous polynucleotide may further include a fourth coding sequence encoding a cis-active proteinase present between the second coding sequence encoding the transactivator and the third coding sequence encoding the selectable marker, and the second coding sequence, the fourth coding sequence, and the third coding sequence together encode a fusion polypeptide.

The present invention further provides replication competent HCV polynucleotides that include a first coding sequence encoding a subgenomic hepatitis C virus polyprotein, and a heterologous polynucleotide containing a second coding sequence encoding a transactivator, wherein the heterologous polynucleotide is located 5' of the first coding sequence. In another aspect, the present invention provides a replication competent HCV polynucleotide containing a first coding sequence encoding a hepatitis C virus polyprotein, and a heterologous polynucleotide.

The present invention also provides kits. The kits include a replication competent HCV polynucleotide containing a heterologous polynucleotide that has a first coding sequence encoding a transactivator, and a vertebrate cell that includes a polynucleotide containing a transactivated coding sequence encoding a detectable marker and an operator sequence operably linked to the transactivated coding sequence. The transactivator interacts with the operator sequence and alters expression of the transactivated coding sequence.

Definitions

As used herein, the term "HCV" refers to a hepatitis C virus, e.g., a viral particle, or a polynucleotide that includes a hepatitis C viral genome or a portion thereof. Preferably, the polynucleotide is RNA.

As used herein, the term "replication competent" refers to an HCV RNA that replicates, e.g., HCV nucleic acid is synthesized, for instance synthesis of the negative-sense strand, in vitro or in vivo. As used herein, the term "replicates in vitro" indicates the HCV RNA replicates in a cell that is growing in culture. The cultured cell can be one that has been selected to grow in culture, including, for instance, an immortalized or a transformed cell. Alternatively, the cultured cell can be one that has been explanted from an animal. "Replicates in vivo" indicates the HCV RNA replicates in a cell within the body of an animal, for instance a primate (including a chimpanzee) or a human. In some aspects of the present invention, replication in a cell can include the production of infectious viral particles, i.e., viral particles that can infect a cell and result in the production of more infectious viral particles.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences and/or non-translated regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. The term "heterologous polynucleotide" refers to a polynucleotide that has been inserted into the HCV genome, typically by using recombinant DNA techniques, and is not naturally occurring.

The terms "3' non-translated RNA," "3' non-translated region," and "3' untranslated region" are used interchangeably, and are terms of art. The term refers to the nucleotides that are at the 3' end of the positive-sense strand of the HCV polynucleotide, the complement thereof (i.e., the negative-sense RNA), and the corresponding DNA sequences of the positive-sense and the negative-sense RNA sequences. The 3' non-translated RNA includes, from 5' to 3', nucleotides of variable length and sequence (referred to as the variable region), a poly-pyrimidine tract (the poly U-UC region), and a highly conserved sequence of about 100 nucleotides (the conserved region) (see FIG. 2). The variable region begins at the first nucleotide following the stop codon of the NS5B coding region, and ends immediately before the nucleotides of the poly U-UC region. The poly U-UC region is a stretch of predominantly U residues, CU residues, or C(U)n-repeats. When the nucleotide sequence of a variable region is compared between members of the same genotype, there is typically a great deal of similarity; however, there is typically very little similarity in the nucleotide sequence of the variable regions between members of different genotypes (see, for instance, Yamada et al., *Virology*, 223, 255-261 (1996)). The length of the variable region can vary.

The terms "5' non-translated RNA," "5' non-translated region," "5' untranslated region" and "5' noncoding region" are used interchangeably, and are terms of art (see Bukh et al., Proc. Nat. Acad. Sci. USA, 89, 4942-4946 (1992)). The term refers to the nucleotides that are at the 5' end of the positive-sense strand of the HCV polynucleotide, the complement thereof (i.e., the negative-sense RNA), and the corresponding DNA sequences of the positive-sense and the negative-sense RNA sequences. The 5' NTR includes about 341 nucleotides. The last nucleotide of the 5' NTR is immediately upstream and adjacent to the first nucleotide of the coding sequence encoding the hepatitis C virus polyprotein.

A "coding region" or "coding sequence" is a nucleotide region that encodes a polypeptide and, when placed under the control of appropriate regulatory sequences, expresses the encoded polypeptide. The boundaries of a coding region are generally determined by a translation start codon at its 5 end and a translation stop codon at its 3' end. A coding region can encode one or more polypeptides. For instance, a coding region can encode a polypeptide that is subsequently processed into several polypeptides. A regulatory sequence or regulatory region is a nucleotide sequence that regulates expression of a coding region to which it is operably linked. Nonlimiting examples of regulatory sequences include promoters, transcription initiation sites, translation start sites, internal ribosome entry sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

As used herein the term "marker" refers to a molecule, for instance, a polypeptide. A "selectable marker" is a polypeptide that inhibits a compound, for instance an antibiotic, from preventing cell growth. A "detectable marker" is a polypeptide that can be detected. A marker can be both selectable and detectable.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

As used herein a "fusion polypeptide" refers to a polypeptide encoded by a coding region that is made up of two coding regions that have been joined together in frame, typically using recombinant DNA techniques, such that the two coding regions now encode a single polypeptide.

As used herein, a "transactivator" is a polypeptide that affects in trans the expression of a transactivated coding region. A "transactivated coding region" is a coding region to which is operably linked an operator sequence. As used herein, the term "operator sequence" is a type of regulatory region and includes a polynucleotide with which a transactivator can interact to alter expression of an operably linked transactivated coding region.

An "isolated" virus means a virus that has been removed from its natural environment. For instance, a virus that has been removed from an animal is an isolated virus. Another example of an isolated virus is one that has been removed from the cultured cells in which the virus was propagated, for instance by removing media containing the virus. A virus of this invention may be purified, i.e., essentially free from any other associated cellular products or other impurities. The term "purified" is defined as encompassing preparations of a virus having less than about 50%, more preferable less than about 25% contaminating associated cellular products or other impurities.

As used herein, the phrase "selecting a replication competent HCV RNA" refers to identifying a cell that includes a replication competent HCV RNA under conditions that prevent the replication of cells that do not include a replication competent HCV RNA.

A "hepatitis C virus polyprotein" refers to a polypeptide that is post-translationally cleaved to yield more than one polypeptide. Unless noted otherwise, a hepatitis C virus polyprotein yields the polypeptides core (also referred to as nucleocapsid), E1, E2, P7, NS2, NS3, NS4A, NS4B, NS5A, and NS5B. Optionally, a hepatitis C virus polyprotein also yields protein F (see Xu et al., *EMBO J*, 20, 3840-3848 (2001).

A "subgenomic" HCV polynucleotide, preferably an RNA, refers to an HCV RNA that does not include the entire HCV genome. A subgenomic HCV RNA typically includes a coding region encoding only a portion of a hepatitis C virus polyprotein, e.g., the nucleotides encoding one or more polypeptide is not present. Such a hepatitis C virus polyprotein is referred to as a "subgenomic hepatitis C virus polyprotein." In some aspects of the invention, an HCV RNA contains a subgenomic hepatitis C virus polyprotein that does not include polypeptides encoded by the 5' end of the hepatitis C virus polyprotein. Thus, a subgenomic hepatitis C virus polyprotein may encode the polypeptides NS3, NS4A, NS4B, NS5A, and NS5B; NS2, NS3, NS4A, NS4B, NS5A, and NS5B; P7, NS2, NS3, NS4A, NS4B, NS5A, and NS5B; E2, P7, NS2, NS3, NS4A, NS4B, NS5A, and NS5B; or E1, E2, P7, NS2, NS3, NS4A, NS4B, NS5A, and NS5B. In other aspects of the invention, an HCV RNA contains a subgenomic hepatitis C virus polyprotein that does not include polypeptides present in an internal portion of a hepatitis C virus polyprotein. Thus, a subgenomic hepatitis C virus polyprotein may encode, for instance, the polypeptides NS3, NS4A, NS4B, and NS5B. Replication of a subgenomic HCV RNA in a cell includes the synthesis of viral nucleic acid, for instance synthesis of the negative-sense strand, and typically does not include the production of infectious viral particles Unless otherwise specified, "a," "an," "the," and "at least one" are used interchangeably and mean one or more than one.

BRIEF DESCRIPTION OF THE FIGURES

FIG. 4. SEAP activity in medium collected from cells following transfection with RNAs. (A) Huh7-SEAP-o10 cells. (B) Huh7-SEAP-N7 cells. The smaller graph A and B each depict days 1 and 6, but use different scales. Mock, cells exposed to transfection conditions but not RNA; 3'ETZ, MK0-Z, and dS-MK0-Z, the constructs shown in FIG. 1; y-axis, units of secretory alkaline phosphatase activity measured by luminescent signal detected by a TD-20/20 Luminometer (Turner Design, Sunnyvale, Calif.).

FIG. 9. Nucleotide sequence of MK0-Z (SEQ ID NO:17). The initiation codon of the viral polyprotein which undergoes post-translational cleavage is the ATG at nucleotides 342-344. The initiation codon of the inserted heterologous polynucleotide is the ATG at nucleotides 9907-9909.

Figure 10A:
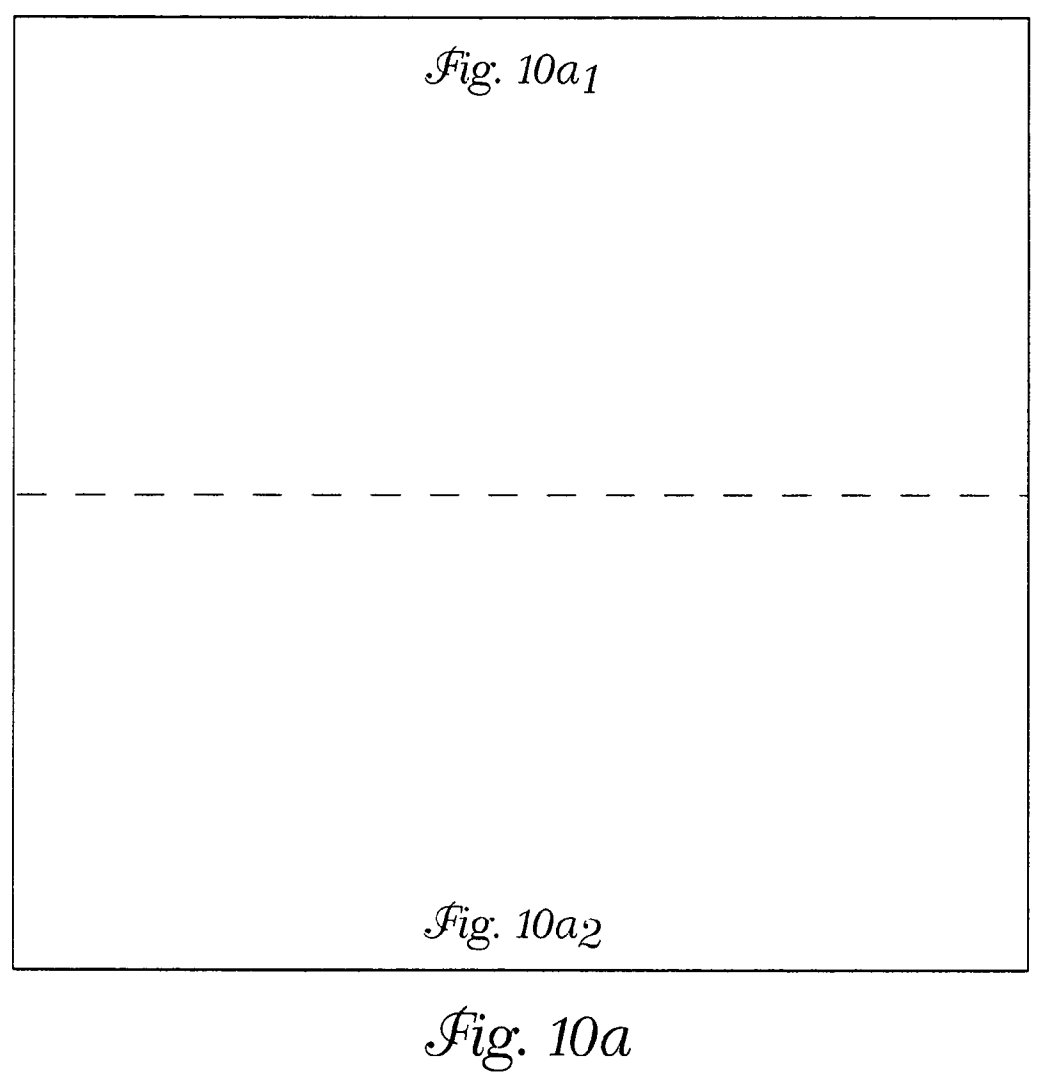
Figure 10G:
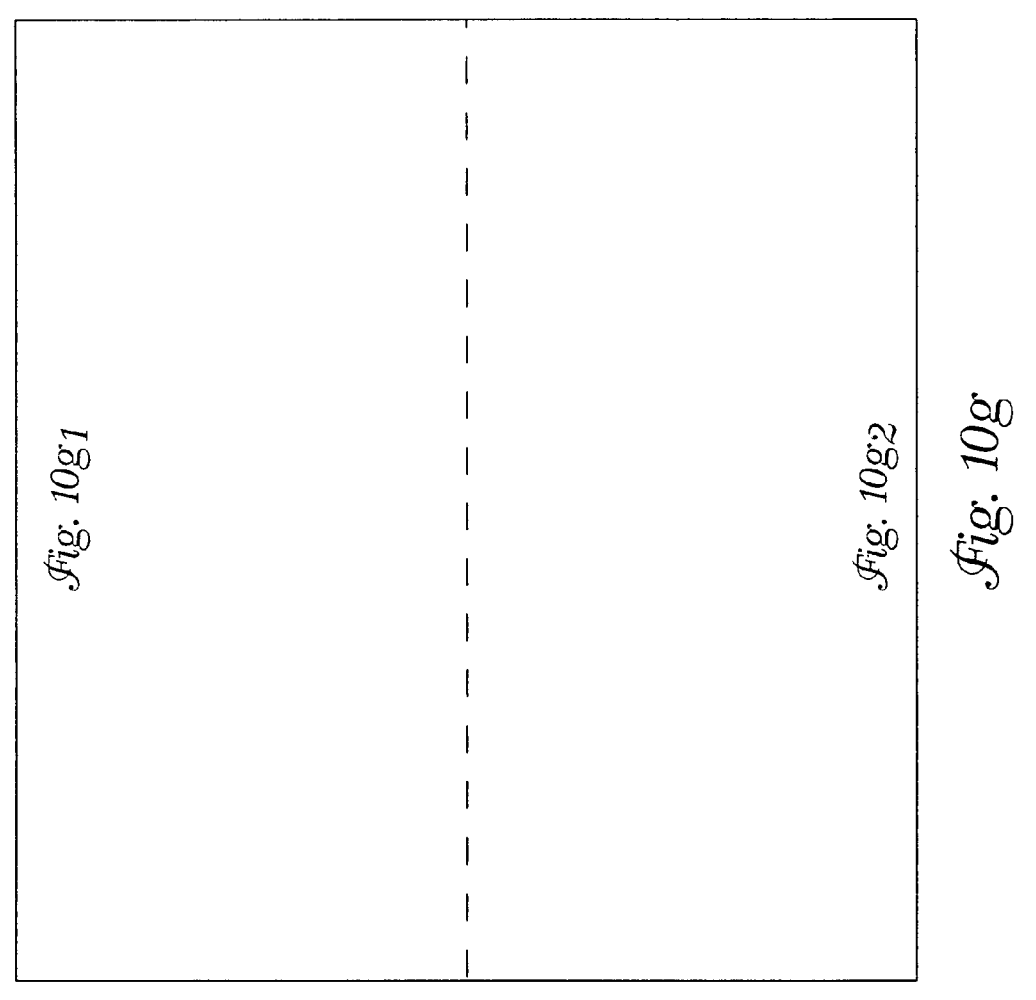

FIG. 10. Nucleotides 342-10,803 of SEQ ID NO:17, and the polyprotein (SEQ ID NO:20). The amino acid sequences SEQ ID NO:32, SEQ ID NO:33, and SEQ ID NO:34 encoded by nucleotides 9,390-9,485, nucleotides 9,489-9,794, and nucleotides 9,798-9,887 of SEQ ID NO:17, respectively, are shown. The amino acid sequence (SEQ ID NO:21) encoded by the heterologous polynucleotide (i.e., nucleotides 9907-10,602 of SEQ ID NO:17) is also shown.

FIG. 12. Nucleotide sequence of HIVSEAP (SEQ ID NO:18). The HIV long terminal repeat (LTR) is depicted at nucleotides 1-719, and secretory alkaline phosphatase is encoded by the nucleotides 748-2239.

FIG. 15. Alignment of the amino acid sequences of the NS5A proteins encoded by NNeo/3-5B and Neo/3-5B. The ISDR is shaded, with the 4-amino-acid SSYN (SEQ ID NO: 75) insertion in NNeo/3-5B shown in boldface type and enclosed in a box. Arrows indicate the location of single-base substitutions and insertions and the large 47-amino-acid deletion that has been shown previously to enhance the replication capacity of BNeo/3-5B (Blight et al., Science, 290, 1972-1974 (2000), Krieger et al., J Virol., 75, 4614-4624 (2001), Lohmann et al., J Virol., 75, 1437-1449 (2002)). The asterisk indicates the S2005I mutation.

FIG. 16. Enzyme reporter system. (A) Organization of pEt2AN. A solid square represents the CMV promoter region; a solid arrow the T7 promoter; a thick line the EMCV IRES and the open box for the open reading frame encoding the fusion polypeptide tat-2A-Neo. (B) SEAP expression following pEt2AN DNA transfection into En5-3 cells (▲). The expression of tat from this plasmid is dependent on the CMV promoter. Note that SEAP activity is reported in arbitrary units. SEAP expression from En5-3 cells without DNA transfection was also shown (■). (C) SEAP expression following electroporation of En5-3 cells with RNA transcribed in vitro from pEt2AN (▲). SEAP expression from En5-3 cells without RNA transfection was also shown (■).

Figure 24B:
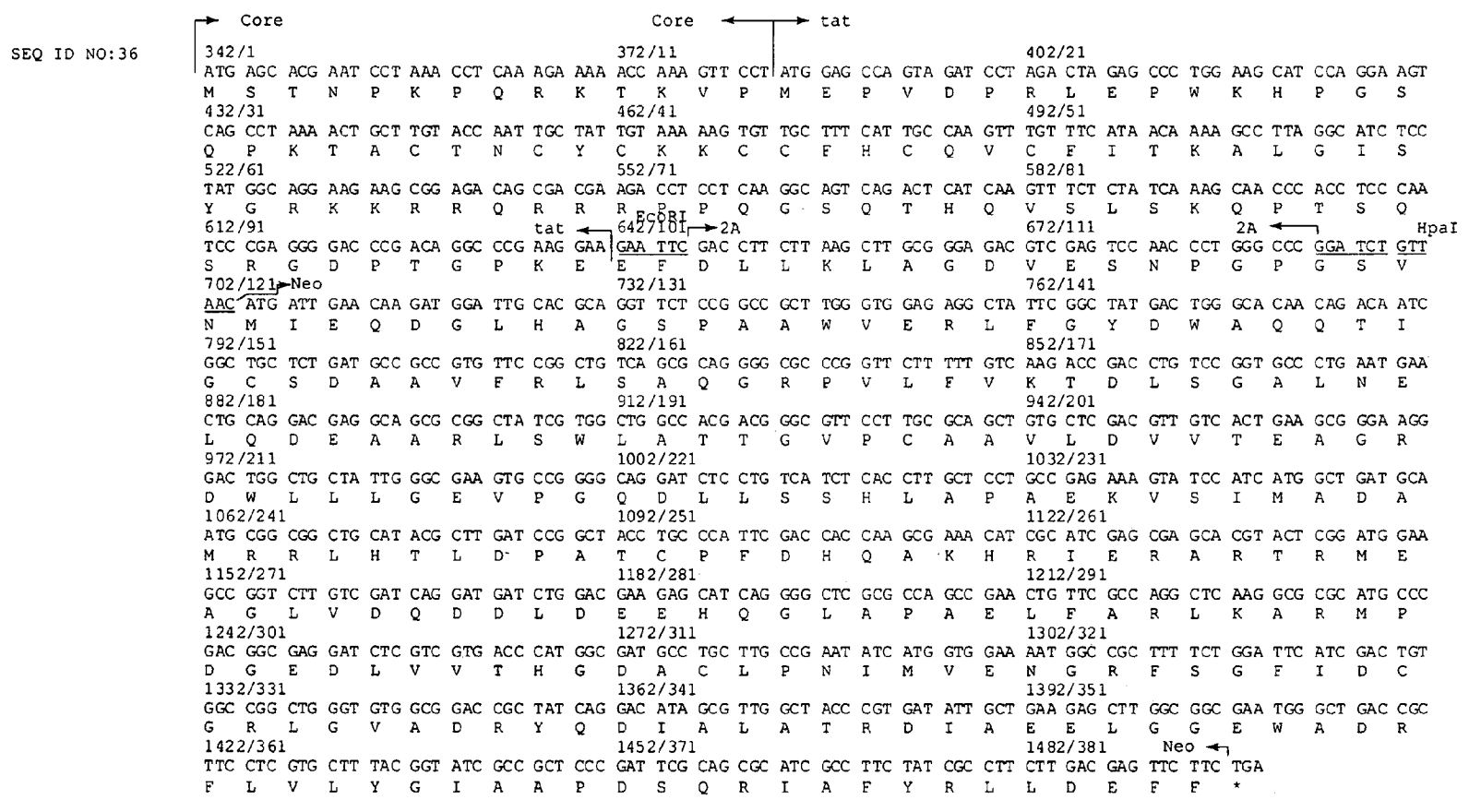
Figure 24C:
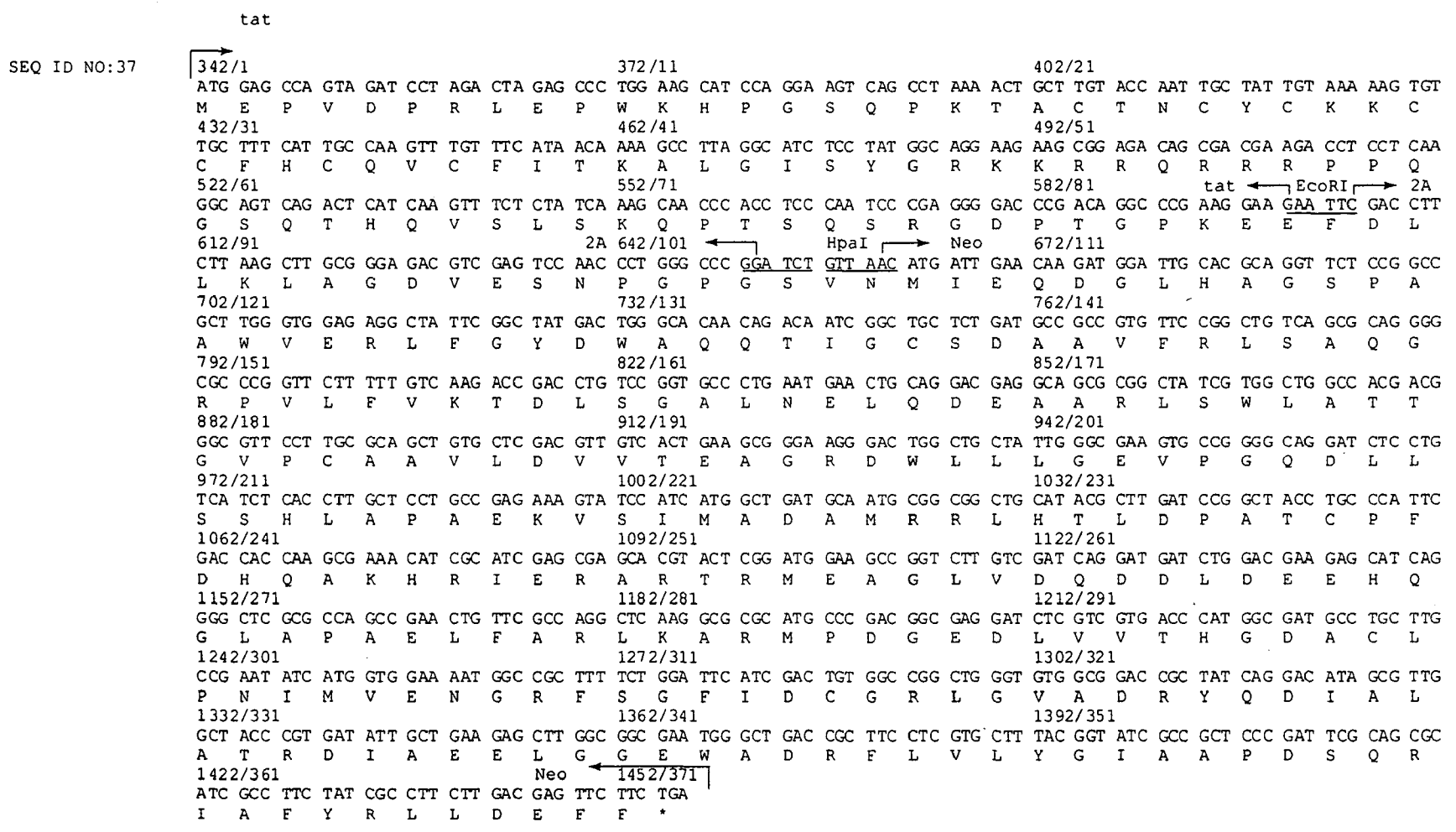
Figure 24D:
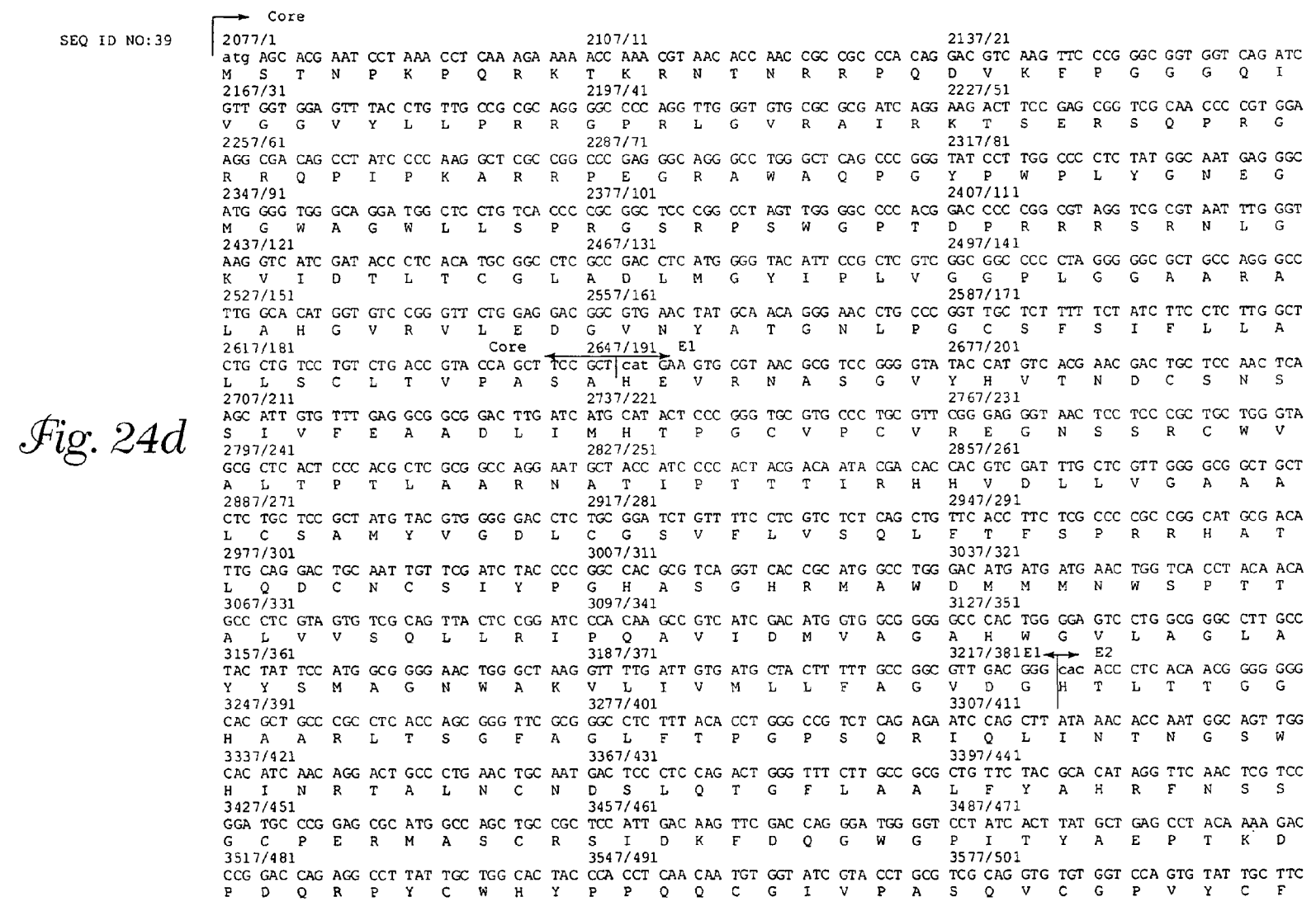
Figure 24D-1:
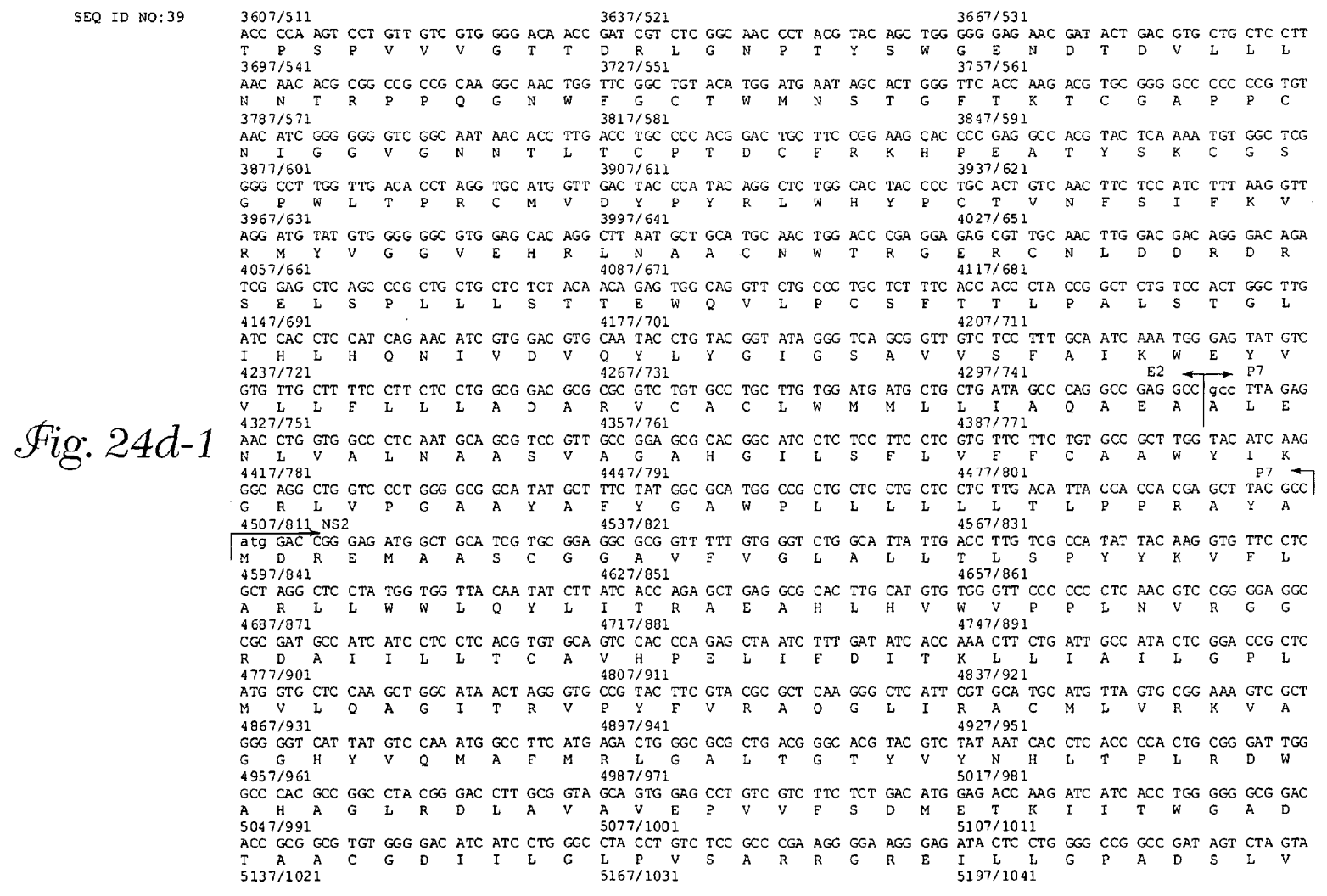
Figure 24D-3:
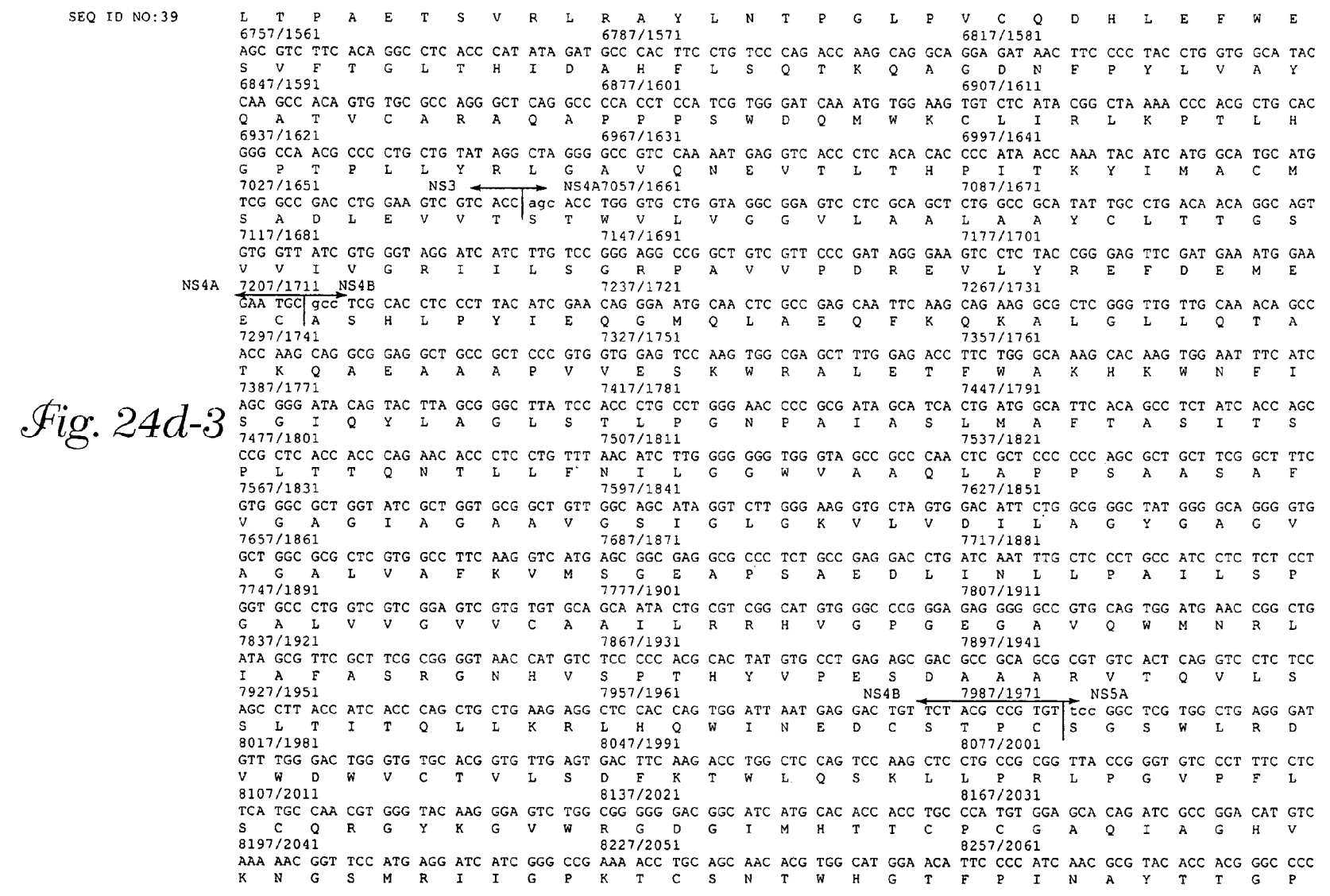
Figure 24D-4:
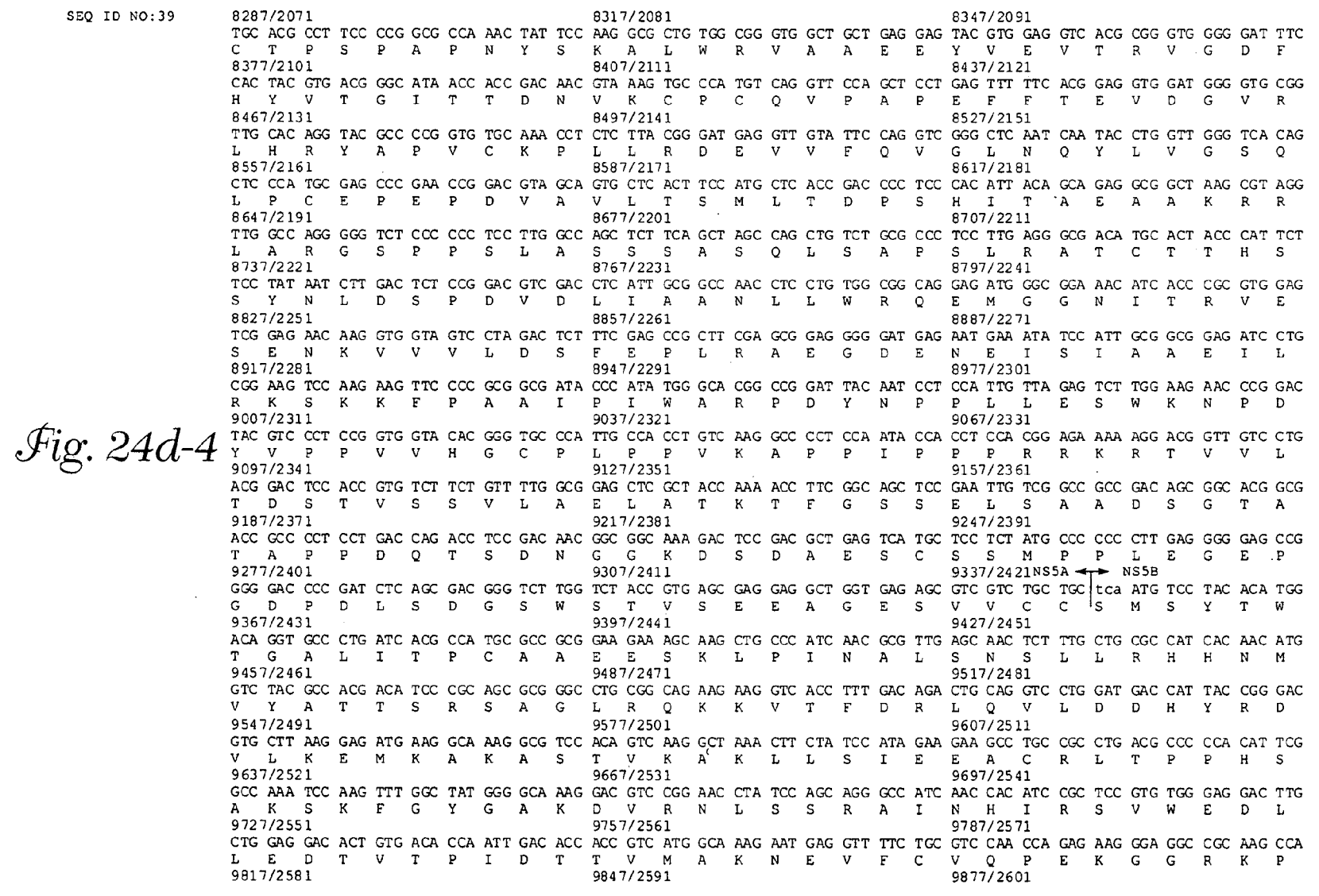
Figure 24D-5:
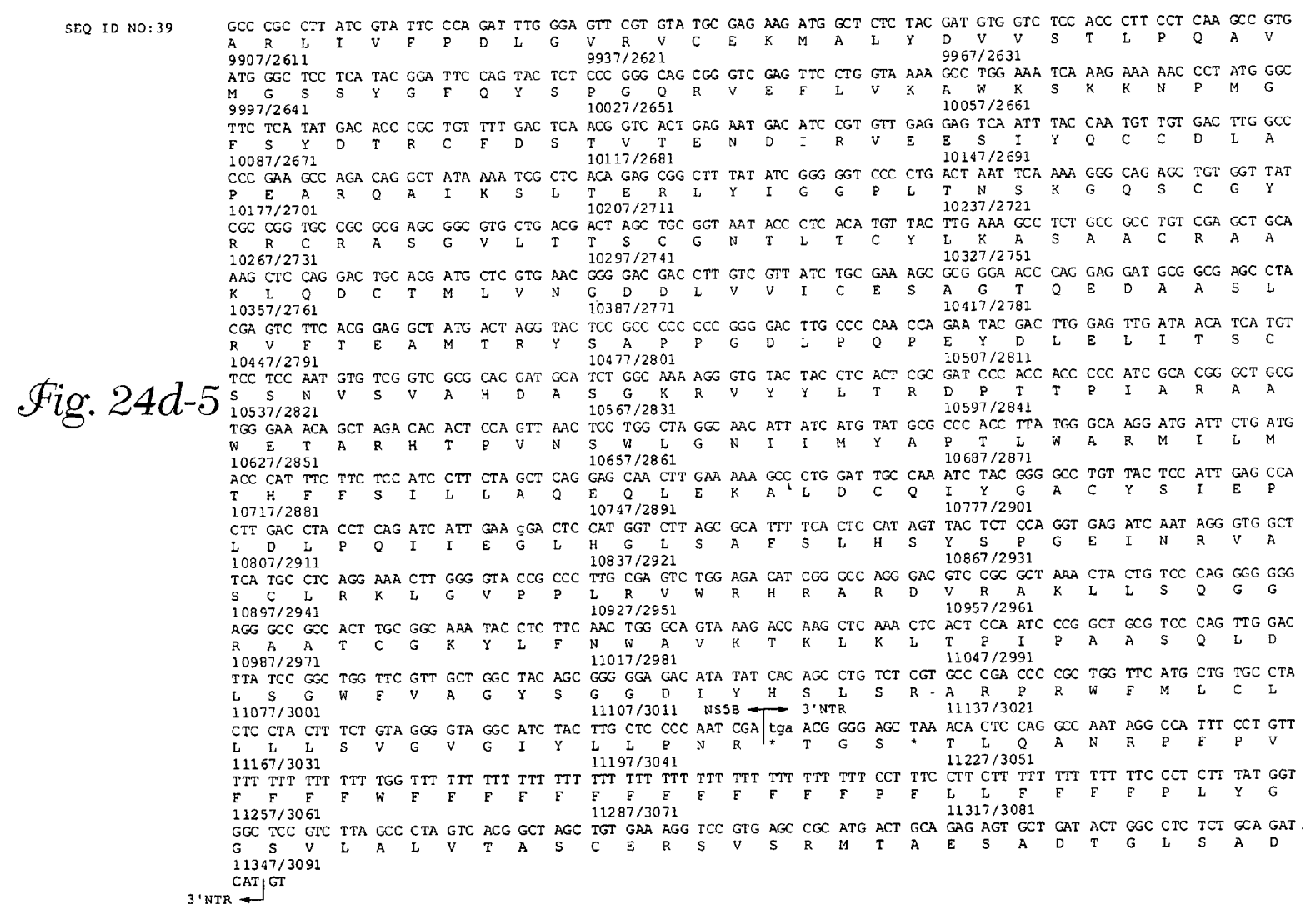
Figure 24E:
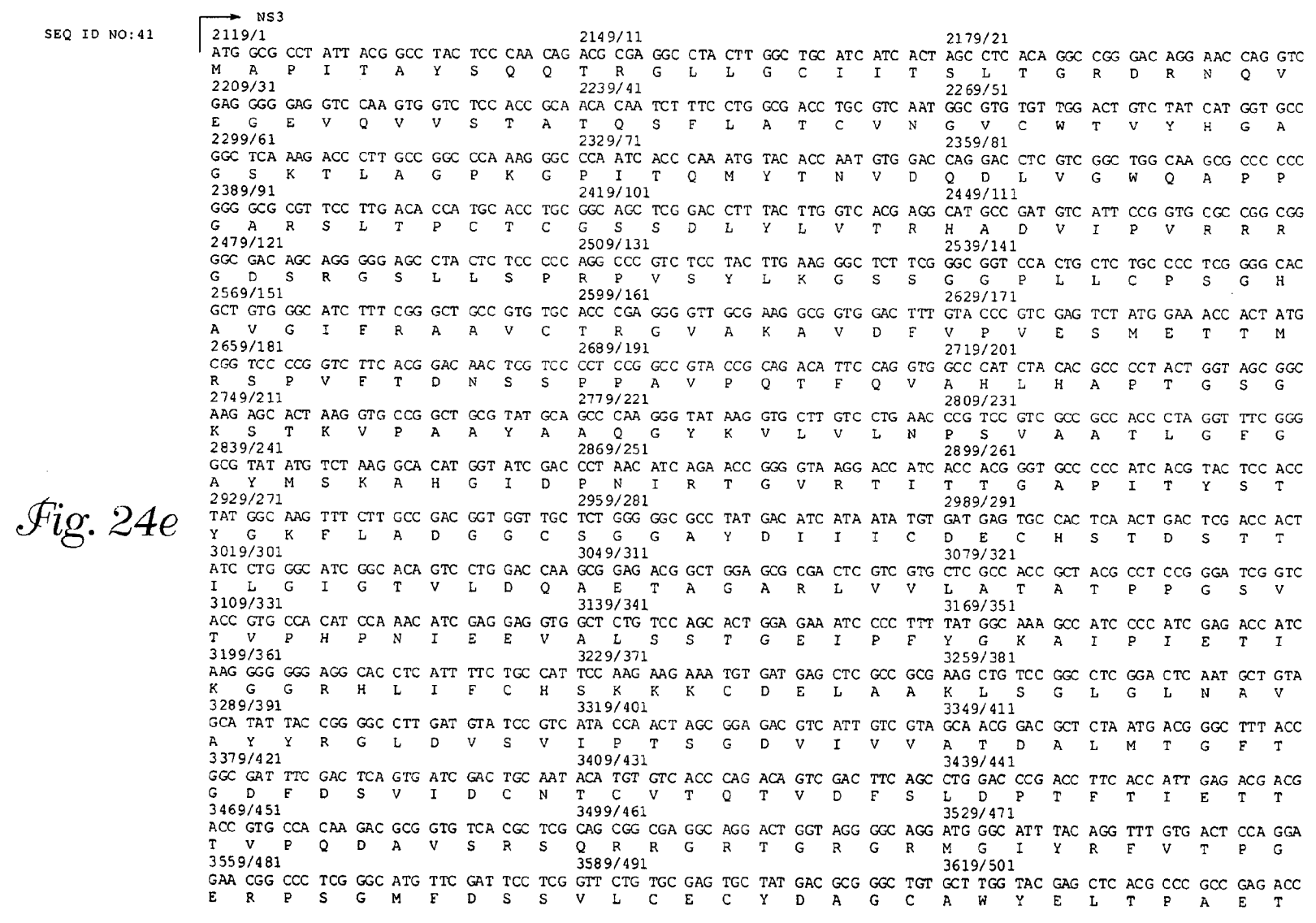
Figure 24E-1:
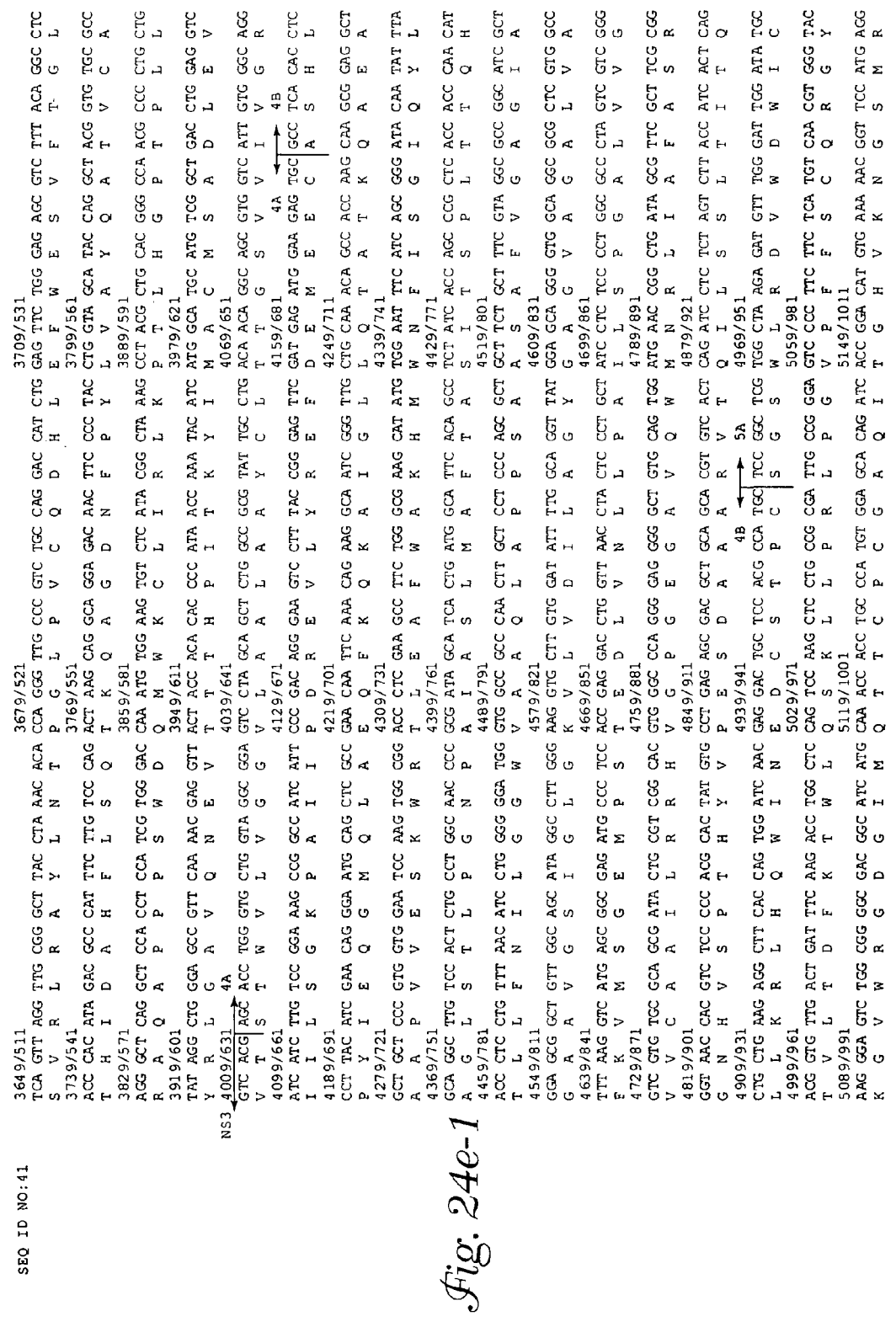
Figure 24E-2:
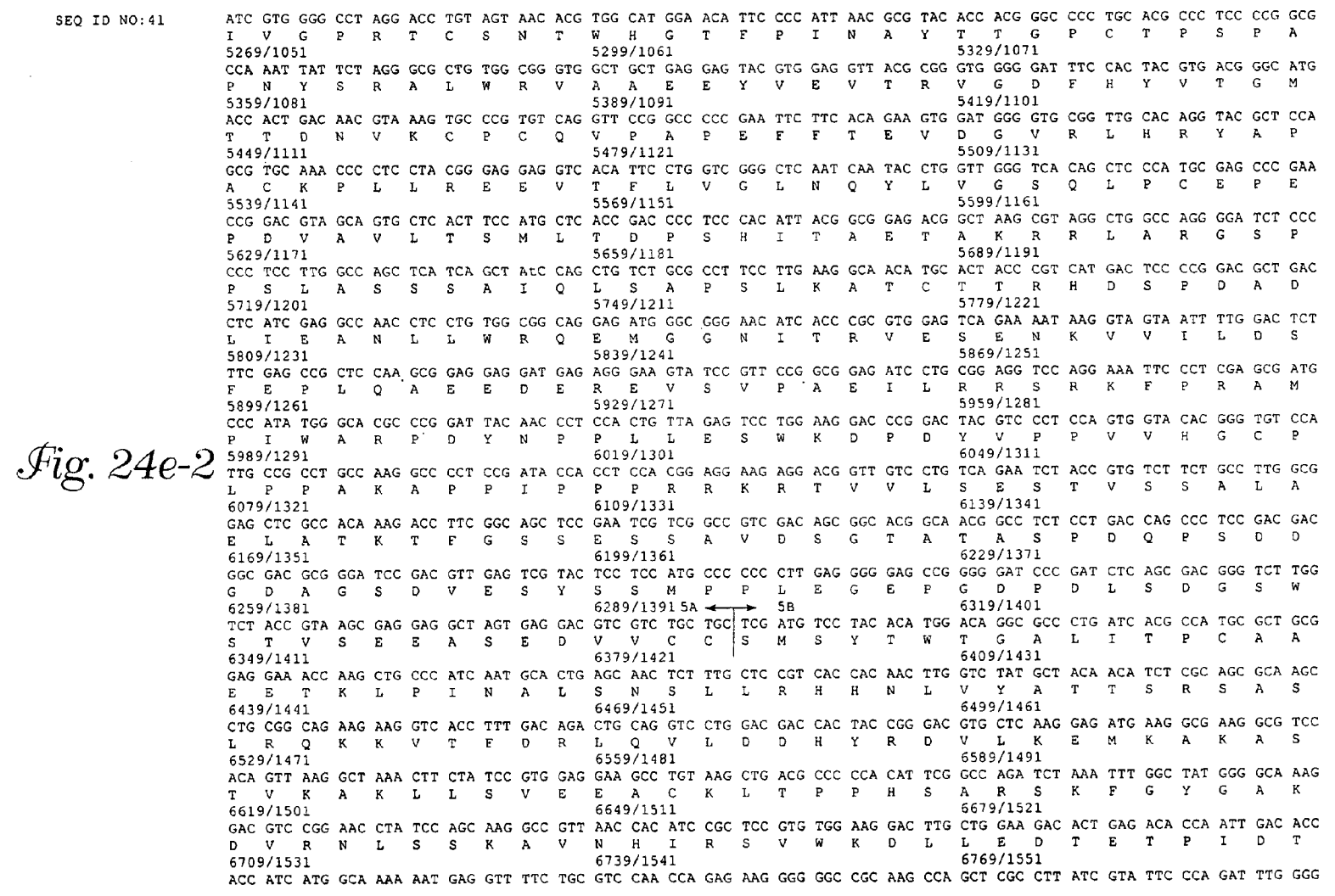
Figure 24E-3:
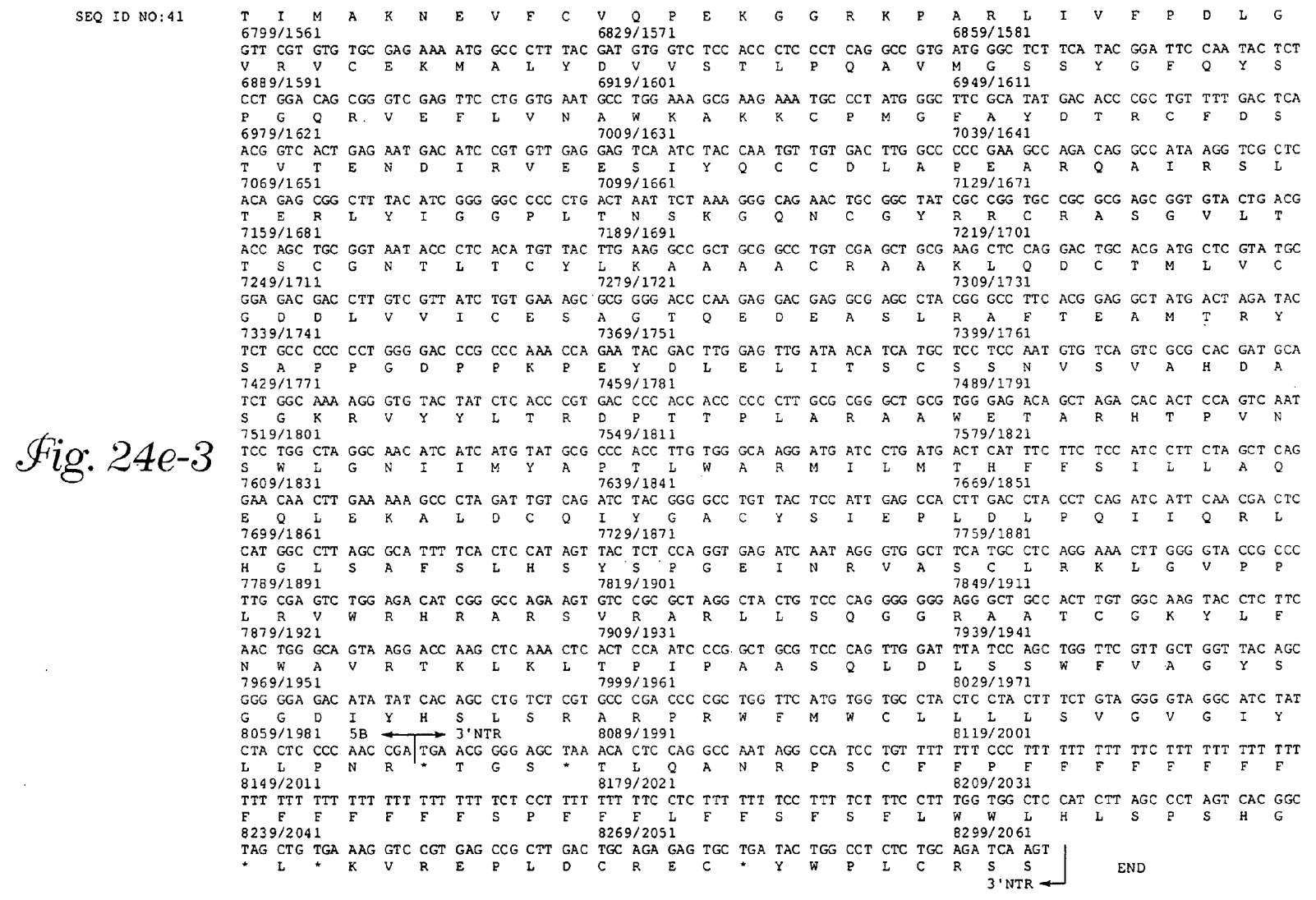

FIG. 24. Nucleotide sequences of constructs described in FIG. 17. The nucleotide sequence of the 5' NTR is disclosed at SEQ ID NO:35, the nucleotide sequence of the ΔCtat2ANeo is disclosed at SEQ ID NO:36, the nucleotide sequence of the tat2ANeo is disclosed at SEQ ID NO:37, the nucleotide sequence of the EMCV IRES located between the two cistrons is disclosed at SEQ ID NO:38. The nucleotide sequence encoding hepatitis C virus polyprotein derived from HCV-N is disclosed at SEQ ID NO:39, and the amino acid sequence (SEQ ID NO:40) of the polyprotein encoded by the nucleotides 2077-11121 is also shown. The nucleotide sequence encoding hepatitis C virus polyprotein derived from Con1 is disclosed at SEQ ID NO:41, and the amino acid sequence (SEQ ID NO:42) of the polyprotein encoded by the nucleotides 2119-8073 is also shown. The nucleotide sequence of the 3'NTR that is present in those replicons having an hepatitis C virus polyprotein derived from HCV-N is disclosed at nucleotides 11122-11349 of SEQ ID NO:39. The nucleotide sequence of the 3'NTR that is present in those replicons having an hepatitis C virus polyprotein derived from Con1 is disclosed at nucleotides 8074-8307 of SEQ ID NO:41.

DETAILED DESCRIPTION OF THE INVENTION

Hepatitis C Virus

Figure 1:
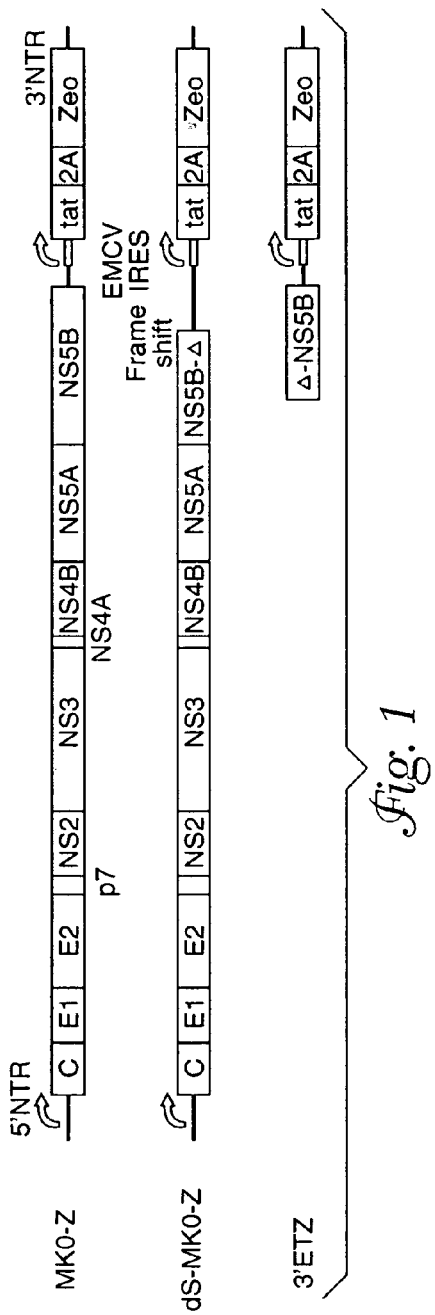
FIG. 1. Genomic organization of MK0-Z, ds-MK0-Z, and 3'ETZ. The rightward facing arrows, location and direction of transcription initiation; 5'NTR, 5' non-translated RNA; C, core protein; E1, envelope protein 1; E2, envelope protein 2; E2-p7, a polypeptide of about 7 kDa; NS2, non-structural protein 2; NS3, non-structural protein 3; NS4A, non-structural protein 4A; NS4B, non-structural protein 4B; NS5A, non-structural protein 5A; NS5B, non-structural protein 5B; EMCV IRES, encephalomyocarditis virus internal ribosome entry site; tat, portion of the human immunodeficiency virus I (HIV 1) tat protein; 2A, 2A proteinase of foot-and-mouth disease virus (FMDV); Zeo, polypeptide encoding resistance to phleomycin; 3'NTR, 3' non-translated RNA.

The present invention provides HCV polynucleotides, preferably RNA, that include a heterologous polynucleotide. In some aspects of the invention, the HCV includes a coding sequence encoding an hepatitis C virus polyprotein, and in other aspects the HCV includes a coding region encoding a portion of an HCV polyprotein. Preferably, the HCV are replication competent. Preferably the HCV are isolated, more preferably, purified. Unless otherwise noted, HCV polynucleotide, and other terms that refer to all or a part of an HCV polynucleotide (including, for instance, "3' non-translated RNA") include an RNA sequence of the positive-sense genome RNA, the complement thereof (i.e., the negative-sense RNA), and the DNA sequences corresponding to the positive-sense and the negative-sense RNA sequences.

It is expected that HCV polynucleotides from different sources, including molecularly cloned laboratory strains, for instance cDNA clones of HCV, and clinical isolates can be used in the methods described below to yield replication competent HCV of the present invention. Examples of molecularly cloned laboratory strains include the HCV that is encoded by pCV-H77C (Yanagi et al., *Proc. Natl. Acad. Sci., USA,* 94, 8738-8743 (1997)), and pHCV-N as modified by Beard et al. (*Hepatol.,* 30, 316-324 (1999)). Clinical isolates can be from a source of infectious HCV, including tissue samples, for instance from blood, plasma, serum, liver biopsy, or leukocytes, from an infected animal, including a human or a primate.

It is expected that the HCV polynucleotides of the present invention are not limited to a specific genotype. For instance, an HCV of the present invention can be genotype 1a, 1b, 1c, 2a, 2b, 2c, 3a, 3b, 4, 5a, or 6a (as defined by Simmons, *Hepatology,* 21, 570-583 (1995)). It is also expected that HCV used in the methods described below can be prepared by recombinant, enzymatic, or chemical techniques. In some aspects, an HCV that is modified as described herein to include a heterologous polynucleotide is able to replicate in vivo, preferably in a chimpanzee, prior to inserting the heterologous polypeptide. Methods for determining whether an HCV is able to replicate in a chimpanzee are described herein.

In some aspects of the present invention, the nucleotide sequence of an HCV polynucleotide used in the methods of the present invention is similar to the nucleotide sequence of an HCV, preferable an HCV of genotype 1a, 1b, 2a, or 2b. An example of an HCV of genotype 1a is present at Genbank accession AF011751. Examples of an HCV of genotype I b are present at Genbank accession AF139594, Genbank accession AJ238799, or the sequences present at FIG. 24. An example of an HCV of genotype 2a is present at Genbank accession AF238481. An example of an HCV of genotype 2b is present at Genbank accession AB030907. The similarity is referred to as structural similarity and may be determined by aligning the residues of the two polynucleotides (i.e., the nucleotide sequence of a candidate nucleotide sequence and the nucleotide sequence of HCV, or a portion thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate nucleotide sequence is the nucleotide sequence being compared to the nucleotide sequence of the HCV, or a portion thereof. Two nucleotide sequences can be compared using standard software algorithms. Preferably, two nucleotide sequences are compared using the Blastn program of the BLAST 2 search algorithm, as described by Tatusova, et al. (*FEMS Microbiol Lett* 1999, 174:247-250), and available at ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with the coding region of an HCV, or a portion thereof, of at least about 66%, at least about 77%, at least about 91%, at least about 94%, at least about 96%, or at least about 99% identity.

Specific mutations increasing the replicative capacity of HCV polynucleotides have been characterized for HCV 1b subgenomic RNA replicons (see, for instance, Blight et al., *Science,* 290, 1972-1975 (2000); Lohmann et al., "Adaptation of selectable HCV replicon to a human hepatoma cell line," Abstract P038, 7th International Meeting on Hepatitis C virus and Related viruses (Molecular Virology and Pathogenesis), The Marriott resort Hotel, Gold coast, Queensland, Australia, December 3-7 (2000); and Guo et al., "Identification of a novel RNA species in cell lines expressing HCV subgenomic replicons," Abstract P045, 7th International Meeting on Hepatitis C virus and Related viruses (Molecular Virology and Pathogenesis), The Marriott resort Hotel, Gold coast, Queensland, Australia, December 3-7 (2000)). Such mutations are referred to herein as "cell culture adaptive mutations." It is expected that the introduction of these individual mutations may enhance the replication capacity of an HCV of some aspects of the present invention. The approximate locations and types of some mutations are shown in Table 1. The precise location of these cell culture adaptive mutations can vary between members of different genotypes, and between members of the same genotype. For instance, with mutations 2442 and 2884 listed in Table 1, in HCV genotype 1a the locations of these mutations are 2443 and 2885, respectively. The location of a mutation introduced into an HCV of the present invention to enhance replication is expected to be within 4 amino acids, preferably within 3 amino acids, more preferably within 2 amino acids, most preferably within 1 amino acid of the positions listed in Table 1. Another example of an adaptive mutation of HCV-N is the insertion of amino acids SSYN (SEQ ID NO: 75) present at position 2220-2223.

TABLE 1

Adaptive mutations in an HCV of genotype 1b.

| Amino acid position[1] | Mutation[2] |
|---|---|
| 1202 | E to G |
| 1281 | T to I |
| 1283 | R to G |
| 1383 | E to A |
| 1577 | K to R |
| 1609 | K to E |
| 1757 | L to I |
| 1936 | P to S |
| 2163 | E to G |
| 2177 | D to H, or D to N |
| 2189 | R to G |
| 2196 | P to S |
| 2197 | S to P, or S to C |
| 2199 | A to S, or A to T |
| 2201 | deletion of S |
| 2204[3] | S to I |
| 2207-2254 | Deletion of 48 amino acids |
| 2330 | K to E |
| 2442 | I to V |
| 2884[4] | R to G |

[1] Amino acid position refers to amino acid number where the first amino acid is the first amino acid of the polyprotein expressed by the HCV at Genbank Accession number AJ238799.
[2] Amino acids are listed in the single letter code. The first amino acid is the wild-type amino acid, and the second amino acid is the residue present in the mutant.
[3] Amino acid 2205 in the polyprotein expressed by the HCV at Genbank Accession number AF139594.
[4] Amino acid 2889 in the polyprotein expressed by the HCV at Genbank Accession number AF139594.

Cell culture adaptive mutations can be introduced into an HCV polynucleotide of the present invention by mutagenesis of the nucleotide sequence of the HCV in the form of plasmid DNA. Methods for targeted mutagenesis of nucleotide sequences are known to the art, and include, for instance, PCR mutagenesis.

In some aspects of the invention, the heterologous polynucleotide is present in the HCV 3' non-translated RNA, for instance, in the variable region of the 3' non-translated RNA. In some aspects of the invention, the heterologous polynucleotide is inserted into the variable region such that the variable region is not removed. Alternatively, deletions of the variable region can be made, in whole or in part, and replaced with the heterologous polynucleotide. Preferably, in some aspects of the invention, when the HCV has the genotype 1a, more preferably, the strain H77C, the heterologous polynucleotide is inserted in the variable region between nucleotides 5 and 6 of the sequence 5' CUCUUAAGC 3', where the sequence shown corresponds to the positive-strand.

A heterologous polynucleotide can include a non-coding region and/or a coding region, preferably a coding region. The coding region can encode a polypeptide including, for instance, a marker, including a detectable marker and/or a selectable marker. Examples of detectable markers include secretory alkaline phosphatase, green fluorescent protein, and molecules that can be detected by antibody. Examples of selectable markers include molecules that confer resistance to antibiotics, including the antibiotics kanamycin, ampicillin, chloramphenicol, tetracycline, neomycin, and formulations of phleomycin D1 including, for example, the formulation available under the trade-name ZEOCIN (Invitrogen, Carlsbad, Calif.). Other examples of polypeptides that can be encoded by the coding region include a transactivator, and/or a fusion polypeptide. Preferably, when the polypeptide is a fusion polypeptide, the coding region includes nucleotides encoding a marker, more preferably, nucleotides encoding a fusion between a transactivator and a marker. Optionally, the coding region can encode an immunogenic polypeptide. When the heterologous polynucleotide includes a coding region, the HCV is typically dicistronic, i.e., the coding region of the heterologous polynucleotide and the coding region encoding the HCV polyprotein or portion thereof are separate.

An "immunogenic polypeptide" refers to a polypeptide which elicits an immunological response in an animal. An immunological response to a polypeptide is the development in a subject of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed specifically to an epitope or epitopes of the polypeptide fragment.

A transactivator is a polypeptide that affects in trans the expression of a coding region, preferably a coding region integrated in the genomic DNA of a cell. Such coding regions are referred to herein as "transactivated coding regions." The cells containing transactivated coding regions are described in detail herein in the section "Methods of use." Transactivators useful in the present invention include those ihat can interact with a regulatory region, preferably an operator sequence, that is operably linked to a transactivated coding region. As used herein, the term "transactivator" includes polypeptides that interact with an operator sequence and either prevent transcription from initiating at, activate transcription initiation from, or stabilize a transcript from, a transactivated coding region operably linked to the operator sequence. Examples of useful transactivators include the HIV tat polypeptide (see, for example, the polypeptide SEQ ID NO:19, MEPVDPRLEPWKHPGSQPKTACTNCYCK-KCCFHCQVCFITKALGISYGRKK RRQRRRAHQN-SQTHQASLSKQPTSQPRGDPTGPKE which is encoded by nucleotides 5377 to 5591 and 7925 to 7970 of Genbank accession number AF033819), and MEPVDPRLEPWKH-PGSQPKTACTNCYCKKCCFHCQVCFITKALGISY GR KK RRQRRRPPQGSQTHQVSLSKQPTS QSRGDPTG-PKE, the polypeptide present at amino acids 4-89 of SEQ ID NO:21. The HIV tat polypeptide interacts with the HIV long terminal repeat. Other useful transactivators include human T cell leukemia virus tax polypeptide (which binds to the operator sequence tax response element, Fujisawa et al., *J. Virol.*, 65, 4525-4528 (1991)), and transactivating polypeptides encoded by spumaviruses in the region between env and the LTR, such as the bel-1 polypeptide in the case of human foamy virus (which binds to the U3 domain of these viruses, Rethwilm et al., *Proc. Natl. Acad. Sci. USA*, 88, 941-945 (1991)). Alternatively, a post-transcriptional transactivator, such as HIV rev, can be used. HIV rev binds to a 234 nucleotide RNA sequence in the env gene (the rev-response element, or RRE) of HIV (Hadzopolou-Cladaras et al., *J. Virol.*, 63, 1265-1274 (1989)).

Other transactivators that can be used are those having similarity with the amino acid sequence of SEQ ID NO:19 or amino acids 4-89 of SEQ ID NO:21. The similarity is referred to as structural similarity and is generally determined by aligning the residues of the two amino acid sequences (i.e., a candidate amino acid sequence and the amino acid sequence of SEQ ID NO:19 or amino acids 4-89 of SEQ ID NO:21) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO:19 or amino acids 4-89 of SEQ ID NO:21. A candidate amino acid sequence can be isolated from a virus, or can be produced using recombinant techniques, or chemically or enzymatically synthesized. Preferably, two amino acid sequences are compared using the Blastp program of the BLAST 2 search algorithm, as described by Tatusova, et al. (*FEMS Microbiol Lett* 1999, 174:247-250). Preferably, the default values for all BLAST 2 search parameters are used, including matrix=BLOSUM62; open gap penalty=11, extension gap penalty=1, gap x_dropoff=50, expect=10, word-size=3, and filter on. In the comparison of two amino acid sequences using the BLAST search algorithm, structural similarity is referred to as "identities." Preferably, a transactivator includes an amino acid sequence having a structural similarity with SEQ ID NO:19 or amino acids 4-89 of SEQ ID NO:21 of at least about 70%, at least about 80%, at least about 90%, at least about 94%, at least about 96%, or at least about 99% identity. Typically, an amino acid sequence having a structural similarity with SEQ ID NO:19 or amino acids 4-89 of SEQ ID NO:21 has tat activity. Whether such a polypeptide has activity can be evaluated by determining if the amino acid sequence can interact with an HIV LTR, preferably, alter transcription from a coding sequence operably linked to an HIV LTR.

Active analogs or active fragments of a transactivator can be used in the invention. An active analog or active fragment of a transactivator is one that is able to interact with an operator sequence and either prevent transcription from initiating at, activate transcription initiation from, or stabilize a transcript from, a transactivated coding region operably linked to the operator sequence.

Active analogs of a transactivator include polypeptides having conservative amino acid substitutions that do not eliminate the ability to interact with an operator and alter transcription. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, aspartate, and glutamate. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Active fragments of a transactivator include a portion of the transactivator containing deletions or additions of about 1, about 2, about 3, about 4, or at least about 5 contiguous or noncontiguous amino acids such that the resulting transactivator will alter expression of an operably linked transactivated coding region. A preferred example of an active fragment of the HIV tat polypeptide includes amino acids amino acids 1-48 of SEQ ID NO:19, or amino acids 4-51 of SEQ ID NO:21.

In those aspects of the invention where the heterologous polynucleotide includes a coding region that encodes a fusion polypeptide, the fusion polypeptide can further include amino acids corresponding to a cis-active proteinase. When the fusion polypeptide is a fusion between a transactivator and a marker, preferably the fusion polypeptide also includes amino acids corresponding to a cis-active proteinase. Preferably the amino acids corresponding to a cis-active proteinase are present between the amino acids corresponding to the transactivator and the marker. A cis-active proteinase in this position allows the amino acids corresponding to the transactivator and the marker to be physically separate from each other in the cell within which the HCV is present. Examples of cis-active proteinases that are useful in the present invention include the cis-active 2A proteinase of foot-and-mouth disease (FMDV) virus (see, for example, U.S. Pat. No. 5,846,767 (Halpin et al.) and U.S. Pat. No. 5,912,167 (Palmenberg et al.)), ubiquitin (see, for example, Tauz et al., *Virology*, 197, 74-85 (1993)), and the NS3 recognition site GADTEDV-VCCSMSY (SEQ ID NO:31) (see, for example, Lai et al., *J. Virol.*, 74, 6339-6347 (2000)).

Active analogs and active fragments of cis-active proteinases can also be used. Active analogs of a cis-acting proteinase include polypeptides having conservative amino acid substitutions that do not eliminate the ability of the proteinase to catalyze cleavage. Active fragments of a cis-active proteinase include a portion of the cis-active proteinase containing deletions or additions of one or more contiguous or noncontiguous amino acids such that the resulting cis-active proteinase will catalyze the cleavage of the proteinase.

In some aspects of the invention, the heterologous polynucleotide may further include a regulatory region that is operably linked to the coding region of the heterologous polynucleotide. Preferably, a regulatory region located 5' of the operably linked coding region provides for the translation of the coding region.

A preferred regulatory region located 5' of an operably linked coding region is an internal ribosome entry site (IRES). An IRES allows a ribosome access to mRNA without a requirement for cap recognition and subsequent scanning to the initiator AUG (Pelletier, et al., *Nature*, 334, 320-325 (1988)). An IRES is located upstream of the translation initiation codon, e.g., ATG or AUG, of the coding sequence to which the IRES is operably linked. The distance between the IRES and the initiation codon is dependent on the type or IRES used, and is known to the art. For instance, poliovirus IRES initiates a ribosome translocation/scanning process to a downstream AUG codon. For other IRES elements, the initiator codon is generally located at the 3' end of the IRES sequence. Examples of an IRES that can be used in the invention include a viral IRES, preferably a picornaviral IRES or a flaviviral IRES. Examples of poliovirus IRES elements include, for instance, poliovirus IRES, encephalomyocarditis virus IRES, or hepatitis A virus IRES. Examples of preferred flaviviral IRES elements include hepatitis C virus IRES, GB virus B IRES, or a pestivirus IRES, including but not limited to bovine viral diarrhea virus IRES or classical swine fever virus IRES. Other IRES elements with similar secondary and tertiary structure and translation initiation activity can either be generated by mutation of these viral sequences, by cloning of analogous sequences from other viruses (including picornaviruses), or prepared by enzymatic synthesis techniques.

The size of the heterologous polynucleotide is not critical to the invention. It is expected there is no lower limit on the size of the heterologous polynucleotide. It is expected that there is an upper limit on the size of the heterologous polynucleotide. This upper limit can be easily determined by a person skilled in the art, as heterologous polynucleotides that are greater than this upper limit adversely affect replication of an HCV polynucleotide. In increasing order of preference, the heterologous polynucleotide is at least about 10 nucleotides, at least about 20 nucleotides, at least about 30 nucleotides, most preferably at least about 40 nucleotides.

In some aspects of the invention, the heterologous polynucleotide is present in an HCV downstream of the 5' NTR. For instance, the first nucleotide of the heterologous polynucleotide may be immediately downstream and adjacent to the last nucleotide of the 5' NTR. Alternatively, the first nucleotide of the heterologous polynucleotide may be about 33 to about 51 nucleotides, more preferably, about 36 to about 48 nucleotides, downstream of the last nucleotide of the 5' NTR. Typically, when the first nucleotide of the heterologous polynucleotide is not immediately downstream of the last nucleotide of the 5' NTR, the nucleotides in between the 5' NTR and the heterologous polynucleotide encode the amino terminal amino acids of the HCV core polypeptide.

In those aspects of the invention where the heterologous polynucleotide present in an HCV is inserted downstream of the 5' NTR and upstream of the coding region encoding the HCV polyprotein or a portion thereof, the heterologous polynucleotide typically includes a regulatory region operably linked to the downstream coding region. Preferably, the regulatory region provides for the translation of the downstream coding region. The size of the regulatory region may be from about 400 nucleotides to about 800 nucleotide, more preferably, about 600 nucleotides to about 700 nucleotides. Preferably, the regulatory region is an IRES. Examples of IRES elements are described herein.

In those aspects of the invention where the HCV polynucleotide includes a portion of the hepatitis C virus polyprotein, the 5' end of the coding region encoding the HCV polyprotein may further include about 33 to about 51 nucleotides, more preferably, about 36 to about 48 nucleotides, that encode the first about 11 to about 17, more preferably, about 12 to about 16, amino acids of the core polypeptide. The result is a fusion polypeptide between the amino terminal amino acids of the core polypeptide and the first polypeptide encoded by the heterologous polnucleotide.

The replication competent HCV polynucleotide of the invention can be present in a vector. When a replication competent HCV is present in a vector the HCV is DNA, including the 5' non-translated RNA and the 3' non-translated RNA. Methods for cloning an HCV and inserting it into a vector are known to the art (see, e.g., Yanagi et al., *Proc. Natl. Acad. Sci., USA,* 94, 8738-8743 (1997); and Rice et al., (U.S. Pat. No. 6,127,116)). Such constructs are often referred to as molecularly cloned laboratory strains, and an HCV that is inserted into a vector is typically referred to as a cDNA clone of the HCV. If the RNA encoded by the HCV is able to replicate in vivo, the HCV present in the vector is referred to as an infectious cDNA clone. A vector is a replicating polynucleotide, such as a plasmid, phage, cosmid, or artificial chromosome to which another polynucleotide may be attached so as to bring about the replication of the attached polynucleotide. A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Preferably the vector is a plasmid. Preferably the vector is able to replicate in a prokaryotic host cell, for instance *Escherichia coli*. Preferably, the vector can integrate in the genomic DNA of a eukaryotic cell.

An expression vector optionally includes regulatory sequences operably linked to the HCV such that the HCV is transcribed to produce RNA molecules. These RNA molecules can be used, for instance, for introducing an HCV to a cell that is in an animal or growing in culture. The terms "introduce" and "introducing" refer to providing an HCV to a cell under conditions that the HCV is taken up by the cell in such a way that the HCV can then replicate. The HCV can be a virus particle, or a nucleic acid molecule, preferably RNA. The invention is not limited by the use of any particular promoter, and a wide variety are known. Promoters act as regulatory signals that bind RNA polymerase in a cell to initiate transcription of a downstream (3' direction) HCV. The promoter used in the invention can be a constitutive or an inducible promoter. A preferred promoter for the production of HCV is T7 promoter.

Preferred examples of HCV polynucleotide of the present invention are shown in FIGS. 9, 10, and 17. It should be noted that while these sequences are DNA sequences, the present invention contemplates the corresponding RNA sequence, and RNA and DNA complements thereof, as well.

Methods of Use

The present invention is directed to methods for identifying a replication competent HCV polynucleotide, including detecting and/or selecting for cells containing a replication competent HCV polynucleotide. Typically, the cells used in this aspect of the invention are cells growing in culture. Useful cultured cells will support the replication of the HCV of the present invention, and include primary human or chimpanzee hepatocytes, peripheral mononuclear cells, cultured human lymphoid cell lines (for instance lines expressing B-cell and T-cell markers such as Bjab and Molt-4 cells), and continuous cell lines derived from such cells, including Huh-7, HepG2, and PH5CH-8. The cells may be primate or human cells, preferably human cells. In general, useful cells include those that support replication of HCV RNA, including, for instance, replication of the HCV encoded by pCV-H77C, or replication of the HCV encoded by pHCV-N as modified by Beard et al. (*Hepatol.,* 30, 316-324 (1999)). A preferred cultured cell is HuH-7, which is known to workers in the field of HCV (see, for instance, Lohmann et al., *Science,* 285, 570-574 (1999)).

In some aspects of the invention, the cultured cell includes a polynucleotide that includes a coding region, the expression of which is controlled by a transactivator. Such a coding region is referred to herein as a transactivated coding region. A transactivated coding region encodes a marker, preferably a detectable marker, for example, secretory alkaline phosphatase. In some aspects of the invention, the detectable marker is secretory alkaline phospahtase (SEAP). An example of an SEAP is encoded by nucleotides 748-2239 of SEQ ID NO:18. Typically, a cultured cell that includes a polynucleotide having a transactivated coding region is used in conjunction with an HCV polynucleotide that includes a coding region encoding a transactivator.

The polynucleotide that includes the transactivated coding region can be present integrated into the genomic DNA of the cell, or present as part of a vector that is not integrated. Preferably, the polynucleotide is integrated into the genomic DNA of the cell. Methods of modifying a cell to contain an integrated DNA are known to the art. An example of making such a cell is described in Example 3 and Example 9.

Operably linked to the transactivated coding region is an operator sequence. The interaction of a transactivator can alter transcription of the operably linked transactivated coding region. In those aspects of the invention where a transactivator increases transcription, preferably there is low transcription of the transactivated coding region in the absence of a transactivator, more preferably, essentially no transcription. An operator sequence can be present upstream (5') or downstream (3') of a transactivated coding region. An operator sequence can be a promoter, or can be a nucleotide sequence that is present in addition to a promoter.

In some aspects of the invention, the operator sequence that is operably linked to a transactivated coding sequence is an HIV long terminal repeat (LTR). An example of an HIV LTR is depicted in nucleotides 1-719 of SEQ ID NO:18. Also included in the present invention are operator sequences having similarity to nucleotides 1-719 of SEQ ID NO: 18. The similarity between two nucleotides sequences may be determined as described above, however, the candidate nucleotide sequence is compared to the nucleotides 1-719 of SEQ ID NO:18. Preferably, an operator sequence includes a nucleotide sequence having a structural similarity with the nucleotides 1-719 of SEQ ID NO:18 of at least about 80%, more preferably at least about 90%, most preferably at least about 95% identity. Typically, an operator sequence having structural similarity with the nucleotides I-719 of SEQ ID NO:18 has transcriptional activity. Whether such an operator sequence has transcriptional activity can be determined by evaluating the ability of the operator sequence to alter transcription of an operably linked coding sequence in response to the presence of a polypeptide having tat activity, preferably, a polypeptide including the amino acids of SEQ ID NO:19 or amino acids 4-89 of SEQ ID NO:21.

In some aspects of the present invention, the replication of cultured cells may be inhibited by a selecting agent. Examples of selecting agents include antibiotics, including kanamycin, ampicillin, chloramphenicol, tetracycline, neomycin, and formulations of phleomycin D1. A selecting agent can act to prevent replication of a cell while the agent is present and the cell does not express a molecule that provides resistance to the selecting agent. Alternatively and preferably, a selecting agent can act to kill a cell that does not express a molecule that provides resistance to the selecting agent. Typically, the molecule providing resistance to a selecting agent is expressed in the cell by an HCV polynucleotide of the present invention. Alternatively, the molecule providing resistance to a selecting agent is expressed by the cell but the expression of the molecule is controlled by an HCV polynucleotide of the present invention that is present in the cell. The concentration of the selecting agent is typically chosen such that a cell that does not contain a molecule providing resistance to a selecting agent does not replicate. The appropriate concentration of a selecting agent varies depending on the particular selecting agent, and can be easily determined by one having ordinary skill in the art using known techniques.

When a polynucleotide that includes a replication competent HCV polynucleotide is introduced into a cell that is growing in culture, the polynucleotide can be introduced using techniques known to the art. Such techniques include, for instance, liposome and non-liposome mediated transfection. The Examples describe the use of one type of liposome mediated transfection. Non-liposome mediated transfection methods include, for instance, electroporation.

In some aspects of the invention, when a replication competent HCV polynucleotide is identified using cultured cells, its ability to replicate may be verified by introducing the HCV to a cell present in an animal, preferably a chimpanzee. When the cell is present in the body of an animal, the polynucleotide that includes a replication competent HCV can be introduced by, for instance, subcutaneous, intramuscular, intraperitoneal, intravenous, or percutaneous intrahepatic administration, preferably by percutaneous intrahepatic administration. Methods for determining whether an HCV polynucleotide is able to replicate in a chimpanzee are known to the art (see, for example, Yanagi et al., *Proc. Natl Acad. Sci. USA,* 94, 8738-8743 (1997), and Example 2). In general, the demonstration of infectivity is based on the appearance of the virus in the circulation (blood) of the chimpanzee over the days and weeks following the intrahepatic injection of the HCV. The presence of the virus can be confirmed by reverse transcription-polymerase chain reaction (RT-PCR) detection of the viral RNA, by inoculation of a second chimpanzee with transfer of the hepatitis C virus infection as indicated by the appearance of liver disease and seroconversion to hepatitis C virus in ELISA tests, or possibly by the immunologic detection of components of the hepatitis C virus (e.g., the core protein) in the circulation of the inoculated animal. It should be noted that seroconversion by itself would not be a useful indicator of infection in an animal injected with a viral RNA produced using a molecularly cloned laboratory strain, as this RNA may have immunizing properties and be capable of inducing HCV-specific antibodies to proteins translated from an input RNA that is non-replicating. Similarly, the absence of seroconversion does not exclude the possibility of viral replication and infection of a chimpanzee with HCV.

Whether an HCV polynucleotide of the present invention is replication competent can be determined using methods known to the art, including methods that use nucleic acid amplification to detect the result of increased levels of HCV replication. In some aspects of the invention, another method for detecting a replication competent HCV polynucleotide includes measuring the production of viral particles by a cell. The measurement of viral particles can be accomplished by passage of supernatant from media containing a cell culture that may contain a replication competent HCV, and using the supernatant to infect a second cell. Detection of HCV in the second cell indicates the initial cell contains a replication competent HCV. The production of infectious virus particles by a cell can also be measured using antibody that specifically binds to an HCV viral particle. As used herein, an antibody that can "specifically bind" an HCV viral particle is an antibody that interacts only with the epitope of the antigen (e.g., the viral particle or a polypeptide that makes up the particle) that induced the synthesis of the antibody, or interacts with a structurally related epitope. "Epitope" refers to the site on an antigen to which specific B cells and/or T cells respond so that antibody is produced. An epitope could includes about 3 amino acids in a spatial conformation which is unique to the epitope. Generally an epitope includes at least about 5 such amino acids, and more usually, consists of at least about 8-10 such amino acids. Antibodies to HCV viral particles can be produced as described herein.

In another aspect, identifying a replication competent HCV polynucleotide includes incubating a cultured cell that includes an HCV of the present invention. In those aspects of the invention where the heterologous polynucleotide encodes a detectable marker, cells containing a replication competent HCV can be identified by observing individual cells that contain the detectable marker. Alternatively, if the detectable marker is secreted by the cell, the presence of the marker in the medium in which the cell is incubated can be detected. Methods for observing the presence or absence of a detectable marker in a cell or in liquid media are known to the art.

Another aspect of the invention provides for the positive selection of cells that include a replication competent HCV polynucleotide. The marker expressed by the HCV is a selectable marker, and the cell, which includes the HCV, is incubated in the presence of a selecting agent. Those cells that can replicate in the presence of the selecting agent contain an HCV that is replication competent. Typically, the cells that can replicate are detected by allowing resistant cells to grow in the presence of the selecting agent.

In some aspects, the method may further include isolating virus particles from the cells that contain a replication competent HCV polynucleotide and exposing a second cell to the isolated virus particle under conditions such that the virus particle is introduced to the cell. After providing time for expression of the selectable marker, the second cell is then incubated with the selecting agent. The presence of a cell that replicates indicates the replication competent HCV produces infectious virus particles. Preferably, virus particles are isolated by removing a volume of the media in which the first cells are incubated.

In another aspect, the invention provides a method for detecting a replication competent HCV polynucleotide. The method includes incubating a cell that contains an HCV of the present invention. The cell includes a transactivated coding region and an operator sequence operably linked to the transactivated coding region. The transactivated coding region encodes a detectable marker.

The heterologous polynucleotide present in the HCV polynucleotide encodes a transactivator that interacts with the operator sequence present in the cell. The interaction of the transactivator to the operator sequence can decrease transcription or increase transcription of the operably linked transactivated coding region. Preferably, binding of the transactivator to the operator sequence increases transcription. Preferably, the HCV also encodes a marker, more preferably, a fusion polypeptide that includes a transactivator and a marker. Most preferably, the fusion polypeptide further includes a cis-acting proteinase located between the nucleotides encoding the transactivator and the nucleotides encoding the marker.

The method further includes detecting the presence or absence of the detectable marker encoded by the transactivated coding region present in the cell. The presence of the detectable marker indicates the cell includes a replication competent HCV. Preferably, the detectable marker is one that is secreted by the cell, for instance secretory alkaline phosphatase.

The methods described above for identifying replication competent HCV polynucleotide can also be used for identifying a variant HCV polynucleotide, i.e., an HCV that is derived from a replication competent HCV of the present invention. Preferably, a variant HCV has a faster replication rate than the parent or input HCV. The method takes advantage of the inherently high mutation rate of RNA replication. It is expected that during continued culture of a replication competent HCV in cultured cells, the HCV of the present invention may mutate, and some mutations will result in HCV with greater replication rates. The method includes identifying a cell that has greater expression of a polypeptide encoded by a replication competent HCV. An HCV of the present invention that replicates at a faster rate will result in more of the polypeptide(s) that is encoded by the heterologous polynucleotide present in the HCV. For instance, when an HCV encodes a selectable marker, a cell containing a variant HCV having a greater replication rate will be resistant to higher levels of an appropriate selecting agent. When an HCV encodes a transactivator, a cell containing a variant HCV having a greater replication rate than the parent or input HCV will express higher amounts of the transactivated coding region that is present in the cell. The observed increases in resistance to phleomycin D1 (for instance, ZEOCIN) suggest the accumulation of mutations that allow increased rates of replication.

A cDNA molecule of a variant HCV polynucleotide can be cloned using methods known to the art (see, for instance, Yanagi et al., Proc. Nail. Acad. Sci., USA, 94, 8738-8743 (1997)). The nucleotide sequence of the cloned cDNA can be determined using methods known to the art, and compared with that of the input RNA. This allows identification of mutations that have occurred in association with passage of the HCV in cell culture. For example, using methods known to the art, including longrange RT-PCR, extended portions of a variant HCV genome can be obtained. Multiple clones could be obtained from each segment of the genome, and the dominant sequence present in the culture determined. Mutations that are identified by this approach can then be reintroduced into the background of the HCV cDNA encoding the parent or input HCV. This may be used to produce a replication competent HCV that does not contain a heterologous polynucleotide. Such an HCV would have superior replication properties in cell culture compared to the parent HCV and the variant HCV because it would not carry the burden of an additional coding region within its 3' non-translated RNA.

The present invention also provides methods for identifying a compound that inhibits replication of an HCV polynucleotide, preferably a replication competent HCV as described herein in the section "Hepatitis C Virus." The method includes contacting a cell containing a replication competent HCV polynucleotide with a compound and incubating the cell under conditions that permit replication of the replication competent HCV polynucleotide in the absence of the compound. After a period of time sufficient to allow replication of the HCV polynucleotide, the replication competent HCV polynucleotide is detected. A decrease in the presence of replication competent HCV polynucleotide in the cell contacted with the compound relative to the presence of replication competent HCV polynucleotide in a cell not contacted by the compound indicates the compound inhibits replication of a replication competent HCV. A compound that inhibits replication of an HCV includes compounds that completely prevent replication, as well as compounds that decrease replication. Preferably, a compound inhibits replication of a replication competent HCV by at least about 50%, more preferably at least about 75%, most preferably at least about 95%.

The compounds added to a cell can be a wide range of molecules and is not a limiting aspect of the invention. Compounds include, for instance, a polyketide, a non-ribosomal peptide, a polypeptide, a polynucleotide (for instance an antisense oligonucleotide or ribozyme), or other organic molecules. The sources for compounds to be screened include, for example, chemical compound libraries, fermentation media of *Streptomycetes*, other bacteria and fungi, and extracts of eukaryotic or prokaryotic cells. When the compound is added to the cell is also not a limiting aspect of the invention. For instance, the compound can be added to a cell that contains a replication competent HCV. Alternatively, the compound can be added to a cell before or at the same time that the replication competent HCV is introduced to the cell.

Typically, the ability of a compound to inhibit replication of a replication competent HCV polynucleotide is measured using methods described herein. For instance, methods that use nucleic acid amplification to detect the amount of HCV nucleic acid in a cell can be used. Alternatively, methods that detect or select for a marker encoded by a replication competent HCV or encoded by a cell containing a replication competent HCV can be used.

In some aspects of the invention, the replication competent HCV polynucleotide of the invention can be used to produce infectious viral particles. For instance, a cell that includes a replication competent HCV can be incubated under conditions that allow the HCV to replicate, and the infectious viral particles that are produced can be isolated, preferably purified. The infectious viral particles can be used as a source of virus particles for various assays, including evaluating methods for inactivating particles, excluding particles from serum, identifying a neutralizing compound, and as an antigen for use in detecting anti-HCV antibodies in an animal. An example of using a viral particle as an antigen includes use as a positive-control in assays that test for the presence of anti-HCV antibodies.

For instance, the activity of compounds that neutralize or inactivate the particles can be evaluated by measuring the ability of the molecule to prevent the particles from infecting cells growing in culture or in cells in an animal. Inactivating compounds include detergents and solvents that solubilize the envelope of a viral particle. Inactivating compounds are often used in the production of blood products and cell-free blood products. Examples of compounds that can be neutralizing include a polyketide, a non-ribosomal peptide, a polypeptide (for instance, an antibody), a polynucleotide (for instance, an antisense oligonucleotide or ribozyme), or other organic molecules. Preferably, a neutralizing compound is an antibody, including polyclonal and monoclonal antibodies, as well as variations thereof including, for instance, single chain antibodies and Fab fragments.

Viral particles produced by replication competent HCV polynucleotide of the invention can be used to produce antibodies. Laboratory methods for producing polyclonal and monoclonal antibodies are known in the art (see, for instance, Harlow E. et al. *Antibodies: A laboratory manual* Cold Spring Harbor Laboratory Press, Cold Spring Harbor (1988) and Ausubel, R. M., ed. *Current Protocols* in Molecular Biology (1994)), and include, for instance, immunizing an animal with a virus particle. Antibodies produced using the viral particles of the invention can be used to detect the presence of viral particles in biological samples. For instance, the presence of viral particles in blood products and cell-free blood products can be determined using the antibodies.

The present invention further includes methods of treating an animal including administering neutralizing antibodies. The antibodies can be used to prevent infection (prophylactically) or to treat infection (therapeutically), and optionally can be used in conjunction with other molecules used to prevent or treat infection. The neutralizing antibodies can be mixed with pharmaceutically acceptable excipients or carriers. Suitable excipients include but are not limited to water, saline, dextrose, glycerol, ethanol, or the like and combinations thereof. In addition, if desired, neutralizing antibodies and pharmaceutically acceptable excipients or carriers may contain minor amounts of auxiliary substances such as wetting or emulsifying agents, pH buffering agents, and/or adjuvants which enhance the effectiveness of the neutralizing antibodies. Such additional formulations and modes of administration as are known in the art may also be used.

The virus particles produced by replication competent HCV polynucleotide of the invention can be used as a source of viral antigen to measure the presence and amount of antibody present in an animal. Assays are available that measure the presence in an animal of antibody directed to HCV, and include, for instance, ELISA assays, and recombinant immunoblot assay. These types of assays can be used to detect whether an animal has been exposed to HCV, and/or whether the animal may have an active HCV infection. However, these assays do not use virus particles, but rather individual or multiple viral polypeptides expressed from recombinant cDNA that are not in the form of virus particles. Hence they are unable to detect potentially important antibodies directed against surface epitopes of the envelope polypeptides, nor are they measures of functionally important viral neutralizing antibodies. Such antibodies could only be detected with the use of infectious virus particles, such as those that are produced in this system. The use of infectious viral particles as antigen in assays that detect the presence of specific antibodies by virtue of their ability to block the infection of cells with HCV viral particles, or that possibly bind to whole virus particles in an ELISA assay or radioimmunoassay, will allow the detection of functionally important viral neutralizing antibodies The present invention also provides a kit for identifying a compound that inhibits replication of a replication competent HCV polynucleotide. The kit includes a replication competent HCV polynucleotide as described herein, and a cell that contains a polynucleotide including a transactivated coding sequence encoding a detectable marker and an operator sequence operably linked to the transactivated coding sequence in a suitable packaging material. Optionally, other reagents such as buffers and solutions needed to practice the invention are also included. Instructions for use of the packaged materials are also typically included.

As used herein, the phrase "packaging material" refers to one or more physical structures used to house the contents of the kit. The packaging material is constructed by well known methods, preferably to provide a sterile, contaminant-free environment. The packaging material may include a label which indicates that the replication competent HCV polynucleotide can be used for identifying a compound that inhibits replication of an HCV. In addition, the packaging material may contain instructions indicating how the materials within the kit are employed. As used herein, the term "package" refers to a solid matrix or material such as glass, plastic, and the like, capable of holding within fixed limits the replication competent virus and the vertebrate cell.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of the Infectious MK0-Z RNA

Figure 2:
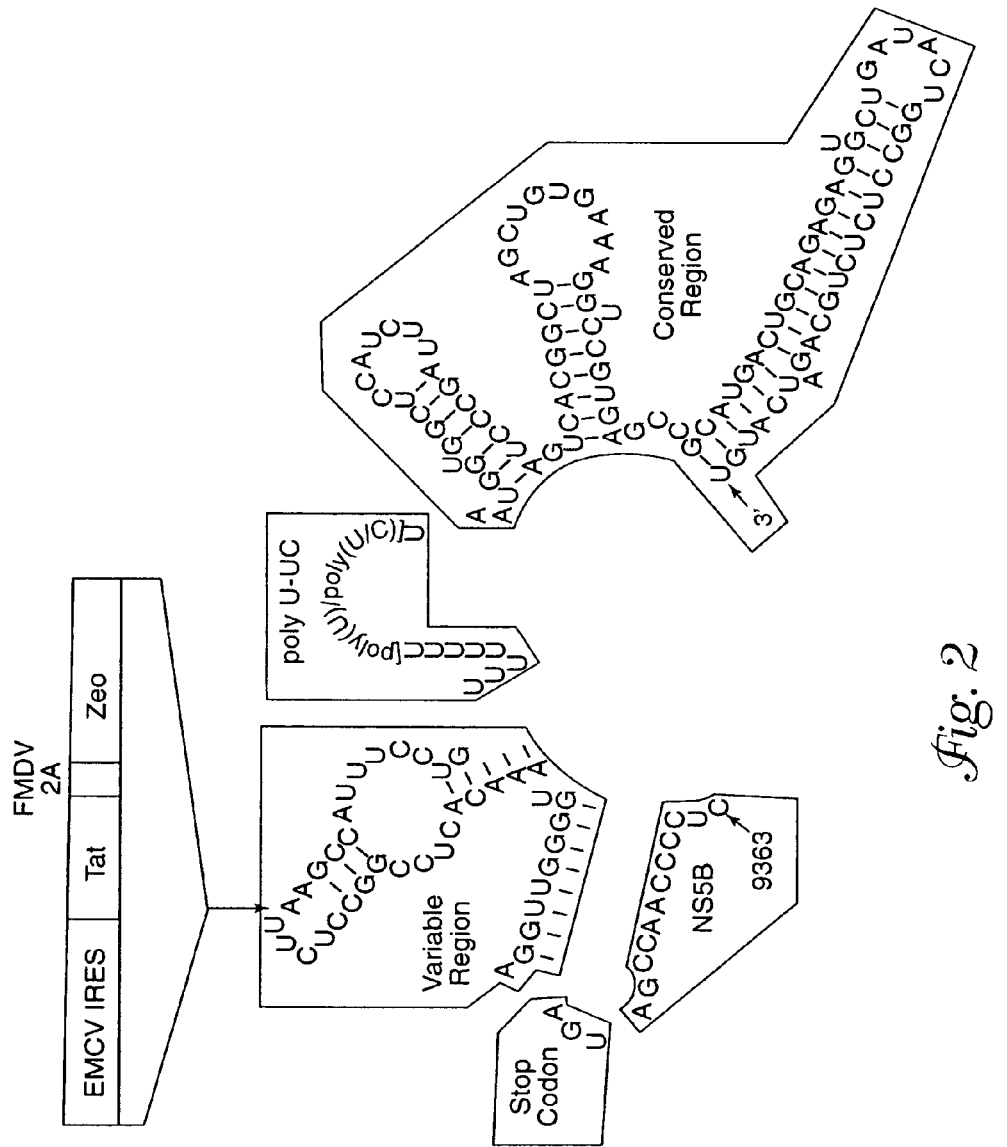
FIG. 2. Site of insertion of heterologous sequence within the 3'NTR (3' non-translated RNA) of H77C strain (pCV-H77C). Variable region, poly U-UC, and Conserved region of the sequence (SEQ ID NO:76) depicted in the Figure refer to regions of the 3' non-translated RNA; EMCV IRES, tat, FMDV 2A, and Zeo, see legend to FIG. 1; NS5B refers to the last 12 nucleotides that encode NS5B.
Figure 9A2:
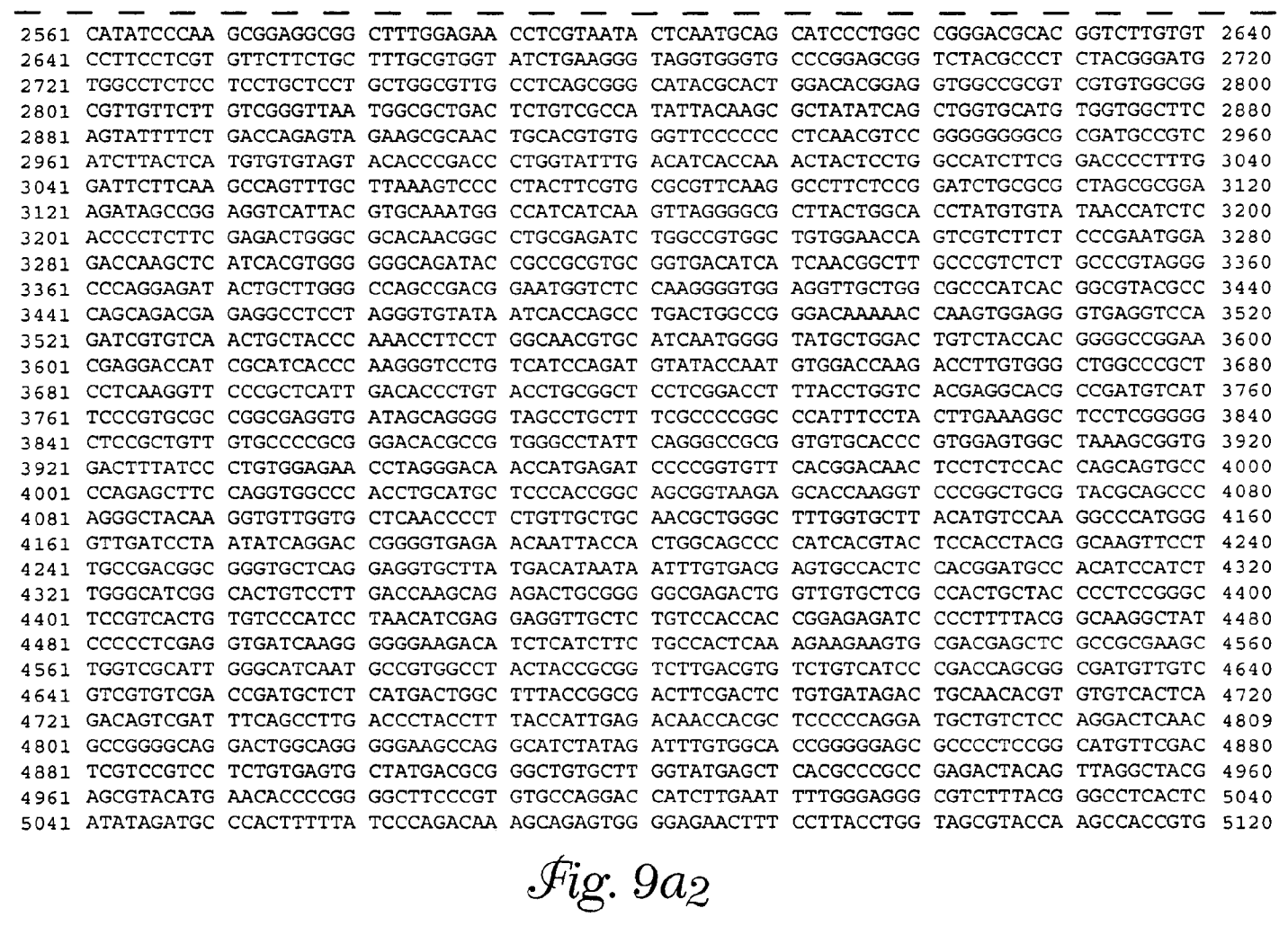

FIG. 1 shows the full-length modified HCV cDNA (MK0-Z) that was constructed by modification of pCV-H77C. The nucleotide sequence of MK0-Z is shown in FIG. 9. A coding region encoding a polypeptide conferring resistance to neomycin has been expressed under control of the EMCV IRES from a second reading frame inserted within the 3' non-translated RNA in subgenomic Kunjin virus replicons. However, the specific placement of the foreign sequence could not be used as a guide for the placement of a coding region in HCV since the 3' non-translated RNA of these viruses share no sequence identity. In the case of MK0-Z, the heterologous sequence functions as a unique 3' cistron, with the internal ribosome entry site (IRES) of encephalomyocarditis virus (EMCV) directing the cap independent translation of a novel polyprotein composed of Tat and the ZEOCIN (phleomycin, Invitrogen) resistance protein, Zeo, separated by the cis-active 2A proteinase of foot-and-mouth disease (FMDV) virus. The Asn-Pro-Gly sequence at the carboxy terminus of FMDV 2A mediates proteolytic cleavage at the 2AZeo junction, effectively separating the upstream Tat and downstream Zeo polypeptides (Ryan et al., *EMBO J,* 13, 928-933 (1994)). The heterologous sequence is placed within the 3'NTR of HCV, a genomic region that contains highly conserved sequences that cannot be deleted without loss of infectivity. More specifically, the heterologous sequence was placed within the variable region of the 3'NTR (FIG. 2). As a control, a replication-incompetent variant of MK0-Z, dS-MK0-Z, was constructed by opening the clone at two closely positioned Sma I sites within the NS5B coding region, then religating the plasmid. This resulted in a frame-shift deletion in the HCV sequence, upstream of the GDD motif in the polymerase encoded by the NS5B coding region, that is lethal to viral replication. The novel 3' reading frame in MK0-Z, has been shown to be active translationally in in vitro translation reactions carried out in rabbit reticulocyte lysates. These experiments also demonstrated that the 2A proteinase effectively cleaved the resulting polyprotein, releasing Tat-2A from the Zeo protein.

a. Construction of pUC HCV3'-EMCV-tat-2A-Zeo

To make pHCV3', full length HCV 1a (present on the plasmid pCV-H77C) (provided by Dr. Purcell at NIH) was digested with HindIII-XbaI. A DNA fragment of about 1.7 kilobases, corresponding to nucleotides 7861-9599 of the HCV nucleotide sequence available at Genbank Accession number AF011751, was isolated and ligated into the vector pBluescript (Stratagene) that had been digested with HindIII and XbaI. The resulting plasmid was designated pHCV3'.

A DNA fragment containing the EMCV IRES was generated by the polymerase chain reaction (PCR). The plasmid pEMCV-CAT, described in Whetter et al., (*Arch. Virol. Suppl.* 9, 291-298 (1994)) was amplified using the sense primer 5'-GGCCTCTTAAGGTTATTTTCCACCATATTGCC (SEQ ID NO:22) which contained a BfrI site, and the anti-sense primer 5'-TCC CCGCGGAAGGCCTCATATTATCATCGTGTTTTC (SEQ ID NO:23) which contained a SacI and StuI site. The italicized nucleotides are those which are not present in the DNA to be amplified, and the underlined nucleotides indicate a restriction endonuclease site. The PCR conditions were: 94° C. for 30 seconds, 55° C. for 30 seconds, and 72° C. for 1 minute, for 35 cycles.

pHCV3'-EMCV was generated by ligating EMCV IRES fragment digested with BfrI-SacI and vector from pHCV3' digested with same enzymes.

A DNA fragment containing the nucleotides encoding 85 amino acids from the HIV I Tat protein was generated by PCR. The amino acid sequence of the HIV I Tat protein is shown at amino acids 4-89 of SEQ ID NO:21 The plasmid used was pCTAT (provided by Dr. Bryan Cullen, Duke University, Durham, N.C. Dept. of Microbiology) (see Bieniasz et al., *Molecular Cellular Biology,* 19, 4592-4599); was amplified using the sense primer 5'-GA AGGCCTATGGAGCCAGTAGATCCTAGA (SEQ ID NO:28), which contained a StuI site, and anti-sense primer 5'-CGGAATTCTTCCTTCGGGCCTGTCGGGTCC (SEQ ID NO:29), which contained an EcoRI site. The italicized nucleotides are those which are not present in the DNA to be amplified, and the underlined nucleotides indicate a restriction endonuclease site. The PCR conditions were: 94° C. for 30 seconds, 55° C. for 30 seconds, and 72° C. for 1 minute, for 35 cycles.

A DNA fragment containing the nucleotides encoding 15 amino acids of FMDV 2A was generated by annealing 51 mer primer set; sense primer 5'-AATTCGACCTTCTTAAGCTTGCGGGAGACGTCGAG TCCAACCCTGGGCCC G (SEQ ID NO:24) and anti-sense primer 5'-GATCCGGGCCCA GGGTUGGACTC-GACGTCTCCCGC AAGCTTAAGAAGGT CG (SEQ ID NO:25) with putative digested form of EcoRI and BamHI site at its 5' and 3' end, respectively. The result was a DNA fragment encoding the 15 amino acids of FMDV 2A. The amino acid sequence encoded by the DNA fragment was FDLLKLAGDVESNPG (SEQ ID NO:30).

A DNA fragment containing the coding region encoding resistance to phleomycin was generated by the polymerase chain reaction (PCR). The plasmid pZeoSV (Invitrogen) was amplified using the sense primer 5'-CCGCTCGAGGCCT GGATCCATGGCCAAGTTGACCAGTGCC (SEQ ID NO:26) which contained a Bam HI site, and anti-sense primer 5'-GGCCTCTTAAGTCAGTCCTGCTCCTCGGCCACG (SEQ ID NO:27) which contained a BfrI site. The italicized nucleotides are those which are not present in the DNA to be amplified, and the underlined nucleotides indicate a restriction endonuclease site. The PCR conditions were: 94° C. for 30 seconds, 55° C. for 30 seconds, and 72° C. for 1 minute, for 35 cycles.

pΔHCV3'-2A-Zeo was generated by digesting the DNA fragment containing the coding region encoding resistance to phleomycin with BfrI-BamHI, and pHCV3' was with EcoRI-BfrI. These two fragments and the FMDV 2A fragment (which contains an EcoRI site with staggered ends and a BamH site with staggered ends) were then ligated to form pΔHCV3'-2A-Zeo.

pUC HCV3'-EMCV-tat-2A-Zeo was generated by ligating 4 fragments together. A DNA fragment containing the EMCV IRES was obtained by digesting pHCV3'-EMCV with SphI-StuI. The amplified DNA fragment encoding a portion of the HIV I Tat protein was digested with StuI-EcoRI. pΔHCV3'-2A-Zeo was digested with EcoRI and XbaI to yield a DNA fragment containing the nucleotides encoding the FMVD 2A and phleomycin resistance. pUC20 vector digested with SphI-XbaI. These were ligated together and the resulting plasmid was designated pUC HCV3'-EMCV-tat-2A-Zeo.

b. Construction of pUC HCV3'-EMCV-tat-2A Containing New HCV 3'Fragment

Original full length HCV 1a (present on the plasmid pCV-H77C) was digested with SphI-BfrI and a 342 nucleotide fragment (corresponding to nucleotides 9060-9427 of HCV) was isolated. pUC HCV3'-EMCV-tat-2A-Zeo was digested StuI-BamHI and a fragment of 317 nucleotides containing tat-2A was isolated. The remaining portion of the plasmid was digested with BfrI, and a 508 nucleotide BfrI-StuI fragment containing the EMCV IRES was isolated. The remaining 361 nucleotide fragment, which contained the nucleotides encoding phleomycin resistance was isolated and reserved for later use in the construction of pUC Zeo-HCV3'NTR containing new HCV3'NTR fragment (see section c below).

pUC HCV3'-EMCV-tat-2A was generated by ligating the 3 fragments described above, i.e., the 342 nucleotide SphI-BfrI fragment corresponding to nucleotides 9060-9427 of HCV, the 508 nucleotide BfrI-StuI fragment containing the EMCV IRES, and the 317 nucleotide StuI-BamHI fragment containing tat-2A, with the vector pUC20 that had been digested with SphI-BamHI. The resulting plasmid was designated pUC HCV3'-EMCV-tat-2A.

c. Construction of pUC Zeo-HCV3'NTR Containing New HCV3'NTR Fragment pUC Zeo-HCV3'NTR was constructed by ligating the 361 nucleotide BamHI-BfrI fragment encoding phleomycin resistance (see above), a 198 nucleotide fragment (corresponding to nucleotides 9427-9625 of HCV) generated by digesting original full length HCV 1a with BfrI-XbaI, and the vector pUC20 that had been digested with BamHI-XbaI.

d. Construction of MK0-Z RNA

Steps b and c above were repeated to produce a second pUC HCV3'-EMCV-tat-2A and a second pUC Zeo-HCV3'NTR containing new HCV3'NTR fragment for use in the construction of MK0-Z RNA.

MK0-Z was generated by the ligation of 4 fragments. Full length HCV was digested with HindIII-SphI and a 1,199 nucleotide fragment (corresponding to nucleotides 7861-9060 of HCV) was isolated. A SphI-BamHI DNA fragment containing HCV3'-EMCV-tat-2A was isolated from pUC HCV3'-EMCV-tat-2A. A BamHI-XbaI DNA fragment containing Zeo-HCV3'NTR was isolated from pUC Zeo-HCV3'NTR. Nucleotides corresponding to nucleotides 1-7860 were isolated from pCV-H77C by digestion with HindIII-XbaI. Ligation of these 4 fragments resulted in MK0-Z.

e. Construction of ds-MK0-Z RNA

The plasmid pHCV3' was digested with SmaI and ligated under conditions to result in self-ligation. The result of the self ligation was loss of the nucleotides corresponding to nucleotides 8497-8649 of HCV. The resulting plasmid was designated pds-HCV3'.

ds-MK0-Z was generated by ligation of 4 DNA fragments. pds-HCV3' was digested with HindIII-SphI to yield a DNA fragment corresponding to nucleotides 7861-9060 of HCV and containing the SmaI fragment deletion. pUC HCV3'-EMCV-tat-2A was digested with SphI-BamHI to yield a fragment containing HCV3'-EMCV-tat-2A. pUC Zeo-HCV3'NTR was digested with BamHI-XbaI to yield a fragment containing the nucleotides encoding Zeo-HCV3'NTR. Nucleotides corresponding to nucleotides 1-7860 were isolated from pCV-H77C by digestion with HindIII-XbaI. Ligation of these 4 fragments resulted in ds-MK0-Z.

Example 2

Production of the Virus by Chimpanzee

This demonstrates the insertion of a heterologous sequence into an HCV does not destroy the ability of the HCV to replicate and produce infectious virus.

MK0-Z plasmid was linearized with XbaI and RNA was synthesized with T7 mega transcription kit from Ambion. The reaction was analysed by gel electrophoresis before injecting into the liver of an HCV-naive Chimpanzee. RNA was frozen at −70° C. overnight before used. About 300 μg of RNA was injected. When injecting, the RNA, which was in 100 ml of transcription reaction mixture, was diluted in 1 ml PBS. The RNA was administered to a Chimpanzee by percutaneous intrahepatic injection guided by ultrasound. Several sites and injections were done in single day. The levels of ALT in the chimpanzee were monitored and were in normal ranges throughout the experiment. Sera from the chimpanzee were collected weekly, and the presence of HCV in each 1 ml of those sera, were checked by RT-PCR, using either the TaqMan or Light Cycler RT-PCR methods.

The primers and probe used for the TaqMan RT-PCR were sense primer, AAGACTGCTAGCCGAGTAGTGTT nt 243 to 265 (SEQ ID NO: 1); anti-sense primer: GGTTGGTGTTACGTTTGGTTT nt 390 to 370 (SEQ ID NO:2); and probe: TGCACCATGAGCACGAATCCTAAA nt 336 to 359 (SEQ ID NO:3), where "nt 243 to 265," "nt 390 to 370," and "nt 336 to 359" refers to the HCV nucleotides (at Genbank Accession number AF011751) to which the primers hybridize. All single-tube EZ RT-PCR reactions were carried out in optical MicroAmp reaction tubes with optical lids in 50 microliter (μl) volume (96 well format). The RNA amplification was done using the TaqMan EZ RT-PCR Kit. Briefly, reactions contained 1× amplification buffer (TaqMan EZ Buffer), 3 mM manganese, 0.5 U AmpErase uracil-N-glycosylate, 7.5 U rTth DNA polymerase, RNA, 200 nM forward and reverse primers, 200 μM each dNTP, and 500 uM of dUTP. Thermocycling conditions were one cycle at 50° C. for 2 minutes, one cycle at 60° C. for 30 minutes, one cycle at 95° C. for 5 minutes, and 40 cycles of 95° C. for 20 seconds, 60° C. for 1 minute. Amplifications were evaluated by ABI7700 Sequence Detector version 1.6.3 software (Applied Biosystems), as suggested by the manufacturer.

The primers and probe used for Light Cycler RT-PCR were forward primer, ACACTCCACCATGAATCACTC, nt 22 to 41, (SEQ ID NO:4); reverse primer, GATCGGGCTCATCACAACCC, nt 268 to 250, (SEQ ID NO:5); fluor probe, GCGTCTAGCCATGGCGTTAGTATGAGT(fluor), nt 75 to 101 (SEQ ID NO:6); and red probe, (LC640) TCGTGCAGCCTCCAGGACCCC(phosphate), nt 103 to 123 (SEQ ID NO:7). The terms "nt 22 to 41," "nt 268 to 250," "nt 75 to 101" and "nt 103 to 123" refer to the HCV nucleotides (at Genbank Accession number AF011751) to which the primers hybridize. The "fluor probe" is labeled at the 3' end with fluorescein, and the "red probe" is labeled at the 5' with LightCycler Red 640 dye.

Single-tube RT-PCR reactions were carried out in capillary tubes in a reaction volume of 20 μl using the core reagents of RNA Amplification Kit Hybridization Probes (Roche) as suggested by the manufacturer. A master mix was made according to the manufacturer's suggestions, containing Lightcycler-RT-PCR Reaction Mix Hybridization probe solution, LightCycler RT-PCR Enzyme mix, 7 mM $MgCl_2$, 0.5 μM of forward primer, 0.9 μM of reverse primer and 0.5 μM of fluor probe, 0.9 μM of red probe, and $H_2O$ is added to make it total 20 μl. This master mix was added directly to the RNA pellet and after dissolve the RNA, it was loaded into glass capillary tube. After adding the 5 ul wash, the tube was snap sealed with a plastic cap. The RT-PCR conditions were 55° C. for 15 minutes, 95° C. for 30 seconds, and 40 cycles of 94° C. for 0 seconds, 60° C. annealing for 15 seconds, and 72° C. extension for 15 seconds.

The signal acquisition was at the end of the annealing step for 100 milliseconds (ms). After amplification was complete, a melting curve was performed by cooling to 55° C., holding at 55° C. for 30 seconds, and then heating slowly at the rate of 0.2 C/second until 90° C. Signal was collected continuously during this melting to monitor the dissociation of the 5'-LC640-labeled probe. The signal was the result of fluorescence resonance energy transfer (FRET) between the fluor probe and the red probe. These probes hybridize to an internal sequence of the amplified fragment during the annealing phase of the PCR cycle. One probe is labeled at the 5' end with a LightCycler—Red fluorophore (LC-Red 640 or LC-Red 705), and to avoid extension, modified at the 3' end by phosphorylation. The other probe is labeled at the 3' end with fluorescein. Only after hybridization to the template, do the two probes come in close proximity, resulting in FRET between the two fluorophores. During FRET, fluorescein, the donor fluorophore, is excited by the light source of the Light-Cycler Instrument. Part of the excitation energy is transferred to LightCycler—Red, the acceptor fluorophore. The emitted fluorescence of the LightCycler—Red fluorophore is measured. The melting curves were then displayed as –dF/d T vs T plots as calculated by LightCycler software version 3.

Figure 11:
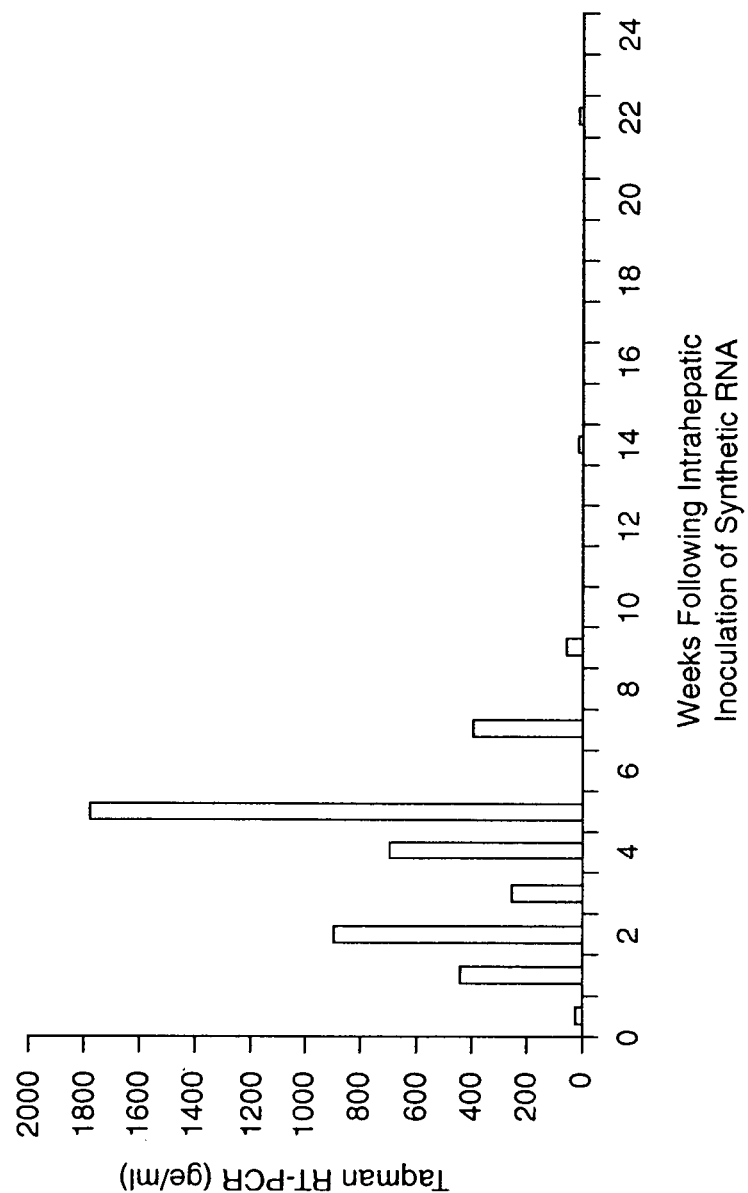
FIG. 11. The results of Taqman RT-PCR of a chimpanzee inoculated with MK0-Z RNA. The term ge/ml refers to genomic equivalents per milliliter.

The results of TaqMan RT-PCR are shown in FIG. 11. They demonstrate that MK0-Z RNA is infectious in a chimpanzee.

Example 3

Construction of a Cellular Enzyme Reporter System for Detection of Replicating HCV A major difficulty in evaluating the outcome of experiments in which cultured cells are transfected with candidate infectious RNAs lies in the detection of newly synthesized viral RNAs against the large background of transfected input RNA. While this is less of a problem, with very robustly replicating viral RNAs, only Lohmann et al. (*Science,* 285, 110-113 (1999)) and Blight et al. (*Science,* 290, 1972-1975 (2000)) have thus far reported levels of replication detectable by northern analysis, using subgenomic RNA replicons that are not capable of producing infectious virus. Moreover, these authors observed such replication only in a small number of cell clones that were isolated over a period of weeks by a stringent antibiotic selection protocol. RT-PCR is difficult to use to detect newly replicated nucleic acid in recently transfected cells due to the persistence of input RNA (in our experience, RNA transfected by liposome-mediated methods remains detectable for weeks). The use of a negative-strand "specific" assay reduces, but does not eliminate this problem, since such assays have no more than a –1.000-fold relative specificity for detection of the negative strand vs. detection of the positive-strand (see, for instance, Lanford et al., *J. Virol.,* 69, 8079-8083 (1995)).

Figure 3:
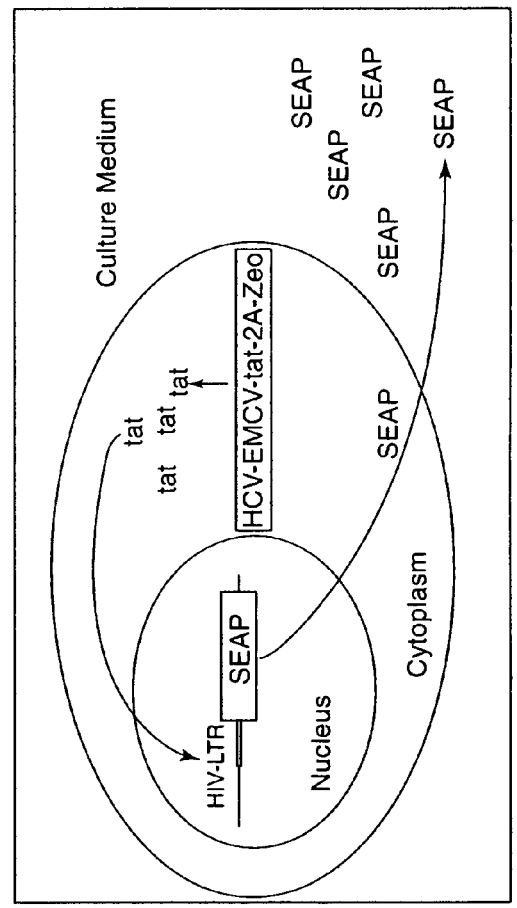
FIG. 3. Schematic depicting release of SEAP from a reporter cell line by expression of Tat from a modified HCV RNA. EMCV, tat, 2A, and Zeo, see legend to FIG. 1; HIV- LTR, HIV I long terminal repeat transcriptional regulator; SEAP, secretory alkaline phosphatase.

This Example details the construction of a cell line that allows the detection of replicating synthetic HCV RNA. The detection is based on the detection of a protein product expressed from the RNA. The system uses the incorporation of the sequence encoding the HIV I Tat protein within modified viral RNAs (see FIG. 1). The Tat protein is a strong transactivator of the HIV I long terminal repeat (LTR) transcriptional regulator. For use as cell substrates in this system, multiple stably transformed cell lines were established. The transformed cell lines were derived from Huh-7 cells that express secretory alkaline phosphatase (SEAP) under transcriptional control of the HIV I LTR. These cell lines were established using either Neomycin or Blastocidin selection, so that either of these antibiotics or Zeocin can be used for subsequent selection of replicating full-length HCV RNAs. The expression of Tat within these cells leads to measurable increases in SEAP activity within the culture medium, as depicted schematically in FIG. 3.

For establishment of neomycin resistant SEAP cell lines, the HIV-SEAP sequence was PCR amplified from pBCHIVSEAP plasmid (provided by Dr. Bryan Cullen, Duke University, Durham, N.C. Dept. of Microbiology) (see Cullen, *Cell,* 46, 973-982 (1986), and Berger et al., *Gene,* 66, 1-10 (1988)) using the primer pairs 5'-CTAGCTAGCCTC-GAGACCTGGAAAAACATGGAG (SEQ ID NO:8) and 5'-ATAAGAATGCGGCCGCTTAACCCGGGTGCGCGG (SEQ ID NO:9). The non-italicized nucleotides in SEQ ID NOs:8 and 9 hybridize with nucleotides present in the target DNA, and the italicized nucleotides in SEQ ID NO:9 represent additional nucleotides that do not hybridize with the target DNA. The underlined nucleotides indicate introduced restriction endonuclease sites. The nucleotide sequence of the amplified fragment is shown in FIG. 12 (SEQ ID NO:18).

After filling in to repair the possible PCR overhang, this fragment was digested with NotI and ligated to vector derived from pRcCMV (Invitrogen) digested with NruI-NotI removing CMV promoter. The resulting plasmid was designated pRcHIVSEAP The nucleotide sequence of the pRcHIVSEAP was used to transfect Huh-7 cells using a non-liposomal transfection reagent commercially available under the trade name FUGENE (Boerhinger Manheim). Tranfectants were selected using G418 (neomycin). The ability of a cell to express SEAP in the presence of tat was tested by transfecting cells with the plasmid pCTAT, which expresses the tat protein. Two resulting cell lines which expressed high levels of SEAP were designated Huh-o10 (also referred to as Huh7-SEAP-o10) and Huh7-SEAP-N7, and were used for subsequent experiments.

A Blasticidin resistant SEAP cell line was constructed as follows. pcDNA6/V5-His (Invitrogen) was digested with BglII-BamHI to remove the CMV promoter. The vector was then self-ligated and subsequently digested with EcoRV-NotI and ligated to the HIV-SEAP DNA fragment that was PCR amplified from pBCHIVSEAP fragment mentioned. The resulting plasmid was used to transfect Huh-7 cells using a non-liposomal transfection reagent commercially available under the trade name FUGENE (Boerhinger Manheim). Tranfectants were selected using Blastocidin (Invitrogen). A blastocidin resistant cell was selected and designated Huh-SEAP-Bla-EN.

Example 4

Evaluation of the Cellular Enzyme Reporter System for Detection of Replicating HCV This Example demonstrates the feasibility and utility of the SEAP cellular reporter system, and demonstrates the expression of Tat by the genetically modified HCV RNA.

To test the SEAP cellular reporter system, MK0-Z RNA was synthesized and transfected into two different SEAP reporter cell lines, Huh7-SEAP-o 10 and Huh7-SEAP-N7 (another cell line that resulted from neomycin selection), on the same day. To provide adequate controls for this experiment, cells from both cell lines were transfected with RNAs synthesized from each of the plasmid DNAs shown in FIG. 1. These include MK0-Z, its replication incompetent control dS-MK0-Z, and a subgenomic transcript, 3'ETZ, each of which encode the novel polyprotein consisting of Tat and Zeo separated by the 19 amino acid 2A proteinase from FMDV 4. Fifteen of the amino acids were the FMDV 2A sequence, and 4 additional amino acids were encoded by nucleotides present to introduce restriction endonuclease sites. In each of the transfected RNAs, this polyprotein is under the translational control of the EMCV IRES.

DNA was linearized with Xba I and RNA was synthesized with T7 mega transcription kit (Ambion, Madison, Wis.). Transfection of RNA was done using Lipofectin (Gibco BRL, Rockville, Md.). Briefly, about 5 µg of RNA was added to a mixture (1 hour incubation prior to transfection) of 15 µl of Lipofectin and 200 µl OPTIMEM (Gibco BRL), incubated for 15 min, and applied to cells. The cells were in 6 well plates which had been plated one day before transfection. The cells were washed two times with OPTIMEM before addition of the RNA, followed by the addition of 1 ml of OPTIMEM.

After overnight incubation, cells were washed with PBS two times and growth medium (DMEM with 2% FBS as above) was added.

Transfection of these RNAs was associated with striking increases in SEAP secreted into the cell culture supernatant, as measured by assay of SEAP. SEAP was assayed using Tropix Phospha-Light Chemiluminescent Reporter Assay for secreted Alkine Phosphatase reagent (Tropix, Foster City, Calif.), according to the manufacturer's suggested protocol, but reduced ⅓ in scale. Luminescent signal detected by a TD-20/20 Luminometer (Turner Design).

The increase in SEAP occurred as a result of transfection with either MK0-Z or the replication deficient dS-MK0-Z RNA, indicating that the SEAP released in the initial weeks after transfection was expressed from the input RNA, not newly replicated RNA. High expression of SEAP was observed from 3'ETZ, reflecting greater transfection efficiency of this small RNA transcript. This experiment demonstrates the feasibility and utility of the SEAP cellular reporter system, and demonstrates the expression of Tat by the genetically modified HCV RNA.

Figure 5:
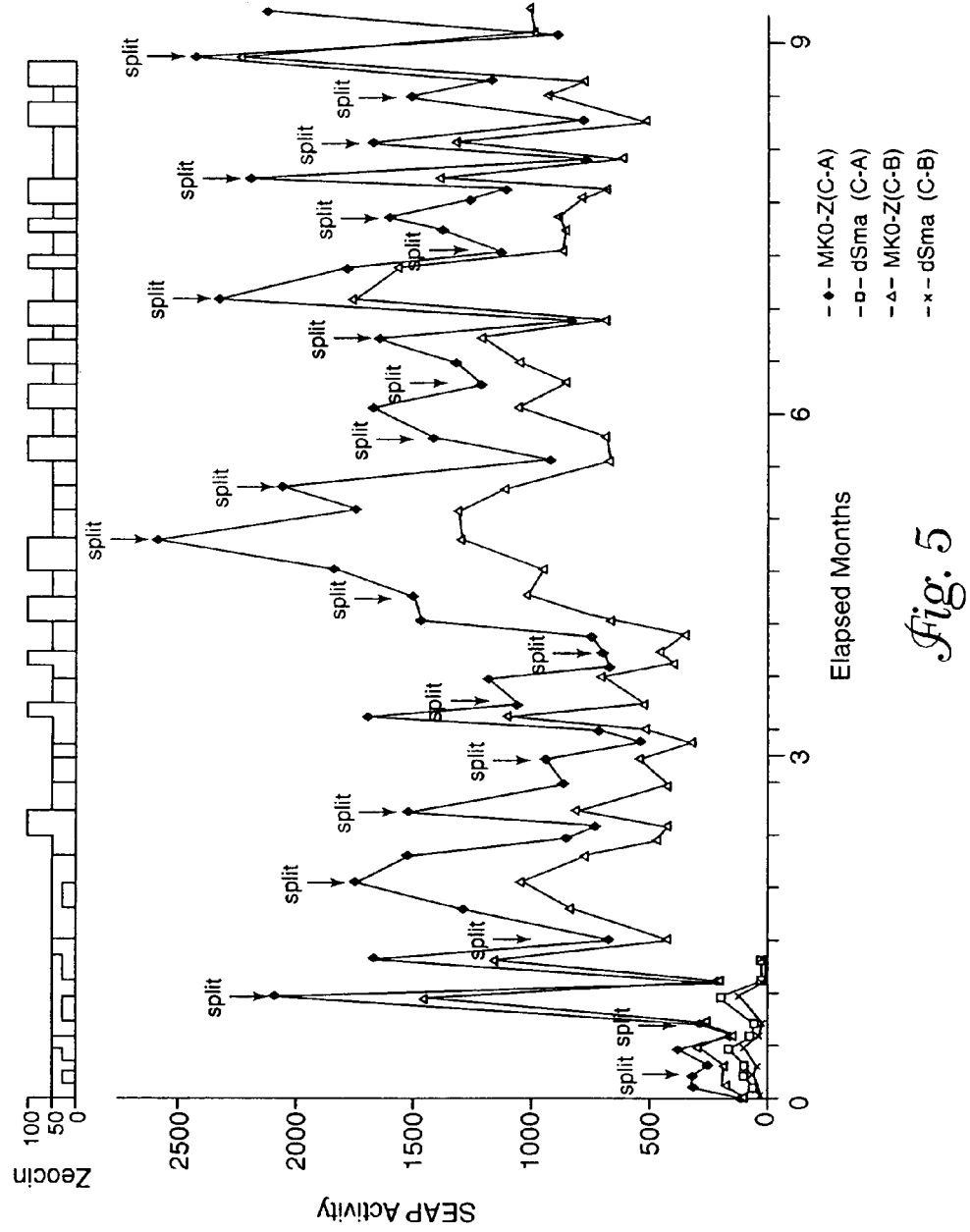
FIG. 5. The passage history of two Huh-SEAP-o10 cell sublines (MK0-Z.C-A and MK0-Z.C-B) that were infected with MK0-K and the secretory alkaline phosphatase (SEAP) activity in supernatant media collected at approximately weekly intervals from both surviving cell lines. dSma (C-A) and dSma (C-B) are two Huh-SEAP-o10 cell sublines infected with supernatant fluids collected from cells transfected in parallel with dS-MK0-Z (NS5B-deletion mutant) RNA. Split, points at which the cultures were split are indicated by arrows. The top panel shows the timing and magnitude of Zeocin selection pressure (top panel, mg/ml).

Proof that infection had been accomplished by the transfection of MK0-Z RNA and that virus adaptation to replication in cultured cells had occurred under antibiotic selection pressure accumulated over the ensuring several months, as follows. FIG. 4 (left panel) shows the results of SEAP assays on media harvested from these cells during the first month after transfection with MK0-Z, and the pol(−) mutant dSMk0-Z. These cells were subsequently maintained in medium with a low concentration of fetal calf serum (2%) over the ensuing 3 months, during which the cells were split periodically and intermittently exposed to low concentrations of the antibiotic Zeocin as tolerated (about 10 to 25 µg/ml). There was no significant difference in cell survival in the presence of Zeo between cells transfected with MK0-Z, and those transfected with dSMK0-Z, but the former usually expressed somewhat higher levels of SEAP in the media (about 1.5 times to about 2 times higher than the control cells). At approximately 3 months, these cells (both MK0Z and ds-MKM0-Z transfected cells) underwent a spontaneous crisis with loss of viability. The supernatant fluids were collected and placed on replicate cultures of fresh Huh-SEAPo 10 cells in an attempt at blind passage of virus. Antibiotic selection was continued intermittently, with gradually intensifying Zeocin selection (intermittent exposure ultimately to 50 µg/ml). With the increase to 50 µg/ml Zeocin, sudden marked increases in SEAP expression were noted from replicate cultures of cells that had been inoculated with medium from the MK0-Z transfected cells, but not cells inoculated with the pol(−) mutant, dS-MK0-Z. This occurred about 7 months after the original transfection, and 4 months after the attempt at cell-free passage of virus. All cells were unable to survive the higher concentration of Zeo, however and the cultures were lost at this point. However, cells that had been previously frozen from the putative passage were recovered from the freezer, and subjected to intermittent concentrations of Zeocin ranging from 25-50 µg/ml. Results are shown in FIG. 5, and summarized in Table 2.

TABLE 2

Passage history of vMK0-Z -infected Huh-SEAP-o10 C-A and C-B sublines.[1]

| Passage | Approximate elapsed time (days) | Comments |
|---|---|---|
| P1 | 1 | Huh-SEAP-o10 cells transfected with MK0-Z RNA, maintained in the absence of antibiotic selection. |
| | 33 | Start intermittent Zeocin selection pressure, 10-25 mg/ml. |
| | 75 | Cells entered crisis and were lost |
| P2 | 68 | Fresh Huh-SEAP-o10 cells infected with P1 day 68 supernatant, and maintained in intermittent Zeocin 25 mg/ml. |
| | 190 | Increase Zeocin to 25-50 mg/ml, with resulting increase in SEAP expression. |
| | 197 | Cells frozen (continuously cultured cells lost within about 1.5 months) |
| | 283 | Cells frozen on P2 day 197 were replated, cultured in intermittent Zeocin 50-100 mg/ml, with marked increase in SEAP expression. P2 cells infected with P1 supernatant from control dS-MK0-Z did not survive. |
| | 547 | Two cell lines (C-A and C-B), both established on P2 day 283, maintained in intermittent Zeocin 50-100 mg/ml with high SEAP. |
| P3 | 514 | Fresh Huh-SEAP-o10 cells infected with 0.45 m-filtered supernatant media from P2 C-A and C-B cell lines on day 544, maintained in intermittent Zeocin 25 mg/ml. |

[1]The term "vMK0-Z" is used to refer to the viral form of MK0-Z after passage.

As observed previously, striking increases occurred in the level of SEAP secreted from 12 of 12 replicate cultures of cells infected with medium from the MK0-Z-transfected cells, but not from any cultures of cells infected in parallel with medium from dS-MK0-Z transfected cells. Moreover, all of the control cell cultures were lost under exposure to 50 µg/ml Zeocin, while each of the cultures infected with MK0-Z material remained viable. Significantly, there was no increase in SEAP released into the medium from the dying cell lines (FIG. 5, dSma (C-A) and dSma (C-B)), consistent with the fact that all SEAP produced is actively secreted from the cells into the medium. This result confirms that cell death does not result in a false elevation of SEAP activity in culture supernatant fluids. The Zeocin resistance and SEAP expression displayed by these cells cannot be explained by fortuitous integration of DNA from the transfected material, since the cells shown in FIG. 5 were never transfected, only exposed to medium from transfected cells. Cell survival and SEAP expression also cannot be explained by cellular mutations in these experiments, as these events have occurred in multiple cultures exposed to the supernatant fluid of MK0-Z transfected cells, but not in related control cell cultures that were similarly exposed to media from dS-MK0-Z transfected cells.

Fluctuations in SEAP activity correlated in part with cell density, and cell viability. At times, these cultures demonstrated considerable cytopathology. However, it was demonstrated that there was minimal intracellular SEAP activity and that most SEAP is actively secreted from the cells. Thus, peaks of SEAP activity reflect peaks of SEAP synthesis, not release from dying cells.

The results shown in FIG. 5 indicate that these cells express two heterologous proteins encoded by MK0-Z, RNA. The Huh-SEAP-o 10 cells have acquired relative Zeocin resistance, indicating the expression of the Zeocin resistance protein, and they secrete 5- to 10-fold greater quantities of SEAP than control cells, indicating the expression of Tat. Moreover, RT-PCR has been used to successfully detect the presence of HCV RNA in samples of the supernatant fluids collected from these cells, using a primer set derived from the viral 5'NTR (see Example 5). Detection of the signal was dependent on Southern blotting of first round RT-PCR products, and amplification was dependent upon the inclusion of reverse transcriptase in the reaction. The results suggest that only small quantities of RNA are present, but confirm that the RT-PCR products are amplified from RNA and not contaminating DNA. The sequence of the amplified product was identical to the H77C strain 5'NTR, the virus from which the MK0-Z clone was derived. These results thus represent the first successful attempt at recovery of HCV from cells transfected with synthetic RNA.

One of the more important features of the experiment depicted in FIG. 5 is the significant change in the behavior of these HCV infected cells over the months of observation, both in terms of their increasing Zeocin resistance and increasing SEAP secretion. This is consistent with adaptation of the viral RNA to more efficient replication within these cells, as would be expected for a positive-strand RNA virus. Furthermore, since at this point all of the cells exposed to medium from cells transfected with the pol(−) mutant dS-MK0-7 have failed to survive Zeocin selection, it can now be assumed that all of the surviving cells harbor viral RNA. Thus, any further increases in SEAP expression must be indicative of greater abundance of the RNA and enhanced replication of the virus.

In summary, these two cell lines continue to demonstrate substantial Zeocin resistance and high level SEAP activity, two independent measures of protein expression from the second open reading frame of the modified vMK0-Z genome, more than 12 months after their infection with supernatant fluids taken from RNA-transfected cells. This is strong evidence of continued replication of the viral RNA in these cells.

Example 5

Passage of vMK0-Z to Fresh Huh-SEAP-o 10 Cells

A third passage of vMK0-Z was carried out using supernatant media collected from the C-A and C-B cell lines on P2 day 540 (see Table 2). These media samples were passed through a 0.45µ filter and then used to feed fresh Huh-SEAP-o10 cells. Control cell cultures (n=6) were mock infected with normal media. One hundred and twenty hours after inoculation, these cells were exposed to intermittent Zeocin selection pressure (25 µg/ml). When treated with high concentrations of drug, or when maintained in continuous drug condition, these cells tend to die. Accordingly, drug exposure was intermittent, and not at high concentrations. The mock-infected cells were lost due to Zeocin toxicity by about day 546 (relative SEAP activity of infected to control cells at this point was 42658 and 31510, respectively, and is not shown in FIG. 6).

Figures 6A, 6B:
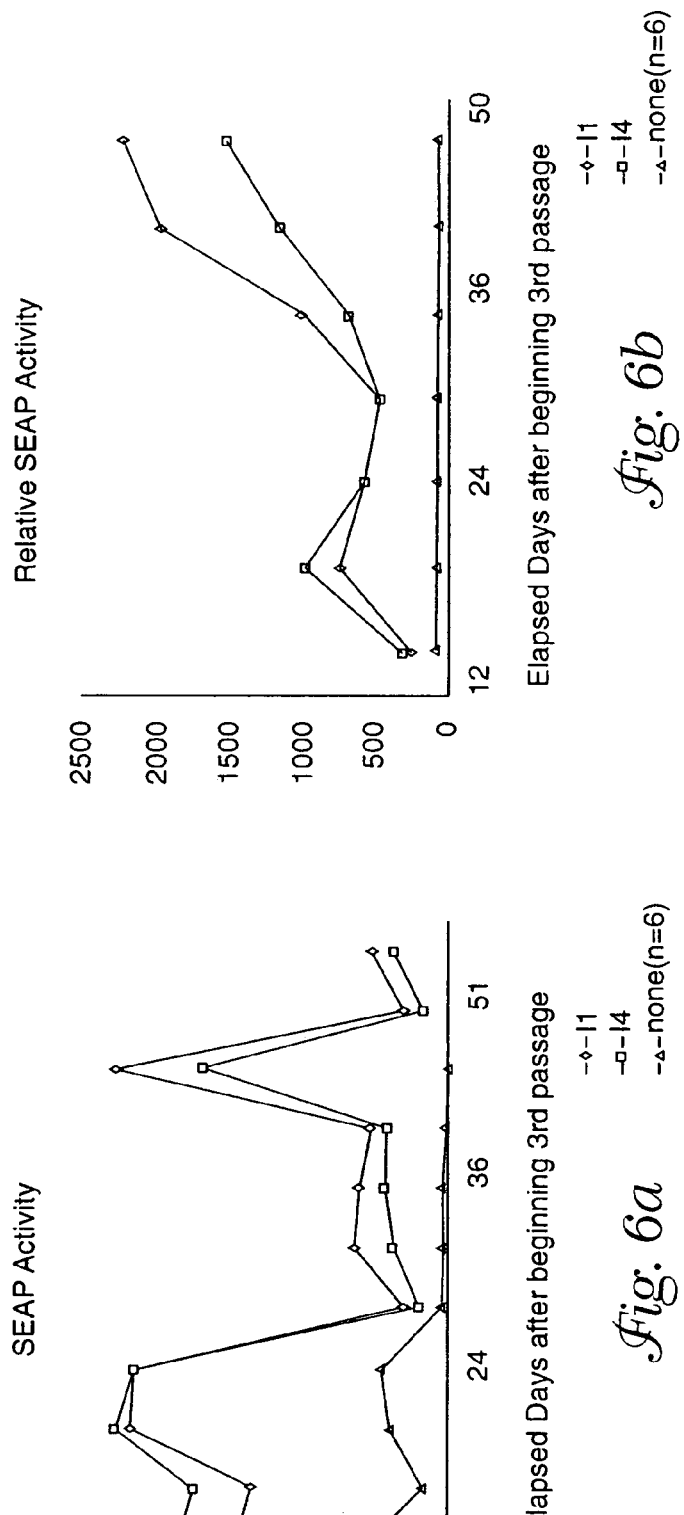
FIG. 6. SEAP expression profiles of Huh-SEAP-o10 cells. (A) Absolute SEAP activities of supernatant media from cells inoculated with supernatant fluids of C-A and C-B MK0-Z infected cell lines. "11" inoculum=media from C-A subline, "14" inoculum=media from C-B subline. None=mock infections. (B) SEAP activity relative to SEAP activity of mock-infected control Huh-SEAP-o 10 cells (lost during Zeocin selection).

The results shown in FIG. 6 demonstrate the passage of SEAP expression activity and Zeocin resistance to fresh Huh-SEAP-o10 cells following inoculation of these cells with supernatant medium collected from vMK0-Z-infected cells.

Example 6

Detection of Viral RNA in Huh-SEAP-o10 Cell Lines

Despite the results described above, and the demonstration of viral antigen in MK0-Z infected cells (see Example 7), it has proven difficult to consistently demonstrate viral RNA in these cells. This Example describes methods for detecting the presence of viral RNA in Huh-SEAP-o 10 cell lines.

Two different quantitative RT-PCR assays (LightCycler and TaqMan) have been used in recent efforts to detect viral RNA in lysates of the cells or in supernatant media. Greatest consistency of success has been in detection of viral RNA in supernatant media following PEG precipitation. This technique works very well, allowing concentration of 130 genome copies equivalent from 1 milliliter (ml) supernatant with 80% recovery. Viral RNA has been reproducibly but intermittently detected in the supernatant fluids; however, reliable detection of viral RNA in cell lysates has not been possible.

The primers and probes that have been used for these assays were as follows:
LightCycler RT-PCR This method used the Lightcycler thermal cycler manufactured by Roche.

```
Primers:
                                            (SEQ ID NO: 10)
Forward 5'-GACACTCCACCATGAATCACT, nt 21 to 41, (SEQ ID NO: 11)
Reverse 5'-GTTCCGCAGACCACTATGG, nt 156 to 139, Probes for fluorescence resonance energy transfer
(FRET):

(SEQ ID NO: 12)
       5'-AGAAAGCGTCTAGCCATGGCGTTAG(Fluor)

(SEQ ID NO: 13)
       5'(LC640)ATGAGTGTCGTGCAGCCTCCAG(phosphate)
```

Briefly, the HCV virus was precipitated with PEG (Sigma, St. Louis, Mo.) prior to extraction with QIAamp serum kit Qiagen, Valencia, Calif.). Supernatant (1.3 ml) was mixed with 0.3 ml of 40% PEG and was placed in an ice bath for 4 hours. The mixture was then centrifuged at 10000×g for 30 minutes at 4° C. The supernatant was removed from the white pellet and 140 µl of TE was added to it. The RNA was then extracted from the viral pellet by following the manufacturers instructions. The eluate was treated with Dnase I as was instructed by the T7 mega transcription kit (Ambion), precipitated with 60 µg glycogen in 130 µl IPA, and stored at −80° C. The positive serum control was a volume of serum containing 5000 genome equivalents, added to media (1.3 ml TE) before precipitation with 0.3 ml PEG and extraction as discussed above. The HCV genome equivalents were determined by National Genetics Institute (Los Angeles, Calif.). The negative serum control was 1 µl of serum from an uninfected volunteer. The serum was treated in the same way as the positive control serum.

The single-tube RT-PCR reactions were carried out in capillary tubes in a reaction volume of 20 µl using the core reagents of RNA Amplification Kit Hybridization Probes (Roche). A 20 µl RT-PCR mixture contained 0.05 µM forward primer, 0.9 µM of reverse primer, RNA sample and 5 µl tube wash of purified sample RNA. The precipitated RNA was first reconstituted with RT-PCR master mix then was loaded into a glass capillary tube, after adding the 5 µl wash the tube was snap sealed with a plastic cap. The RT-PCR conditions were 55° C. for 15 minutes, 95° C. for 30 seconds, and 40 cycles of 94° C. for 0 seconds, 60° C. annealing for 15 seconds, and 72° C. extension for 15 seconds. The signal acquisition was at the end of the annealing step for 100 ms. After amplification was complete, a melting curve was performed by cooling to 55°, holding at 55° C. for 30 seconds, and then heating slowly at 0.2 C/seconds until 90° C. Signal was collected continuously during this melting to monitor the dissociation of the 5'-LC640-labeled probe. The melting curves were then displayed as –dF/dT vs T plots by LightCyler software version 3.

Figure 7:
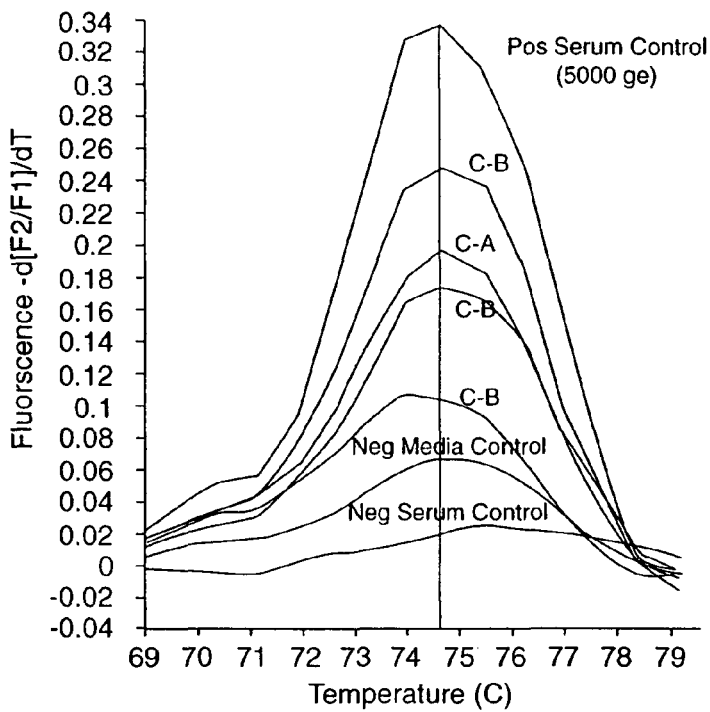
FIG. 7. LightCycler RT-PCR detection of viral RNA in supernatant fluids of C-A and C-B cells. The plot demonstrates the melting curves of the fluorescence resonance energy transfer signal from products generated from the cell culture samples and associated controls. Fluorescence –d[F2/F1]/dT, the melting curve as calculated by the LightCycler thermal cycler.

Results obtained in the LightCycler assay with PEG-precipitated supernatant media collected from the C-A and C-B cell sublines are shown in FIG. 7, which shows the melting curve detected by the FRET method. The melting curve indicates the specificity of product. Both C-A and C-B's curve matches that of positive control. The height of the curve correlates with the amount of the product produced. The negative media control was cell culture media maintained in the isolation room in which the C-A and C-B cell sublines are maintained. The negative serum control was contributed by a volunteer.

TaqMan RT-PCR

Primers (see Takeuchi et al., *Gastroenterol.*, 116, 636-642 (1999)):

Forward 5'-CGGGAGAGCCATAGTGG (SEQ ID NO: 14)

Reverse 5'-AGTACCACAAGGCCTTTCG (SEQ ID NO: 15)

TaqMan probe:
5'-(FAM)-CTGCGGAACCGGTGAGTACAC(TAMRA)-3' (SEQ ID NO: 16)

RNA was obtained from cells as described above for PCR with the Lightcycler thermal cycler. This experiment was set up according to the protocol provided in TaqMan EZ RT-PCR Core Reagents Protocol (product number 402877, Applied Biosystems, Foster City, Calif.). Briefly, All single-tube EZ RT-PCR reactions were carried out in optical MicroAmp reaction tubes with optical lids and in 50 µl volume in a 96-well format. The RNA amplification contained 1× amplification buffer, 3 mM manganese, 0.5 Units (U) AmpErase uracil-N-glycosylate, 7.5 U rTth DNA polymerase, RNA, 200 nM forward and reverse primers, 200 µM each dNTP, 500 µM of d UTP. ABI7700 Sequence Detector version 1.6.3 software was used for sample analysis. Thermocycling conditions were one cycle at 50° C. for 2 minutes, one cycle at 60° C. for 30 minutes, one cycle at 95° C. for 5 minutes, 40 cycles at 95° C. for 20 seconds and 60° C. for 1 minutes.

Figure 8:
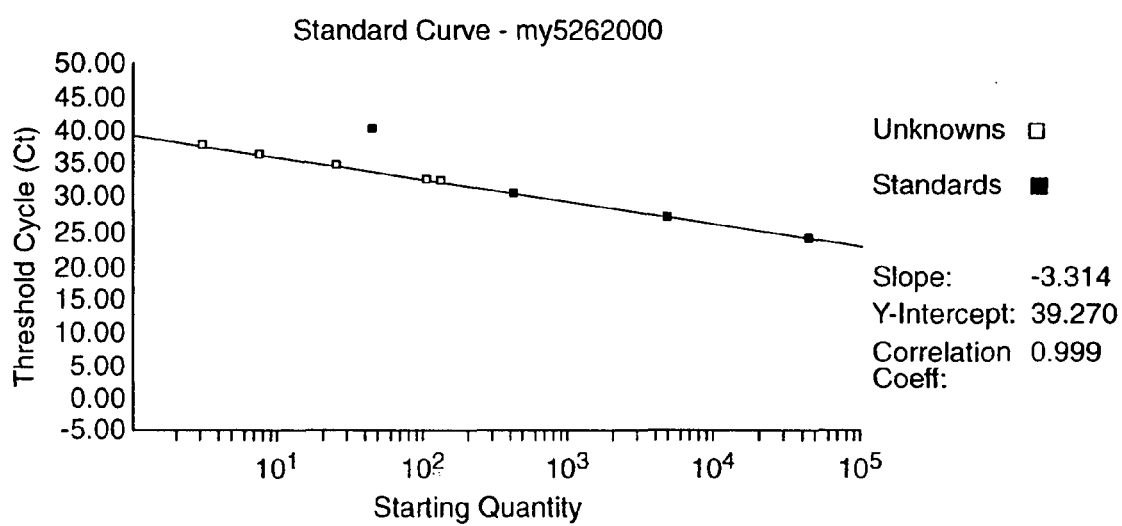
FIG. 8. TaqMan RT-PCR detection of HCV RNA in C-A and C-B cell culture supernatants.

FIG. 8 shows results of TaqMan RT-PCR The C-A and C-B product as detected according to program is aligned along with a known concentration of positive control HCV. The approximate number of HCV protracted from this graph is shown in Table 3.

TABLE 3

TaqMan quantitation of HCV RNA in supernatant media.

| Supernatant from: | Number of genome equivalents |
|---|---|
| Positive serum control (5000 ge[1]) | 4188 |
| C-B | 109 |
| C-A | 136 |
| C-B (unhealthy culture)[2] | 3 |
| C-A (unhealthy culture)[2] | 7 |
| Negative control media | 24[3] |
| Medium | 0 |
| Negative control | 0 |

[1]ge, genome equivalents.
[2]Cultures were losing viability.
[3]This is believed to be the result of contamination.

There was good correlation between the TaqMan and LightCycler results on these specimens.

Example 7

Demonstration of Viral Antigens in vMK0-Z-Infected Huh-SEAP-o10 Cell Lines

Viral antigens expressed from both coding regions (i.e., the coding region encoding the viral polypeptides and the coding region inserted in the 3' NTR) in the modified HCV genome have been demonstrated in vMK0-Z infected Huh-SEAP-o10 cells by indirect immunofluorescence. Negative controls for these experiments were uninfected Huh-SEAP-o10 cells. Cells were grown in tissue culture chamber slides and fixed in acetone-methanol at room temperature prior to staining. Cells were fixed in 50% methanol/50% Acetone for 10 minutes. Blocking agent was 3% BSA in PBS. The primary antibodies used were a mouse monoclonal antibody against HCV core protein, (anti-core antibody, provided by Johnson Lau, Schering-Plough Research Institute, Kennilworth, N.J.) used at a dilution of 1:100, a rabbit polyclonal antibody raised against Sh Ble protein (anti-Zeo antibody, CAYLA, France) used at a dilution of 1:250. The secondary antibodies were fluorescene conjugated anti-mouse or anti-rabbit. Antibodies were incubated with cells for 1 hour each. Between each incubation, the cells were washed three times for 5 minutes each with PBS. Nuclear counterstain was done using DAPI. Dapi staining to detect nucleus was done in 1:10,000 dilution in PBS. It was incubated for 5 minutes, followed by three washes for 5 minutes each in PBS. Photographic exposure times and contrast enhancements were identical for the infected cells and control cell images.

Exposure of cells to an anti-core antibody demonstrated the presence of HCV core protein in vMK0-Z infected cells. Exposure of cell to an anti-zeocin resistance protein demonstrated the presence of the Zeocin resistance protein in vMK0-Z infected cells.

Example 8

Construction of Subgenomic and Genome-Length Dicistronic RNAs

This example demonstrates the successful construction of replication competent, selectable dicistronic replicons from an infectious clone of a Japanese genotype 1b HCV virus (HCV-N) (Beard et al., *Hepatol.,* 30, 316-324, (1999)). Unlike other replicons, adaptive mutations are not required for efficient replication of these HCV-N replicons in Huh7 cells or for the selection of Huh7 clones under G418 selection. We also demonstrate the replication competence of similar selectable, dicistronic RNAs incorporating the NS2-NS5B, E1-NS5B, or complete core-NS5B sequences of this virus. Our findings extend the range of replication competent HCV replicons to a second, genotype 1b virus and show that a natural 4-amino-acid insertion within the NS5A protein of the wild-type HCV-N virus has a controlling role in determining the replication capacity of this RNA in cultured Huh7 cells.

Materials and Methods

Plasmids.

The plasmid pBNeo/3-5B (FIG. 13) contains the Con1 sequence of the $I_{377}$neo/NS3-3' replicon of Lohmann et al. (Lohmann et al., Science, 285, 110-113 (1999), GenBank accession no. AJ242652) downstream of the T7 promoter which is present in the vector upstream of the 5' untranslated region (FIG. 13) (obtained from M. Murray, Schering-Plough Research Institute, Kenilworth, N.J.). pNNeo/3-5B (FIG. 13) contains the sequence of a similar HCV replicon in which almost all of the NS3-NS5B sequence of the 3' cistron is derived from an infectious molecular clone of the genotype 1b virus, HCV-N (GenBank accession no. AF139594) (Beard et al., Hepatol., 30, 316-324, (1999)). It was constructed by replacing the large BsrGI-XbaI fragment of pBNeo/3-5B with the analogous HCV sequence derived from the plasmid pHCV-N. This fragment swap results in the NS3-NS5B sequence in pNNeo/3-5B being identical to that of HCV-N, with the exception of substitutions at 2 amino acid residues that retain the Con1 sequence: a Lys-to-Arg substitution at residue 1053 and an Ala-to-Thr substitution at residue 1099 (where the numbering system is based on the location within the original full length polyprotein as described at GenBank AF139594), near the N-terminus (proteinase domain) of the NS3 protein. The 5' untranslated region ('UTR) and N-terminal core protein sequences of HCV-N and the BNeo/3-5B replicon are identical.

The mutant pNNeo/3-5BΔi5A (FIG. 13) was derived from pNNeo/3-5B by an in-frame deletion removing a unique 4-amino-acid insertion that is present in the NS5A sequence of HCV-N in comparison to the consensus genotype 1b sequence (Beard et al., Hepatol., 30, 316-324, (1999)). This was accomplished by QuickChange mutagenesis (Stratagene, La Jolla, Calif.). By similar methods, additional mutations were created within the background of pNNeo/3-5B and pNNeo/3-5BΔi5A incorporating single-amino-acid substitutions within NS5A or NS5B that have previously been reported to enhance the replication capacity of the $I_{377}$/NS3-3' replicon (BNeo/3-5B) by others: the R2884G mutation described by Lohmann et al. (J. Virol., 75, 1437-1449 (2001)), and the S1179I mutation described by Blight et al. (Blight et al., Science, 290, 1972-1974 (2000)). These mutations are referred to as R2889G and S2005I, respectively, for the purposes of this study, according to the location of these residues within the original full-length HCV-N polyprotein sequence. The resulting mutants were designated NNeo/3-5B(RG) and NNeo/3-5B(SI). Similar substitutions were introduced into the background of pBNeo/3-5B to generate BNeo/3-5B(RG) and BNeo/3-5B(SI). Two additional mutants, NNeo/3-5BΔGDD and BNeo/3-5BΔGDD, each possess an in-frame deletion of 10 amino acids (MLVNGDDLVV); (SEQ ID NO: 74) spanning the GDD motif (underlined) within the NS5B RNA-dependent RNA polymerase of both wild-type replicons. DNA sequencing of the manipulated regions of the plasmids verified all mutations.

Figure 14:
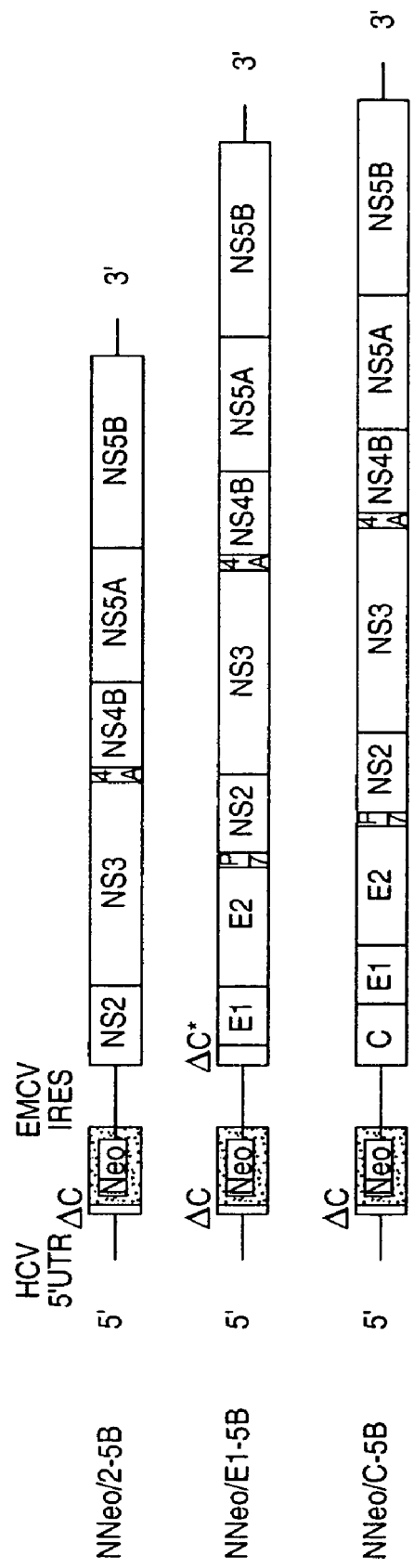
FIG. 14. Organization of selectable dicistronic RNAs containing HCV-N sequence encoding NS2, the envelope proteins E1 and E2, and/or the core protein within the 3' cistron. NTR, nontranslated region.

Selectable, dicistronic replicons containing part or all of the HCV-N structural protein-coding sequence within the 3' cistron were generated as follows. The plasmid pNNeo/C-5B contains the full-length HCV-N polyprotein-coding sequence downstream of the EMCV IRES (see FIG. 14). To construct it, DNA fragments representing the EMCV IRES and HCV core protein-coding sequence were fused by overlapping PCR. Briefly, the primer set to amplify the EMCVIRES-core fusion were as follows. For EMCV and part of core sequence containing fragment, sense primer, 5'-TCCCTCTAGA CGGACCGCTA TCAGGACATA GC (SEQ ID NO:43) (which corresponds to nucleotides 1030-1051 of I377/NS3-3'UTR (AJ242652), within the EMCV coding region, and italics indicate non HCV replicon sequence) and antisense primer, 5'-ATTCGTGCTC ATGGTATTAT CGTGTTTTC AAAGG (SEQ ID NO:44) (where the italicized nucleotides correspond to nucleotides 342-353 of HCV-N, and the remainder correspond to nucleotides 1778-1800 of I377/NS3-3'UTR. For part of the EMCV and core containing fragment; the sense primer was 5'-CACGATAATA CCATGAGCAC GAATCCTAAA CCTC (SEQ ID NO:45), which corresponds to nucleotides 1789-1800 of I377/NS3-3'UTR (AJ242652) within EMCV coding region, and italics indicate HCV N core coding region nucleotides 342-363) and antisense primer, 5'-CCGCTCGAGG CAGTCGTTCG TGACATGGTA TACC (SEQ ID NO:46) (italics indicate non HCV replicon nucleotides, and the remainder correspond to nucleotides 938-962 of HCV-N). The resulting DNA was digested with RsrII and BstZ17I and then ligated with the XbaI-RsrII fragment of pBNeo/3-5B and the BsIZ17I-XbaI fragment of pHCV-N.

pNNeo/E1-5B contains sequence encoding the C-terminal 22 amino acids of the core protein, the downstream E1 and E2 sequences and the remainder of the HCV-N polyprotein coding sequence. To construct it, a DNA fragment containing the EMCV sequence was fused to the E1 sequence by an overlapping PCR. Briefly, the primer set to amplify the EMCVIRES-E1 fusion were as follows. For EMCV and part of the E1 containing fragment, the sense primer was 5'-TCCCTCTAGA CGGACCGCTA TCAGGACATA GC (SEQ ID NO:47) (which corresponds to nucleotides 1030-1051 of I377/NS3-3'UTR (AJ242652), within EMCV coding region, and italics indicate non HCV replicon nucleotides) and antisense primer, 5'-AGAGCAACCG GGCATGGTAT TATCGTGTTT TTCAAAGG (SEQ ID NO:48) (where italics correspond to E1 sequence (nucleotides 849-861 of HCV-N) and the remaining nucleotides correspond to nucleotides 1778-1803 of I377/NS3-3'UTR. For part of the EMCV and E1 containing fragment; the sense primer was 5'-CACGATAATA CCATGCCCGG TTGCTCTTTT TCTATCTTCC (SEQ ID NO:49) (which corresponds to nucleotides 1789-1803 of I377/NS3-3'UTR (AJ242652), within EMCV coding region, and italics indicate nucleotides 849-873 of the HCV N E1) and antisense primer, 5'-ATGTACAGCC GAACCAGTTG CC (SEQ ID NO:50) (which corresponds to nucleotides 1983-2004 of HCV-N). The resulting DNA was digested with RsrII and NotI, and then ligated to the XbaI-RsrII fragment of pBNeo/3-5B and NotI-XbaI fragment of pHCV-N.

The 3' cistron of pNNeo/2-5B contains sequence encoding the NS2-NS5B proteins of HCV-N, immediately downstream of the EMCV IRES. It was constructed in a fashion similar to pNNeo/C-5B and pNNeo/E1-5B, with fusion of the EMCV and NS2 sequences by an overlapping PCR. Briefly, the primer set to amplify the EMCVIRES-NS2 fusion were as follows. For EMCV and part of the NS2 sequence containing fragment, the sense primer was 5'-TCCCTCTAGA CGGAC-CGCTA TCAGGACATA GC (SEQ ID NO:51) (which corresponds to nucleotides 1030-1051 of I377/NS3-3'UTR (AJ242652), within EMCV coding region, and italics indicate non HCV replicon sequence) and antisense primer, 5'-CTCCCGGTCC ATGGTATTAT CGTGTTTTTC AAAGG (SEQ ID NO:52) (where the italics indicate NS2 sequence of HCV-N (nucleotides 2772-2783) and the remainder of the sequence corresponds to nucleotides 1778-1800 of I377/NS3-3'UTR. For part of the EMCV and NS2 containing fragment; the sense primer was 5'-CACGATAATA CCATG-GACCG GGAGATGGCT GC (SEQ ID NO:53) (which corresponds to nucleotides 1789-1800 of I377/NS3-3'UTR (AJ242652), within EMCV coding region, and italics indicate nucleotides 2772-2791 of the HCV-N NS2) and antisense primer, 5'-GAGCGGTCCG AGTATGGCAA TCAG (SEQ ID NO:54) (which corresponds to nucleotides 3018-3041 of HCV-N). The resulting DNA was digested with RsrII and EcoRV, and ligated to the XbaI-RsrII fragment of pBNeo/3-5B and EcoRV-XbaI fragment from pHCV-N.

Cells

Huh7 cells were cultured in Dulbecco's modified Eagle's medium (Gibco-BRL, Invitrogen Life Technologies, Carlsbad, Calif.) supplemented with 10% fetal calf serum, penicillin, and streptomycin. Transfected cells supporting the replication of HCV replicons were maintained in the presence of 1 mg of G418 (Geneticin) per ml and passaged two or three times per week at a 4:1 split ratio.

In vitro Transcription and Transfection of Synthetic RNA.

Plasmid DNAs were linearized by XbaI and purified by passage through a column (PCR Purification Kit; Qiagen, Valencia, Calif.) prior to transcription. RNA was synthesized with T7 MEGAScript reagents (Ambion, Austin, Tex.) following the manufacturer's suggested protocol, and the reaction was stopped by digestion with RNase-free DNase. Following precipitation with lithium chloride, RNA was washed with 75% ethanol and dissolved in RNase-free water. For electroporation, Huh7 cells were washed twice with ice-cold phosphate-buffered saline (PBS) and resuspended at $10^7$ cells/ml in PBS. RNA (1 to 10 µg) was mixed with 500 µl of the cell suspension in a cuvette with a gap width of 0.2 cm (GenePulser II System; Bio-Rad, Hercules, Calif.). The mixture was immediately subjected to two pulses of current at 1.5 kV, 25 µF, and maximum resistance. Following 10 minutes (min) of incubation at room temperature, the cells were transferred into 9 ml of growth medium and the number of viable cells assessed by staining with trypan blue. Cells were seeded into 10-cm-diameter cell culture dishes. For selection of Neo-expressing cells, the medium was replaced with fresh medium containing 1 mg of G418 per ml after 24 to 48 hours (h) in culture.

Indirect Immunofluorescence.

Cells were grown on chamber slides until 70 to 80% confluent, washed three times with PBS, and fixed in methanol-acetone (1:1 [vol/vol]) for 10 min at room temperature. Dilutions of primary, murine monoclonal antibodies to residues 1 to 61 of the core protein (MAB7013; Maine Biotechnology Services, Portland) (1:25), E2 (obtained from Y. Matsuura and T. Miyamura, National Institute of Health, Tokyo, Japan) (1:400), or NS5A (MAB7022P; Maine Biotechnology Services) (1:10) were prepared in PBS containing 3% bovine serum albumin and incubated with fixed cells for 2 h at room temperature. After additional washes with PBS, specific antibody binding was detected with a goat anti-mouse immunoglobulin G-fluorescein isothiocyanate-conjugated secondary antibody (Sigma-Aldrich, St. Louis, Mo.) diluted 1:70. Cells were washed with PBS, counterstained with 4,6-diamidino-2-phenylindole (DAPI), and mounted in Vectasbield mounting medium (Vector Laboratories, Burlingame, Calif.) prior to examination by a Zeiss AxioPlan2 fluorescence microscope.

Northern Analysis.

To minimize potential variation in the intracellular abundance of HCV RNAs that might occur due to variation in the growth status of cells, RNA was extracted from freshly plated cultures after cells had reached 70 to 80% confluence. Total cellular RNAs were extracted with TRIzol reagent (Gibco-BRL) and quantified by spectrophotometry at 260 nm. RNAs were separated by denaturing agarose-formaldehyde gel electrophoresis and transferred to positively charged Hybond-N+ nylon membranes (Amersham-Pharmacia Biotec, Piscataway, N.J.) with reagents provided with the NorthernMax kit (Ambion) and the manufacturer's suggested protocol. RNAs were immobilized on the membranes by UV cross-linking (Stratagene) and stained with ethidium bromide to locate 28S rRNA on the membrane. The upper part of the membrane containing HCV replicon RNA (size greater than 28S) was hybridized with a digoxigenin-labeled, negative-sense RNA riboprobe complementary to the NS5B sequence of HCV-N, while the lower part of the membrane containing β-actin mRNA was hybridized with a digoxigenin-labeled, β-actin-specific riboprobe. For detection of the bound riboprobes, membranes were incubated with antidigoxigenin-alkaline phosphatase conjugate, reacted with CSPD (Roche Molecular Biochemicals, Indianapolis, Ind.), and exposed to X-ray film.

RT-PCR Amplification and Sequencing of cDNA from Replicating HCV RNAs.

Total cellular RNA was extracted from replicon-bearing cell lines as described above and used as a template for the amplification of cDNA fragments spanning the NS3-NS5B segment of the NNeo/3-5B replicon. Reverse transcription (RT) was carried out with 1 µg of RNA, 200 U of SuperScript II reverse transcriptase (Gibco-BRL), and two HCV-specific primers (N6700R, 5'-AGCCTCTTCAGC AGCTG (SEQ ID NO:55) and N9411R 5'-AGGAAATGGCCTATTGGC (SEQ ID NO:56), 1 µM), complementary to sequence in the NS4B and 3'UTR segments of the genome, in a total reaction volume of 10 µl for 60 min at 42° C. cDNAs were subsequently amplified with Pfu Turbo DNA polymerase (Stratagene) by 30 PCR cycles involving annealing at 60° C. for 60 seconds (s), extension at 72° C. for 120 s, and denaturation at 95° C. for 30 s, followed by a final extension reaction at 72° C. for 2 min. Eight separate PCR primer sets were used to amplify nested segments spanning the NS3-NS5B region of the genome (see Table 4).

TABLE 4

Primer pairs.

| Primer sequence | Corresponds to: |
|---|---|
| TTTCCACCATATTGCCGTC (SEQ ID NO: 57) | nucleotides 1307-1325 of 1377/NS3-3'UTR |

TABLE 4-continued

Primer pairs.

| Primer sequence | Corresponds to: |
|---|---|
| TTGACGCAGGTCGCCAGG | (SEQ ID NO: 58) nucleotides 3551-3568 of HCV-N |
| GAACCAGGTCGAGGGGGAGG | (SEQ ID NO: 59) nucleotides 3499-3519 of HCV-N |
| TCGATGGGGATGGCTTTGCC | (SEQ ID NO: 60) nucleotides 4473-4492 of HCV-N |
| CTCGCCACCGCTACGCCTCC | (SEQ ID NO: 61) nucleotides 3551-3568 of HCV-N |
| ACTCCGCCTACCAGCACCC | (SEQ ID NO: 62) nucleotides 5323-5341 of HCV-N |
| ACCCCATAACCAAATACATC | (SEQ ID NO: 63) nucleotides 5260-5279 of HCV-N |
| AGCCTCTTCAGCAGCTG | (SEQ ID NO: 64) nucleotides 6207-6223 of HCV-N |
| TATGTGCCTGAGAGCGACGC | (SEQ ID NO: 65) nucleotides 6144-6163 of HCV-N |
| TATGTGCCTGAGAGCGACGC | (SEQ ID NO: 66) nucleotides 7116-7132 of HCV-N |
| AACCTTCTGTGGCGGCAGG | (SEQ ID NO: 67) nucleotides 7044-7062 of HCV-N |
| CTGGTTGGACGCAGAAAACC | (SEQ ID NO: 68) nucleotides 8042-8061 of HCV-N |
| AACCACATCCGCTCCGTGTG | (SEQ ID NO: 70) nucleotides 7962-7981 of HCV-N |
| TGGCTCAATGGAGTAACAGG | (SEQ ID NO: 71) nucleotides 8962-8981 of HCV-N |
| TTCTCCATCCTTCTAGCT | (SEQ ID NO: 72) nucleotides 8901-8918 of HCV-N |
| AACAGGAAATGGCCTATTG | (SEQ ID NO: 73) nucleotides 9412-9431 of HCV-N |

The sequence of each amplified cDNA segment was determined directly with an ABI 9600 automatic DNA sequencer. The existence of mutations was confirmed by sequencing the products of at least two separate RT-PCRs.

Results

Autonomous Replication of Subgenomic HCV Replicons Derived from HCV-N

Figure 13A:
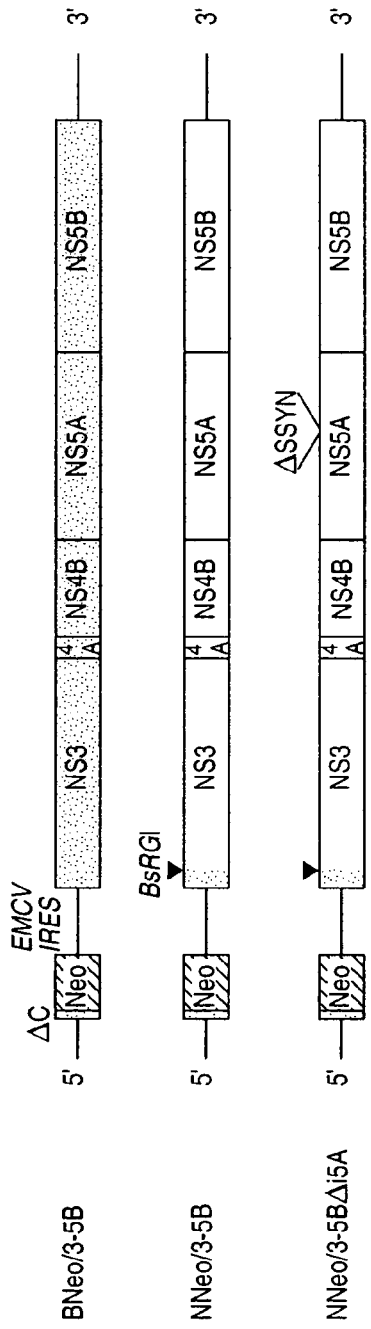
FIG. 13. (A) Organization of the subgenomic HCV RNA replicons. Open reading frames are depicted as boxes, and untranslated segments of the dicistronic RNAs are depicted as solid lines. The sequence of BNeo/3-5B (shaded box) is identical to that of I377NS3-3/wt, described previously by Lohmann et al. (Science, 285, 110-113 (1999)). NNeo/3-5B contains mostly HCV-N-derived sequence (open boxes). The amino acid sequence of NS3 in NNeo/3-5B differs from that of HCV-N at only 2 amino acid residues while the 5'- and 3' UTR sequences are identical. "ΔC" indicates the N-terminal segment of the HCV core protein that is expressed as a fusion with Neo in these replicons. Nneo/3-5BΔi5A includes a SSYN (SEQ ID NO:75) deletion. (B) Locations of the S2205I and R2889G BNeo/3-5B-adaptive mutations and the MLVNGDDLVV deletion (SEQ ID NO:74) introduced into the replicons shown in panel A.
Figure 13B:
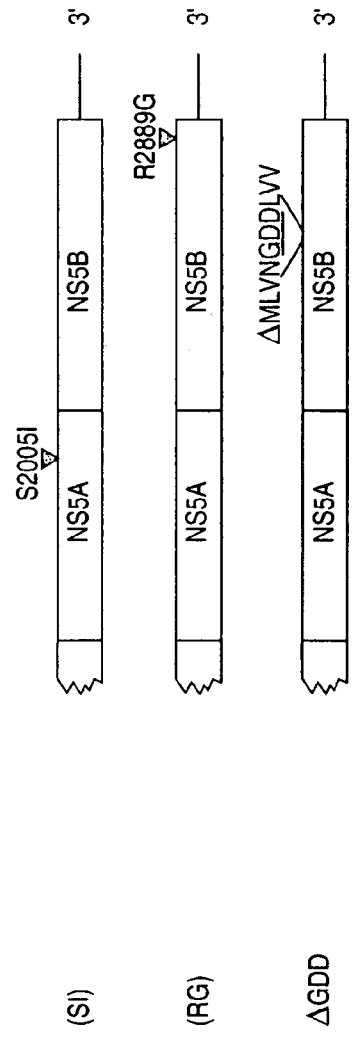

HCV-N is a genotype 1b virus (Beard et al., *Hepatol.*, 30, 316-324, (1999)) that shares only about 90% nucleotide identity in the NS3-NS5B region with the Con1 sequence present in the replicon RNAs described by Lohmann et al. (Lohmann et al., *Science*, 285, 110-113 (1999)) and Blight et al. (*Science*, 290, 1972-1974 (2000)). To determine whether subgenomic RNAs derived from a previously constructed molecular clone of this virus are capable of replication in Huh7 cells, a plasmid was constructed with a T7 transcriptional unit containing the sequence of a candidate replicon, NNeo/3-5B (FIG. 13). The organization of RNA transcripts generated from this plasmid is identical to that of the $I_{377}$neo/NS3-3' replicon of Lohmann et al. (Lohmann et al., *Science*, 285, 110-113 (1999)) (designated BNeo/3-5B in this study), with the 5'UTR of HCV and immediately downstream sequence encoding the N-terminal 12 amino acids of the core protein fused in-frame to the selectable marker, Neo, followed by the IRES of EMCV fused to the NS3-coding sequence and downstream regions of the HCV genome, including the 3'UTR (FIG. 13). The sequences of the proteins expressed by both the 5' and 3' cistrons of NNeo/3-5B are identical to those of HCV-N, with the exception of substitutions at 2 amino acid residues near the amino terminus of NS3, a Lys-to-Arg substitution at residue 1053 and an Ala-to-Thr substitution at residue 1099. These substitutions derive from the Con1 sequence employed in construction of this plasmid.

In initial experiments, NNeo/3-5B transcripts were transfected into Huh7 cells, and the cells were grown in the presence of G418 to select cells with active expression of Neo from replicon RNAs undergoing amplification. BNeo/3-5B transcripts were transfected in parallel. Numerous G418-resistant cell colonies survived the selection process in Huh7 cultures transfected with NNeo/3-5B RNA, with the number of cell colonies isolated proportional to the quantity of RNA electroporated into the cells. However, there were no surviving G418-resistant cell colonies following transfection of NNeo/3-5BΔGDD, a mutated replicon containing an in-frame deletion spanning the GDD motif in the NS5B RNA-dependent RNA polymerase. The absence of surviving cell colonies following transfection of this RNA indicates that amplification of the NNeo/3-5B replicon is essential for G418 resistance. Despite reproducible isolation of greater than 1,000 colonies from cultures transfected with 1 μg of NNeo/3-5B RNA, we were unable to isolate any colonies from cells transfected with an equivalent quantity of either BNeo/3-5B or BNeo/ΔGDD RNA. The failure to recover G418-resistant colonies following transfection of BNeo/3-5B suggests strongly that this previously described RNA replicates significantly less efficiently than NNeo/3-5B in these Huh7 cells.

To confirm the presence of replicating subgenomic RNAs in cells selected for G418 resistance following transfection with NNeo/3-5B, three G418-resistant cell colonies were selected at random and clonally isolated. These clonal cell lines were then examined for the presence of HCV RNA by Northern analysis. The presence of a substantial abundance of HCV-specific RNA with a length approximating 8 kb was detected in extracts of total cellular RNA prepared from each of these stable cell lines (data shown only for clones 1 and 2). Although the abundance of the replicon RNA was significantly greater in the BNeo/3-5B(RG) cell line than in other cell lines studied in this particular experiment, we noted no consistent trends in the abundance of replicon RNA among cell lines derived with different replicon constructs. Abundant NS5A protein was also demonstrated in each of the cell lines by indirect immunofluorescence. These data confirm the ability of wild-type HCV-N subgenomic replicons to undergo autonomous replication in Huh7 cells and represent an important confirmation of the results of Lohmann et al. (Lohmann et al., *Science,* 285, 110-113 (1999)) with a second, independent isolate of HCV.

Adaptive Mutations are not Required for Efficient Replication of NNeo/3-5B RNA.

Data reported both by Lohmann et al. (*J. Virol.,* 75, 1437-1449 (2002)) and by Blight et al. (*Science,* 290, 1972-1974 (2000)) suggest that spontaneously arising, cell culture-adaptive mutations are required for efficient replication of BNeo/3-5B in Huh7 cells. Such mutations appear to be present within each replicon-bearing cell line that has been clonally isolated and characterized in detail (Blight et al., *Science,* 290, 1972-1974 (2000), Krieger et al., *J. Virol.,* 75, 4614-4624 (2001), Lohman et al., *J. Virol.,* 75, 1437-1449 (2002)). Cell culture-adaptive mutations have been identified within NS3, NS5A, and NS5B and have been shown to dramatically increase the efficiency of colony formation when cells are transfected and subjected to G418 selection. To determine whether such adaptive mutations are also required with NNeo/3-5B replicons derived from HCV-N, we determined the nucleotide sequences of the NS3-NS5B segment of the replicons present in the three clonal cell lines described in the preceding section. RNA extracted from these cells were reverse transcribed into cDNA and amplified by RT-PCR for direct DNA sequencing as described in Materials and Methods.

Replicon RNAs in two of the three cell lines contained single-amino-acid mutations: a 3-base insertion resulting in a new Lys residue at position 2040 (NS5A) in clone 2, and a single-base change leading to a Cys-to-Ser substitution at residue 1519 (NS3 helicase domain) in clone 3. Remarkably, there were no mutations identified in the amino acid sequence of the nonstructural proteins in clone 1, despite the fact that the replicon RNA abundance in these cells was approximately equivalent to that in other G418-resistant cell lines, including clone 2, in which there was the insertion of an additional residue in NS5A. These results confirm that NNeo/3-5B RNA is capable of efficient autonomous replication in the absence of adaptive mutations and suggest that the two mutations may have relatively little impact on the replication of this RNA.

Effect of BNeo/3-5B Adaptive Mutations on Replication of NNeo/3-5B.

To determine whether mutations in NS5A or NS5B that have been reported previously to enhance the replication of BNeo/3-5B would further enhance the replication of NNeo/3-5B replicons, we constructed NNeo/3-5B-derived replicons with a Ser-to-Ile substitution at residue 2005, NNeo/3-5B(SI), comparable to the Con1 replicons containing the S117931 mutation in NS5A described by Blight et al. (*Science,* 290, 1972-1974 (2000)), or an Arg-to-Gly substitution at residue 2889, NNeo/3-5B(RG), comparable to the replicon containing the R2884G mutation in NS5B reported by Lohmann et al. (*J. Virol.,* 75, 1437-1449 (2002)). Identical mutations were also introduced into BNeo/3-5B, leading to the creation of BNeo/3-5B(SI) and BNeo/3-5B(RG), respectively, and the modified NNeo/3-5B and BNeo/3-5B RNAs were transfected into Huh7 cells in parallel experiments.

The results of these experiments confirmed the cell culture adaptive activities of these NS5A and NS5B mutations on Con1-derived replicons. The introduction of S20051 into the background of BNeo/3-5B increased the efficiency of G418-resistant colony formation substantially more than the introduction of R2884G. The number of colonies generated following transfection of Huh7 cells with BNeo/3-5B(SI) RNA approximated that obtained with NNeo/3-5B RNA. These results thus confirmed the importance of the S20051 substitution for replication of the BNeo/3-5B replicon, as reported previously (Blight et al., *Science,* 290, 1972-1974 (2000)). However, they also demonstrated that the wild-type NNeo/3-5B RNA is comparable to BNeo/3-5B RNAs containing adaptive mutations such as S20051 in terms of its ability to replicate in Huh7 cells and lead to the selection of G418-resistant colonies. In fact, there was no apparent difference in the abundance of HCV RNA in cell lines selected following transfection of BNeo/3-5B(SI) and NNeo/3-5B (clone 1, which contains no adaptive mutations). Interestingly, however, a cell line selected following transfection with BNeo/3-5B(RG) had a greater abundance of viral RNA despite the substantially lower number of G418-resistant cell colonies generated with this RNA. We did not determine whether this particular cell line contained additional adaptive mutations.

The introduction of either of these two mutations into the background of NNeo/3-5B also resulted in an increase in the number of G418-resistant colonies, but proportionately this increase was much less than that observed with the introduction of these mutations into the BNeo/3-5B background. The S20051 and R2889G mutations resulted in comparable increases in the numbers of G418-resistant colonies, although the density of colony formation made their enumeration difficult even when only 1 μg of RNA was transfected per culture dish. However, we also compared the effects of these two mutations when introduced into the background of a similar subgenomic HCV-N replicon containing blastocidin rather than Neo as a selection marker (NBla/3-5B). In this case, where blastocidin is generally less efficient than Neo as a selectable marker, the introduction of R2889G was shown to result in an ~5-fold higher number of G418-resistant cell colonies than the introduction of S2005I . Importantly, the introduction of these mutations increased the number of G418-resistant colonies obtained with NNeo/3-5B replicons no more than several fold, and far less than the 1,000-fold or greater increases seen with the comparable BNeo/3-5B replicons. Neither mutation resulted in an increase in the abundance of replicon RNA in G418-resistant cell lines selected following transfection with NNeo/3-5B RNAs.

Enhanced Replication Capacity of HCV-N RNA is Due to a Natural 4-Amino-Acid Insertion in NS5A.

As mentioned above, the sequence of the infectious HCV-N cDNA clone contains a unique 4-amino-acid insertion (-Ser-Ser-Tyr-Asn-;SEQ ID NO:75) within the ISDR segment of the NS5A protein in alignments with other HCV sequences (Beard et al., *Hepatol.,* 30,316-324, (1999)). This insertion includes amino acid residues 2220 to 2223 in the HCV-N polyprotein and, although unique in the database, was present in cDNA cloned directly from the Japanese patient who served as the source of the HCV-N isolate (Hayashi et al., *J Hepatol.,* 17, S94-S107 (1993)). It is thus representative of the wild-type sequence of this virus. Since mutations that enhance the replication of the BNeo/3-5B replicon have been suggested to cluster near the ISDR of NS5, we questioned whether the presence of this unique insertion in the ISDR might contribute to the ability of NNeo/3-5B replicons to replicate efficiently in the absence of additional cell culture-adaptive mutations. To address this question, we deleted the 4-amino-acid insertion from NNeo/3-5B (generating NNeo/3-5BΔi5A) and assessed the ability of this NS5A deletion mutant to support the selection of G418-resistant colonies following transfection of Huh7 cells. Additional deletion mutants were generated by removal of the 4-aminoacid insertion from NNeo/3-5B(SI) and NNeo/3-5B(RG), designated NNeo/3-5B(SI) i5A and NNeo/3-5B(RG) i5A, respectively.

The number of G418-resistant colonies selected following transfection with NNeo/3-5BΔi5A was much lower than after transfection with NNeo/3-5B. Only a small number of colonies were generated following transfection with a large amount of RNA (20 µg per culture dish), confirming the importance of this insertion to replication of this RNA in Huh7 cells. In contrast, the deletion of these 4 amino acids from the NS5A sequences of NNeo/3-5B(SI) resulted in only a modest decrease in the efficiency of colony formation, with large numbers of G418-resistant colonies selected after transfection of relatively small amounts of NNeo/3-5B(SI) i5A RNA (1 µg/culture dish). Similar results were obtained with the NNeo/3-5B(RG) i5A replicon, although the number of surviving G418-resistant colonies was less than that with NNeo/3-5B(SI). The fact that efficient G418-resistant colony-forming activity could be preserved by either of these previously described cell culture adaptive mutations in the absence of the 4-amino-acid insertion in NS5A provides further evidence that the 4-amino-acid insertion is responsible for the inherent ability of NNeo/3-5B RNA to replicate efficiently in Huh7 cells.

Since many of the mutations that enhance the replication of BNeo/3-5B have been localized to the NS5A sequence (Blight et al., *Science,* 290, 1972-1974 (2000), 14), we compared the NS5A sequences of NNeo/3-5B and BNeo/3-5B. The proteins are predicted to differ at 49 of 451 (11%) amino acid residues (FIG. 15). Amino acid differences are scattered across the length of the protein sequence, although they are somewhat more frequent within the ISDR and C-terminal half of the protein. Interestingly, there are no differences at any of the residues at which single-amino-acid substitutions have previously been reported to enhance the replication capacity of BNeo/3-5B.

The most striking difference in the NS5A sequences of these replicons is the presence of the 4-amino-acid insertion within the ISDR of NNeo/3-5B. This insertion and, in fact, the entire ISDR are within a 47-amino-acid segment that was shown to have been spontaneously deleted in a cell line bearing a BNeo/3-5B replicon isolated by Blight et al. (*Science,* 290, 1972-1974 (2000)). This large deletion mutation significantly increased the numbers of G418-resistant cell colonies selected following transfection of BNeo/3-5B RNA (Blight et al., *Science,* 290, 1972-1974 (2000)). When the 4-amino-acid insertion was deleted from NNeo/3-5B, its capacity to generate G418-resistant colonies was substantially, although not completely, eliminated. However, the ability of the RNA to efficiently generate G418-resistant colonies was preserved by introduction of the BNeo/3-5B-adaptive S2005I mutation in NS5A and, to a slightly lesser extent, the R2889G mutation in NS5B. The 4-amino-acid insertion in NS5A thus accounts, at least in part, for the unique ability of the wild-type HCV-N RNA to replicate in these cells. It thus represents a natural cell culture-adaptive mutation. Although present in the synthetic HCV-N RNA that gave rise to infection in a chimpanzee, as described above (Beard et al., *Hepatol.,* 30, 316-324, (1999)), the persistence of this sequence polymorphism was not studied in this animal. Thus, it is not possible to comment further on its contribution to replication in vivo.

Replication Competence of Selectable Dicistronic HCV-N RNAs Encoding the Structural Proteins of HCV Lohmann et al. (Lohmann et al., *Science,* 285, 110-113 (1999)) demonstrated that subgenomic Con1 replicons containing the NS2-NS5B segment of HCV also were capable of autonomous replication in Huh7 cells, although the number of G418-resistant colonies selected was somewhat less than that obtained after transfection of cells with replicon RNA containing only the NS3-NS5B segment. To determine whether the replication capacity of the HCV-N RNA would be influenced by the inclusion of NS2-coding sequence or sequences encoding the envelope and core proteins of HCV-N, we constructed a series of plasmids with transcriptional units encoding the selectable, dicistronic RNAs shown in FIG. 14. In addition to the NS3-NS5B coding sequence present in NNeo/3-5B, the 3' cistrons of these dicistronic RNAs contain upstream wild-type HCV-N sequence encoding NS2 (NNeo/2-5B), the envelope proteins as well as NS2 (NNeo/E1-5B), or the entire polyprotein (NNeo/C-5B). RNA transcripts prepared from these plasmids were transfected into Huh7 cells, as described above, and in each case gave rise to G418-resistant colonies after several weeks of culture in G418-containing media. The number of colonies produced from each RNA diminished with the increasing length of the second cistron, with ~160 colonies obtained with NNeo/2-5B, ~60 colonies with NNeo/E1-5B, and only 22 colonies from NNeo/C-5B. However, stable G418-resistant cell lines were clonally isolated from transfections with each of these RNAs, indicating that the RNA remained replication competent despite the inclusion of the additional sequence.

Total cellular RNA extracted from these G418-resistant cell lines was analyzed by Northern analysis for HCV RNA. Each cell line contained HCV-specific RNA of the appropriate length, confirming the ongoing replication of HCV RNA in cell lines selected after transfection with each of the RNAs shown in FIG. 14. However, cells selected following transfection with NNeo/C-5B contained a demonstrably lower abundance of replicon RNA than cells selected following transfection with NNeo/2-5B or NNeo/E1-5B. These latter cell lines were comparable in replicon abundance to cells selected following transfection with NNeo/3-5B. Furthermore, 6418-resistant cells selected with the NNeo/C-5B replicon grew slowly and failed to become completely confluent after several weeks in culture. Colonies of cells selected from one of the NNeo/C-5B cell lines were subcloned and, after passage for an additional month, demonstrated improved growth properties. Northern analysis of total cellular RNA extracted from three of these NNeo/C-5B subclones contained viral RNA of the appropriate length, with an abundance approximating that of replicon RNA in cell lines selected following transfection with NNeo/3-5B.

G418-resistant cell lines selected following transfection with NNeo/E1-5B or NNeo/C-5B were examined for the presence of structural protein antigens by indirect immunofluorescence. In addition to NS5A antigen, cells selected following transfection with NNeo/E1-5B contained detectable E2 antigen, while cells selected following transfection with NNeo/C-5B RNA stained positively for core antigen. In both cases, only a proportion of the cells present in the clonally isolated cell lines contained a detectable abundance of these antigens at any single point in time. This result was different from what was observed with G418-resistant cell lines selected following transfection with NNeo/3-5B, in which almost all cells contained detectable NS5A antigen. It is possible that this may reflect cell cycle dependence of the replication of these RNAs (Pietschmann et al., J. Virol., 75, 1252-1264 (2001)), because the cell lines were clonally derived and stable. Together, however, these data provide strong confirmatory evidence of the replication competence of genome-length, selectable, dicistronic HCV-N RNAs in Huh7 cells.

Example 9

Subgenomic Hepatitis C Virus Replicons Inducing Expression of a Secreted Enzymatic Reporter Protein This Example describes a useful refinement of these subgenomic replicons that simplifies detection of HCV RNA replication in both transiently-transfected cells and established cell clones selected under antibiotic pressure. By modifying the upstream cistron so that it expresses the tat protein of human immunodeficiency virus (HIV) in addition to the Neo resistance marker, replicon RNAs were developed that are capable of signaling their presence and abundance in cells by the secretion of placental alkaline phosphatase (SEAP), expressed under transcriptional control of the HIV LTR. This system permits the autonomous replication of the viral RNA to be monitored in intact cells by an enzymatic assay of SEAP activity in the media bathing the cells. Using these novel reporter replicons, we show the effect of interferon-α on the replication of RNAs derived from two different strains of HCV in stably transformed cell cultures.

Materials and Methods

Cells. En5-3 cells are a clonal cell line derived from Huh7 cells by stable transformation with the plasmid pLTR-SEAP (see below). These cells were cultured in Dulbecco's modified Eagle's medium (Gibco BRL) supplemented with 10% fetal calf serum, 2 µg/ml blasticidin (Invitrogen), penicillin and streptomycin. Following transfection with replicon RNAs, cells supporting replicon amplification were selected and maintained in the above media containing in addition 400 µg/ml G418 (geneticin). Cell lines were passaged once or twice per week.

Plasmids. The plasmid pLTR-SEAP was generated as follows. pcDNA6/V5-His (Invitrogen) was digested with BglII-BamHI to remove the CMV promoter. The vector was then self-ligated, digested with EcoRV-NotI, and religated to a DNA fragment encoding SEAP under transcriptional control of the HIV LTR that was amplified from pBCHIVSEAP (obtained from B. Cullen, Duke University, Durham, N.C.) using the oligonucleotide primer pairs; 5'-CTAGCTAGC-CTCGAGACCTGGAAAAACATGGAG (SEQ ID NO:8) and 5'-ATAAGAATGCGGCCGCTTAACCCGGGT-GCGCGG (SEQ ID NO:9). The resulting plasmid was transfected into Huh7 cells using a non-liposomal transfection reagent (FUGENE, Boerhinger Manheim), and stably resistant cells were selected in the presence of blasticidin (Invitrogen). Blasticidin-resistant cell colonies were clonally selected and subjected to further characterization. One, designated En5-3, was selected for subsequent use due to a low basal level of SEAP activity and efficient induction of SEAP following expression of the HIV tat protein.

To construct the plasmid pEt2AN, a DNA fragment containing the EMCV IRES was amplified by PCR from pEMCV-CAT (Whetter et al., Arch Viol., 136, 291-298 (1994)) using paired primers containing HindIII and StuI sites, respectively. DNA encoding the tat protein was similarly amplified from pCTAT (also a generous gift of Dr. Cullen) with paired primers containing StuI and EcoRI sites, respectively. Finally, a DNA fragment encoding 15 amino acids of the foot-and-mouth disease virus (FMDV) 2A protein was generated by annealing the complementary primers 5'-AATTCGACCTTCTTAAGCTTGCGG-GAGACGTCGAGTCCAACCCTGGGC CCG (SEQ ID NO:24) and 5'-GATCCGGGCCCAGGGTTGGACTC-GACGTCTCCCGCAAGCTTAAGAAG GCG (SEQ ID NO:74) to form a duplex DNA molecule with EcoRI and BamHI sticky ends, respectively. The neo sequence was amplified from pRcCMV (Invitrogen) with primer pairs containing BglII and NotI. These fragments were ligated to pcDNA6/V5-His (Invitrogen) digested with HindIII and NotI to generate pEt2AN.

To construct the replicon plasmid pBΔCtat2Aneo, the genotype 1a infectious clone, pCV-H77c (generously provided by Dr. Robert Purcell, National Institutes of Health, Bethesda, Md.) was digested with SphI and the small fragment was religated. A single T to A nucleotide change was engineered in this plasmid at nucleotide 444 of the HCV sequence of H77c (GenBank accession number AF011751) using QuickChange (Statagene) mutagenesis, generating a novel HpaI site at this position. This resulting plasmid was digested with HpaI and XbaI to generate a DNA fragment representing the HCV 1a 5'NTR and immediately downstream sequence encoding the first 14 amino acids of the HCV polyprotein. A second DNA fragment representing the tat, 2A, and partial neo sequence was excised from pEt2AN by digestion with StuI and SphI. Finally, the plasmid pBNeo/wt (FIG. 16), containing the sequence of the I377neo/NS3-3' replicon of Lohmann et al. (obtained form Michael Murray, Schering-Plough Research Institute) was digested with SphI and XbaI to generate a fragment representing the C-terminal neo sequence, EMCV IRES, and downstream elements of the HCV replicon. These three fragments were ligated to generate pBΔCtat2Aneo (FIG. 16), which contains the 5'NTR and downstream 42 nts of core-coding sequence of the H77 strain of HCV (genotype 1a) and the NS3-5B and 3'NTR sequence of the Con1 strain of HCV (genotype 1b). The plasmid pBtat2Aneo was generated by QuickChange mutagenesis of pBΔCtat2Aneo, with deletion of the 42 nucleotides of core-coding sequence and fusion of the tat sequence directly downstream of 5'NTR of HCV. pNtat2Aneo was constructed by exchanging the large BsrGI-XbaI fragment of pBtat2Aneo with the analogous HCV sequence derived from the plasmid pHCV-N resulting in replacement of most of the NS3-NS5B and 3'NTR sequence. A similar strategy was employed for the construction of variants of these replicon plasmids containing various cell culture-adaptive mutations or a deletion of the GDD motif in the NS5B protein, as described in Example 8.

RNA Transcription and transfection. RNA was synthesized with T7 MEGAScript reagents (Ambion), after linearizing plasmids with XbaI. Following treatment with RNase-free Dnase to remove template DNA and precipitation of the RNA with lithium chloride, the RNA was transfected into En5-3 cells. Transfection was done by electroporation, as described previously. Briefly, 10 µg RNA was mixed with $5 \times 10^6$ cells suspended in 500 µl phosphate buffered saline, in a cuvette with a gap width of 0.2 cm (Bio-Rad). Electroporation was with two pulses of current delivered by the Gene Pulser II electroporation device (Bio-Rad), set at 1.5 kV, 25 µF, and maximum resistance.

In vitro translation. In vitro transcribed RNA, prepared as described above, was used to program in vitro translation reactions in rabbit reticulocyte lysate (Promega). About 1 mg of each RNA, 2 µl of [$^{35}$S]-methionine (1,000 Ci/mmol at 10 mCi/ml), and 1 ml of an amino acid mixture lacking methionine were included in each 50 ml reaction mixture. Translation was carried out at 30° C. for 90 min. Translation products were separated by SDS-PAGE followed by autoradiography or PhosphorImager (Molecular Dynamics) analysis.

Northern analysis for HCV RNA. We seeded replicon-bearing cells into 6 well plates at a density of $2 \times 10^5$ cells/well, and harvested the RNA from individual wells at daily intervals. Total cellular RNAs were extracted with TRizol reagent (Gibco-BRL) and quantified by spectrophotometry at 260 nm. One half of the total RNA extracted from each well was loaded onto a denaturing agarose-formaldehyde gel, subjected to electrophoresis and transferred to positively-charged Hybond-N+nylon membranes (Amersham-Pharmacia Biotec) using reagents provided with the NorthernMax Kit (Ambion). RNAs were immobilized on the membranes by UV-crosslinking. The membrane was hybridized with a [$^{32}$P]-labeled antisense riboprobe complementary to the 3'-end of NS5B sequence (HCV nucleotides 8990-9275 corresponding to GenBank accession number AF139594), and the hybridized probe was detected by exposure to X-ray film.

Indirect immunofluorescence analysis. Cells were grown on chamber slides until 70-80% confluent, washed 3 times with PBS, and fixed in methanol/acetone (1:1 V/V) for 10 min at room temperature. A 1:10 dilution of a primary, murine monoclonal antibody to NS5A (MAB7022P, Maine Biotechnology Services) was prepared in PBS containing 3% bovine serum albumin, and incubated with the fixed cells for 1 hr at room temperature. Following additional washes with PBS, specific antibody binding was detected with a goat anti-mouse IgG FITC-conjugated secondary antibody (Sigma) diluted 1:70. Cells were washed with PBS, counterstained with DAPI, and mounted in Vectashield mounting medium (Vector Laboratories) prior to examination by a Zeiss AxioPlan2 fluorescence microscope.

Alkaline phosphatase assay. SEAP activity was measured in 20 μl aliquots of the supernatant culture fluids using the Phospha-Light Chemiluminescent Reporter Assay (Tropix), and the manufacturer's suggested protocol reduced ⅓ in scale. The luminescent signal was read using a TD-20/20 Luminometer (Turner Designs, Inc.). In most time course experiments, the culture medium was replaced every 24 hrs. Thus, the SEAP activity measured in these fluids reflected the daily production of SEAP by the cells.

Real-time quantitative RT-PCR anaysis of HCV RNA. Quantitative RT-PCR assays were carried out using TaqMan chemistry on a PRISM 7700 instrument (ABI). For detection and quantitation of HCV RNA, we used primers complementary to the 5'NTR region of HCV (Takeuchi et al., *Gastroenterology*, 116, 636-642 (1999)), with in vitro transcribed HCV RNA included in the assays as a standard. Results were normalized to the estimated total RNA content of the sample, as determined by the abundance of cellular GAPDH mRNA detected in a similar real-time RT-PCR assay using reagents provided with Taqman GAPDH Control Reagents (Human) (Applied Biosystems).

Sequence analysis of cDNA from replicating HCV RNAs. HCV RNA was extracted from cells, converted to cDNA and amplified by PCR as described previously (see Example 8). First-strand cDNA synthesis was carried out with Superscript II reverse transcriptase (Gibco-BRL), and pfu-Turbo DNA polymerase (Stratagene) was used for PCR amplification of the DNA. The amplified DNAs were subjected to direct sequencing using an ABI 9600 automatic DNA sequencer.

Interferon treatment of cell cultures. Selected replicon-bearing cell lines were seeded into 12 well plates. The media was replaced 24 hrs later with fresh, G418 free media containing various concentrations of recombinant interferon-α2B ranging from 0 to 100 units/ml. The medium was subsequently completely removed every 24 hrs, the cells washed, and refed with fresh interferon-containing media. SEAP activity was measured in the media removed from the cells as described above.

Results

Tat-SEAP enzyme reporter system. The HIV tat protein is a potent transcriptional transactivator of its LTR promoter element. Unlike most known eukaryotic transcriptional transactivators, tat functions via an interaction with an RNA structure, the transactivation responsive element (TAR), rather than through interaction with DNA (Naryshkin et al., *Biochemistry*, 63, 189-503 (1998); Cullen, *Cell*, 93, 685-692 (1998)). In the absence of tat, almost all RNA transcripts initiated by the LTR promoter are terminated prematurely within ~60-70 nucleotides of the start site. Tat acts to promote the efficient elongation of premature transcripts, thereby transactivating the transcription of functional mRNAs from sequences placed under control of the HIV LTR promoter. We have taken advantage of the small size of the tat protein, and the manner in which it functionally regulates the LTR promoter, to develop a system in which a replication-competent, subgenomic HCV RNA expressing tat induces the expression of secreted alkaline phosphatase (SEAP) placed under transcriptional control of the LTR in stably transformed liver cells.

pEt2AN is an expression plasmid in which the HIV tat coding sequence is fused to sequence encoding the FMDV 2A proteinase and the positive, selectable marker neomycin phosphotransferase (Neo) (FIG. 16A). The small FMDV 2A polypeptide sequence possesses autocatalytic activity (Ryan et al., *EMBO J.*, 13, 928-933 (1994)), resulting in the scission of the peptide backbone at its C-terminus and the release of Neo. The translation of this minipolyprotein is driven by the EMCV IRES sequence located just upstream of the protein coding sequence (FIG. 16A), while transcription is directed by a composite CMV/T7 promoter. We used this plasmid to determine the level of SEAP expressed by stably transformed Huh7 cells (selected for blasticidin resistance) in which the SEAP sequence had been integrated under transcriptional control of the HIV LTR. SEAP activity was measured in the supernatant culture medium before and after transfection of the cells with pEt2AN. Results obtained with one clonally-isolated cell line, En5-3, are shown in FIG. 16B.

This cell line produced a minimal basal level of SEAP activity, while transfection of the cells with pEt2AN DNA led to an approximately 100 fold increase in the secretion of SEAP into the medium in response to tat expression (FIG. 16B). The secretion of SEAP from En5-3 cells began to increase between 24 and 48 hrs after DNA transfection, and reached maximal levels at 72 to 96 hrs. In contrast, the transfection of En5-3 cells with RNA transcribed in vitro from pEt2AN led to an immediate increase in SEAP activity that was maximal when first assayed at 24 hrs post-transfection and subsequently decreased over time, reaching background levels 72 hours later (FIG. 16C). Since the cell culture medium bathing these transfected cells was replaced at 24 hr intervals in these experiments (see Materials and Methods), the SEAP activity measured at each time point reflected the amount of the reporter protein secreted into the medium over the preceding 24 hr period. The delay in SEAP secretion following DNA versus RNA transfection is likely to represent the time required for RNA transcription to occur, while the rapid decline of SEAP following RNA transfection reflects degradation of the transfected RNA and the tat protein translated from it. These encouraging results suggested that the expression of tat from a replicating subgenomic HCV RNA could provide a simple and useful approach to monitoring the presence and abundance of replicon RNA in En5-3 cells.

Figure 17A:
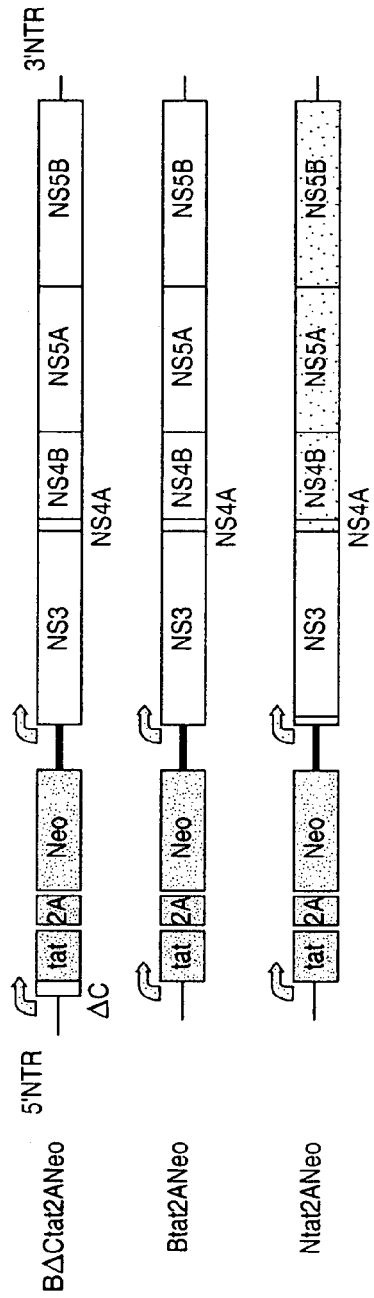
FIG. 17. (A) Organization of subgenomic HCV RNA replicons encoding tat. Open reading frames are depicted as boxes, and nontranslated segments of the dicistronic RNAs as solid lines. AC indicates the N-terminal 14 amino acid core protein segment. (B) Additional mutations engineered into the replicons.

Subgenomic HCV replicons expressing tat. To test this hypothesis, we constructed a plasmid with a transcriptional unit containing a dicistronic, subgenomic HCV replicon similar to that reported originally by Lohmann et al. (*Science*, 285, 110-113 (1999)), but in which the 5' cistron encodes the tat-2A-Neo minipolyprotein present in pEt2AN (FIG. 16), fused in frame downstream of the N-terminal 14 amino acid residues of the HCV core protein sequence (FIG. 17, BΔCtat2ANeo). The second cistron in this replicon contained the NS3-5B segment of the Con1 HCV sequence placed under the translational control of the ECMV IRES, as in the original HCV replicons (Lohmann et al., *Science*, 285, 110-113 (1999)). We also constructed a variant in which the 5' cistron contained no HCV protein-coding sequence, and in which HCV IRES-directed translation initiated at the tat coding sequence (FIG. 17, Btat2ANeo). To enhance the potential replication of these replicons in Huh7 cells, additional variants were engineered to contain the S2205I (SI) cell culture-adaptive mutation described by Blight et al. (*Science*, 290, 1972-1974 (2000)), and the R2889G (RG) mutation described by Krieger et al. (*J. Virol*, 75, 4614-4624 (2001)), respectively (these mutations are numbered according to the location of the cognate residue within the HCV-N sequence) (see Example 8) (FIG. 17).

Figure 18B:
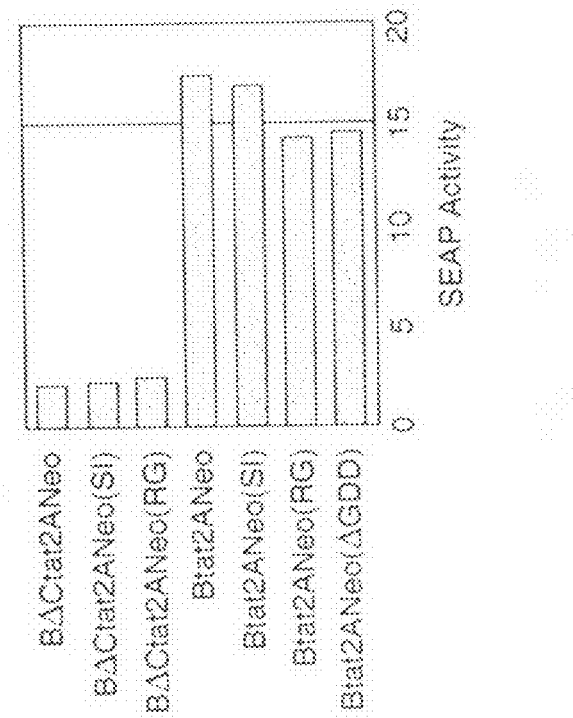
FIG. 18. (A) Product of in vitro translation reactions programmed with the indicated RNAs. (*) indicates the expected positions of the major protein products anticipated to be produced from the dicistronic RNAs. (B) SEAP activity present in tissue culture media 72 hrs following transient transfection with synthetic RNAs transcribed from the indicated plasmids.
Figure 18A:
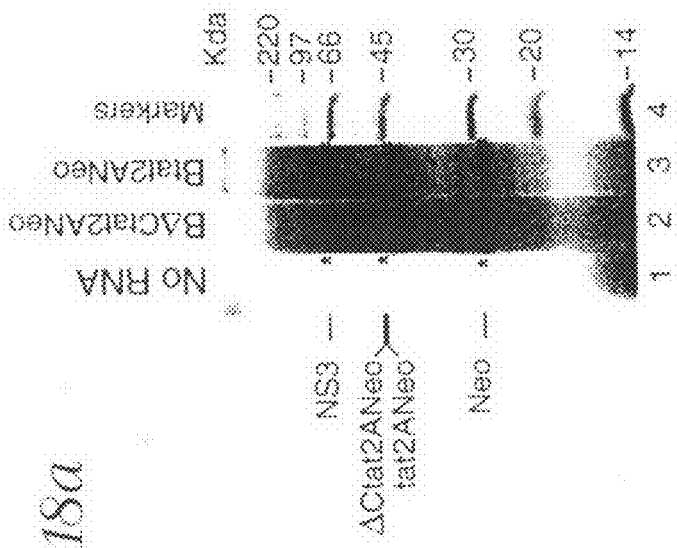

Since the fusion of heterologous sequence directly downstream of the HCV IRES may reduce the ability of the HCV IRES to direct the internal initiation of translation on a hybrid RNA (Reynolds et al., *EMBO J*, 14, 6010-6020 (1995); Rijinbrand et al., *RNA*, 7, 585-597 (2001)), we evaluated the translational activity of these replicons by programming rabbit reticulocyte lysates for translation with RNAs transcribed from these plasmids. The results of these experiments confirmed the activity of the FMDV 2A proteinase within the minipolyprotein, as protein species migrating with the mobilities expected for both the unprocessed DCtat2ANeo and tat2ANeo precursor proteins, and the fully processed Neo protein, were evident in SDS-PAGE gels of the translation products from BΔCtat2ANeo and Btat2ANeo, respectively (FIG. 18A, lanes 2 and 3). The tat2A cleavage product was not observed due to its small size. The results also suggested that the absence of the core protein-coding sequence in Btat2ANeo did in fact result in a significant reduction in translation of the upstream cistron, as reflected in reduced quantities of Neo and the tat2ANeo precursor protein in lysate programmed with Btat2ANeo RNA (FIG. 18A, compare lane 3 with lane 2). In contrast, the quantity of NS3 produced from the downstream cistron was relatively increased in lysates programmed with Btat2ANeo RNA compared to BΔCtat2ANeo, suggesting that the reduction in the activity of the HCV IRES in the former RNA may have a complementary, beneficial effect on the downstream EMCV IRES. This suggests that there may be intercistronic competition for translation factors between the HCV and EMCV IRES elements in these replicon RNAs, as noted previously with other dicistronic RNAs (Whetter et al., *J. Virol.*, 68, 5253-5263 (1994)).

Figure 17B:
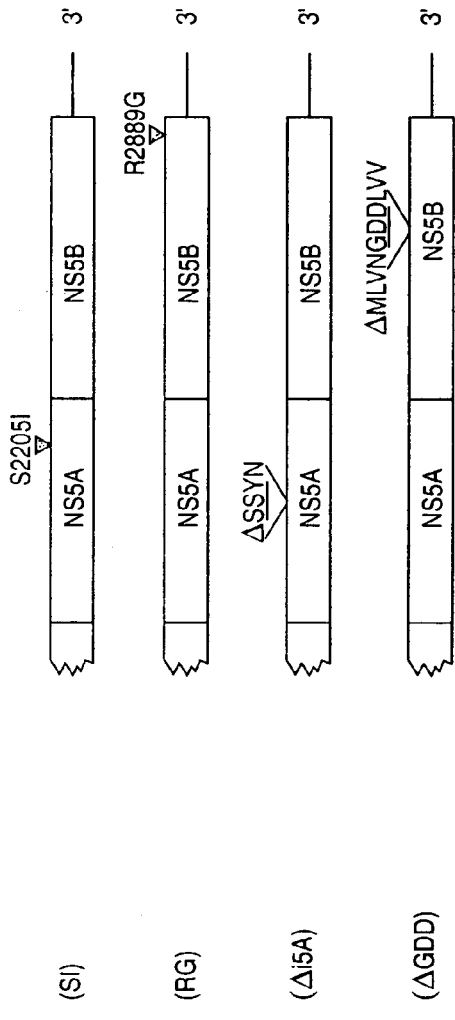

We next assessed the activities of tat proteins expressed from the upstream cistron in the BΔCtat2ANeo and Btat2ANeo replicons (FIG. 17) in transient transfections of these replicon RNAs in En5-3 cells. SEAP activity was monitored in the supernatant media at 72 hrs post-transfection, in the absence of Neo selection. The results of these experiments indicated that the tat protein was significantly less active when expressed as a fusion protein with the N-terminal 14 amino acid segment of core (FIG. 18B, compare BΔCtat2ANeo, BΔCtat2ANeo(SI) and BΔCtat2ANeo(RG), with Btat2ANeo, Btat2ANeo(SI) and Btat2ANeo(RG) RNAs). Although the tat proteins expressed from these RNAs also have a C-terminal fusion with the FMDV 2A proteinase, this C-terminal fusion does not abrogate the transactivating activity of tat, as evidenced in the experiments shown in FIGS. 16B and 16C. Replication of the RNAs did not contribute to the expression of SEAP in the transient transfection experiment shown in FIG. 18B, as the amount of SEAP induced by transfection of an NS5B deletion mutant, Btat2ANeo(ΔGDD), was only slightly less than that induced by its parent, Btat2ANeo. Similarly, the cell culture-adaptive NS5A S2205I and NS5B R2889G mutations (FIG. 17) engineered into these RNAs had no effect on the level of SEAP expression under these conditions (FIG. 18B).

Stable cell lines expressing SEAP under control of replicon-mediated tat expression. Efforts to select stable, G418-resistant colonies following transfection of En5-3 cells with Btat2ANeo or BΔCtat2ANeo were unsuccessful. These results are consistent with the very low frequency of colony formation with the unmodified Con1 NS3-5B sequence, as reported by Lohmann and others (Lohmann et al., *Science*, 285, 110-113 (1999); Blight et al., *Science*, 290, 1972-1974 (2000)). However, it was possible to select G418-resistant En5-3 clones following transfection of the modified Btat2ANeo containing the adaptive S2205I mutation and BΔCtat2ANeo RNAs containing the adaptive S2205I and R2889G mutations in NS5A and NS5B (FIG. 17), respectively. The efficiency of colony formation was substantially lower with these replicons, even with the adaptive mutations, than what has been reported in the literature (Lohmann et al., *J. Virol.*, 75, 1437-1449 (2001); Blight et al., *Science*, 290, 1972-1974 (2000)) or what we have observed previously (see Example 8) with dicistronic, subgenomic HCV replicons. This may reflect the use of the clonal, blasticidin-resistant En5-3 cell line rather than the parental Huh7 cells. Moreover, the number of colonies selected with Btat2ANeo(SI) RNA was approximately 10-fold lower than with BΔCtat2ANeo (SI), suggesting that the absence of the short, AC core protein-coding sequence in Btat2ANeo(SI) decreases the efficiency of colony selection. This could be due to the lower level of Neo expressed from this RNA (FIG. 18), or potentially to other effects on replication of the subgenomic RNA.

Figure 19B:
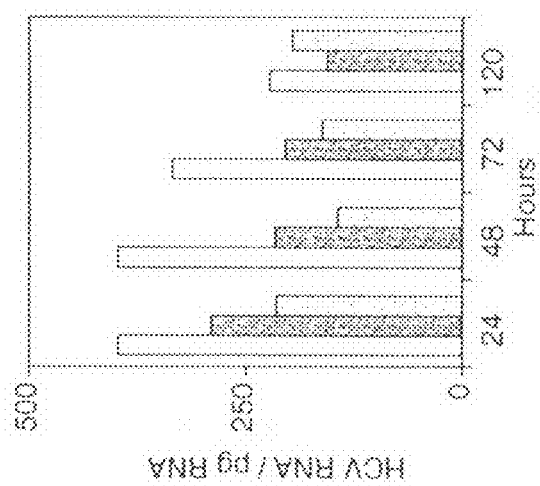
FIG. 19. (A) Northern Blot analysis of replicon RNAs following passage of stable G418-resistant cell clones. (B) HCV RNA abundance detected by TaqMan RT-PCR, normalized to a total cellular RNA standard, and presented as copies of HCV RNA per pg total cellular RNA. The same RNA samples were used as in northern blot analysis in FIG. 19A. Open bar represents BΔCtat2ANeo(SI), solid bar represents Btat2ANeo(SI); gray bar, for Ntat2ANeo(RG).
Figure 19A:
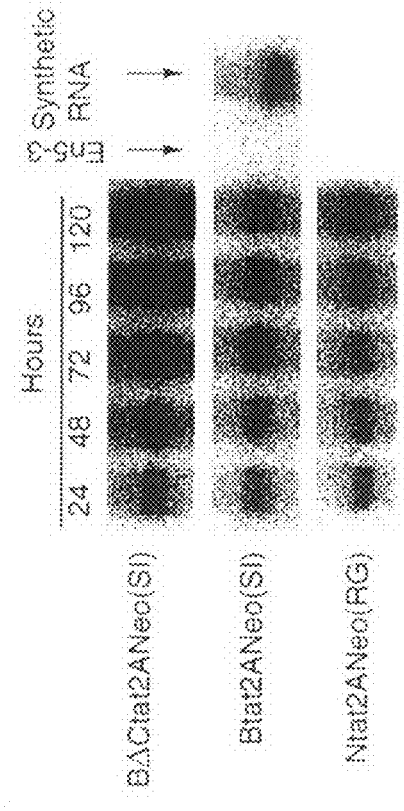

Because replicons containing the genotype 1b, HCV-N sequence have proven to be substantially superior to Con1 replicons in their ability to induce the selection of G418-resistant Huh7 cell clones (see Example 8), we constructed a parallel series of replicons containing the tat2ANeo sequence in the upstream cistron with the downstream cistron, NS3-NS5B sequence derived from HCV-N: Ntat2ANeo, Ntat2ANeo(SI) and Ntat2ANeo(RG) (FIG. 17). Transfection with each of these RNAs led to the selection of stable, G418-resistant colonies. The number of G418-resistant colonies selected with Ntat2ANeo(RG) was at least 100-fold higher than with Btat2ANeo(SI). Overall, the efficiency of colony selection observed with replicon RNAs that lacked any core protein coding sequence (FIG. 17) could be ordered as follows, from high to low: Ntat2ANeo(SI), Ntat2ANeo(RG), Ntat2ANeo, Btat2ANeo(SI). This is consistent with our previous observations with subgenomic HCV replicons expressing only Neo from the upstream cistron (see Example 8). Replicon RNA was readily detected by northern analysis of G418-resistant cell lines selected following transfection with BΔCtat2ANeo(SI), Btat2ANeo(SI) and Ntat2ANeo(RG) (FIG. 19A). The abundance of the viral RNA was significantly greater in the BΔCtat2ANeo(SI) cell line selected for testing, than in cell lines supporting replication of Btat2ANeo (SI) and Ntat2ANeo(RG). While the total abundance of the replicon RNAs (see Materials and Methods) increased in each of the cell lines studied over a 120 hr period following passage of the cells (FIG. 19A), quantitative real-time RT-PCR assays showed a trend toward a reduction in the intracellular abundance of the replicon RNA relative to the abundance of GAPDH mRNA as the cells approached confluence at 120 hrs (FIG. 19B). This is similar to the reduction in intracellular abundance of replicon RNAs reported recently by Pietschmann et al. (*J. Virol*, 75, 1252-1264 (2001)). Once confluent, the intracellular abundance of the replicon RNAs appeared to be similar in all three cell lines studied. These results confirm that there is no requirement for core-protein coding sequence for replication of these dicistronic, subgenomic viral RNAs.

Figure 20B:
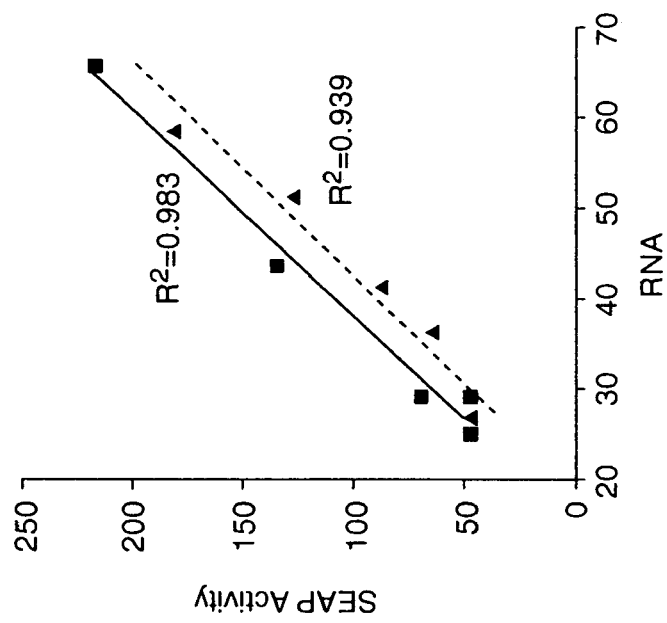
FIG. 20. (A) SEAP activity present in supernatant culture media at various time point following passage of stable cell lines. Btat2ANeo(SI) (▲), Ntat2ANeo(RG) (■), BΔCtat2ANeo(SI) (●), En5-3 (◊). Bars show the range of SEAP activity from duplicate experiments. (B) Linear regression analysis of SEAP activity vs. abundance of replicon RNA in the culture, as determined by densitometry of northern blots. Btat2ANeo(SI) (▲ - - - ), Ntat2ANeo(RG) (■ - - - ).
Figure 20A:
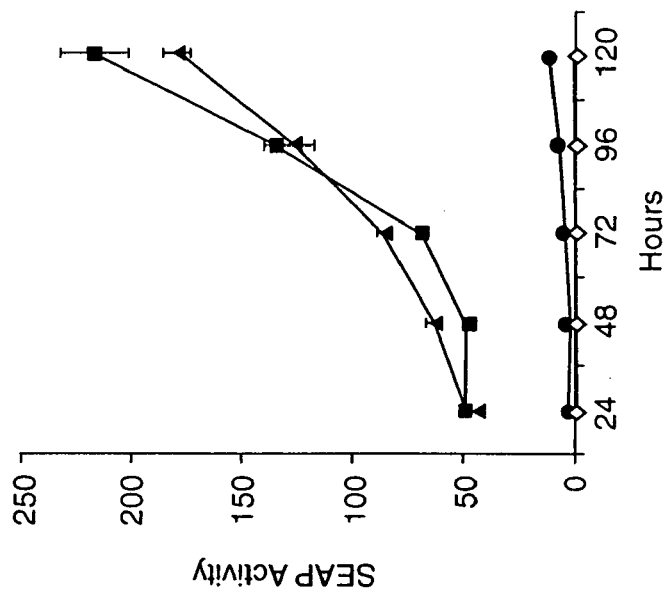

We also examined the cell lines shown in FIG. 19 for viral protein expression as well as secretion of SEAP. NS5A antigen was readily detected within the cytoplasm in each cell line, while no NS5A antigen was detectable in normal En5-3 cells stained in parallel. The abundance of the viral protein was significantly greater in cells containing BΔCtat2ANeo (SI) than Btat2ANeo(SI) or Ntat2ANeo(RG), consistent with the greater abundance of replicon RNA detected in the former by northern analysis (FIG. 19A). In contrast, the SEAP activities expressed by these cell lines showed a very different relationship to the abundance of the replicon RNA. Each of the cell lines secreted increased amounts of SEAP that were detectable above the low background activity present in En5-3 media (FIG. 20A). However, the level of SEAP activity expressed by the BΔCtat2A(SI) cell line was minimally above background and much lower than that secreted by the Btat2ANeo(SI) or Ntat2ANeo(RG) cell lines, despite a higher abundance of viral RNA and viral proteins in the former. Sequencing of cDNA amplified by RT-PCR from the replicon RNAs present in the BΔCtat2A(SI) cells did not identify any mutations within the upstream, ΔCtat2ANeo cistron, ruling out adventitious mutations as a potential cause for the minimal level of SEAP expressed by these cells. The Btat2ANeo(SI) and Ntat2ANeo(RG) cell lines demonstrated robust secretion of the reporter protein, reaching levels at least 100-fold above background after 5 days in culture (FIG. 20A). These results are consistent with the results of the transient transfections presented above (FIG. 18B), and serve to confirm that the fusion of tat to the N-terminal segment of the core protein sharply diminishes its ability to functionally transactivate the HIV LTR.

In the experiment shown in FIG. 20A, it is important to note that the media was completely replaced at 24 hr intervals, and that the cells were thoroughly washed before being refed with fresh media. Thus, the results shown represent the quantity of SEAP secreted by the Btat2ANeo(SI) and Ntat2ANeo(RG) cells during successive 24 hr periods. The secretion of SEAP correlated closely with the abundance of replicon RNA in the Btat2ANeo(SI) and Ntat2ANeo(RG) cells as determined by densitometry of northern blots (FIG. 20B, R2=0.983 and 0.939 by linear regression analysis, respectively). In aggregate, these results demonstrate that the expression of tat from subgenomic HCV RNAs that are replicating in En5-3 cells effectively signals the secretion of SEAP, thereby providing an easily measurable and accurate marker of viral RNA replication that does not require lysis or destruction of the cell monolayer.

Impact of cell culture-adaptive mutations on the replication of tat-expressing HCV replicons in transient transfection assays. Further studies of these replicons focused on those with no core protein sequence fused to tat, since the fusion with the core sequence effectively inactivated the transactivating function of tat. To determine whether the activation of SEAP expression in En5-3 cells by tat was sufficiently sensitive for detection of the replication of subgenomic RNAs in transient transfection assays, replicon RNAs were transfected into En5-3 cells using electroporation, and the cells were followed for a period of 20 days in the absence of G418 selection. Included in this experiment were the Btat2ANeo and Ntat2ANeo replicons, and mutants containing cell culture-adaptive mutations that were derived from them, as shown schematically in FIG. 17B. The supernatant media bathing the transfected cells was removed and replaced with fresh media at 24 hr intervals, as in the experiment shown in FIG. 20A, and the cells were collected by trypsinization and passaged into fresh culture vessels at 7 and 14 days. The levels of SEAP activity present in the media that was removed from cells transfected with the replicon RNAs based on the Btat2ANeo (Con1) sequence (FIG. 17) are shown in FIG. 21A, while FIG. 21B shows SEAP activities in media collected from cells transfected with replicons derived from the HCV-N sequence.

Figure 21B:
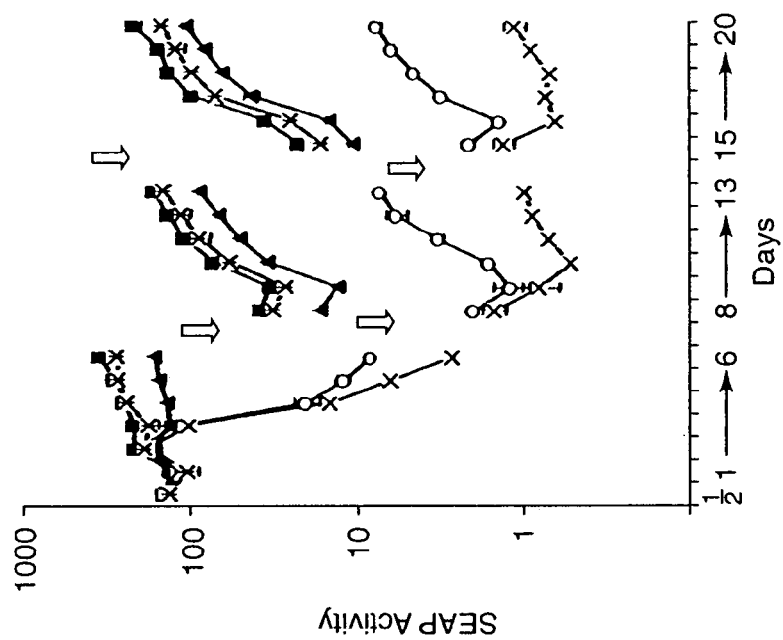
FIG. 21. SEAP activity following transient transfection of En5-3 cells with (A) Btat2Aneo and (B) Ntat2Aneo with various mutations. Wt(○), SI (■), RG (▲), ΔGDD (X), N-Δ5ASI (*). Arrow indicates trypsinization and passage of cells.
Figure 21A:
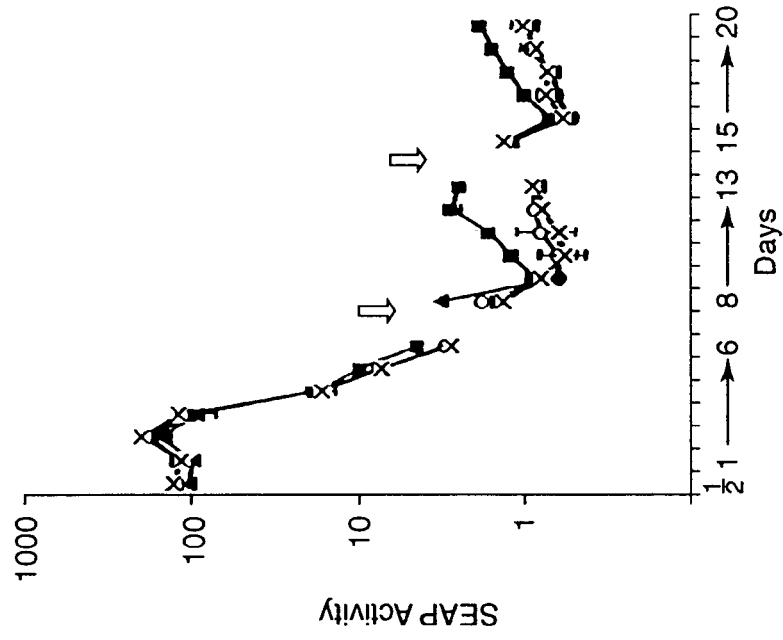

The transfection of any of these replicon RNAs into En5-3 cells resulted in a high initial level of SEAP expression that was present in the culture media as early as 12 hrs after electroporation (FIGS. 21A and 21B). This early, high level of SEAP secretion persisted for approximately 3 days, and was due to translation of the transfected input RNA, as in the experiment shown in FIG. 18C. This high initial SEAP level was also observed with replication-defective mutants containing a deletion in the NS5B sequence involving the GDD polymerase motif (ΔGDD mutants) (FIGS. 21A and 21B). The SEAP activity secreted into the media of cells transfected with Btat2ANeo(ΔGDD) and Ntat2ANeo(ΔGDD) began to decrease by day 4, and reached baseline values similar to those observed with normal En5-3 cells by 8 days after electroporation (FIGS. 21A and 21B). In contrast, other, replication competent RNAs, particularly those derived from the HCV-N sequence, demonstrated increased levels of SEAP expression at later time points that were significantly above the En5-3 cell background and thus indicative of replication of the transfected RNA.

In experiments with replicon RNAs derived from the Con1 sequence, significant increases in SEAP activity above that observed with the Btat2ANeo(ΔGDD) mutant were seen only in cells transfected with Btat2ANeo(SI). There was no apparent difference in the levels of SEAP expressed by cells transfected with the Btat2ANeo and Btat2ANeo(RG) replicons. Cells transfected with Btat2ANeo(SI) demonstrated a low level but sustained increase in SEAP activity above background beginning about 10 days after transfection (FIG. 21A). However, the secretion of SEAP was modest in magnitude, and never more than several-fold above background. In sharp contrast, the HCV-N based replicons were remarkably more potent in terms of their abilities to elicit sustained increases in SEAP expression (FIG. 21B). Levels of SEAP secretion up to 100-fold above background were observed with Ntat2ANeo(SI) and Ntat2ANeo(RG), as well as Ntat2ANeo(SIΔi5A). This latter replicon contains both the S2205I substitution in NS5A as well as the deletion of a natural 4 amino acid insertion that is present in the NS5A sequence of HCV-N (FIG. 17B). This natural insertion in NS5A, which was present in cDNA cloned from human serum (Beard et al., *Hepatology*, 30, 316-324 (1999)), has been shown to contribute substantially to the replication capacity of replicons containing the wild-type HCV-N sequence in Huh7 cells (Example 8). The results shown in FIG. 21 are consistent with those disclosed in Example 8 concerning the relative abilities of subgenomic RNAs containing the Con1 and HCV-N NS3-NS5B sequences (with or without cell culture adaptive mutations in NS5A and NS5B) to transduce the selection of G418-resistant cell clones. These results also provide independent confirmation of the ability of the S2205I and R2889G mutations to enhance the replication capacity of subgenomic, genotype I b RNAs in cultured cells (Blight et al., *Science*, 290, 1972-1974 (2000); Krieger et al., *J. Virol.*, 75, 4614-4624 (2001); Example 8).

We also examined transiently transfected cells for expression of NS5A antigen at 12 and 19 days after electroporation.

These studies demonstrated that the proportion of cells containing a detectable abundance of NS5A was significantly greater following transfection with Ntat2ANeo(RG) and Ntat2ANeo(SI), than Ntat2ANeo or Btat2ANeo(SI). Thus, these results parallel closely the results of the SEAP assays shown in FIG. 21. Interestingly, the intensity of staining of individual positive cells appeared similar with each of the replicon RNAs, suggesting that the level of SEAP expression may correlate with the proportion of cells in which replicon amplification is occurring, rather than the intracellular abundance of the replicon under these conditions. As this experiment was carried out in the absence of G418 selection, it is uncertain whether those cells that did not stain positively for NS5A antigen contained levels of the viral protein that were below the threshold of detection or, alternatively, none at all.

Figure 22B:
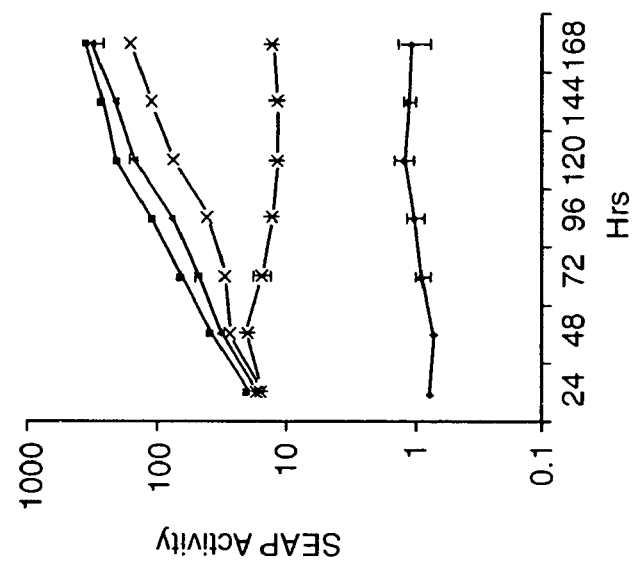
FIG. 22. Suppression of HCV replicon amplification by interferon-α2b. (A) SEAP activity secreted from cells supporting replication of Btat2ANeo(SI) over successive 24 hr intervals following addition of interferon to the medium. (B) SEAP secretion from Ntat2ANeo(RG) cells. Interferon concentrations were: (*) 100 units/ml; (X) 10 units/ml; (▲) 1 unit/ml; (■) no interferon. SEAP expression from En5-3 cells without interferon treatment was also shown (♦). SEAP expression from En5-3 cells was not affected by interferon treatment.

Interferon suppression of HCV RNA replication. To demonstrate the utility of the tat-expressing HCV replicons, we assessed the ability of recombinant interferon-α2b to suppress the replication of Btat2ANeo(SI) and Ntat2ANeo(RG) in stable, G418 resistant cell clones. Recently seeded cell cultures were fed with media containing various concentrations of recombinant interferon-α2B ranging from 0 to 100 units/ml. The medium was subsequently removed completely at 24 hr intervals, and the cells were washed thoroughly and refed with fresh interferon-containing media. Results are shown in FIG. 22 and demonstrate dose-dependent inhibition of SEAP secretion in both cell lines. As shown, cells cultured in the absence of interferon, or at the lowest concentration of interferon, showed an increasing level of SEAP secretion over successive 24 hr intervals, consistent with the growth of the cells. At the highest concentration of interferon tested (100 units/ml), this trend was reversed and SEAP expression declined over time in the absence of demonstrable cellular cytotoxicity. Independent quantitative RT-PCR assays for HCV RNA demonstrated that the decline in SEAP secretion was closely matched by similar decreases in the intracellular abundance of RNA (compare FIG. 22 and FIG. 23). The decline in intracellular RNA preceded the decreases in SEAP secretion by approximately 24 hrs, most likely reflecting the kinetic delay in tat signaling of SEAP secretion.

Figure 22A:
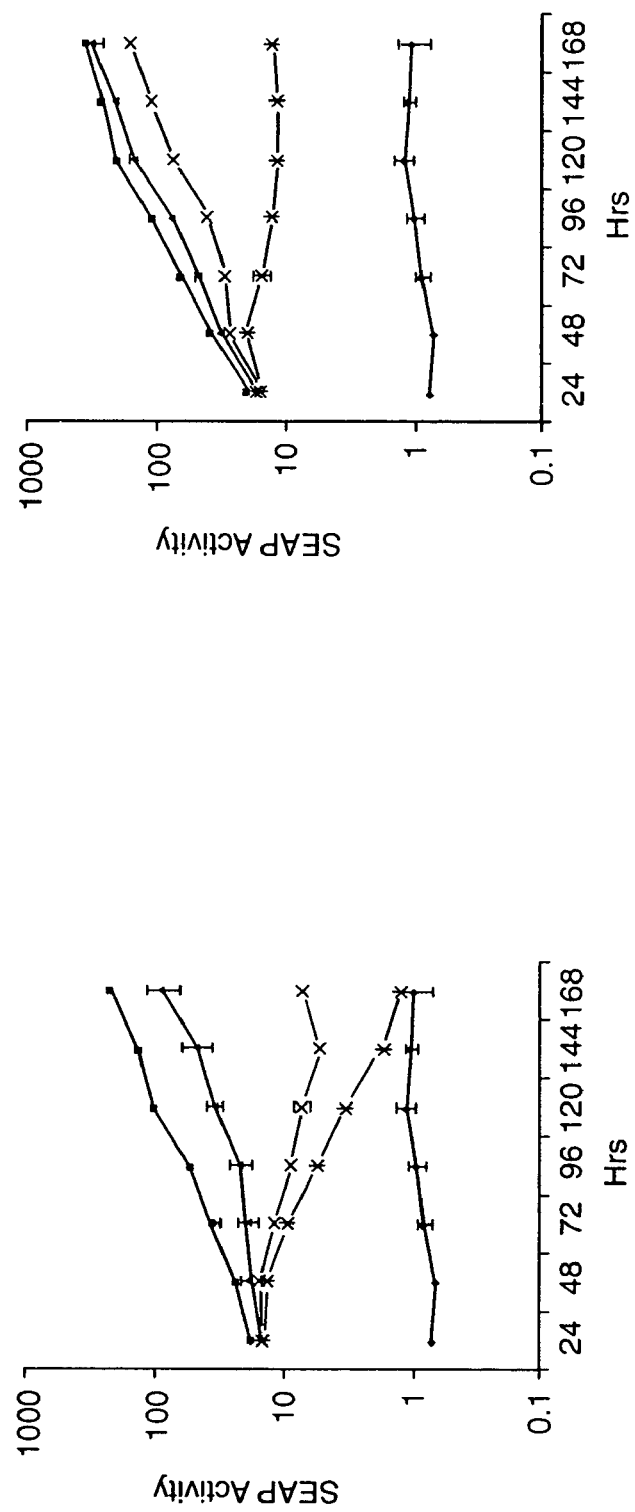
Figure 23B:
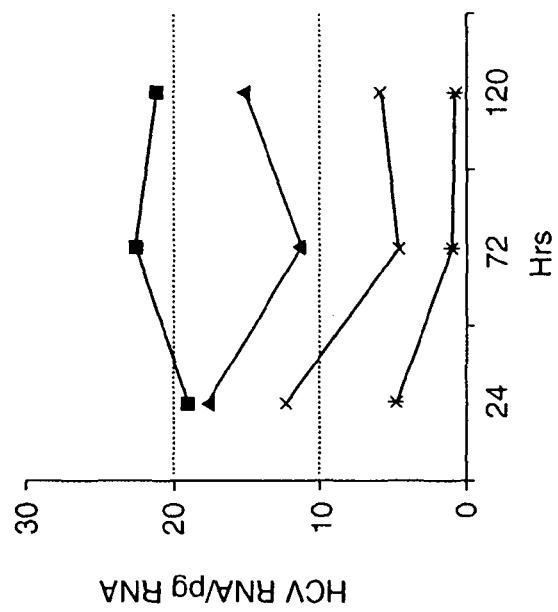
FIG. 23. Suppression of HCV replicon RNA abundance by interferon-α2b in the cell cultures depicted in FIG. 22. (A) Intracellular abundance of HCV RNA in cells supporting replication of Btat2ANeo(SI) at 24, 72 and 120 hrs following addition of interferon to the medium. (B) RNA abundance in Ntat2ANeo(RG) cells under similar conditions. HCV RNA was quantified by RT-PCR analysis, and normalized to a total cellular RNA standard (see legend to FIG. 19B). Interferon concentrations were: (*) 100 units/ml; (X) 10 units/ml; (▲) 1 unit/ml; (■) no interferon.
Figure 23A:
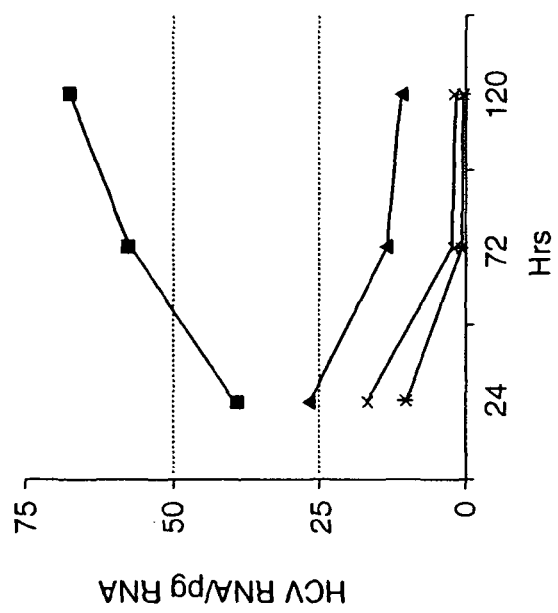

Surprisingly, the Ntat2ANeo(RG) replicon (FIG. 22B) was approximately 10-fold more resistant to interferon than the Btat2ANeo(SI) replicon (FIG. 22A). This relative interferon resistance was reflected also in differences in the degree of suppression of the intracellular abundance of HCV RNA following interferon treatment of these cells (compare the decrease in Btat2ANeo(SI) RNA abundance at different interferon concentrations in FIG. 23A, with the decreases in Ntat2ANeo(RG) RNA abundance shown in FIG. 23B). A similar level of interferon resistance was observed in separate experiments with an independently selected, G418-resistant clone supporting the replication of the Ntat2ANeo(RG) replicon, suggesting that the resistance observed in FIGS. 22B and 23B was not an idiosyncratic feature of the particular cell clone tested. Studies are currently in progress to determine the molecular basis of this difference in the response of the two replicons to interferon-α2b.

Discussion

We have described here an enzymatic reporter system that permits the detection and quantitation of HCV RNA replication in intact cell monolayers. The system is based on the expression of the tat transactivator protein by replicating subgenomic RNA replicons, and the subsequent induction of SEAP synthesis in En5-3 cells that contain the SEAP gene under transcriptional control of the HIV LTR promoter. SEAP is secreted efficiently into the medium bathing these cells, where it is readily quantified as an accurate marker of viral RNA abundance. We adapted both Con-1 and HCV-N replicons for use in this system, and have shown that the induction of SEAP is a useful measure of the replicon RNA abundance in stable, G418-resistant cell lines (FIG. 20), as well as in cells that have been transiently transfected by these RNAs (FIG. 21). Parallel measurements of RNA abundance and SEAP expression in two separate stable cell lines demonstrated a remarkable degree of correlation (FIG. 20B), providing strong validation of the system.

We have utilized this system to document the inhibition of HCV-N and Con-1 HCV RNA replication in En5-3 cells following treatment with recombinant interferon-α2B (FIG. 22 and FIG. 23). We found Ntat2ANeo(RG) to be about 10-fold less sensitive to interferon than Btat2ANeo(SI). These results differ from those reported recently by Guo et al. (*J. Virol.*, 75, 8516-8523 (2001)), who found comparable interferon sensitivities with simple subgenomic dicistronic replicons constructed from these two viral sequences. We are currently investigating the molecular basis of the difference we observed in the interferon responsiveness of these replicons. Using the tat-expressing replicons, we have also been able to demonstrate the inhibition of viral RNA replication by prototype antiviral compounds that have activity against the viral NS3 proteinase or NS5B RNA-dependent, RNA polymerase. Thus, we believe that this unique and simple system for monitoring viral RNA replication is likely to prove useful in future antiviral drug discovery efforts.

Because measurements of SEAP are technically simpler and considerably less expensive than quantitative RT-PCR assays for viral RNA, this system is likely to prove advantageous for high throughput screening for compounds with antiviral activity. An additional technical advantage over HCV replicons that express luciferase or most other conventional reporter proteins is that SEAP activity is measured in supernatant culture fluids and does not require the lysis of cells. This permits serial measurements of the kinetics of RNA amplification in single cultures of cells (FIG. 21). One potential drawback of this system is that suppression of SEAP activity by candidate antiviral compounds could result from inhibition of the activity of either the 2A protease or tat, or even (as with other published dicistronic HCV replicons) the EMCV IRES. To address this issue, we established a stably transformed cell line that constitutively expresses the tat2ANeo polyprotein under the translational control of the EMCV IRES. This cell line (Et2AN) was established by transfection of pEt2AN DNA (FIG. 16) into En5-3 cells, followed by selection with G418. In contrast to the results shown in FIG. 22, where interferon-α2B suppressed the secretion of SEAP from the replicon-bearing cell lines, there was no suppression of the secretion of SEAP by the Et2AN cell line at comparable concentrations of interferon. This indicates that the effect of interferon-α2B on SEAP secretion from the replicon cell line was due to specific suppression of the replication of HCV RNA, and not the fortuitous suppression of 2A, tat, or EMCV IRES activity. It also demonstrates the absence of nonspecific toxicity at the concentrations of interferon tested, and is consistent with the suppression of HCV RNA abundance in these cells shown in FIG. 23.

In developing these replicons, we have shown that none of the viral core protein-coding sequence is required for replication of HCV RNA. There has been considerable controversy over the role of this sequence in viral translation since Reynolds et al. (*RNA*, 2, 867-878 (1996)) first suggested that the 5' proximal 33 nts of the core sequence were an integral part of the viral IRES and required for efficient cap-independent translation. Recently, however, Rijinbrand et al. (*RNA*, 7, 585-597 (2001)) demonstrated that the requirement is not for any specific sequence, but rather for a lack of secondary RNA structure within the core-coding sequence immediately downstream of the initiator AUG. This is consistent with prior work by Honda et al. (*RNA*, 2, 955-968 (1996)) that indicated that stable RNA structure within the vicinity of the AUG is very detrimental to IRES-directed translation. Because of concerns that the 5' proximal core coding sequence might be required for optimal activity of the HCV IRES, the original dicistronic, subgenomic HCV replicons that were constructed by Lohmann et al. (*Science*, 285, 110-113 (1999)) contained RNA encoding 12 or 16 amino acids of the core protein fused in-frame to the Neo gene in the upstream cistron. We found that replicons in which the tat sequence was fused directly to the HCV IRES had reduced translation of the upstream tat2ANeo mini-polyprotein (FIG. 17A), but were nonetheless capable of replication and the transduction of G418-resistant cell lines. These results demonstrate that none of the core coding sequence is required for viral RNA replication. Other subgenomic HCV replicons have recently been described in which all core protein sequence had been removed, but in these replicons translation of the upstream cistron was driven by a picornaviral IRES and the HCV 5'NTR sequence functioned only in template recognition by the RNA replicase complex (Kim et al., *Biochem Biophys Res Commun*, 290, 105-112 (2002)).

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the beading, unless so specified.

What is claimed is:

1. An isolated replication competent HCV polynucleotide comprising:
a first coding sequence encoding a subgenomic hepatitis C virus polyprotein;

a heterologous polynucleotide comprising a second coding sequence encoding a transactivator, wherein the HCV comprises a 3' non-translated RNA, and wherein the heterologous polynucleotide is located in the 3' non-translated RNA or 5' of the first coding sequence, wherein the first coding sequence is operably linked to a first regulatory region and the second coding sequence is operably linked to a second regulatory region, and wherein the first and second regulatory regions each comprise an internal ribosome entry segment.

2. The replication competent HCV polynucleotide of claim 1 wherein the heterologous polynucleotide further comprises a third coding sequence encoding a selectable marker, and wherein the second coding sequence and the third coding sequence together encode a fusion polypeptide.

3. The replication competent HCV polynucleotide of claim 2 wherein the heterologous polynucleotide further comprises a fourth coding sequence encoding a cis-active proteinase present between the second coding sequence encoding the transactivator and the third coding sequence encoding the selectable marker, and wherein the second coding sequence, the fourth coding sequence, and the third coding sequence together encode a fusion polypeptide.

4. The replication competent HCV polynucleotide of claim 1 wherein the transactivator comprises an amino acid sequence comprising at least about 95% identity with an amino acid sequence selected from the group consisting of SEQ ID NO:19 and amino acids 4-89 of SEQ ID NO:21, and wherein the transactivator has tat activity.

5. The replication competent HCV polynucleotide of claim 1 wherein the polynucleotide is an RNA polynucleotide.

6. The replication competent HCV polynucleotide of claim 1 wherein the polynucleotide is a DNA polynucleotide.

7. The replication competent HCV polynucleotide of claim 6 wherein the DNA polynucleotide is present in a vector.

8. The replication competent HCV polynucleotide of claim 1 wherein the replication competent HCV polynucleotide is genotype 1a or 1b.

9. The replication competent HCV polynucleotide of claim 1 wherein the second coding sequence does not comprise nucleotides encoding viral core protein.

10. An isolated replication competent HCV polynucleotide comprising a first coding sequence encoding a hepatitis C virus polyprotein, and a heterologous polynucleotide, wherein the heterologous polynucleotide comprises a second coding sequence, and wherein the second coding sequence encodes a transactivator, wherein the first coding sequence is operably linked to a first regulatory region and the second coding sequence is operably linked to a second regulatory region, and wherein the first and second regulatory regions each comprise an internal ribosome entry segment.

11. The replication competent HCV polynucleotide of claim 10 wherein the HCV comprises a 3' non-translated RNA, and wherein the heterologous polynucleotide is present in the 3' non-translated RNA or 5' of the coding sequence.

12. The replication competent HCV polynucleotide of claim 10 wherein the second coding sequence encodes a selectable marker or a detectable marker.

13. The replication competent HCV polynucleotide of claim 10 wherein the transactivator comprises an amino acid sequence comprising at least about 95% identity with an amino acid sequence selected from the group consisting of SEQ ID NO:19 and amino acids 4-89 of SEQ ID NO:21, and wherein the transactivator has tat activity.

14. The replication competent HCV polynucleotide of claim 10 wherein the heterologous polynucleotide further comprises a third coding sequence encoding a selectable marker, and wherein the second coding sequence and the third coding sequence together encode a fusion polypeptide.

15. The replication competent HCV polynucleotide of claim 14 wherein the heterologous polynucleotide further comprises a fourth coding sequence encoding a cis-active proteinase present between the second coding sequence encoding the transactivator and the third coding sequence encoding the selectable marker, and wherein the second coding sequence, the fourth coding sequence, and the third coding sequence together encode a fusion polypeptide.

16. The replication competent HCV polynucleotide of claim 10 wherein the replication competent HCV polynucleotide is an RNA polynucleotide.

17. The replication competent HCV polynucleotide of claim 10 wherein the replication competent HCV polynucleotide is a DNA polynucleotide.

18. The replication competent HCV polynucleotide of claim 17 wherein the DNA polynucleotide is present in a vector.

19. The replication competent HCV polynucleotide of claim 10 wherein the replication competent HCV polynucleotide is genotype 1a or 1b.

20. The replication competent HCV polynucleotide of claim 10 wherein the second coding sequence does not comprise nucleotides encoding viral core protein.

* * * * *

SEQUENCE LISTING

```
<160> NUMBER OF SEQ ID NOS: 76

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
aagactgcta gccgagtagt gtt                                           23

<210> SEQ ID NO 2
<211> LENGTH: 21
<212> TYPE: DNA
<213> ORGANISM: artificial
<220> FEATURE:
<223> OTHER INFORMATION: Primer

<400> SEQUENCE: 2
ggttggtgtt acgtttggtt t                                             21

<210> SEQ ID NO 3
<211> LENGTH: 24
<212> TYPE: DNA
<213> ORGANISM: artificial
<220> FEATURE:
<223> OTHER INFORMATION: Probe

<400> SEQUENCE: 3
tgcaccatga gcacgaatcc taaa                                          24

<210> SEQ ID NO 4
<211> LENGTH: 21
<212> TYPE: DNA
<213> ORGANISM: artificial
<220> FEATURE:
<223> OTHER INFORMATION: Primer

<400> SEQUENCE: 4
acactccacc atgaatcact c                                             21

<210> SEQ ID NO 5
<211> LENGTH: 20
```

-continued

<212> TYPE: DNA
<213> ORGANISM: artificial
<220> FEATURE:
<223> OTHER INFORMATION: Primer

<400> SEQUENCE: 5
gatcgggctc atcacaaccc                                           20

<210> SEQ ID NO 6
<211> LENGTH: 27
<212> TYPE: DNA
<213> ORGANISM: artificial
<220> FEATURE:
<223> OTHER INFORMATION: Fluor probe
<220> FEATURE:
<221> NAME/KEY: misc_difference
<222> LOCATION: (27)..(27)
<223> OTHER INFORMATION: Labeled with fluorescein

<400> SEQUENCE: 6
gcgtctagcc atggcgttag tatgagt                                   27

<210> SEQ ID NO 7
<211> LENGTH: 21
<212> TYPE: DNA
<213> ORGANISM: artificial
<220> FEATURE:
<223> OTHER INFORMATION: Red probe
<220> FEATURE:
<221> NAME/KEY: misc_difference
<222> LOCATION: (1)..(1)
<223> OTHER INFORMATION: LC640 labeled

<400> SEQUENCE: 7
tcgtgcagcc tccaggaccc c                                         21

<210> SEQ ID NO 8
<211> LENGTH: 33
<212> TYPE: DNA
<213> ORGANISM: artificial
<220> FEATURE:
<223> OTHER INFORMATION: Primer

<400> SEQUENCE: 8
ctagctagcc tcgagacctg gaaaaacatg gag                            33

<210> SEQ ID NO 9
<211> LENGTH: 33
<212> TYPE: DNA
<213> ORGANISM: artificial
<220> FEATURE:
<223> OTHER INFORMATION: Primer

<400> SEQUENCE: 9
ataagaatgc ggccgcttaa cccgggtgcg cgg                            33

<210> SEQ ID NO 10
<211> LENGTH: 21
<212> TYPE: DNA
<213> ORGANISM: artificial
<220> FEATURE:
<223> OTHER INFORMATION: Primer

<400> SEQUENCE: 10
gacactccac catgaatcac t                                         21

<210> SEQ ID NO 11
<211> LENGTH: 19

```
<212> TYPE: DNA
<213> ORGANISM: artificial
<220> FEATURE:
<223> OTHER INFORMATION: Primer

<400> SEQUENCE: 11
gttccgcaga ccactatgg                                              19

<210> SEQ ID NO 12
<211> LENGTH: 25
<212> TYPE: DNA
<213> ORGANISM: artificial
<220> FEATURE:
<223> OTHER INFORMATION: Probe
<220> FEATURE:
<221> NAME/KEY: misc_difference
<222> LOCATION: (25)..(25)
<223> OTHER INFORMATION: Labeled with fluorescein

<400> SEQUENCE: 12
agaaagcgtc tagccatggc gttag                                       25

<210> SEQ ID NO 13
<211> LENGTH: 22
<212> TYPE: DNA
<213> ORGANISM: artificial
<220> FEATURE:
<223> OTHER INFORMATION: Probe
<220> FEATURE:
<221> NAME/KEY: misc_difference
<222> LOCATION: (1)..(1)
<223> OTHER INFORMATION: LC640 labeled
<220> FEATURE:
<221> NAME/KEY: misc_difference
<222> LOCATION: (22)..(22)
<223> OTHER INFORMATION: phosphate

<400> SEQUENCE: 13
atgagtgtcg tgcagcctcc ag                                          22

<210> SEQ ID NO 14
<211> LENGTH: 17
<212> TYPE: DNA
<213> ORGANISM: artificial
<220> FEATURE:
<223> OTHER INFORMATION: Primer

<400> SEQUENCE: 14
cgggagagcc atagtgg                                                17

<210> SEQ ID NO 15
<211> LENGTH: 19
<212> TYPE: DNA
<213> ORGANISM: artificial
<220> FEATURE:
<223> OTHER INFORMATION: Primer

<400> SEQUENCE: 15
agtaccacaa ggcctttcg                                              19

<210> SEQ ID NO 16
<211> LENGTH: 21
<212> TYPE: DNA
<213> ORGANISM: artificial
<220> FEATURE:
<223> OTHER INFORMATION: Probe
<220> FEATURE:
<221> NAME/KEY: misc_difference
<222> LOCATION: (21)..(21)
<223> OTHER INFORMATION: Labeled with TAMRA
```

<400> SEQUENCE: 16
ctgcggaacc ggtgagtaca c                                          21

<210> SEQ ID NO 17
<211> LENGTH: 10803
<212> TYPE: DNA
<213> ORGANISM: artificial
<220> FEATURE:
<223> OTHER INFORMATION: Nucleotide sequence of MK0-Z

<400> SEQUENCE: 17
gccagccccc tgatgggggc gacactccac catgaatcac tccctgtga ggaactactg      60 tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg ataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtaccttgg cccctctatg    600 gcaatgaggg ttgcgggtgg gcgggatggc tcctgtctcc ccgtggctct cggcctagct    660
ggggccccac agaccccgg cgtaggtcgc gcaatttggg taaggtcatc gatacccta    720 cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtcgcaatt cctcgggct ttaccatgtc accaatgatt     960
gccctaactc gagtattgtg tacgaggcgg ccgatgccat cctgcacact ccggggtgtg    1020
tcccttgcgt tcgcgagggt aacgcctcga ggtgttgggt ggcggtgacc cccacggtgg    1080
ccaccaggga cggcaaactc cccacaacgc agcttgacg tcatatcgat ctgcttgtcg    1140
ggagcgccac cctctgctcg gccctctacg tgggggacct gtgcgggtct gtctttcttg    1200
ttggtcaact gtttaccttc tctcccaggc gccactggac gacgcaagac tgcaattgtt    1260
ctatctatcc cggccatata acgggtcatc gcatggcatg ggatatgatg atgaactggt    1320 ccctacggc agcgttggtg gtagctcagc tgctccggat cccacaagcc atcatggaca    1380
tgatcgctgg tgctcactgg ggagtcctgg cgggcatagc gtatttctcc atggtgggga    1440
actgggcgaa ggtcctggta gtgctgctgc tatttgccgg cgtcgacgcg gaaacccacg    1500
tcaccggggg aaatgccggc cgcaccacgg ctgggcttgt tggtctcctt acaccaggcg    1560
ccaagcagaa catccaactg atcaacacca acggcagttg gcacatcaat gcacggcct    1620 tgaattgcaa tgaaagcctt aacaccggct ggttagcagg gctcttctat caacacaaat    1680
tcaactcttc aggctgtcct gagaggttgg ccagctgccg acgccttacc gattttgccc    1740
agggctgggg tcctatcagt tatgccaacg gaagcggcct cgacgaacgc ccctactgct    1800
ggcactaccc tccaagacct tgtggcattg tgcccgcaaa gagcgtgtgt ggcccggtat    1860
attgcttcac tcccagcccc gtggtggtgg gaacgaccga caggtcgggc gcgcctacct    1920
acagctgggg tgcaaatgat acggatgtct tcgtccttaa caacaccagg ccaccgctgg    1980

```
gcaattggtt cggttgtacc tggatgaact caactggatt caccaaagtg tgcggagcgc   2040
ccccttgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctaccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata tcaatgcag catccctggc cgggacgcac ggtcttgtgt   2640
ccttcctcgt gttcttctgc tttgcgtggt atctgaaggg taggtgggtg cccggagcgg   2700
tctacgccct ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
agtattttct gaccagagta gaagcgcaac tgcacgtgtg ggttcccccc ctcaacgtcc   2940
ggggggggcg cgatgccgtc atcttactca tgtgtgtagt acacccgacc ctggtatttg   3000
acatcaccaa actactcctg gccatcttcg gaccccttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc accctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgt acctgcggct   3720
cctcggacct ttacctggtc acgaggcacg ccgatgtcat tcccgtgcgc cggcgaggtg   3780
atagcagggg tagcctgctt tcgccccggc ccatttccta cttgaaaggc tcctcggggg   3840
gtccgctgtt gtgccccgcg ggacacgccg tgggcctatt cagggccgcg gtgtgcaccc   3900
gtggagtggc taaagcggtg gactttatcc ctgtggagaa cctagggaca accatgagat   3960
ccccggtgtt cacggacaac tcctctccac cagcagtgcc ccagagcttc caggtggccc   4020
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
```

```
ccactgctac ccctccgggc tccgtcactg tgtcccatcc taacatcgag gaggttgctc    4440
tgtccaccac cggagagatc ccctttacg gcaaggctat cccctcgag gtgatcaagg     4500 ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccggggagc   4860 gccctccgg catgttcgac tcgtccgtcc tctgtgagtg ctatgacgcg ggctgtgctt   4920
ggtatgagct cacgcccgcc gagactacag ttaggctacg agcgtacatg aacacccgg   4980 ggcttcccgt gtgccaggac catcttgaat tttgggaggg cgtctttacg ggcctcactc   5040
atatagatgc ccactttta tcccagacaa agcagagtgg ggagaacttt ccttacctgg    5100
tagcgtacca agccaccgtg tgcgctaggg ctcaagcccc tccccatcg tgggaccaga    5160 tgtggaagtg tttgatccgc cttaaaccca ccctccatgg gccaacaccc ctgctataca   5220
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggatcg   5400
tcttgtccgg gaagccggca attatacctg acagggaggt tctctaccag gagttcgatg   5460
agatggaaga gtgctctcag cacttaccgt acatcgagca agggatgatg ctcgctgagc   5520
agttcaagca gaaggcccctc ggcctcctgc agaccgcgtc ccgccatgca gaggttatca   5580
cccctgctgt ccagaccaac tggcagaaac tcgaggtctt tgggcgaag cacatgtgga   5640 atttcatcag tgggatacaa tacttggcgg gcctgtcaac gctgcctggt aaccccgcca   5700
ttgcttcatt gatggctttt acagctgccg tcaccagccc actaaccact ggccaaaccc   5760
tcctcttcaa catattgggg gggtgggtgg ctgcccagct cgccgccccc ggtgccgcta   5820
ctgcctttgt gggtgctggc ctagctggcg ccgccatcgg cagcgttgga ctggggaagg   5880
tcctcgtgga cattcttgca gggtatgcgc cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccggggga   6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg gggtctggcg aggagacggc attatgcaca   6420
ctcgctgcca ctgtggagct gagatcactg gacatgtcaa aaacgggacg atgaggatcg   6480
tcggtcctag gacctgcagg aacatgtgga gtgggacgtt ccccattaac gcctacacca   6540
cgggcccctg tactcccctt cctgcgccga ctataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga ttttttcaca gaattggacg   6720
gggtgcgcct acacaggttt gcgccccctt gcaagccctt gctgcgggag gaggtatcat   6780
```

```
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcacccccctt ctatggccag ctcctcggct agccagctgt   6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acctgcagaa attctgcgga agtctcggag attcgcccgg gccctgcccg    7200
tctgggcgcg gccggactac aaccccccgc tagtagagac gtggaaaaag cctgactacg    7260
aaccacctgt ggtccatggc tgcccgctac cacctccacg gtcccctcct gtgcctccgc    7320
ctcggaaaaa gcgtacggtg gtcctcaccg aatcaaccct atctactgcc ttggccgagc    7380
ttgccaccaa aagttttggc agctcctcaa cttccggcat tacgggcgac aatacgacaa    7440
catcctctga gcccgcccct tctggctgcc ccccgactc cgacgttgag tcctattctt    7500
ccatgccccc cctggagggg gagcctgggg atccggatct cagcgacggg tcatggtcga    7560
cggtcagtag tggggccgac acggaagatg tcgtgtgctg ctcaatgtct tattcctgga    7620
caggcgcact cgtcaccccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga aagggggggt cgtaagccag ctcgtctcat cgtgttcccc gacctgggcg    8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccgatggggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacacctc acttgctaca tcaaggcccg ggcagcctgt cgagccgcag    8520
ggctccagga ctgcaccatg ctcgtgtgtg gcgacgactt agtcgttatc tgtgaaagtg    8580
cgggggtcca ggaggacgcg gcgagcctga gagccttcac ggaggctatg accaggtact    8640
ccgccccccc cggggacccc ccacaaccag aatacgactt ggagcttata acatcatgct    8700
cctccaacgt gtcagtcgcc cacgacgcg ctggaaagag ggtctactac cttacccgtg    8760
accctacaac ccccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacgcgag ctgctactcc atagaaccac tggatctacc tccaatcatt caaagactcc    9000
atggcctcag cgcattttca ctccacagtt actctccagg tgaaatcaat agggtggccg    9060
catgcctcag aaaacttggg gtcccgccct tgcgagcttg agacaccgg gcccggagcc    9120 tccgcgctag gcttctgtcc agaggaggca gggctgccat atgtggcaag tacctcttca    9180
```

```
actgggcagt aagaacaaag ctcaaactca ctccaatagc ggccgctggc cggctggact      9240
tgtccggttg gttcacggct ggctacagcg ggggagacat ttatcacagc gtgtctcatg      9300
cccggccccg ctggttctgg ttttgcctac tcctgctcgc tgcaggggta ggcatctacc      9360
tcctccccaa ccgatgaagg ttggggtaaa cactccggcc tcttaaggtt attttccacc      9420
atattgccgt cttttggcaa tgtgagggcc cggaaacctg gccctgtctt cttgacgagc      9480
attcctaggg gtctttcccc tctcgccaaa ggaatgcaag gtctgttgaa tgtcgtgaag      9540
gaagcagttc ctctggaagc ttcttgaaga caaacaacgt ctgtagcgac cctttgcagg      9600
cagcggaacc ccccacctgg cgacaggtgc ctctgcggcc aaaagccacg tgtataagat      9660
acacctgcaa aggcggcaca accccagtgc cacgttgtga gttggatagt tgtgaaaga      9720 gtcaaatggc tctcctcaag cgtattcaac aaggggctga aggatgccca gaaggtaccc      9780
cattgtatgg gatctgatct ggggcctcgg tgcacatgct ttacgtgtgt ttagtcgagg      9840
ttaaaaaacg tctaggcccc ccgaaccacg ggacgtggt tttcctttga aaaacacgat      9900
gataatatga ggcctatgga gccagtagat cctagactag agccctggaa gcatccagga      9960
agtcagccta aaactgcttg taccaattgc tattgtaaaa agtgttgctt tcattgccaa      10020
gtttgtttca taacaaaagc cttaggcatc tcctatggca ggaagaagcg gagacagcga      10080
cgaagacctc ctcaaggcag tcagactcat caagtttctc tatcaaagca cccacctcc      10140 caatcccgag gggacccgac aggcccgaag gaagaattcg accttcttaa gcttgcggga      10200
gacgtcgagt ccaaccctgg gcccggatcc atggccaagt tgaccagtgc cgttccggtg      10260
ctcaccgcgc gcgacgtcgc cggagcggtc gagttctgga ccgaccggct cgggttctcc      10320
cgggacttcg tggaggacga cttcgccggt gtggtccggg acgacgtgac cctgttcatc      10380
agcgcggtcc aggaccaggt ggtgccggac aacaccctgg cctgggtgtg ggtgcgcggc      10440
ctggacgagc tgtacgccga gtggtcgag gtcgtgtcca cgaacttccg ggacgcctcc      10500
gggccggcca tgaccgagat cggcgagcag ccgtgggggc gggagttcgc cctgcgcgac      10560
ccggccggca actgcgtgca cttcgtggcc gaggagcagg actgacttaa gccatttcct      10620
gttttttttt tttttttttt tttttttttc tttttttttt tctttccttt ccttcttttt      10680
ttcctttctt tttcccttct ttaatggtgg ctccatctta gccctagtca cggctagctg      10740
tgaaaggtcc gtgagccgca tgactgcaga gagtgctgat actggcctct ctgcagatca      10800
tgt                                                                   10803
```

<210> SEQ ID NO 18
<211> LENGTH: 2239
<212> TYPE: DNA
<213> ORGANISM: artificial
<220> FEATURE:
<223> OTHER INFORMATION: Nucleotide sequence of HIVSEAP

<400> SEQUENCE: 18

```
acctggaaaa acatggagca atcacaagta gcaatacagc agctaccaat gctgcttgtg        60
cctggctaga agcacaagag gaggaggagg tgggttttcc agtcacacct caggtacctt       120
taagaccaat gacttacaag gcagctgtag atcttagcca cttttaaaa gaaaaggggg        180 gactggaagg gctaattcac tcccaaagaa gacaagatat ccttgatctg tggatctacc       240
acacacaagg ctacttccct gattagcaga actacacacc agggccaggg gtcagatatc       300
cactgacctt tggatggtgc tacaagctag taccagttga gccagataag atagaagagg       360
ccaataaagg agagaacacc agcttgttac accctgtgag cctgcatggg atggatgacc       420
```

```
cggagagaga agtgttagag tggaggtttg acagccgcct agcatttcat cacgtggccc    480
gagagctgca tccggagtac ttcaagaact gctgacatcg agcttgctac aagggacttt    540
ccgctgggga cttccaggg aggcgtggcc tgggcgggac tggggagtgg cgagccctca     600
gatcctgcat ataagcagct gcttttgcc tgtactgggt ctctctggtt agaccagatc     660
tgagcctggg agctctctgg ctaactaggg aacccactgc ttaagcctca ataaagcttc    720
tgcatgctgc tgctgctgct gctgctgggc ctgaggctac agctctccct gggcatcatc    780
ccagttgagg aggagaaccc ggacttctgg aaccgcgagg cagccgaggc cctgggtgcc    840
gccaagaagc tgcagcctgc acagacagcc gccaagaacc tcatcatctt cctgggcgat    900
gggatggggg tgtctacggt gacagctgcc aggatcctaa aagggcagaa gaaggacaaa    960
ctggggcctg agatacccct ggccatggac cgcttcccat atgtggctct gtccaagaca   1020
tacaatgtag acaaacatgt gccagacagt ggagccacag ccacggccta cctgtgcggg   1080
gtcaagggca acttccagac cattggcttg agtgcagccg cccgctttaa ccagtgcaac   1140
acgacacgcg gcaacgaggt catctccgtg atgaatcggg ccaagaaagc agggaagtca   1200
gtgggagtgg taaccaccac acgagtgcag cacgcctcgc cagccggcac ctacgcccac   1260
acggtgaacc gcaactggta ctcggacgcc gacgtgcctg cctcggcccg ccaggagggg   1320
tgccaggaca tcgctacgca gctcatctcc aacatggaca ttgacgtgat cctaggtgga   1380
ggccgaaagt acatgtttcc catgggaacc ccagaccctg agtacccaga tgactacagc   1440
caaggtggga ccaggctgga cgggaagaat ctggtgcagg aatggctggc gaagcgccag   1500
ggtgcccggt atgtgtggaa ccgcactgag ctcatgcagg cttccctgga cccgtctgtg   1560
acccatctca tgggtctctt tgagcctgga gacatgaaat acgagatcca ccgagactcc   1620
acactggacc cctccctgat ggagatgaca gaggctgccc tgcgcctgct gagcaggaac   1680
ccccgcggct tcttcctctt cgtggagggt ggtcgcatcg accatggtca tcatgaaagc   1740
agggcttacc gggcactgac tgagacgatc atgttcgacg acgccattga gagggcgggc   1800
cagctcacca gcgaggagga cacgctgagc ctcgtcactg ccgaccactc ccacgtcttc   1860
tccttcggag gctaccccct gcgagggagc tccatcttcg ggctggcccc tggcaaggcc   1920
cgggacagga aggcctacac ggtcctccta tacggaaacg gtccaggcta tgtgctcaag   1980
gacggcgccc ggccggatgt taccgagagc gagagcggga gccccgagta tcggcagcag   2040
tcagcagtgc ccctggacga agagacccac gcaggcgagg acgtggcggt gttcgcgcgc   2100
ggcccgcagg cgcacctggt tcacggcgtg caggagcaga ccttcatagc gcacgtcatg   2160
gccttcgccg cctgcctgga gcctacacc gcctgcgacc tggcgccccc cgccggcacc   2220
accgacgccg cgcacccgg                                                2239

<210> SEQ ID NO 19
<211> LENGTH: 86
<212> TYPE: PRT
<213> ORGANISM: HIV

<400> SEQUENCE: 19

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45
```

Arg Lys Lys Arg Arg Gln Arg Arg Ala His Gln Asn Ser Gln Thr
50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 20
<211> LENGTH: 3011
<212> TYPE: PRT
<213> ORGANISM: artificial
<220> FEATURE:
<223> OTHER INFORMATION: Polyprotein

<400> SEQUENCE: 20

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln

-continued

```
                325                 330                 335
Leu Leu Arg Ile Pro Gln Ala Ile Met Asp Met Ile Ala Gly Ala His
            340                 345                 350
Trp Gly Val Leu Ala Gly Ile Ala Tyr Phe Ser Met Val Gly Asn Trp
            355                 360                 365
Ala Lys Val Leu Val Val Leu Leu Phe Ala Gly Val Asp Ala Glu
            370                 375                 380
Thr His Val Thr Gly Gly Asn Ala Gly Arg Thr Thr Ala Gly Leu Val
385                 390                 395                 400
Gly Leu Leu Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Glu Ser
                420                 425                 430
Leu Asn Thr Gly Trp Leu Ala Gly Leu Phe Tyr Gln His Lys Phe Asn
        435                 440                 445
Ser Ser Gly Cys Pro Glu Arg Leu Ala Ser Cys Arg Arg Leu Thr Asp
    450                 455                 460
Phe Ala Gln Gly Trp Gly Pro Ile Ser Tyr Ala Asn Gly Ser Gly Leu
465                 470                 475                 480
Asp Glu Arg Pro Tyr Cys Trp His Tyr Pro Arg Pro Cys Gly Ile
                485                 490                 495
Val Pro Ala Lys Ser Val Cys Gly Pro Val Tyr Cys Phe Thr Pro Ser
                500                 505                 510
Pro Val Val Val Gly Thr Thr Asp Arg Ser Gly Ala Pro Thr Tyr Ser
                515                 520                 525
Trp Gly Ala Asn Asp Thr Asp Val Phe Val Leu Asn Asn Thr Arg Pro
            530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Val Gly Asn
                565                 570                 575
Asn Thr Leu Leu Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Met
        595                 600                 605
Val Asp Tyr Pro Tyr Arg Leu Trp His Tyr Pro Cys Thr Ile Asn Tyr
    610                 615                 620
Thr Ile Phe Lys Val Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Gln Trp
            660                 665                 670
Gln Val Leu Pro Cys Ser Phe Thr Thr Leu Pro Ala Leu Ser Thr Gly
        675                 680                 685
Leu Ile His Leu His Gln Asn Ile Val Asp Val Gln Tyr Leu Tyr Gly
    690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
            740                 745                 750
```

-continued

```
Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Leu Gln Tyr
                835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Ile
                915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
            995                 1000                1005

Glu Ile Leu Leu Gly Pro Ala Asp Gly Met Val Ser Lys Gly Trp
        1010                1015                1020

Arg Leu Leu Ala Pro Ile Thr Ala Tyr Ala Gln Gln Thr Arg Gly
        1025                1030                1035

Leu Leu Gly Cys Ile Ile Thr Ser Leu Thr Gly Arg Asp Lys Asn
        1040                1045                1050

Gln Val Glu Gly Glu Val Gln Ile Val Ser Thr Ala Thr Gln Thr
        1055                1060                1065

Phe Leu Ala Thr Cys Ile Asn Gly Val Cys Trp Thr Val Tyr His
        1070                1075                1080

Gly Ala Gly Thr Arg Thr Ile Ala Ser Pro Lys Gly Pro Val Ile
        1085                1090                1095

Gln Met Tyr Thr Asn Val Asp Gln Asp Leu Val Gly Trp Pro Ala
        1100                1105                1110

Pro Gln Gly Ser Arg Ser Leu Thr Pro Cys Thr Cys Gly Ser Ser
        1115                1120                1125

Asp Leu Tyr Leu Val Thr Arg His Ala Asp Val Ile Pro Val Arg
        1130                1135                1140

Arg Arg Gly Asp Ser Arg Gly Ser Leu Leu Ser Pro Arg Pro Ile
        1145                1150                1155

Ser Tyr Leu Lys Gly Ser Ser Gly Gly Pro Leu Leu Cys Pro Ala
        1160                1165                1170
```

```
Gly His Ala Val Gly Leu Phe Arg Ala Ala Val Cys Thr Arg Gly
    1175                1180                1185

Val Ala Lys Ala Val Asp Phe Ile Pro Val Glu Asn Leu Gly Thr
    1190                1195                1200

Thr Met Arg Ser Pro Val Phe Thr Asp Asn Ser Ser Pro Pro Ala
    1205                1210                1215

Val Pro Gln Ser Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Met Ser Lys Ala His Gly Val Asp Pro Asn Ile
    1265                1270                1275

Arg Thr Gly Val Arg Thr Ile Thr Thr Gly Ser Pro Ile Thr Tyr
    1280                1285                1290

Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ala
    1310                1315                1320

Thr Ser Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Val Thr Val Ser His Pro Asn Ile Glu Glu Val Ala Leu Ser
    1355                1360                1365

Thr Thr Gly Glu Ile Pro Phe Tyr Gly Lys Ala Ile Pro Leu Glu
    1370                1375                1380

Val Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Val Ser Thr Asp Ala Leu Met Thr Gly
    1430                1435                1440

Phe Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Thr Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Met Asn Thr Pro Gly Leu
    1535                1540                1545

Pro Val Cys Gln Asp His Leu Glu Phe Trp Glu Gly Val Phe Thr
    1550                1555                1560

Gly Leu Thr His Ile Asp Ala His Phe Leu Ser Gln Thr Lys Gln
```

-continued

```
              1565                1570                1575

Ser Gly Glu Asn Phe Pro Tyr Leu Val Ala Tyr Gln Ala Thr Val
    1580                1585                1590

Cys Ala Arg Ala Gln Ala Pro Pro Ser Trp Asp Gln Met Trp
    1595                1600                1605

Lys Cys Leu Ile Arg Leu Lys Pro Thr Leu His Gly Pro Thr Pro
    1610                1615                1620

Leu Leu Tyr Arg Leu Gly Ala Val Gln Asn Glu Val Thr Leu Thr
    1625                1630                1635

His Pro Ile Thr Lys Tyr Ile Met Thr Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Ser Thr Gly Cys Val Val Ile Val
    1670                1675                1680

Gly Arg Ile Val Leu Ser Gly Lys Pro Ala Ile Ile Pro Asp Arg
    1685                1690                1695

Glu Val Leu Tyr Gln Glu Phe Asp Glu Met Glu Glu Cys Ser Gln
    1700                1705                1710

His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg His Ala
    1730                1735                1740

Glu Val Ile Thr Pro Ala Val Gln Thr Asn Trp Gln Lys Leu Glu
    1745                1750                1755

Val Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ala Val Thr Ser Pro Leu Thr Thr
    1790                1795                1800

Gly Gln Thr Leu Leu Phe Asn Ile Leu Gly Gly Trp Val Ala Ala
    1805                1810                1815

Gln Leu Ala Ala Pro Gly Ala Ala Thr Ala Phe Val Gly Ala Gly
    1820                1825                1830

Leu Ala Gly Ala Ala Ile Gly Ser Val Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Val Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965
```

-continued

Thr Thr Pro Cys Ser Gly Ser Trp Leu Arg Asp Ile Trp Asp Trp
    1970            1975            1980

Ile Cys Glu Val Leu Ser Asp Phe Lys Thr Trp Leu Lys Ala Lys
    1985            1990            1995

Leu Met Pro Gln Leu Pro Gly Ile Pro Phe Val Ser Cys Gln Arg
    2000            2005            2010

Gly Tyr Arg Gly Val Trp Arg Gly Asp Gly Ile Met His Thr Arg
    2015            2020            2025

Cys His Cys Gly Ala Glu Ile Thr Gly His Val Lys Asn Gly Thr
    2030            2035            2040

Met Arg Ile Val Gly Pro Arg Thr Cys Arg Asn Met Trp Ser Gly
    2045            2050            2055

Thr Phe Pro Ile Asn Ala Tyr Thr Thr Gly Pro Cys Thr Pro Leu
    2060            2065            2070

Pro Ala Pro Asn Tyr Lys Phe Ala Leu Trp Arg Val Ser Ala Glu
    2075            2080            2085

Glu Tyr Val Glu Ile Arg Arg Val Gly Asp Phe His Tyr Val Ser
    2090            2095            2100

Gly Met Thr Thr Asp Asn Leu Lys Cys Pro Cys Gln Ile Pro Ser
    2105            2110            2115

Pro Glu Phe Phe Thr Glu Leu Asp Gly Val Arg Leu His Arg Phe
    2120            2125            2130

Ala Pro Pro Cys Lys Pro Leu Leu Arg Glu Glu Val Ser Phe Arg
    2135            2140            2145

Val Gly Leu His Glu Tyr Pro Val Gly Ser Gln Leu Pro Cys Glu
    2150            2155            2160

Pro Glu Pro Asp Val Ala Val Leu Thr Ser Met Leu Thr Asp Pro
    2165            2170            2175

Ser His Ile Thr Ala Glu Ala Ala Gly Arg Arg Leu Ala Arg Gly
    2180            2185            2190

Ser Pro Pro Ser Met Ala Ser Ser Ser Ala Ser Gln Leu Ser Ala
    2195            2200            2205

Pro Ser Leu Lys Ala Thr Cys Thr Ala Asn His Asp Ser Pro Asp
    2210            2215            2220

Ala Glu Leu Ile Glu Ala Asn Leu Leu Trp Arg Gln Glu Met Gly
    2225            2230            2235

Gly Asn Ile Thr Arg Val Glu Ser Glu Asn Lys Val Val Ile Leu
    2240            2245            2250

Asp Ser Phe Asp Pro Leu Val Ala Glu Glu Asp Glu Arg Glu Val
    2255            2260            2265

Ser Val Pro Ala Glu Ile Leu Arg Lys Ser Arg Arg Phe Ala Arg
    2270            2275            2280

Ala Leu Pro Val Trp Ala Arg Pro Asp Tyr Asn Pro Pro Leu Val
    2285            2290            2295

Glu Thr Trp Lys Lys Pro Asp Tyr Glu Pro Pro Val Val His Gly
    2300            2305            2310

Cys Pro Leu Pro Pro Arg Ser Pro Pro Val Pro Pro Pro Arg
    2315            2320            2325

Lys Lys Arg Thr Val Val Leu Thr Glu Ser Thr Leu Ser Thr Ala
    2330            2335            2340

Leu Ala Glu Leu Ala Thr Lys Ser Phe Gly Ser Ser Ser Thr Ser
    2345            2350            2355

Gly Ile Thr Gly Asp Asn Thr Thr Thr Ser Ser Glu Pro Ala Pro
    2360            2365            2370

-continued

Ser Gly Cys Pro Pro Asp Ser Asp Val Glu Ser Tyr Ser Ser Met
    2375            2380            2385

Pro Pro Leu Glu Gly Glu Pro Gly Asp Pro Asp Leu Ser Asp Gly
    2390            2395            2400

Ser Trp Ser Thr Val Ser Ser Gly Ala Asp Thr Glu Asp Val Val
    2405            2410            2415

Cys Cys Ser Met Ser Tyr Ser Trp Thr Gly Ala Leu Val Thr Pro
    2420            2425            2430

Cys Ala Ala Glu Glu Gln Lys Leu Pro Ile Asn Ala Leu Ser Asn
    2435            2440            2445

Ser Leu Leu Arg His His Asn Leu Val Tyr Ser Thr Thr Ser Arg
    2450            2455            2460

Ser Ala Cys Gln Arg Gln Lys Lys Val Thr Phe Asp Arg Leu Gln
    2465            2470            2475

Val Leu Asp Ser His Tyr Gln Asp Val Leu Lys Glu Val Lys Ala
    2480            2485            2490

Ala Ala Ser Lys Val Lys Ala Asn Leu Leu Ser Val Glu Glu Ala
    2495            2500            2505

Cys Ser Leu Thr Pro Pro His Ser Ala Lys Ser Lys Phe Gly Tyr
    2510            2515            2520

Gly Ala Lys Asp Val Arg Cys His Ala Arg Lys Ala Val Ala His
    2525            2530            2535

Ile Asn Ser Val Trp Lys Asp Leu Leu Glu Asp Ser Val Thr Pro
    2540            2545            2550

Ile Asp Thr Thr Ile Met Ala Lys Asn Glu Val Phe Cys Val Gln
    2555            2560            2565

Pro Glu Lys Gly Gly Arg Lys Pro Ala Arg Leu Ile Val Phe Pro
    2570            2575            2580

Asp Leu Gly Val Arg Val Cys Glu Lys Met Ala Leu Tyr Asp Val
    2585            2590            2595

Val Ser Lys Leu Pro Leu Ala Val Met Gly Ser Ser Tyr Gly Phe
    2600            2605            2610

Gln Tyr Ser Pro Gly Gln Arg Val Glu Phe Leu Val Gln Ala Trp
    2615            2620            2625

Lys Ser Lys Lys Thr Pro Met Gly Phe Ser Tyr Asp Thr Arg Cys
    2630            2635            2640

Phe Asp Ser Thr Val Thr Glu Ser Asp Ile Arg Thr Glu Glu Ala
    2645            2650            2655

Ile Tyr Gln Cys Cys Asp Leu Asp Pro Gln Ala Arg Val Ala Ile
    2660            2665            2670

Lys Ser Leu Thr Glu Arg Leu Tyr Val Gly Gly Pro Leu Thr Asn
    2675            2680            2685

Ser Arg Gly Glu Asn Cys Gly Tyr Arg Arg Cys Arg Ala Ser Gly
    2690            2695            2700

Val Leu Thr Thr Ser Cys Gly Asn Thr Leu Thr Cys Tyr Ile Lys
    2705            2710            2715

Ala Arg Ala Ala Cys Arg Ala Ala Gly Leu Gln Asp Cys Thr Met
    2720            2725            2730

Leu Val Cys Gly Asp Asp Leu Val Val Ile Cys Glu Ser Ala Gly
    2735            2740            2745

Val Gln Glu Asp Ala Ala Ser Leu Arg Ala Phe Thr Glu Ala Met
    2750            2755            2760

Thr Arg Tyr Ser Ala Pro Pro Gly Asp Pro Pro Gln Pro Glu Tyr

```
                  2765                2770                2775

Asp Leu Glu Leu Ile Thr Ser Cys Ser Ser Asn Val Ser Val Ala
        2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
2840                2845                2850

Ile Ala Arg Asp Gln Leu Glu Gln Ala Leu Asn Cys Glu Ile Tyr
    2855                2860                2865

Gly Ala Cys Tyr Ser Ile Glu Pro Leu Asp Leu Pro Pro Ile Ile
2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
2900                2905                2910

Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys
2930                2935                2940

Tyr Leu Phe Asn Trp Ala Val Arg Thr Lys Leu Lys Leu Thr Pro
    2945                2950                2955

Ile Ala Ala Ala Gly Arg Leu Asp Leu Ser Gly Trp Phe Thr Ala
2960                2965                2970

Gly Tyr Ser Gly Gly Asp Ile Tyr His Ser Val Ser His Ala Arg
    2975                2980                2985

Pro Arg Trp Phe Trp Phe Cys Leu Leu Leu Leu Ala Ala Gly Val
2990                2995                3000

Gly Ile Tyr Leu Leu Pro Asn Arg
    3005                3010

<210> SEQ ID NO 21
<211> LENGTH: 232
<212> TYPE: PRT
<213> ORGANISM: artificial
<220> FEATURE:
<223> OTHER INFORMATION: Amino acid sequence encoded by the
      heterologous polynucleotide

<400> SEQUENCE: 21

Met Arg Pro Met Glu Pro Val Asp Pro Arg Leu Glu Pro Trp Lys His
1               5                   10                  15

Pro Gly Ser Gln Pro Lys Thr Ala Cys Thr Asn Cys Tyr Cys Lys Lys
                20                  25                  30

Cys Cys Phe His Cys Gln Val Cys Phe Ile Thr Lys Ala Leu Gly Ile
            35                  40                  45

Ser Tyr Gly Arg Lys Lys Arg Arg Gln Arg Arg Pro Pro Gln Gly
    50                  55                  60

Ser Gln Thr His Gln Val Ser Leu Ser Lys Gln Pro Thr Ser Gln Ser
65                  70                  75                  80

Arg Gly Asp Pro Thr Gly Pro Lys Glu Glu Phe Asp Leu Leu Lys Leu
                85                  90                  95

Ala Gly Asp Val Glu Ser Asn Pro Gly Pro Gly Ser Met Ala Lys Leu
```

```
                    100                 105                 110
Thr Ser Ala Val Pro Val Leu Thr Ala Arg Asp Val Ala Gly Ala Val
        115                 120                 125

Glu Phe Trp Thr Asp Arg Leu Gly Phe Ser Arg Asp Phe Val Glu Asp
    130                 135                 140

Asp Phe Ala Gly Val Val Arg Asp Asp Val Thr Leu Phe Ile Ser Ala
145                 150                 155                 160

Val Gln Asp Gln Val Val Pro Asp Asn Thr Leu Ala Trp Val Trp Val
                165                 170                 175

Arg Gly Leu Asp Glu Leu Tyr Ala Glu Trp Ser Glu Val Val Ser Thr
            180                 185                 190

Asn Phe Arg Asp Ala Ser Gly Pro Ala Met Thr Glu Ile Gly Glu Gln
        195                 200                 205

Pro Trp Gly Arg Glu Phe Ala Leu Arg Asp Pro Ala Gly Asn Cys Val
    210                 215                 220

His Phe Val Ala Glu Glu Gln Asp
225                 230

<210> SEQ ID NO 22
<211> LENGTH: 32
<212> TYPE: DNA
<213> ORGANISM: artificial
<220> FEATURE:
<223> OTHER INFORMATION: Primer

<400> SEQUENCE: 22
ggcctcttaa ggttattttc caccatattg cc                                32

<210> SEQ ID NO 23
<211> LENGTH: 37
<212> TYPE: DNA
<213> ORGANISM: artificial
<220> FEATURE:
<223> OTHER INFORMATION: Primer

<400> SEQUENCE: 23
tccccgcgga aggcctcata ttatcatcgt gtttttc                           37

<210> SEQ ID NO 24
<211> LENGTH: 51
<212> TYPE: DNA
<213> ORGANISM: artificial
<220> FEATURE:
<223> OTHER INFORMATION: Primer

<400> SEQUENCE: 24
aattcgacct tcttaagctt gcgggagacg tcgagtccaa ccctgggccc g            51

<210> SEQ ID NO 25
<211> LENGTH: 51
<212> TYPE: DNA
<213> ORGANISM: artificial
<220> FEATURE:
<223> OTHER INFORMATION: Primer

<400> SEQUENCE: 25
gatccgggcc cagggttgga ctcgacgtct cccgcaagct taagaaggtc g            51

<210> SEQ ID NO 26
<211> LENGTH: 40
<212> TYPE: DNA
<213> ORGANISM: artificial
<220> FEATURE:
```

-continued

<223> OTHER INFORMATION: Primer

<400> SEQUENCE: 26
ccgctcgagg cctggatcca tggccaagtt gaccagtgcc        40

<210> SEQ ID NO 27
<211> LENGTH: 33
<212> TYPE: DNA
<213> ORGANISM: artificial
<220> FEATURE:
<223> OTHER INFORMATION: Primer

<400> SEQUENCE: 27
ggcctcttaa gtcagtcctg ctcctcggcc acg        33

<210> SEQ ID NO 28
<211> LENGTH: 29
<212> TYPE: DNA
<213> ORGANISM: artificial
<220> FEATURE:
<223> OTHER INFORMATION: Primer

<400> SEQUENCE: 28
gaaggcctat ggagccagta gatcctaga        29

<210> SEQ ID NO 29
<211> LENGTH: 30
<212> TYPE: DNA
<213> ORGANISM: artificial
<220> FEATURE:
<223> OTHER INFORMATION: Primer

<400> SEQUENCE: 29
cggaattctt ccttcgggcc tgtcgggtcc        30

<210> SEQ ID NO 30
<211> LENGTH: 15
<212> TYPE: PRT
<213> ORGANISM: artificial
<220> FEATURE:
<223> OTHER INFORMATION: Fifteen amino acids of FMDV 2A

<400> SEQUENCE: 30

Phe Asp Leu Leu Lys Leu Ala Gly Asp Val Glu Ser Asn Pro Gly
1 5 10 15

<210> SEQ ID NO 31
<211> LENGTH: 14
<212> TYPE: PRT
<213> ORGANISM: artificial
<220> FEATURE:
<223> OTHER INFORMATION: NS3 recognition site

<400> SEQUENCE: 31

Gly Ala Asp Thr Glu Asp Val Val Cys Cys Ser Met Ser Tyr
1 5 10

<210> SEQ ID NO 32
<211> LENGTH: 32
<212> TYPE: PRT
<213> ORGANISM: artificial
<220> FEATURE:
<223> OTHER INFORMATION: Amino acid sequence

<400> SEQUENCE: 32

Thr Leu Arg Pro Leu Lys Val Ile Phe His His Ile Ala Val Phe Trp
1 5 10 15

```
Gln Cys Glu Gly Pro Glu Thr Trp Pro Cys Leu Leu Asp Glu His Ser
            20                  25                  30

<210> SEQ ID NO 33
<211> LENGTH: 102
<212> TYPE: PRT
<213> ORGANISM: artificial
<220> FEATURE:
<223> OTHER INFORMATION: Amino acid sequence

<400> SEQUENCE: 33

Gly Ser Phe Pro Ser Arg Gln Arg Asn Ala Arg Ser Val Glu Cys Arg
1               5                   10                  15

Glu Gly Ser Ser Ser Gly Ser Phe Leu Lys Thr Asn Asn Val Cys
            20                  25                  30

Ser Asp Pro Leu Gln Ala Ala Glu Pro Pro Thr Trp Arg Gln Val Pro
            35                  40                  45

Leu Arg Pro Lys Ala Thr Cys Ile Arg Tyr Thr Cys Lys Gly Gly Thr
        50                  55                  60

Thr Pro Val Pro Arg Cys Glu Leu Asp Ser Cys Gly Lys Ser Gln Met
65                  70                  75                  80

Ala Leu Leu Lys Arg Ile Gln Gln Gly Ala Glu Gly Cys Pro Glu Gly
                85                  90                  95

Thr Pro Leu Tyr Gly Ile
            100

<210> SEQ ID NO 34
<211> LENGTH: 30
<212> TYPE: PRT
<213> ORGANISM: artificial
<220> FEATURE:
<223> OTHER INFORMATION: Amino acid sequence

<400> SEQUENCE: 34

Ser Gly Ala Ser Val His Met Leu Tyr Val Cys Leu Val Glu Val Lys
1               5                   10                  15

Lys Arg Leu Gly Pro Pro Asn His Gly Asp Val Val Phe Leu
            20                  25                  30

<210> SEQ ID NO 35
<211> LENGTH: 341
<212> TYPE: DNA
<213> ORGANISM: ARTIFICIAL
<220> FEATURE:
<223> OTHER INFORMATION: nucleotide sequence of 5' NTR

<400> SEQUENCE: 35
gccagccccc tgatgggggc gacactccac catgaatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg   300
gtgcttgcga gtgccccggg aggtctcgta gaccgtgcac c                         341

<210> SEQ ID NO 36
<211> LENGTH: 1158
<212> TYPE: DNA
<213> ORGANISM: ARTIFICIAL
<220> FEATURE:
<223> OTHER INFORMATION: nucleotide sequence of delta Ctat2ANeo
```

<400> SEQUENCE: 36

```
atgagcacga atcctaaacc tcaaagaaaa accaaagttc ctatggagcc agtagatcct      60
agactagagc cctggaagca tccaggaagt cagcctaaaa ctgcttgtac caattgctat     120
tgtaaaaagt gttgctttca ttgccaagtt tgtttcataa caaaagcctt aggcatctcc     180
tatggcagga agaagcggag acagcgacga agacctcctc aaggcagtca gactcatcaa     240
gtttctctat caaagcaacc cacctcccaa tcccgagggg acccgacagg cccgaaggaa     300
gaattcgacc ttcttaagct tgcgggagac gtcgagtcca accctgggcc cggatctgtt     360
aacatgattg aacaagatgg attgcacgca ggttctccgg ccgcttgggt ggagaggcta     420
ttcggctatg actgggcaca acagacaatc ggctgctctg atgccgccgt gttccggctg     480
tcagcgcagg ggcgcccggt tctttttgtc aagaccgacc tgtccggtgc cctgaatgaa     540
ctgcaggacg aggcagcgcg gctatcgtgg ctggccacga cgggcgttcc ttgcgcagct     600
gtgctcgacg ttgtcactga agcgggaagg gactggctgc tattgggcga agtgccgggg     660
caggatctcc tgtcatctca ccttgctcct gccgagaaag tatccatcat ggctgatgca     720
atgcggcggc tgcatacgct tgatccggct acctgcccat tcgaccacca agcgaaacat     780
cgcatcgagc gagcacgtac tcggatggaa gccggtcttg tcgatcagga tgatctggac     840
gaagagcatc aggggctcgc gccagccgaa ctgttcgcca ggctcaaggc gcgcatgccc     900
gacggcgagg atctcgtcgt gacccatggc gatgcctgct tgccgaatat catggtggaa     960
aatggccgct tttctggatt catcgactgt ggccggctgg gtgtggcgga ccgctatcag    1020
gacatagcgt tggctacccg tgatattgct gaagagcttg gcggcgaatg ggctgaccgc    1080
ttcctcgtgc tttacggtat cgccgctccc gattcgcagc gcatcgcctt ctatcgcctt    1140
cttgacgagt tcttctga                                                  1158
```

<210> SEQ ID NO 37
<211> LENGTH: 1116
<212> TYPE: DNA
<213> ORGANISM: ARTIFICIAL
<220> FEATURE:
<223> OTHER INFORMATION: nucleotide sequence of tat2ANeo

<400> SEQUENCE: 37

```
atggagccag tagatcctag actagagccc tggaagcatc aggaagtca gcctaaaact      60
gcttgtacca attgctattg taaaaagtgt gctttcatt gccaagtttg tttcataaca     120
aaagccttag gcatctccta tggcaggaag aagcggagac agcgacgaag acctcctcaa     180
ggcagtcaga ctcatcaagt ttctctatca aagcaaccca cctcccaatc cgaggggac     240
ccgacaggcc cgaaggaaga attcgacctt cttaagcttg cgggagacgt cgagtccaac     300
cctgggcccg atctgttaa catgattgaa caagatggat tgcacgcagg ttctccggcc     360
gcttgggtgg agaggctatt cggctatgac tgggcacaac agacaatcgg ctgctctgat     420
gccgccgtgt tccggctgtc agcgcagggg cgcccggttc tttttgtcaa gaccgacctg     480
tccggtgccc tgaatgaact gcaggacgag gcagcgcggg tatcgtggct ggccacgacg     540
ggcgttcctt gcgcagctgt gctcgacgtt gtcactgaag cgggaaggga ctggctgcta     600
ttgggcgaag tgccggggca ggatctcctg tcatctcacc ttgctcctgc cgagaaagta     660
tccatcatgg ctgatgcaat gcggcggctg catacgcttg atccggctac ctgcccattc     720
gaccaccaag cgaaacatcg catcgagcga gcacgtactc ggatggaagc cggtcttgtc     780
gatcaggatg atctggacga agagcatcag gggctcgcgc cagccgaact gttcgccagg     840
```

```
ctcaaggcgc gcatgcccga cggcgaggat ctcgtcgtga cccatggcga tgcctgcttg      900
ccgaatatca tggtggaaaa tggccgcttt tctggattca tcgactgtgg ccggctgggt      960
gtggcggacc gctatcagga catagcgttg gctacccgtg atattgctga agagcttggc     1020
ggcgaatggg ctgaccgctt cctcgtgctt tacggtatcg ccgctcccga ttcgcagcgc     1080
atcgccttct atcgccttct tgacgagttc ttctga                              1116
```

<210> SEQ ID NO 38
<211> LENGTH: 610
<212> TYPE: DNA
<213> ORGANISM: ARTIFICIAL
<220> FEATURE:
<223> OTHER INFORMATION: nucleotide sequence of EMCV IRES

<400> SEQUENCE: 38

```
agaccacaac ggtttccctc tagcgggatc aattccgccc ctctccctcc ccccccccta       60
acgttactgg ccgaagccgc ttggaataag gccggtgtgc gtttgtctat atgttatttt      120
ccaccatatt gccgtctttt ggcaatgtga gggcccggaaa cctggccctg tcttcttgac      180
gagcattcct agggggtcttt ccctctcgc caaaggaatg caaggtctgt tgaatgtcgt      240
gaaggaagca gttcctctgg aagcttcttg aagacaaaca acgtctgtag cgacccttg      300 caggcagcgg aacccccac ctggcgacag gtgcctctgc ggccaaaagc cacgtgtata      360
agatacacct gcaaaggcgg cacaaccccca gtgccacgtt gtgagttgga tagttgtgga      420
aagagtcaaa tggctctcct caagcgtatt caacaagggg ctgaaggatg cccagaaggt      480
accccattgt atgggatctg atctggggcc tcggtgcaca tgctttacat gtgtttagtc      540
gaggttaaaa aacgtctagg ccccccgaac cacggggacg tggttttcct ttgaaaaaca      600
cgataatacc                                                             610
```

<210> SEQ ID NO 39
<211> LENGTH: 9275
<212> TYPE: DNA
<213> ORGANISM: ARTIFICIAL
<220> FEATURE:
<223> OTHER INFORMATION: nucleotide sequence encoding hepatitis C virus
polyprotein derived from HCV-N

<400> SEQUENCE: 39
atgagcacga atcctaaacc tcaaagaaaa accaaacgta acaccaaccg ccgcccacag 60
gacgtcaagt tcccgggcgg tggtcagatc gttggtggag tttacctgtt gccgcgcagg 120
ggccccaggt tgggtgtgcg cgcgatcagg aagacttccg agcggtcgca accccgtgga 180
aggcgacagc ctatccccaa ggctcgccgg cccgagggca gggcctgggc tcagcccggg 240
tatccttggc ccctctatgg caatgagggc atggggtggg caggatggct cctgtcaccc 300
cgcggctccc ggcctagttg gggccccacg gacccccggc gtaggtcgcg taatttgggt 360
aaggtcatcg ataccctcac atgcggcctc gccgacctca tggggtacat tccgctcgtc 420
ggcggccccc tagggggcgc tgccagggcc ttggcacatg gtgtccgggt tctggaggac 480
ggcgtgaact atgcaacagg gaacctgccc ggttgctctt tttctatctt cctcttggct 540
ctgctgtcct gtctgaccgt accagcttcc gctcatgaag tgcgtaacgc gtccggggta 600
taccatgtca cgaacgactg ctccaactca agcattgtgt ttgaggcggc ggacttgatc 660
atgcatactc ccgggtgcgt gccctgcgtt cgggagggta actcctcccg ctgctgggta 720
gcgctcactc ccacgctcgc ggccaggaat gctaccatcc ccactacgac aatacgacac 780

```
cacgtcgatt tgctcgttgg ggcggctgct ctctgctccg ctatgtacgt gggggacctc    840
tgcggatctg ttttcctcgt ctctcagctg ttcaccttct cgccccgccg gcatgcgaca    900
ttgcaggact gcaattgttc gatctacccc ggccacgcgt caggtcaccg catggcctgg    960
gacatgatga tgaactggtc acctacaaca gccctcgtag tgtcgcagtt actccggatc   1020
ccacaagccg tcatcgacat ggtggcgggg gcccactggg gagtcctggc gggccttgcc   1080
tactattcca tggcggggaa ctgggctaag gttttgattg tgatgctact ttttgccggc   1140
gttgacgggc acaccctcac aacggggggg cacgctgccc gcctcaccag cgggttcgcg   1200
ggcctcttta cacctgggcc gtctcagaga atccagctta taaacaccaa tggcagttgg   1260
cacatcaaca ggactgccct gaactgcaat gactccctcc agactgggtt tcttgccgcg   1320
ctgttctacg cacataggtt caactcgtcc ggatgcccgg agcgcatggc cagctgccgc   1380
tccattgaca agttcgacca gggatggggt cctatcactt atgctgagcc tacaaaagac   1440
ccggaccaga ggccttattg ctggcactac ccacctcaac aatgtggtat cgtacctgcg   1500
tcgcaggtgt gtggtccagt gtattgcttc accccaagtc ctgttgtcgt ggggacaacc   1560
gatcgtctcg gcaaccctac gtacagctgg ggggagaacg atactgacgt gctgctcctt   1620
aacaacacgc ggccgccgca aggcaactgg ttcggctgta catggatgaa tagcactggg   1680
ttcaccaaga cgtgcggggc cccccgtgt aacatcgggg gggtcggcaa taacaccttg   1740
acctgcccca cggactgctt ccggaagcac cccgaggcca cgtactcaaa atgtggctcg   1800
gggccttggt tgacacctag gtgcatggtt gactacccat acaggctctg gcactacccc   1860
tgcactgtca acttctccat cttttaaggtt aggatgtatg tgggggcgt ggagcacagg   1920
cttaatgctg catgcaactg gacccgagga gagcgttgca acttggacga cagggacaga   1980
tcggagctca gcccgctgct gctctctaca acagagtggc aggttctgcc ctgctctttc   2040
accaccctac cggctctgtc cactggcttg atccacctcc atcagaacat cgtggacgtg   2100
caatacctgt acggtatagg gtcagcggtt gtctcctttg caatcaaatg ggagtatgtc   2160
gtgttgcttt tccttctcct ggcggacgcg cgcgtctgtg cctgcttgtg gatgatgctg   2220
ctgatagccc aggccgaggc cgccttagag aacctggtgg ccctcaatgc agcgtccgtt   2280
gccggagcgc acggcatcct ctccttcctc gtgttcttct gtgccgcttg gtacatcaag   2340
ggcaggctgg tccctgggc ggcatatgct ttctatggcg catggccgct gctcctgctc   2400
ctcttgacat taccaccacg agcttacgcc atggaccggg agatggctgc atcgtgcgga   2460
ggcgcggttt ttgtgggtct ggcattattg accttgtcgc catattacaa ggtgttcctc   2520
gctaggctcc tatggtggtt acaatatctt atcaccagag ctgaggcgca cttgcatgtg   2580
tgggttcccc ccctcaacgt ccggggaggc cgcgatgcca tcatcctcct cacgtgtgca   2640
gtccacccag agctaatctt tgatatcacc aaacttctga ttgccatact cggaccgctc   2700
atggtgctcc aagctggcat aactagggtg ccgtacttcg tacgcgctca agggctcatt   2760
cgtgcatgca tgttagtgcg gaaagtcgct gggggtcatt atgtccaaat ggccttcatg   2820
agactgggcg cgctgacggg cacgtacgtc tataatcacc tcaccccact gcgggattgg   2880
gcccacgccg gcctacggga ccttgcggta gcagtggagc ctgtcgtctt ctctgacatg   2940
gagaccaaga tcatcacctg gggggcggac accgcgcgt gtggggacat catcctgggc   3000
ctacctgtct ccgcccgaag gggaagggag atactcctgg ggccggccga tagtctagta   3060
gggcagggt ggcgactcct tgcgcccatc acggcctact cccaacagac ccggggccta   3120
cttggttgca tcatcacgag tctcacaggc cgggacaaga accaggtcga gggggaggtt   3180
```

```
caagtggtct ccaccgcaac acaatctttc ctggcgacct gcgtcaacgg cgtatgttgg    3240
actgtctacc atggtgctgg ctcaaagact ctagccggcc caaaaggccc aatcgcccag    3300
atgtacacta atgtagacca ggatctcgtc ggctggccgg cgcccccgg ggcgcgttcc     3360 ctgacaccat gcacctgtgg cagctcggac ctttacttgg ttacgagaca tgcagatgtt    3420
attccggtgc gccggcgggg cgacaataga gggagcttgc tctcccccag gcctgtctcc    3480
tacttgaagg gctcttcggg tggcccactg ctctgccctt cggggcacgc tgtgggcgtc    3540
ttccgggccg ctgtatgcac ccggggggtt gcaaaggcgg tggattttgt cccgttgag     3600 tccatggaaa ctactatgcg gtccccggtc ttcacagaca actcatctcc cccggccgta    3660
ccgcaaacat tccaagtggc ccatctacac gctcccactg gcagcggcaa gagcactaga    3720
gtgccggccg catatgcggc ccaagggtac aaggtgcttg tcctgaaccc gtctgttgcc    3780
gctaccttag gttttggggc gtatatgtct aaagcacatg gtaccgaccc taacatcagg    3840
actggggtaa ggaccattac cacgggcgcc cccattacgt actccaccta tggcaagttc    3900
cttgccgacg gtggttgctc cgggggcgct tacgacatca taatgtgcga tgagtgccac    3960
tcaactgact caactactat cttgggcatc ggcacagtcc tggaccaagc ggagacggct    4020
ggagcgcggc ttgtcgtgct cgccaccgct acgcctccag gatcggtcac cgtgccacac    4080
cccaatatcg aggaggtggc cctgtcgaac actggagaga tccccttcta cggcaaagcc    4140
atccccatcg aagccatcaa gggggggaagg cacctcattt tctgtcactc caagaagaag    4200
tgcgacgagc ttgccgcaaa gctgtcaggc ctcggaatca atgctgtagc gtattaccgg    4260
ggtcttgatg tgtccgtcat accgaccagc ggagacgtcg ttgtcgtggc aacagacgct    4320
ctaatgacgg gctataccgg tgactttgat tcagtgatcg actgtaatac gtgtgtcacc    4380
cagacagtcg acttcagctt ggaccccacc ttcaccattg agacgacgac cgtgccccaa    4440
gacgcagtgt cgcgctcgca gcggcggggt aggactggca ggggcagggg gggcatatac    4500
aggtttgtaa ctccggggga acggccctcg ggcatgttcg attcctcggt cctgtgcgag    4560
tgctatgacg cgggctgtgc ttggtacgag ctcacccccg ctgagacctc ggttaggttg    4620
cgggcttacc taaatacacc aggattgccc gtttgccagg accatctgga gttctggag     4680 agcgtcttca caggcctcac ccatatagat gcccacttcc tgtcccagac caagcaggca    4740
ggagataact tcccctacct ggtggcatac caagccacag tgtgcgccag ggctcaggcc    4800
ccacctccat cgtgggatca aatgtggaag tgtctcatac ggctaaaacc cacgctgcac    4860
gggccaacgc ccctgctgta taggctaggg gccgtccaaa atgaggtcac cctcacacac    4920
cccataacca aatacatcat ggcatgcatg tcggccgacc tggaagtcgt caccagcacc    4980
tgggtgctgg taggcggagt cctcgcagct ctggccgcat attgcctgac aacaggcagt    5040
gtggttatcg tgggtaggat catcttgtcc gggaggccgg ctgtcgttcc cgatagggaa    5100
gtcctctacc gggagttcga tgaaatggaa gaatgcgcct cgcacctccc ttacatcgaa    5160
cagggaatgc aactcgccga gcaattcaag cagaaggcgc tcgggttgtt gcaaacagcc    5220
accaagcagg cggaggctgc cgctcccgtg gtggagtcca gtggcgagc tttggagacc    5280 ttctgggcaa agcacaagtg gaatttcatc agcgggatac agtacttagc gggcttatcc    5340
accctgcctg gaaccccgc gatagccatca ctgatggcat tcacagcctc tatcaccagc    5400
ccgctcacca cccagaacac cctcctgttt aacatcttgg ggggtgggt agccgcccaa    5460 ctcgctcccc ccagcgctgc ttcggctttc gtgggcgctg gtatcgctgg tgcggctgtt    5520
ggcagcatag gtcttgggaa ggtgctagtg gacattctgg cgggctatgg ggcaggggtg    5580
```

-continued

| | |
|---|---|
| gctggcgcgc tcgtggcctt caaggtcatg agcggcgagg cgccctctgc cgaggacctg | 5640 |
| atcaatttgc tccctgccat cctctctcct ggtgccctgg tcgtcggagt cgtgtgtgca | 5700 |
| gcaatactgc gtcggcatgt gggcccggga gaggggccg tgcagtggat gaaccggctg | 5760 |
| atagcgttcg cttcgcgggg taaccatgtc tccccacgc actatgtgcc tgagagcgac | 5820 |
| gccgcagcgc gtgtcactca ggtcctctcc agccttacca tcacccagct gctgaagagg | 5880 |
| ctccaccagt ggattaatga ggactgttct acgccgtgtt ccggctcgtg gctgagggat | 5940 |
| gtttgggact gggtgtgcac ggtgttgagt gacttcaaga cctggctcca gtccaagctc | 6000 |
| ctgccgcggt taccgggtgt ccctttcctc tcatgccaac gtgggtacaa gggagtctgg | 6060 |
| cgggggggacg gcatcatgca caccacctgc ccatgtggag cacagatcgc cggacatgtc | 6120 |
| aaaaacggtt ccatgaggat catcgggccg aaaacctgca gcaacacgtg gcatggaaca | 6180 |
| ttccccatca acgcgtacac cacgggcccc tgcacgcctt cccggcgcc aaactattcc | 6240 |
| aaggcgctgt ggcgggtggc tgctgaggag tacgtggagg tcacgcgggt gggggatttc | 6300 |
| cactacgtga cgggcataac caccgacaac gtaaagtgcc catgtcaggt tccagctcct | 6360 |
| gagttttttca cggaggtgga tggggtgcgg ttgcacaggt acgccccggt gtgcaaacct | 6420 |
| ctcttacggg atgaggttgt attccaggtc gggctcaatc aatacctggt tgggtcacag | 6480 |
| ctcccatgcg agcccgaacc ggacgtagca gtgctcactt ccatgctcac cgaccctcc | 6540 |
| cacattacag cagaggcggc taagcgtagg ttggccaggg ggtctccccc ctccttggcc | 6600 |
| agctcttcag ctagccagct gtctgcgccc tccttgaggg cgacatgcac tacccattct | 6660 |
| tcctataatc ttgactctcc ggacgtcgac ctcattgcgg ccaacctcct gtggcggcag | 6720 |
| gagatgggcg gaaacatcac ccgcgtggag tcggagaaca aggtggtagt cctagactct | 6780 |
| ttcgagccgc ttcgagcgga gggggatgag aatgaaatat ccattgcggc ggagatcctg | 6840 |
| cggaagtcca agaagttccc cgcggcgata cccatatggg cacggccgga ttacaatcct | 6900 |
| ccattgttag agtcttggaa gaacccggac tacgtccctc cggtgtaca cgggtgccca | 6960 |
| ttgccacctg tcaaggcccc tccaatacca cctccacgga gaaaaaggac ggttgtcctg | 7020 |
| acggactcca ccgtgtcttc tgttttggcg gagctcgcta ccaaaaccctt cggcagctcc | 7080 |
| gaattgtcgg ccgccgacag cggcacggcg accgcccctc ctgaccagac ctccgacaac | 7140 |
| ggcggcaaag actccgacgc tgagtcatgc tcctctatgc ccccccttga ggggagccg | 7200 |
| ggggaccccg atctcagcga cgggtcttgg tctaccgtga gcgaggaggc tggtgagagc | 7260 |
| gtcgtctgct gctcaatgtc ctacacatgg acagtgccc tgatcacgcc atgcgccgcg | 7320 |
| gaagaaagca agctgcccat caacgcgttg agcaactctt tgctgcgcca tcacaacatg | 7380 |
| gtctacgcca cgacatcccg cagcgcgggc ctgcggcaga agaaggtcac ctttgacaga | 7440 |
| ctgcaggtcc tggatgacca ttaccgggac gtgcttaagg agatgaaggc aaaggcgtcc | 7500 |
| acagtcaagg ctaaacttct atccatagaa gaagcctgcc gcctgacgcc cccacattcg | 7560 |
| gccaaatcca gtttggctta tggggcaaag gacgtccgga acctatccag cagggccatc | 7620 |
| aaccacatcc gctccgtgtg ggaggacttg ctggaggaca ctgtgacacc aattgacacc | 7680 |
| accgtcatgg caaagaatga ggtttttctgc gtccaaccag agaagggagg ccgcaagcca | 7740 |
| gcccgcctta tcgtattccc agatttggga gttcgtgtat gcgagaagat ggctctctac | 7800 |
| gatgtggtct ccaccttcc tcaagccgtg atgggctcct catacggatt ccagtactct | 7860 |
| cccgggcagc gggtcgagtt cctggtaaaa gcctggaaat caaagaaaaa ccctatgggc | 7920 |
| ttctcatatg acacccgctg ttttgactca acggtcactg agaatgacat ccgtgttgag | 7980 |

-continued

```
gagtcaattt accaatgttg tgacttggcc cccgaagcca gacaggctat aaaatcgctc   8040
acagagcggc tttatatcgg gggtcccctg actaattcaa aagggcagag ctgtggttat   8100
cgccggtgcc gcgcgagcgg cgtgctgacg actagctgcg gtaataccct cacatgttac   8160
ttgaaagcct ctgccgcctg tcgagctgca aagctccagg actgcacgat gctcgtgaac   8220
ggggacgacc ttgtcgttat ctgcgaaagc gcgggaaccc aggaggatgc ggcgagccta   8280
cgagtcttca cggaggctat gactaggtac tccgccccc ccgggacttg ccccaacca    8340
gaatacgact tggagttgat aacatcatgt tcctccaatg tgtcggtcgc gcacgatgca   8400
tctggcaaaa gggtgtacta cctcactcgc gatcccacca ccccatcgc acgggctgcg   8460
tgggaaacag ctagacacac tccagttaac tcctggctag caacattat catgtatgcg    8520
cccaccttat gggcaaggat gattctgatg acccatttct tctccatcct tctagctcag   8580
gagcaacttg aaaaagcct ggattgccaa atctacgggg cctgttactc cattgagcca    8640
cttgacctac ctcagatcat tgaaggactc catggtctta gcgcattttc actccatagt   8700
tactctccag gtgagatcaa tagggtggct tcatgcctca ggaaacttgg ggtaccgccc   8760
ttgcgagtct ggagacatcg ggccaggggac gtccgcgcta aactactgtc caggggggg   8820
agggccgcca cttgcggcaa atacctcttc aactgggcag taaagaccaa gctcaaactc   8880
actccaatcc cggctgcgtc ccagttggac ttatccggct ggttcgttgc tggctacagc   8940
ggggggagaca tatatcacag cctgtctcgt gcccgacccc gctggttcat gctgtgccta   9000
ctcctacttt ctgtaggggt aggcatctac ttgctcccca atcgatgaac ggggagctaa   9060
acactccagg ccaataggcc atttcctgtt tttttttttt tttggttttt tttttttttt   9120
tttttttttt tttttttttt ttttccttc cttctttttt ttttttttcc ctttatggt    9180
ggctccgtct tagccctagt cacggctagc tgtgaaaggt ccgtgagccg catgactgca   9240
gagagtgctg atactggcct ctctgcagat catgt                              9275
```

<210> SEQ ID NO 40
<211> LENGTH: 2985
<212> TYPE: PRT
<213> ORGANISM: ARTIFICIAL
<220> FEATURE:
<223> OTHER INFORMATION: amino acid sequence encoded by nucleotides
   2077-11121 of SEQ ID NO:39

<400> SEQUENCE: 40

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ile Arg Lys Thr Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Gly Pro Leu
```

-continued

```
                130                 135                 140
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala His
                180                 185                 190

Glu Val Arg Asn Ala Ser Gly Val Tyr His Val Thr Asn Asp Cys Ser
                195                 200                 205

Asn Ser Ser Ile Val Phe Glu Ala Ala Asp Leu Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Thr Ile Pro Thr Thr
                245                 250                 255

Thr Ile Arg His His Val Asp Leu Leu Val Gly Ala Ala Ala Leu Cys
                260                 265                 270

Ser Ala Met Tyr Val Gly Asp Leu Cys Gly Ser Val Phe Leu Val Ser
                275                 280                 285

Gln Leu Phe Thr Phe Ser Pro Arg Arg His Ala Thr Leu Gln Asp Cys
290                 295                 300

Asn Cys Ser Ile Tyr Pro Gly His Ala Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Ile Asp Met Val Ala Gly Ala His
                340                 345                 350

Trp Gly Val Leu Ala Gly Leu Ala Tyr Tyr Ser Met Ala Gly Asn Trp
                355                 360                 365

Ala Lys Val Leu Ile Val Met Leu Leu Phe Ala Gly Val Asp Gly His
                370                 375                 380

Thr Leu Thr Thr Gly Gly His Ala Ala Arg Leu Thr Ser Gly Phe Ala
385                 390                 395                 400

Gly Leu Phe Thr Pro Gly Pro Ser Gln Arg Ile Gln Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Leu Ala Ala Leu Phe Tyr Ala His Arg Phe Asn
                435                 440                 445

Ser Ser Gly Cys Pro Glu Arg Met Ala Ser Cys Arg Ser Ile Asp Lys
450                 455                 460

Phe Asp Gln Gly Trp Gly Pro Ile Thr Tyr Ala Glu Pro Thr Lys Asp
465                 470                 475                 480

Pro Asp Gln Arg Pro Tyr Cys Trp His Tyr Pro Pro Gln Gln Cys Gly
                485                 490                 495

Ile Val Pro Ala Ser Gln Val Cys Gly Pro Val Tyr Cys Phe Thr Pro
                500                 505                 510

Ser Pro Val Val Val Gly Thr Thr Asp Arg Leu Gly Asn Pro Thr Tyr
                515                 520                 525

Ser Trp Gly Glu Asn Asp Thr Asp Val Leu Leu Asn Asn Thr Arg
530                 535                 540

Pro Pro Gln Gly Asn Trp Phe Gly Cys Thr Trp Met Asn Ser Thr Gly
545                 550                 555                 560
```

```
Phe Thr Lys Thr Cys Gly Ala Pro Pro Cys Asn Ile Gly Gly Val Gly
                565                 570                 575

Asn Asn Thr Leu Thr Cys Pro Thr Asp Cys Phe Arg Lys His Pro Glu
            580                 585                 590

Ala Thr Tyr Ser Lys Cys Gly Ser Gly Pro Trp Leu Thr Pro Arg Cys
            595                 600                 605

Met Val Asp Tyr Pro Tyr Arg Leu Trp His Tyr Pro Cys Thr Val Asn
        610                 615                 620

Phe Ser Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Asp
                645                 650                 655

Asp Arg Asp Arg Ser Glu Leu Ser Pro Leu Leu Leu Ser Thr Thr Glu
            660                 665                 670

Trp Gln Val Leu Pro Cys Ser Phe Thr Thr Leu Pro Ala Leu Ser Thr
        675                 680                 685

Gly Leu Ile His Leu His Gln Asn Ile Val Asp Val Gln Tyr Leu Tyr
        690                 695                 700

Gly Ile Gly Ser Ala Val Val Ser Phe Ala Ile Lys Trp Glu Tyr Val
705                 710                 715                 720

Val Leu Leu Phe Leu Leu Leu Ala Asp Ala Arg Val Cys Ala Cys Leu
                725                 730                 735

Trp Met Met Leu Leu Ile Ala Gln Ala Glu Ala Ala Leu Glu Asn Leu
            740                 745                 750

Val Ala Leu Asn Ala Ala Ser Val Ala Gly Ala His Gly Ile Leu Ser
            755                 760                 765

Phe Leu Val Phe Phe Cys Ala Ala Trp Tyr Ile Lys Gly Arg Leu Val
        770                 775                 780

Pro Gly Ala Ala Tyr Ala Phe Tyr Gly Ala Trp Pro Leu Leu Leu Leu
785                 790                 795                 800

Leu Leu Thr Leu Pro Pro Arg Ala Tyr Ala Met Asp Arg Glu Met Ala
                805                 810                 815

Ala Ser Cys Gly Gly Ala Val Phe Val Gly Leu Ala Leu Leu Thr Leu
            820                 825                 830

Ser Pro Tyr Tyr Lys Val Phe Leu Ala Arg Leu Leu Trp Trp Leu Gln
            835                 840                 845

Tyr Leu Ile Thr Arg Ala Glu Ala His Leu His Val Trp Val Pro Pro
        850                 855                 860

Leu Asn Val Arg Gly Gly Arg Asp Ala Ile Ile Leu Leu Thr Cys Ala
865                 870                 875                 880

Val His Pro Glu Leu Ile Phe Asp Ile Thr Lys Leu Leu Ile Ala Ile
                885                 890                 895

Leu Gly Pro Leu Met Val Leu Gln Ala Gly Ile Thr Arg Val Pro Tyr
            900                 905                 910

Phe Val Arg Ala Gln Gly Leu Ile Arg Ala Cys Met Leu Val Arg Lys
            915                 920                 925

Val Ala Gly Gly His Tyr Val Gln Met Ala Phe Met Arg Leu Gly Ala
        930                 935                 940

Leu Thr Gly Thr Tyr Val Tyr Asn His Leu Thr Pro Leu Arg Asp Trp
945                 950                 955                 960

Ala His Ala Gly Leu Arg Asp Leu Ala Val Ala Val Glu Pro Val Val
                965                 970                 975

Phe Ser Asp Met Glu Thr Lys Ile Ile Thr Trp Gly Ala Asp Thr Ala
            980                 985                 990
```

-continued

```
Ala Cys Gly Asp Ile Ile Leu Gly  Leu Pro Val Ser  Ala Arg Arg Gly
        995             1000              1005

Arg Glu  Ile Leu Leu Gly Pro  Ala Asp Ser Leu Val  Arg Asp Lys
    1010             1015             1020

Asn Gln  Val Glu Gly Glu Val  Gln Val Val Ser Thr  Ala Thr Gln
    1025             1030             1035

Ser Phe  Leu Ala Thr Cys Val  Asn Gly Val Cys Trp  Thr Val Tyr
    1040             1045             1050

His Gly  Ala Gly Ser Lys Thr  Leu Ala Gly Pro Lys  Gly Pro Ile
    1055             1060             1065

Ala Gln  Met Tyr Thr Asn Val  Asp Gln Asp Leu Val  Gly Trp Pro
    1070             1075             1080

Ala Pro  Pro Gly Ala Arg Ser  Leu Thr Pro Cys Thr  Cys Gly Ser
    1085             1090             1095

Ser Asp  Leu Tyr Leu Val Thr  Arg His Ala Asp Val  Ile Pro Val
    1100             1105             1110

Arg Arg  Arg Gly Asp Asn Arg  Gly Ser Leu Leu Ser  Pro Arg Pro
    1115             1120             1125

Val Ser  Tyr Leu Lys Gly Ser  Ser Gly Gly Pro Leu  Leu Cys Pro
    1130             1135             1140

Ser Gly  His Ala Val Gly Val  Phe Arg Ala Ala Val  Cys Thr Arg
    1145             1150             1155

Gly Val  Ala Lys Ala Val Asp  Phe Val Pro Val Glu  Ser Met Glu
    1160             1165             1170

Thr Thr  Met Arg Ser Pro Val  Phe Thr Asp Asn Ser  Ser Pro Pro
    1175             1180             1185

Ala Val  Pro Gln Thr Phe Gln  Val Ala His Leu His  Ala Pro Thr
    1190             1195             1200

Gly Ser  Gly Lys Ser Thr Arg  Val Pro Ala Ala Tyr  Ala Ala Gln
    1205             1210             1215

Gly Tyr  Lys Val Leu Val Leu  Asn Pro Ser Val Ala  Ala Thr Leu
    1220             1225             1230

Gly Phe  Gly Ala Tyr Met Ser  Lys Ala His Gly Thr  Asp Pro Asn
    1235             1240             1245

Ile Arg  Thr Gly Val Arg Thr  Ile Thr Thr Gly Ala  Pro Ile Thr
    1250             1255             1260

Tyr Ser  Thr Tyr Gly Lys Phe  Leu Ala Asp Gly Gly  Cys Ser Gly
    1265             1270             1275

Gly Ala  Tyr Asp Ile Ile Met  Cys Asp Glu Cys His  Ser Thr Asp
    1280             1285             1290

Ser Thr  Thr Ile Leu Gly Ile  Gly Thr Val Leu Asp  Gln Ala Glu
    1295             1300             1305

Thr Ala  Gly Ala Arg Leu Val  Val Leu Ala Thr Ala  Thr Pro Pro
    1310             1315             1320

Gly Ser  Val Thr Val Pro His  Pro Asn Ile Glu Glu  Val Ala Leu
    1325             1330             1335

Ser Asn  Thr Gly Glu Ile Pro  Phe Tyr Gly Lys Ala  Ile Pro Ile
    1340             1345             1350

Glu Ala  Ile Lys Gly Gly Arg  His Leu Ile Phe Cys  His Ser Lys
    1355             1360             1365

Lys Lys  Cys Asp Glu Leu Ala  Ala Lys Leu Ser Gly  Leu Gly Ile
    1370             1375             1380

Asn Ala  Val Ala Tyr Tyr Arg  Gly Leu Asp Val Ser  Val Ile Pro
```

-continued

```
              1385                1390                1395
Thr  Ser  Gly  Asp  Val  Val  Val  Ala  Thr  Asp  Ala  Leu  Met  Thr
     1400                1405                1410

Gly  Tyr  Thr  Gly  Asp  Phe  Asp  Ser  Val  Ile  Asp  Cys  Asn  Thr  Cys
     1415                1420                1425

Val  Thr  Gln  Thr  Val  Asp  Phe  Ser  Leu  Asp  Pro  Thr  Phe  Thr  Ile
     1430                1435                1440

Glu  Thr  Thr  Thr  Val  Pro  Gln  Asp  Ala  Val  Ser  Arg  Ser  Gln  Arg
     1445                1450                1455

Arg  Gly  Arg  Thr  Gly  Arg  Gly  Arg  Gly  Gly  Ile  Tyr  Arg  Phe  Val
     1460                1465                1470

Thr  Pro  Gly  Glu  Arg  Pro  Ser  Gly  Met  Phe  Asp  Ser  Ser  Val  Leu
     1475                1480                1485

Cys  Glu  Cys  Tyr  Asp  Ala  Gly  Cys  Ala  Trp  Tyr  Glu  Leu  Thr  Pro
     1490                1495                1500

Ala  Glu  Thr  Ser  Val  Arg  Leu  Arg  Ala  Tyr  Leu  Asn  Thr  Pro  Gly
     1505                1510                1515

Leu  Pro  Val  Cys  Gln  Asp  His  Leu  Glu  Phe  Trp  Glu  Ser  Val  Phe
     1520                1525                1530

Thr  Gly  Leu  Thr  His  Ile  Asp  Ala  His  Phe  Leu  Ser  Gln  Thr  Lys
     1535                1540                1545

Gln  Ala  Gly  Asp  Asn  Phe  Pro  Tyr  Leu  Val  Ala  Tyr  Gln  Ala  Thr
     1550                1555                1560

Val  Cys  Ala  Arg  Ala  Gln  Ala  Pro  Pro  Pro  Ser  Trp  Asp  Gln  Met
     1565                1570                1575

Trp  Lys  Cys  Leu  Ile  Arg  Leu  Lys  Pro  Thr  Leu  His  Gly  Pro  Thr
     1580                1585                1590

Pro  Leu  Leu  Tyr  Arg  Leu  Gly  Ala  Val  Gln  Asn  Glu  Val  Thr  Leu
     1595                1600                1605

Thr  His  Pro  Ile  Thr  Lys  Tyr  Ile  Met  Ala  Cys  Met  Ser  Ala  Asp
     1610                1615                1620

Leu  Glu  Val  Val  Thr  Ser  Thr  Trp  Val  Leu  Val  Gly  Gly  Val  Leu
     1625                1630                1635

Ala  Ala  Leu  Ala  Ala  Tyr  Cys  Leu  Thr  Thr  Gly  Ser  Val  Val  Ile
     1640                1645                1650

Val  Gly  Arg  Ile  Ile  Leu  Ser  Gly  Arg  Pro  Ala  Val  Val  Pro  Asp
     1655                1660                1665

Arg  Glu  Val  Leu  Tyr  Arg  Glu  Phe  Asp  Glu  Met  Glu  Glu  Cys  Ala
     1670                1675                1680

Ser  His  Leu  Pro  Tyr  Ile  Glu  Gln  Gly  Met  Gln  Leu  Ala  Glu  Gln
     1685                1690                1695

Phe  Lys  Gln  Lys  Ala  Leu  Gly  Leu  Leu  Gln  Thr  Ala  Thr  Lys  Gln
     1700                1705                1710

Ala  Glu  Ala  Ala  Ala  Pro  Val  Val  Glu  Ser  Lys  Trp  Arg  Ala  Leu
     1715                1720                1725

Glu  Thr  Phe  Trp  Ala  Lys  His  Lys  Trp  Asn  Phe  Ile  Ser  Gly  Ile
     1730                1735                1740

Gln  Tyr  Leu  Ala  Gly  Leu  Ser  Thr  Leu  Pro  Gly  Asn  Pro  Ala  Ile
     1745                1750                1755

Ala  Ser  Leu  Met  Ala  Phe  Thr  Ala  Ser  Ile  Thr  Ser  Pro  Leu  Thr
     1760                1765                1770

Thr  Gln  Asn  Thr  Leu  Leu  Phe  Asn  Ile  Leu  Gly  Gly  Trp  Val  Ala
     1775                1780                1785
```

```
Ala Gln Leu Ala Pro Pro Ser Ala Ala Ser Ala Phe Val Gly Ala
    1790            1795                1800

Gly Ile Ala Gly Ala Ala Val Gly Ser Ile Gly Leu Gly Lys Val
    1805            1810                1815

Leu Val Asp Ile Leu Ala Gly Tyr Gly Ala Gly Val Ala Gly Ala
    1820            1825                1830

Leu Val Ala Phe Lys Val Met Ser Gly Glu Ala Pro Ser Ala Glu
    1835            1840                1845

Asp Leu Ile Asn Leu Leu Pro Ala Ile Leu Ser Pro Gly Ala Leu
    1850            1855                1860

Val Val Gly Val Val Cys Ala Ala Ile Leu Arg Arg His Val Gly
    1865            1870                1875

Pro Gly Glu Gly Ala Val Gln Trp Met Asn Arg Leu Ile Ala Phe
    1880            1885                1890

Ala Ser Arg Gly Asn His Val Ser Pro Thr His Tyr Val Pro Glu
    1895            1900                1905

Ser Asp Ala Ala Ala Arg Val Thr Gln Val Leu Ser Ser Leu Thr
    1910            1915                1920

Ile Thr Gln Leu Leu Lys Arg Leu His Gln Trp Ile Asn Glu Asp
    1925            1930                1935

Cys Ser Thr Pro Cys Ser Gly Ser Trp Leu Arg Asp Val Trp Asp
    1940            1945                1950

Trp Val Cys Thr Val Leu Ser Asp Phe Lys Thr Trp Leu Gln Ser
    1955            1960                1965

Lys Leu Leu Pro Arg Leu Pro Gly Val Pro Phe Leu Ser Cys Gln
    1970            1975                1980

Arg Gly Tyr Lys Gly Val Trp Arg Gly Asp Gly Ile Met His Thr
    1985            1990                1995

Thr Cys Pro Cys Gly Ala Gln Ile Ala Gly His Val Lys Asn Gly
    2000            2005                2010

Ser Met Arg Ile Ile Gly Pro Lys Thr Cys Ser Asn Thr Trp His
    2015            2020                2025

Gly Thr Phe Pro Ile Asn Ala Tyr Thr Thr Gly Pro Cys Thr Pro
    2030            2035                2040

Ser Pro Ala Pro Asn Tyr Ser Lys Ala Leu Trp Arg Val Ala Ala
    2045            2050                2055

Glu Glu Tyr Val Glu Val Thr Arg Val Gly Asp Phe His Tyr Val
    2060            2065                2070

Thr Gly Ile Thr Thr Asp Asn Val Lys Cys Pro Cys Gln Val Pro
    2075            2080                2085

Ala Pro Glu Phe Phe Thr Glu Val Asp Gly Val Arg Leu His Arg
    2090            2095                2100

Tyr Ala Pro Val Cys Lys Pro Leu Leu Arg Asp Glu Val Val Phe
    2105            2110                2115

Gln Val Gly Leu Asn Gln Tyr Leu Val Gly Ser Gln Leu His Arg
    2120            2125                2130

Tyr Ala Pro Val Cys Lys Pro Leu Leu Arg Asp Glu Val Val Phe
    2135            2140                2145

Gln Val Gly Leu Asn Gln Tyr Leu Val Gly Ser Gln Leu Ala Arg
    2150            2155                2160

Gly Ser Pro Pro Ser Leu Ala Ser Ser Ser Ala Ser Gln Leu Ser
    2165            2170                2175

Ala Pro Ser Leu Arg Ala Thr Cys Thr Thr His Ser Ser Tyr Asn
    2180            2185                2190
```

```
Leu Asp Ser Pro Asp Val Asp Leu Ile Ala Ala Asn Leu Leu Trp
    2195            2200            2205

Arg Gln Glu Met Gly Gly Asn Ile Thr Arg Val Glu Ser Glu Asn
    2210            2215            2220

Lys Val Val Val Leu Asp Ser Phe Glu Pro Leu Arg Ala Glu Gly
    2225            2230            2235

Asp Glu Asn Glu Ile Ser Ile Ala Ala Glu Ile Leu Arg Lys Ser
    2240            2245            2250

Lys Lys Phe Pro Ala Ala Ile Pro Ile Trp Ala Arg Pro Asp Tyr
    2255            2260            2265

Asn Pro Pro Leu Leu Glu Ser Trp Lys Asn Pro Asp Tyr Val Pro
    2270            2275            2280

Pro Val Val His Gly Cys Pro Leu Pro Pro Val Lys Ala Pro Pro
    2285            2290            2295

Ile Pro Pro Pro Arg Arg Lys Arg Thr Val Val Leu Thr Asp Ser
    2300            2305            2310

Thr Val Ser Ser Val Leu Ala Glu Leu Ala Thr Lys Thr Phe Gly
    2315            2320            2325

Ser Ser Glu Leu Ser Ala Ala Asp Ser Gly Thr Ala Thr Ala Pro
    2330            2335            2340

Pro Asp Gln Thr Ser Asp Asn Gly Gly Lys Asp Ser Asp Ala Glu
    2345            2350            2355

Ser Cys Ser Ser Met Pro Pro Leu Glu Gly Glu Pro Gly Asp Pro
    2360            2365            2370

Asp Leu Ser Asp Gly Ser Trp Ser Thr Val Ser Glu Glu Ala Gly
    2375            2380            2385

Glu Ser Val Val Cys Cys Ser Met Ser Tyr Thr Trp Thr Gly Ala
    2390            2395            2400

Leu Ile Thr Pro Cys Ala Ala Glu Glu Ser Lys Leu Pro Ile Asn
    2405            2410            2415

Ala Leu Ser Asn Ser Leu Leu Arg His His Asn Met Val Tyr Ala
    2420            2425            2430

Thr Thr Ser Arg Ser Ala Gly Leu Arg Gln Lys Lys Val Thr Phe
    2435            2440            2445

Asp Arg Leu Gln Val Leu Asp Asp His Tyr Arg Asp Val Leu Lys
    2450            2455            2460

Glu Met Lys Ala Lys Ala Ser Thr Val Lys Ala Lys Leu Leu Ser
    2465            2470            2475

Ile Glu Glu Ala Cys Arg Leu Thr Pro Pro His Ser Ala Lys Ser
    2480            2485            2490

Lys Phe Gly Tyr Gly Ala Lys Asp Val Arg Asn Leu Ser Ser Arg
    2495            2500            2505

Ala Ile Asn His Ile Arg Ser Val Trp Glu Asp Leu Leu Glu Asp
    2510            2515            2520

Thr Val Thr Pro Ile Asp Thr Thr Val Met Ala Lys Asn Glu Val
    2525            2530            2535

Phe Cys Val Gln Pro Glu Lys Gly Gly Arg Lys Pro Ala Arg Leu
    2540            2545            2550

Ile Val Phe Pro Asp Leu Gly Val Arg Val Cys Glu Lys Met Ala
    2555            2560            2565

Leu Tyr Asp Val Val Ser Thr Leu Pro Gln Ala Val Met Gly Ser
    2570            2575            2580

Ser Tyr Gly Phe Gln Tyr Ser Pro Gly Gln Arg Val Glu Phe Leu
```

```
                2585                2590                2595

Val Lys Ala Trp Lys Ser Lys Asn Pro Met Gly Phe Ser Tyr
    2600                2605                2610

Asp Thr Arg Cys Phe Asp Ser Thr Val Thr Glu Asn Asp Ile Arg
    2615                2620                2625

Val Glu Glu Ser Ile Tyr Gln Cys Cys Asp Leu Ala Pro Glu Ala
    2630                2635                2640

Arg Gln Ala Ile Lys Ser Leu Thr Glu Arg Leu Tyr Ile Gly Gly
    2645                2650                2655

Pro Leu Thr Asn Ser Lys Gly Gln Ser Cys Gly Tyr Arg Arg Cys
    2660                2665                2670

Arg Ala Ser Gly Val Leu Thr Thr Ser Cys Gly Asn Thr Leu Thr
    2675                2680                2685

Cys Tyr Leu Lys Ala Ser Ala Ala Cys Arg Ala Ala Lys Leu Gln
    2690                2695                2700

Asp Cys Thr Met Leu Val Asn Gly Asp Asp Leu Val Val Ile Cys
    2705                2710                2715

Glu Ser Ala Gly Thr Gln Glu Asp Ala Ala Ser Leu Arg Val Phe
    2720                2725                2730

Thr Glu Ala Met Thr Arg Tyr Ser Ala Pro Pro Gly Asp Leu Pro
    2735                2740                2745

Gln Pro Glu Tyr Asp Leu Glu Leu Ile Thr Ser Cys Ser Ser Asn
    2750                2755                2760

Val Ser Val Ala His Asp Ala Ser Gly Lys Arg Val Tyr Tyr Leu
    2765                2770                2775

Thr Arg Asp Pro Thr Thr Pro Ile Ala Arg Ala Ala Trp Glu Thr
    2780                2785                2790

Ala Arg His Thr Pro Val Asn Ser Trp Leu Gly Asn Ile Ile Met
    2795                2800                2805

Tyr Ala Pro Thr Leu Trp Ala Arg Met Ile Leu Met Thr His Phe
    2810                2815                2820

Phe Ser Ile Leu Leu Ala Gln Glu Gln Leu Glu Lys Ala Leu Asp
    2825                2830                2835

Cys Gln Ile Tyr Gly Ala Cys Tyr Ser Ile Glu Pro Leu Asp Leu
    2840                2845                2850

Pro Gln Ile Ile Glu Gly Leu His Gly Leu Ser Ala Phe Ser Leu
    2855                2860                2865

His Ser Tyr Ser Pro Gly Glu Ile Asn Arg Val Ala Ser Cys Leu
    2870                2875                2880

Arg Lys Leu Gly Val Pro Pro Leu Arg Val Trp Arg His Arg Ala
    2885                2890                2895

Arg Asp Val Arg Ala Lys Leu Leu Ser Gln Gly Gly Arg Ala Ala
    2900                2905                2910

Thr Cys Gly Lys Tyr Leu Phe Asn Trp Ala Val Lys Thr Lys Leu
    2915                2920                2925

Lys Leu Thr Pro Ile Pro Ala Ala Ser Gln Leu Asp Leu Ser Gly
    2930                2935                2940

Trp Phe Val Ala Gly Tyr Ser Gly Gly Asp Ile Tyr His Ser Leu
    2945                2950                2955

Ser Arg Ala Arg Pro Arg Trp Phe Met Leu Cys Leu Leu Leu Leu
    2960                2965                2970

Ser Val Gly Val Gly Ile Tyr Leu Leu Pro Asn Arg
    2975                2980                2985
```

<210> SEQ ID NO 41
<211> LENGTH: 6189
<212> TYPE: DNA
<213> ORGANISM: ARTIFICIAL
<220> FEATURE:
<223> OTHER INFORMATION: nucleotide sequence encoding hepatitis C virus polyprotein derived from Con1

<400> SEQUENCE: 41

```
atggcgccta ttacggccta ctcccaacag acgcgaggcc tacttggctg catcatcact     60
agcctcacag gccgggacag gaaccaggtc gagggggagg tccaagtggt ctccaccgca    120
acacaatctt tcctggcgac ctgcgtcaat ggcgtgtgtt ggactgtcta tcatggtgcc    180
ggctcaaaga cccttgccgg cccaaagggc ccaatcaccc aaatgtacac caatgtggac    240
caggacctcg tcggctggca agcgcccccc ggggcgcgtt ccttgacacc atgcacctgc    300
ggcagctcgg acctttactt ggtcacgagg catgccgatg tcattccggt gcgccggcgg    360
ggcgacagca gggggagcct actctccccc aggcccgtct cctacttgaa gggctcttcg    420
ggcggtccac tgctctgccc ctcggggcac gctgtgggca tctttcgggc tgccgtgtgc    480
acccgagggg ttgcgaaggc ggtggacttt gtacccgtcg agtctatgga aaccactatg    540
cggtccccgg tcttcacgga caactcgtcc cctccggccg taccgcagac attccaggtg    600
gcccatctac acgcccctac tggtagcggc aagagcacta aggtgccggc tgcgtatgca    660
gcccaagggt ataaggtgct tgtcctgaac ccgtccgtcg ccgccaccct aggtttcggg    720
gcgtatatgt ctaaggcaca tggtatcgac cctaacatca gaaccggggt aaggaccatc    780
accacgggtg cccccatcac gtactccacc tatggcaagt ttcttgccga cggtggttgc    840
tctgggggcg cctatgacat cataatatgt gatgagtgcc actcaactga ctcgaccact    900
atcctgggca tcggcacagt cctggaccaa gcggagacgg ctggagcgcg actcgtcgtg    960
ctcgccaccg ctacgcctcc gggatcggtc accgtgccac atccaaacat cgaggaggtg   1020
gctctgtcca gcactggaga aatccccttt tatggcaaag ccatccccat cgagaccatc   1080
aaggggggga ggcacctcat ttctgccat tccaagaaga aatgtgatga gctcgccgcg   1140
aagctgtccg gcctcggact caatgctgta gcatattacc ggggccttga tgtatccgtc   1200
ataccaacta gcggagacgt cattgtcgta gcaacggacg ctctaatgac gggctttacc   1260
ggcgatttcg actcagtgat cgactgcaat acatgtgtca cccagacagt cgacttcagc   1320
ctggacccga ccttcaccat tgagacgacg accgtgccac aagacgcggt gtcacgctcg   1380
cagcggcgag gcaggactgg taggggcagg atgggcattt acaggtttgt gactccagga   1440
gaacggccct cgggcatgtt cgattcctcg gttctgtgcg agtgctatga cgcgggctgt   1500
gcttggtacg agctcacgcc cgccgagacc tcagttaggt tgcgggctta cctaaacaca   1560
ccagggttgc ccgtctgcca ggaccatctg gagttctggg agagcgtctt tacaggcctc   1620
acccacatag acgcccattt cttgtcccag actaagcagg caggagacaa cttcccctac   1680
ctggtagcat accaggctac ggtgtgcgcc agggctcagg ctccacctcc atcgtgggac   1740
caaatgtgga agtgtctcat acggctaaag cctacgctgc acgggccaac gcccctgctg   1800
tataggctgg gagccgttca aaacgaggtt actaccacac accccataac caaatacatc   1860
atggcatgca tgtcggctga cctggaggtc gtcacgagca cctgggtgct ggtaggcgga   1920
gtcctagcag ctctggccgc gtattgcctg acaacaggca gcgtggtcat tgtgggcagg   1980
atcatcttgt ccggaaagcc ggccatcatt cccgacaggg aagtccttta ccgggagttc   2040
gatgagatgg aagagtgcgc ctcacacctc ccttacatcg aacagggaat gcagctcgcc   2100
```

```
gaacaattca aacagaaggc aatcggyttg ctgcaaacag ccaccaagca agcggaggct    2160
gctgctcccg tggtggaatc caagtggcgg accctcgaag ccttctgggc gaagcatatg    2220
tggaatttca tcagcgggat acaatattta gcaggcttgt ccactctgcc tggcaacccc    2280
gcgatagcat cactgatggc attcacagcc tctatcacca gcccgctcac cacccaacat    2340
accctcctgt ttaacatcct ggggggatgg gtggccgccc aacttgctcc tcccagcgct    2400
gcttctgctt tcgtaggcgc cggcatcgct ggagcggctg ttggcagcat aggccttggg    2460
aaggtgcttg tggatatttt ggcaggttat ggagcagggg tggcaggcgc gctcgtggcc    2520
tttaaggtca tgagcggcga gatgccctcc accgaggacc tggttaacct actccctgct    2580
atcctctccc ctggcgccct agtcgtcggg gtcgtgtgcg cagcgatact gcgtcggcac    2640
gtgggcccag ggaggggggc tgtgcagtgg atgaaccggc tgatagcgtt cgcttcgcgg    2700
ggtaaccacg tctcccccac gcactatgtg cctgagagcg acgctgcagc acgtgtcact    2760
cagatcctct ctagtcttac catcactcag ctgctgaaga ggcttcacca gtggatcaac    2820
gaggactgct ccacgccatg ctccggctcg tggctaagag atgtttggga ttggatatgc    2880
acggtgttga ctgatttcaa gacctggctc cagtccaagc cctgccgcg attgccggga    2940
gtccccttct tctcatgtca acgtgggtac aagggagtct ggcggggcga cggcatcatg    3000
caaaccacct gcccatgtgg agcacagatc accggacatg tgaaaaacgg ttccatgagg    3060
atcgtggggc ctaggacctg tagtaacacg tggcatggaa cattccccat taacgcgtac    3120
accacgggcc cctgcacgcc ctcccggcg ccaaattatt ctagggcgct gtggcgggtg    3180
gctgctgagg agtacgtgga ggttacgcgg gtgggggatt ccactacgt gacgggcatg    3240
accactgaca acgtaaagtg cccgtgtcag gttccggccc ccgaattctt cacagaagtg    3300
gatggggtgc ggttgcacag gtacgctcca gcgtgcaaac ccctcctacg ggaggaggtc    3360
acattcctgg tcgggctcaa tcaatacctg gttgggtcac agctcccatg cgagcccgaa    3420
ccggacgtag cagtgctcac ttccatgctc accgaccct cccacattac ggcggagacg    3480
gctaagcgta ggctggccag gggatctccc ccctccttgg ccagctcatc agctatccag    3540
ctgtctgcgc cttccttgaa ggcaacatgc actacccgtc atgactcccc ggacgctgac    3600
ctcatcgagg ccaacctcct gtggcggcag gagatgggcg gaacatcac ccgcgtggag    3660
tcagaaaata aggtagtaat tttggactct ttcgagccgc tccaagcgga ggaggatgag    3720
agggaagtat ccgttccggc ggagatcctg cggaggtcca ggaaattccc tcgagcgatg    3780
cccatatggg cacgccgga ttacaaccct ccactgttag agtcctggaa ggacccggac    3840
tacgtccctc cagtggtaca cggggtgtcca ttgccgcctg ccaaggcccc tccgatacca    3900
cctccacgga ggaagaggac ggttgtcctg tcagaatcta ccgtgtcttc tgccttggcg    3960
gagctcgcca caaagacctt cggcagctcc gaatcgtcgg ccgtcgacag cggcacggca    4020
acggcctctc ctgaccagcc ctccgacgac ggcgacgcgg atccgacgt tgagtcgtac    4080
tcctccatgc cccccttga ggggagccg gggatcccg atctcagcga cgggtcttgg    4140
tctaccgtaa gcgaggaggc tagtgaggac gtcgtctgct gctcgatgtc ctacacatgg    4200
acaggcgccc tgatcacgcc atgcgctgcg gaggaaacca agctgcccat caatgcactg    4260
agcaactctt tgctccgtca ccacaacttg gtctatgcta caacatctcg cagcgcaagc    4320
ctgcggcaga agaaggtcac ctttgacaga ctgcaggtcc tggacgacca ctaccgggac    4380
gtgctcaagg agatgaaggc gaaggcgtcc acagttaagg ctaaacttct atccgtggag    4440
gaagcctgta agctgacgcc cccacattcg gccagatcta aatttggcta tgggacaaag    4500
```

```
gacgtccgga acctatccag caaggccgtt aaccacatcc gctccgtgtg gaaggacttg      4560
ctggaagaca ctgagacacc aattgacacc accatcatgg caaaaaatga ggttttctgc      4620
gtccaaccag agaaggggg ccgcaagcca gctcgcctta cgtattccc agatttgggg       4680 gttcgtgtgt gcgagaaaat ggcccttac gatgtggtct ccaccctccc tcaggccgtg      4740
atgggctctt catacggatt ccaatactct cctggacagc gggtcgagtt cctggtgaat      4800
gcctggaaag cgaagaaatg ccctatgggc ttcgcatatg cacccgctg ttttgactca      4860 acggtcactg agaatgacat ccgtgttgag gagtcaatct accaatgttg tgacttggcc      4920
cccgaagcca gacaggccat aaggtcgctc acagagcggc tttacatcgg ggccccctg       4980 actaattcta aagggcagaa ctgcggctat cgccggtgcc gcgcgagcgg tgtactgacg      5040
accagctgcg gtaataccct cacatgttac ttgaaggccg ctgcggcctg tcgagctgcg      5100
aagctccagg actgcacgat gctcgtatgc ggagacgacc ttgtcgttat ctgtgaaagc      5160
gcggggaccc aagaggacga ggcgagccta cgggccttca cggaggctat gactagatac      5220 tctgccccc ctggggaccc gcccaaacca gaatacgact tggagttgat aacatcatgc       5280
tcctccaatg tgtcagtcgc gcacgatgca tctggcaaaa gggtgtacta tctcacccgt      5340
gaccccacca ccccccttgc gcgggctgcg tgggagacag ctagacacac tccagtcaat      5400
tcctggctag caacatcat catgtatgcg cccaccttgt gggcaaggat gatcctgatg       5460
actcatttct tctccatcct tctagctcag gaacaacttg aaaaagcccct agattgtcag     5520 atctacgggg cctgttactc cattgagcca cttgacctac ctcagatcat caacgactc      5580 catggcctta gcgcattttc actccatagt tactctccag gtgagatcaa tagggtggct      5640
tcatgcctca ggaaacttgg ggtaccgccc ttgcgagtct ggagacatcg gccagaagt      5700 gtccgcgcta ggctactgtc ccaggggggg agggctgcca cttgtggcaa gtacctcttc      5760
aactgggcag taaggaccaa gctcaaactc actccaatcc cggctgcgtc ccagttggat     5820
ttatccagct ggttcgttgc tggttacagc gggggagaca tatatcacag cctgtctcgt      5880
gcccgacccc gctggttcat gtggtgccta ctcctacttt ctgtaggggt aggcatctat      5940
ctactcccca accgatgaac ggggagctaa acactccagg ccaataggcc atcctgtttt      6000 tttcccttt ttttttcctt tttttttttt tttttttttt tttttttttt ttctcctttt       6060 ttttcctct tttttccctt ttctttcctt tggtggctcc atcttagccc tagtcacggc      6120
tagctgtgaa aggtccgtga gccgcttgac tgcagagagt gctgatactg gcctctctgc      6180
agatcaagt                                                              6189
```

<210> SEQ ID NO 42
<211> LENGTH: 1985
<212> TYPE: PRT
<213> ORGANISM: ARTIFICIAL
<220> FEATURE:
<223> OTHER INFORMATION: amino acid sequence encoded by the nucleotides
       2119-8073 of SEQ ID NO:41

<400> SEQUENCE: 42

```
Met Ala Pro Ile Thr Ala Tyr Ser Gln Gln Thr Arg Gly Leu Leu Gly
1               5                  10                  15

Cys Ile Ile Thr Ser Leu Thr Gly Arg Asp Arg Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
```

```
            50                  55                  60
Leu Ala Gly Pro Lys Gly Pro Ile Thr Gln Met Tyr Thr Asn Val Asp
 65                  70                  75                  80

Gln Asp Leu Val Gly Trp Gln Ala Pro Pro Gly Ala Arg Ser Leu Thr
                     85                  90                  95

Pro Cys Thr Cys Gly Ser Ser Asp Leu Tyr Leu Val Thr Arg His Ala
                    100                 105                 110

Asp Val Ile Pro Val Arg Arg Gly Asp Ser Arg Gly Ser Leu Leu
                115                 120                 125

Ser Pro Arg Pro Val Ser Tyr Leu Lys Gly Ser Gly Gly Pro Leu
130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
                180                 185                 190

Ala Val Pro Gln Thr Phe Gln Val Ala His Leu His Ala Pro Thr Gly
                195                 200                 205

Ser Gly Lys Ser Thr Lys Val Pro Ala Ala Tyr Ala Ala Gln Gly Tyr
210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Ile Thr Tyr Ser Thr Tyr Gly
                260                 265                 270

Lys Phe Leu Ala Asp Gly Gly Cys Ser Gly Gly Ala Tyr Asp Ile Ile
                275                 280                 285

Ile Cys Asp Glu Cys His Ser Thr Asp Ser Thr Thr Ile Leu Gly Ile
                290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Ser Thr Gly Glu Ile Pro Phe Tyr Gly
                340                 345                 350

Lys Ala Ile Pro Ile Glu Thr Ile Lys Gly Gly Arg His Leu Ile Phe
                355                 360                 365

Cys His Ser Lys Lys Lys Cys Asp Glu Leu Ala Ala Lys Leu Ser Gly
                370                 375                 380

Leu Gly Leu Asn Ala Val Ala Tyr Tyr Arg Gly Leu Asp Val Ser Val
385                 390                 395                 400

Ile Pro Thr Ser Gly Asp Val Ile Val Ala Thr Asp Ala Leu Met
                405                 410                 415

Thr Gly Phe Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
                435                 440                 445

Thr Thr Thr Val Pro Gln Asp Ala Val Ser Arg Ser Gln Arg Arg Gly
                450                 455                 460

Arg Thr Gly Arg Gly Arg Met Gly Ile Tyr Arg Phe Val Thr Pro Gly
465                 470                 475                 480
```

-continued

```
Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
    530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Thr Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Lys Pro Ala Ile Ile Pro Asp
            660                 665                 670

Arg Glu Val Leu Tyr Arg Glu Phe Asp Glu Met Glu Glu Cys Ala Ser
        675                 680                 685

His Leu Pro Tyr Ile Glu Gln Gly Met Gln Leu Ala Glu Gln Phe Lys
    690                 695                 700

Gln Lys Ala Ile Gly Leu Leu Gln Thr Ala Thr Lys Gln Ala Glu Ala
705                 710                 715                 720

Ala Ala Pro Val Val Glu Ser Lys Trp Arg Thr Leu Glu Ala Phe Trp
                725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
        755                 760                 765

Thr Ala Ser Ile Thr Ser Pro Leu Thr Thr Gln His Thr Leu Leu Phe
    770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
        835                 840                 845

Pro Ser Thr Glu Asp Leu Val Asn Leu Leu Pro Ala Ile Leu Ser Pro
    850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910
```

-continued

Ser Asp Ala Ala Arg Val Thr Gln Ile Leu Ser Ser Leu Thr Ile
       915                 920                 925

Thr Gln Leu Leu Lys Arg Leu His Gln Trp Ile Asn Glu Asp Cys Ser
    930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
            965                 970                 975

Arg Leu Pro Gly Val Pro Phe Phe Ser Cys Gln Arg Gly Tyr Lys Gly
        980                 985                 990

Val Trp Arg Gly Asp Gly Ile Met Gln Thr Thr Cys Pro Cys Gly Ala
    995                 1000                1005

Gln Ile Thr Gly His Val Lys Asn Gly Ser Met Arg Ile Val Gly
    1010                1015                1020

Pro Arg Thr Cys Ser Asn Thr Trp His Gly Thr Phe Pro Ile Asn
    1025                1030                1035

Ala Tyr Thr Thr Gly Pro Cys Thr Pro Ser Pro Ala Pro Asn Tyr
    1040                1045                1050

Ser Arg Ala Leu Trp Arg Val Ala Ala Glu Glu Tyr Val Glu Val
    1055                1060                1065

Thr Arg Val Gly Asp Phe His Tyr Val Thr Gly Met Thr Thr Asp
    1070                1075                1080

Asn Val Lys Cys Pro Cys Gln Val Pro Ala Pro Glu Phe Phe Thr
    1085                1090                1095

Glu Val Asp Gly Val Arg Leu His Arg Tyr Ala Pro Ala Cys Lys
    1100                1105                1110

Pro Leu Leu Arg Glu Glu Val Thr Phe Leu Val Gly Leu Asn Gln
    1115                1120                1125

Tyr Leu Val Gly Ser Gln Leu Pro Cys Glu Pro Glu Pro Asp Val
    1130                1135                1140

Ala Val Leu Thr Ser Met Leu Thr Asp Pro Ser His Ile Thr Ala
    1145                1150                1155

Glu Thr Ala Lys Arg Arg Leu Ala Arg Gly Ser Pro Pro Ser Leu
    1160                1165                1170

Ala Ser Ser Ser Ala Ile Gln Leu Ser Ala Pro Ser Leu Lys Ala
    1175                1180                1185

Thr Cys Thr Thr Arg His Asp Ser Pro Asp Ala Asp Leu Ile Glu
    1190                1195                1200

Ala Asn Leu Leu Trp Arg Gln Glu Met Gly Gly Asn Ile Thr Arg
    1205                1210                1215

Val Glu Ser Glu Asn Lys Val Val Ile Leu Asp Ser Phe Glu Pro
    1220                1225                1230

Leu Gln Ala Glu Glu Asp Glu Arg Glu Val Ser Val Pro Ala Glu
    1235                1240                1245

Ile Leu Arg Arg Ser Arg Lys Phe Pro Arg Ala Met Pro Ile Trp
    1250                1255                1260

Ala Arg Pro Asp Tyr Asn Pro Pro Leu Leu Glu Ser Trp Lys Asp
    1265                1270                1275

Pro Asp Tyr Val Pro Pro Val Val His Gly Cys Pro Leu Pro Pro
    1280                1285                1290

Ala Lys Ala Pro Pro Ile Pro Pro Arg Arg Lys Arg Thr Val
    1295                1300                1305

Val Leu Ser Glu Ser Thr Val Ser Ser Ala Leu Ala Glu Leu Ala

-continued

```
              1310                1315                1320

Thr Lys Thr Phe Gly Ser Ser Glu Ser Ser Ala Val Asp Ser Gly
    1325                1330                1335

Thr Ala Thr Ala Ser Pro Asp Gln Pro Ser Asp Asp Gly Asp Ala
    1340                1345                1350

Gly Ser Asp Val Glu Ser Tyr Ser Ser Met Pro Pro Leu Glu Gly
    1355                1360                1365

Glu Pro Gly Asp Pro Asp Leu Ser Asp Gly Ser Trp Ser Thr Val
    1370                1375                1380

Ser Glu Glu Ala Ser Glu Asp Val Val Cys Cys Ser Met Ser Tyr
    1385                1390                1395

Thr Trp Thr Gly Ala Leu Ile Thr Pro Cys Ala Ala Glu Glu Thr
    1400                1405                1410

Lys Leu Pro Ile Asn Ala Leu Ser Asn Ser Leu Leu Arg His His
    1415                1420                1425

Asn Leu Val Tyr Ala Thr Thr Ser Arg Ser Ala Ser Leu Arg Gln
    1430                1435                1440

Lys Lys Val Thr Phe Asp Arg Leu Gln Val Leu Asp Asp His Tyr
    1445                1450                1455

Arg Asp Val Leu Lys Glu Met Lys Ala Lys Ala Ser Thr Val Lys
    1460                1465                1470

Ala Lys Leu Leu Ser Val Glu Glu Ala Cys Lys Leu Thr Pro Pro
    1475                1480                1485

His Ser Ala Arg Ser Lys Phe Gly Tyr Gly Ala Lys Asp Val Arg
    1490                1495                1500

Asn Leu Ser Ser Lys Ala Val Asn His Ile Arg Ser Val Trp Lys
    1505                1510                1515

Asp Leu Leu Glu Asp Thr Glu Thr Pro Ile Asp Thr Thr Ile Met
    1520                1525                1530

Ala Lys Asn Glu Val Phe Cys Val Gln Pro Glu Lys Gly Gly Arg
    1535                1540                1545

Lys Pro Ala Arg Leu Ile Val Phe Pro Asp Leu Gly Val Arg Val
    1550                1555                1560

Cys Glu Lys Met Ala Leu Tyr Asp Val Val Ser Thr Leu Pro Gln
    1565                1570                1575

Ala Val Met Gly Ser Ser Tyr Gly Phe Gln Tyr Ser Pro Gly Gln
    1580                1585                1590

Arg Val Glu Phe Leu Val Asn Ala Trp Lys Ala Lys Lys Cys Pro
    1595                1600                1605

Met Gly Phe Ala Tyr Asp Thr Arg Cys Phe Asp Ser Thr Val Thr
    1610                1615                1620

Glu Asn Asp Ile Arg Val Glu Glu Ser Ile Tyr Gln Cys Cys Asp
    1625                1630                1635

Leu Ala Pro Glu Ala Arg Gln Ala Ile Arg Ser Leu Thr Glu Arg
    1640                1645                1650

Leu Tyr Ile Gly Gly Pro Leu Thr Asn Ser Lys Gly Gln Asn Cys
    1655                1660                1665

Gly Tyr Arg Arg Cys Arg Ala Ser Gly Val Leu Thr Thr Ser Cys
    1670                1675                1680

Gly Asn Thr Leu Thr Cys Tyr Leu Lys Ala Ala Ala Cys Arg
    1685                1690                1695

Ala Ala Lys Leu Gln Asp Cys Thr Met Leu Val Cys Gly Asp Asp
    1700                1705                1710
```

```
Leu Val Val Ile Cys Glu Ser Ala Gly Thr Gln Glu Asp Glu Ala
    1715                1720                1725
Ser Leu Arg Ala Phe Thr Glu Ala Met Thr Arg Tyr Ser Ala Pro
    1730                1735                1740
Pro Gly Asp Pro Pro Lys Pro Glu Tyr Asp Leu Glu Leu Ile Thr
    1745                1750                1755
Ser Cys Ser Ser Asn Val Ser Val Ala His Asp Ala Ser Gly Lys
    1760                1765                1770
Arg Val Tyr Tyr Leu Thr Arg Asp Pro Thr Thr Pro Leu Ala Arg
    1775                1780                1785
Ala Ala Trp Glu Thr Ala Arg His Thr Pro Val Asn Ser Trp Leu
    1790                1795                1800
Gly Asn Ile Ile Met Tyr Ala Pro Thr Leu Trp Ala Arg Met Ile
    1805                1810                1815
Leu Met Thr His Phe Phe Ser Ile Leu Leu Ala Gln Glu Gln Leu
    1820                1825                1830
Glu Lys Ala Leu Asp Cys Gln Ile Tyr Gly Ala Cys Tyr Ser Ile
    1835                1840                1845
Glu Pro Leu Asp Leu Pro Gln Ile Ile Gln Arg Leu His Gly Leu
    1850                1855                1860
Ser Ala Phe Ser Leu His Ser Tyr Ser Pro Gly Glu Ile Asn Arg
    1865                1870                1875
Val Ala Ser Cys Leu Arg Lys Leu Gly Val Pro Pro Leu Arg Val
    1880                1885                1890
Trp Arg His Arg Ala Arg Ser Val Arg Ala Arg Leu Leu Ser Gln
    1895                1900                1905
Gly Gly Arg Ala Ala Thr Cys Gly Lys Tyr Leu Phe Asn Trp Ala
    1910                1915                1920
Val Arg Thr Lys Leu Lys Leu Thr Pro Ile Pro Ala Ala Ser Gln
    1925                1930                1935
Leu Asp Leu Ser Ser Trp Phe Val Ala Gly Tyr Ser Gly Gly Asp
    1940                1945                1950
Ile Tyr His Ser Leu Ser Arg Ala Arg Pro Arg Trp Phe Met Trp
    1955                1960                1965
Cys Leu Leu Leu Leu Ser Val Gly Val Gly Ile Tyr Leu Leu Pro
    1970                1975                1980
Asn Arg
    1985

<210> SEQ ID NO 43
<211> LENGTH: 32
<212> TYPE: DNA
<213> ORGANISM: ARTIFICIAL
<220> FEATURE:
<223> OTHER INFORMATION: primer

<400> SEQUENCE: 43
tccctctaga cggaccgcta tcaggacata gc                              32

<210> SEQ ID NO 44
<211> LENGTH: 35
<212> TYPE: DNA
<213> ORGANISM: ARTIFICIAL
<220> FEATURE:
<223> OTHER INFORMATION: primer

<400> SEQUENCE: 44
attcgtgctc atggtattat cgtgttttc aaagg                            35
```

<210> SEQ ID NO 45
<211> LENGTH: 34
<212> TYPE: DNA
<213> ORGANISM: ARTIFICIAL
<220> FEATURE:
<223> OTHER INFORMATION: primer

<400> SEQUENCE: 45
cacgataata ccatgagcac gaatcctaaa cctc                                  34

<210> SEQ ID NO 46
<211> LENGTH: 34
<212> TYPE: DNA
<213> ORGANISM: ARTIFICIAL
<220> FEATURE:
<223> OTHER INFORMATION: primer

<400> SEQUENCE: 46
ccgctcgagg cagtcgttcg tgacatggta tacc                                  34

<210> SEQ ID NO 47
<211> LENGTH: 32
<212> TYPE: DNA
<213> ORGANISM: ARTIFICIAL
<220> FEATURE:
<223> OTHER INFORMATION: primer

<400> SEQUENCE: 47
tccctctaga cggaccgcta tcaggacata gc                                    32

<210> SEQ ID NO 48
<211> LENGTH: 38
<212> TYPE: DNA
<213> ORGANISM: ARTIFICIAL
<220> FEATURE:
<223> OTHER INFORMATION: primer

<400> SEQUENCE: 48
agagcaaccg ggcatggtat tatcgtgttt ttcaaagg                              38

<210> SEQ ID NO 49
<211> LENGTH: 40
<212> TYPE: DNA
<213> ORGANISM: ARTIFICIAL
<220> FEATURE:
<223> OTHER INFORMATION: primer

<400> SEQUENCE: 49
cacgataata ccatgcccgg ttgctctttt tctatcttcc                            40

<210> SEQ ID NO 50
<211> LENGTH: 22
<212> TYPE: DNA
<213> ORGANISM: ARTIFICIAL
<220> FEATURE:
<223> OTHER INFORMATION: primer

<400> SEQUENCE: 50
atgtacagcc gaaccagttg cc                                               22

<210> SEQ ID NO 51
<211> LENGTH: 32
<212> TYPE: DNA
<213> ORGANISM: ARTIFICIAL
<220> FEATURE:
<223> OTHER INFORMATION: primer

```
<400> SEQUENCE: 51
tccctctaga cggaccgcta tcaggacata gc                                32

<210> SEQ ID NO 52
<211> LENGTH: 35
<212> TYPE: DNA
<213> ORGANISM: ARTIFICIAL
<220> FEATURE:
<223> OTHER INFORMATION: primer

<400> SEQUENCE: 52
ctcccggtcc atggtattat cgtgtttttc aaagg                             35

<210> SEQ ID NO 53
<211> LENGTH: 32
<212> TYPE: DNA
<213> ORGANISM: ARTIFICIAL
<220> FEATURE:
<223> OTHER INFORMATION: primer

<400> SEQUENCE: 53
cacgataata ccatggaccg ggagatggct gc                                32

<210> SEQ ID NO 54
<211> LENGTH: 24
<212> TYPE: DNA
<213> ORGANISM: ARTIFICIAL
<220> FEATURE:
<223> OTHER INFORMATION: primer

<400> SEQUENCE: 54
gagcggtccg agtatggcaa tcag                                         24

<210> SEQ ID NO 55
<211> LENGTH: 17
<212> TYPE: DNA
<213> ORGANISM: ARTIFICIAL
<220> FEATURE:
<223> OTHER INFORMATION: primer

<400> SEQUENCE: 55
agcctcttca gcagctg                                                 17

<210> SEQ ID NO 56
<211> LENGTH: 18
<212> TYPE: DNA
<213> ORGANISM: ARTIFICIAL
<220> FEATURE:
<223> OTHER INFORMATION: primer

<400> SEQUENCE: 56
aggaaatggc ctattggc                                                18

<210> SEQ ID NO 57
<211> LENGTH: 19
<212> TYPE: DNA
<213> ORGANISM: ARTIFICIAL
<220> FEATURE:
<223> OTHER INFORMATION: primer

<400> SEQUENCE: 57
tttccaccat attgccgtc                                               19

<210> SEQ ID NO 58
<211> LENGTH: 18
```

```
<212> TYPE: DNA
<213> ORGANISM: ARTIFICIAL
<220> FEATURE:
<223> OTHER INFORMATION: primer

<400> SEQUENCE: 58
ttgacgcagg tcgccagg                                                      18

<210> SEQ ID NO 59
<211> LENGTH: 20
<212> TYPE: DNA
<213> ORGANISM: ARTIFICIAL
<220> FEATURE:
<223> OTHER INFORMATION: primer

<400> SEQUENCE: 59
gaaccaggtc gaggggagg                                                     20

<210> SEQ ID NO 60
<211> LENGTH: 20
<212> TYPE: DNA
<213> ORGANISM: ARTIFICIAL
<220> FEATURE:
<223> OTHER INFORMATION: primer

<400> SEQUENCE: 60
tcgatgggga tggctttgcc                                                    20

<210> SEQ ID NO 61
<211> LENGTH: 20
<212> TYPE: DNA
<213> ORGANISM: ARTIFICIAL
<220> FEATURE:
<223> OTHER INFORMATION: primer

<400> SEQUENCE: 61
ctcgccaccg ctacgcctcc                                                    20

<210> SEQ ID NO 62
<211> LENGTH: 19
<212> TYPE: DNA
<213> ORGANISM: ARTIFICIAL
<220> FEATURE:
<223> OTHER INFORMATION: primer

<400> SEQUENCE: 62
actccgccta ccagcaccc                                                     19

<210> SEQ ID NO 63
<211> LENGTH: 20
<212> TYPE: DNA
<213> ORGANISM: ARTIFICIAL
<220> FEATURE:
<223> OTHER INFORMATION: primer

<400> SEQUENCE: 63
accccataac caaatacatc                                                    20

<210> SEQ ID NO 64
<211> LENGTH: 17
<212> TYPE: DNA
<213> ORGANISM: ARTIFICIAL
<220> FEATURE:
<223> OTHER INFORMATION: primer

<400> SEQUENCE: 64
agcctcttca gcagctg                                                       17
```

<210> SEQ ID NO 65
<211> LENGTH: 20
<212> TYPE: DNA
<213> ORGANISM: ARTIFICIAL
<220> FEATURE:
<223> OTHER INFORMATION: primer

<400> SEQUENCE: 65
tatgtgcctg agagcgacgc                                              20

<210> SEQ ID NO 66
<211> LENGTH: 20
<212> TYPE: DNA
<213> ORGANISM: ARTIFICIAL
<220> FEATURE:
<223> OTHER INFORMATION: primer

<400> SEQUENCE: 66
tatgtgcctg agagcgacgc                                              20

<210> SEQ ID NO 67
<211> LENGTH: 19
<212> TYPE: DNA
<213> ORGANISM: ARTIFICIAL
<220> FEATURE:
<223> OTHER INFORMATION: primer

<400> SEQUENCE: 67
aaccttctgt ggcggcagg                                               19

<210> SEQ ID NO 68
<211> LENGTH: 20
<212> TYPE: DNA
<213> ORGANISM: ARTIFICIAL
<220> FEATURE:
<223> OTHER INFORMATION: primer

<400> SEQUENCE: 68
ctggttggac gcagaaaacc                                              20

<210> SEQ ID NO 69
<211> LENGTH: 50
<212> TYPE: DNA
<213> ORGANISM: ARTIFICIAL
<220> FEATURE:
<223> OTHER INFORMATION: primer

<400> SEQUENCE: 69
gatccgggcc cagggttgga ctcgacgtct cccgcaagct taagaaggcg             50

<210> SEQ ID NO 70
<211> LENGTH: 20
<212> TYPE: DNA
<213> ORGANISM: ARTIFICIAL
<220> FEATURE:
<223> OTHER INFORMATION: primer

<400> SEQUENCE: 70
aaccacatcc gctccgtgtg                                              20

<210> SEQ ID NO 71
<211> LENGTH: 20
<212> TYPE: DNA
<213> ORGANISM: ARTIFICIAL
<220> FEATURE:
<223> OTHER INFORMATION: primer

```
<400> SEQUENCE: 71
tggctcaatg gagtaacagg                                                  20

<210> SEQ ID NO 72
<211> LENGTH: 18
<212> TYPE: DNA
<213> ORGANISM: ARTIFICIAL
<220> FEATURE:
<223> OTHER INFORMATION: primer

<400> SEQUENCE: 72
ttctccatcc ttctagct                                                    18

<210> SEQ ID NO 73
<211> LENGTH: 19
<212> TYPE: DNA
<213> ORGANISM: ARTIFICIAL
<220> FEATURE:
<223> OTHER INFORMATION: primer

<400> SEQUENCE: 73
aacaggaaat ggcctattg                                                   19

<210> SEQ ID NO 74
<211> LENGTH: 10
<212> TYPE: PRT
<213> ORGANISM: artificial
<220> FEATURE:
<223> OTHER INFORMATION: deletion in NS5B

<400> SEQUENCE: 74

Met Leu Val Asn Gly Asp Asp Leu Val Val
1               5                   10

<210> SEQ ID NO 75
<211> LENGTH: 4
<212> TYPE: PRT
<213> ORGANISM: artificial
<220> FEATURE:
<223> OTHER INFORMATION: insertion in NS5A

<400> SEQUENCE: 75

Ser Ser Tyr Asn
1

<210> SEQ ID NO 76
<211> LENGTH: 168
<212> TYPE: DNA
<213> ORGANISM: artificial
<220> FEATURE:
<223> OTHER INFORMATION: 3' NTR of H77C strain

<400> SEQUENCE: 76
cuccccaacc gaugaagguu gggguaaaca cuccggccuc uuaagccauu uccuguuuuu      60
uuuuucuaau ggugggcucca ucuuagcccu agucacggcu agcugugaaa ggccgugag    120 ccgcaugacu gcagagagug cugauacugg ccucucugca gaucaugu                 168
```